United States Patent

Otten et al.

[11] Patent Number: 6,054,414
[45] Date of Patent: Apr. 25, 2000

[54] BENZOYL DERIVATIVES

[75] Inventors: Martina Otten, Ludwigshafen; Wolfgang von Deyn, Neustadt; Stefan Engel, Idstein; Regina Luise Hill, Speyer; Uwe Kardorff; Marcus Vossen, both of Mannheim; Peter Plath, Frankenthal; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 09/029,680

[22] PCT Filed: Aug. 29, 1996

[86] PCT No.: PCT/EP96/03800

§ 371 Date: Feb. 26, 1998

§ 102(e) Date: Feb. 26, 1998

[87] PCT Pub. No.: WO97/09324

PCT Pub. Date: Mar. 13, 1997

[30] Foreign Application Priority Data

Sep. 1, 1995 [DE] Germany .............. 195 32 311

[51] Int. Cl.[7] .............. A01N 43/18; C07D 335/04; C07D 335/06
[52] U.S. Cl. .............. 504/288; 549/23
[58] Field of Search .............. 549/23; 504/288

[56] References Cited

U.S. PATENT DOCUMENTS

| | | | |
|---|---|---|---|
| 3,758,522 | 9/1973 | Feit et al. | 260/397.7 |
| 3,897,476 | 7/1975 | Feit et al. | 260/465 D |
| 4,740,519 | 4/1988 | Shroot et al. | 514/443 |
| 4,780,127 | 10/1988 | Michaely et al. | 71/103 |
| 5,015,658 | 5/1991 | Chandraratna | 514/432 |
| 5,420,273 | 5/1995 | Klaus et al. | 544/148 |
| 5,468,878 | 11/1995 | Nasuno et al. | 549/23 |
| 5,480,858 | 1/1996 | Sakamoto et al. | 504/288 |

FOREIGN PATENT DOCUMENTS

| | | |
|---|---|---|
| 903 254 | 3/1986 | Belgium . |
| 139 578 | 1/1973 | Denmark . |
| 50 957 | 5/1982 | European Pat. Off. . |
| 73 663 | 3/1983 | European Pat. Off. . |
| 090 262 | 10/1983 | European Pat. Off. . |
| 135 191 | 3/1985 | European Pat. Off. . |
| 137 963 | 4/1985 | European Pat. Off. . |
| 186 118 | 7/1986 | European Pat. Off. . |
| 186 119 | 7/1986 | European Pat. Off. . |
| 186 120 | 7/1986 | European Pat. Off. . |
| 283 261 | 10/1988 | European Pat. Off. . |
| 319 075 | 6/1989 | European Pat. Off. . |
| 338 992 | 10/1989 | European Pat. Off. . |
| 350 846 | 1/1990 | European Pat. Off. . |
| 2 321 518 | 11/1973 | Germany . |
| 24 50 193 | 5/1975 | Germany . |
| 44 27 995 | 2/1996 | Germany . |
| 3052862 | 7/1989 | Japan . |
| 90/05712 | 5/1990 | WIPO . |
| 94/04524 | 3/1994 | WIPO . |
| 94/08962 | 4/1994 | WIPO . |
| 94/08988 | 4/1994 | WIPO . |
| 97/08164 | 3/1997 | WIPO . |

OTHER PUBLICATIONS

Abstract JP 3120–202, Oct. 3, 1989.

*Primary Examiner*—Laura L. Stockton
*Attorney, Agent, or Firm*—Keil & Weinkauf

[57] ABSTRACT

Benzoyl derivatives of the formula I

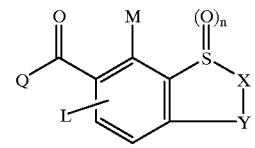

where the substituents L, M, X, Y and n have the meaning given in claim 1 and Q for [sic] a cyclohexane-1,3-dione ring, which is linked in the 2-position, of the formula II,

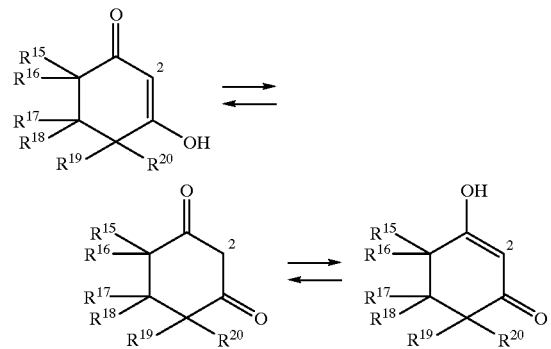

where $R^{15}$, $R^{16}$, $R^{18}$ and $R^{20}$ are hydrogen or $C_1$–$C_4$-alkyl, $R^{19}$ is hydrogen, $C_1$–$C_4$-alkyl or a group —$COOR^{14}$, $R^{17}$ is hydrogen, $C_1$–$C_4$-alkyl, $C_3$–$C_4$-cycloalkyl, it being possible for these groups, if desired, to carry one to three of the following substituents: halogen, $C_1$–$C_4$-alkylthio or $C_1$–$C_4$-alkoxy, or $R^{17}$ is tetrahydropyran-3-yl, tetrahydropyran-4-yl or tetrahydrothiopyran-3-yl or $R^{17}$ and $R^{20}$ together form a bond or a three to six-membered carbocyclic ring, where in the case where Y=C=O, X is not equal to $NR^{23}$, and agriculturally utilizable salts, a process for their preparation and their use as herbicides are described.

11 Claims, No Drawings

BENZOYL DERIVATIVES

This application is a 371 of PCT/EP96/03800 filed Aug. 29, 1996.

The present invention relates to novel benzoyl derivatives having herbicidal action, processes for preparing the benzoyl derivatives, compositions which contain the latter and the use of these derivatives or compositions containing the latter for controlling weeds.

Herbicidally active 2-aroylcyclohexanediones are disclosed in the literature, for example in EP 283261, EP 90262, EP 135191, EP 186118, EP 186119, EP 186120, EP 319075, WO 9005712, WO 9404524, WO 9408988, JO3052862 and JO 3120202.

The herbicidal properties of the known compounds and the tolerability for crop plants, however, are only satisfactory to a limited extent.

It is an object of the present invention to find novel 2-aroylcyclohexanediones having improved properties.

We have found that this object is achieved by the benzoyl derivatives of the formula I

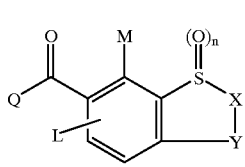

I where the substituents have the following meanings:

L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy; halogen, cyano, nitro, a group —$(A)_m$—$S(O)_n R^1$ or a group —$(A)_m$—CO—$R^2$;

Y is C=O, C=N—$R^3$, $CR^7$—$NR^5 R^6$, $CR^7$—$OR^8$, $CR^{10} R^{11}$, $CR^7$—$SR^8$; 1,3-dioxanyl or 1,3-dioxolanyl substituted by hydrogen or $C_1$–$C_4$-alkyl; a heteroatom selected from the group oxygen, sulfur and nitrogen;

X is a chain (—$CR^{12} R^{13}$—), (—$CR^{12} R^{13}$—$CR^{21} R^{22}$—), (—$CR^{12}$=$CR^{13}$—), (—$CR^{12} R^{13}$—$CR^{12}$=$CR^{13}$—); $NR^{23}$ the bond between X and Y can be saturated or unsaturated;

A is O or $NR^{14}$;

m is zero or one;

n is zero, one or two;

$R^1$ is $C_1$–$C_4$-alkyl, $C_1$–$C_4$-haloalkyl or $NR^{14}$;

$R^2$ is $C_1$–$C_4$-alkyl, $C_1$–$C_4$-haloalkyl, $C_1$–$C_4$-alkoxy or $NR^{14}$;

$R^3$ is hydrogen, —$NR^9 R^4$; $C_1$–$C_6$-alkyl, $C_1$–$C_6$-haloalkyl, $C_1$–$C_6$-alkoxy, $C_1$–$C_6$-haloalkoxy, $C_2$–$C_6$-alkenyl, $C_2$–$C_6$-haloalkenyl, $C_2$–$C_6$-alkynyl; monosubstituted to polysubstituted phenyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro; mono- to polysubstituted benzyloxy, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^4$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$; monosubstituted to polysubstituted phenyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro; mono- to polysubstituted benzyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^9$ is hydrogen, $C_1$–$C_6$-alkyl, $C_1$–$C_6$-haloalkyl, $C_2$–$C_6$-alkenyl, $C_2$–$C_6$-alkynyl, C=O—$NR^{14}$; monosubstituted to polysubstituted phenyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro; mono- to polysubstituted benzyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^5$ and $R^6$ independently of one another are hydrogen, $C_1$–$C_6$-alkyl, $C_2$–$C_6$-alkenyl, $C_1$–$C_4$-haloalkyl, $C_2$–$C_6$-haloalkenyl, $C_1$–$C_6$-alkoxy, $C_1$–$C_6$-haloalkoxy; monosubstituted to polysubstituted phenyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro; mono- to polysubstituted benzyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^7$ is hydrogen, $C_1$–$C_6$-alkyl, $C_1$–$C_4$-alkoxy, $C_1$–$C_4$-haloalkyl, $C_f$–$C_4$-haloalkoxy; substituted or unsubstituted phenyl, it being possible for the substituents to consist of one to three halogens, $C_1$–$C_4$-alkyl, $C_1$–$C_4$-alkoxy, $C_1$–$C_4$-haloalkoxy, nitro; $R^7$ and $R^{21}$ or $R^7$ and $R^{23}$ or $R^7$ and $R^{12}$ can form a bond;

$R^8$ is hydrogen, $C_1$–$C_6$-alkyl, $C_1$–$C_4$-haloalkyl, substituted phenyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro; substituted benzyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{10}$ and $R^{11}$ independently of one another are hydrogen, $C_1$–$C_6$-alkyl; phenyl which is unsubstituted or substituted by one to three halogens, $C_1$–$C_4$-alkyl, $C_1$–$C_4$-alkoxy, $C_1$–$C_4$-haloalkoxy, nitro; $R^{10}$ and $R^{12}$ or $R^{10}$ and $R^{23}$ or $R^{10}$ and $R^{21}$ can form a bond;

$R^{12}$ and $R^{13}$ independently of one another are hydrogen, $C_1$–$C_6$-alkyl, $C_1$–$C_6$-haloalkyl, $C_1$–$C_6$-alkoxy, $C_1$–$C_6$-haloalkoxy; unsubstituted or substituted phenyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{14}$ is $C_1$–$C_4$-alkyl;

$R^{21}$ is hydrogen, $C_1$–$C_6$-alkyl, $C_1$–$C_6$-haloalkyl, $C_1$–$C_6$-alkoxy, $C_1$–$C_6$-haloalkoxy; unsubstituted or substituted phenyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{22}$ is hydrogen, $C_1$–$C_6$-alkyl, $C_1$–$C_6$-haloalkyl, $C_1$–$C_6$-alkoxy, $C_1$–$C_6$-haloalkoxy; unsubstituted or substituted phenyl, it being possible for the substituents to consist of $C_1$–$C_4$-alkyl, $C_1$–$C_4$-alkoxy, $C_1$–$C_4$-haloalkoxy, $C_1$–$C_4$-haloalkyl, halogen, cyano, nitro;

$R^{23}$ is hydrogen, $C_1$–$C_6$-alkyl, $C_2$–$C_6$-alkenyl, $C_1$–$C_6$-alkoxy; phenyl or benzyl which is unsubstituted or substituted by $C_1$–$C_4$-alkyl, $C_1$–$C_4$-alkoxy, $C_1$–$C_4$-haloalkoxy, $C_1$–$C_4$-haloalkyl, halogen, cyano, nitro;

Q is a cyclohexane-1,3-dione ring, which is linked in the 2-position, of the formula II,

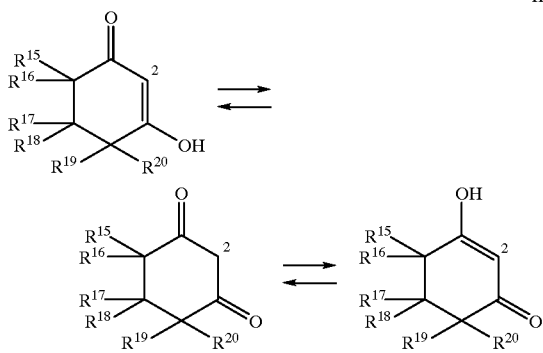

where

R[15], R[16], R[18], and R[20] are hydrogen or $C_1$–$C_4$-alkyl,

R[19] is hydrogen, $C_1$–$C_4$-alkyl or a group —COOR[14],

R[17] is hydrogen, $C_1$–$C_4$-alkyl, $C_3$–$C_4$-cycloalkyl, it being possible for these groups, if desired, to carry one to three of the following substituents: halogen, $C_1$–$C_4$-alkylthio or $C_1$–$C_4$-alkoxy, or R[17] is tetrahydropyran-3-yl, tetrahydropyran-4-yl or tetrahydrothiopyran-3-yl, or R[17] and R[20] together form a bond or a three to six-membered carbocyclic ring, where in the case where Y=C=O, X is not equal to NR[23], and agriculturally customary salts of the compound [sic] I.

Compounds of the formula Ia–Ie are obtained by reacting compounds of the formula II with a benzoic acid derivative of the formula III and rearranging to give benzoyl derivatives of the formula Ia–Ie.

Scheme 1

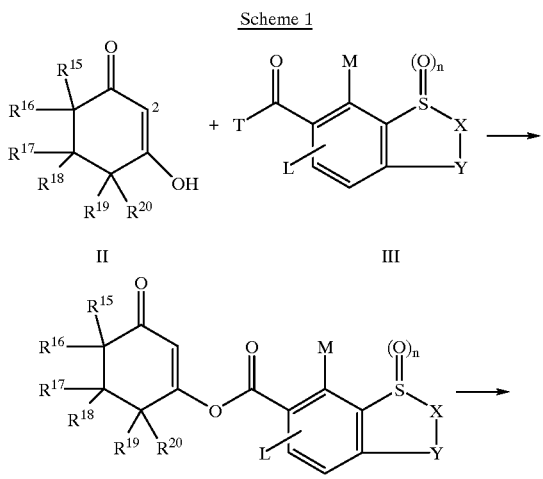

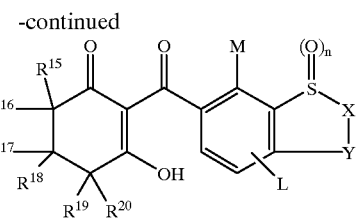

In the above scheme 1, T in said formulae has the meaning halogen or OH and L, M, X, Y and n have the meanings given above.

The first step of the reaction sequence, the acylation, is carried out in a generally known manner, e.g. by adding an acid chloride of the formula III (T=Cl) or a carboxylic acids III (T=OH) activated, for example, with DCC (dicyclocarbodiimides or similar agents known from the literature, e.g. triphenylphosphine/DEAD=diethyl azodicarboxylate, 2-pyridine disulfide/triphenylphosphine to the solution or suspension of a cyclohexanedione II, if appropriate in the presence of an auxiliary base. The reactants and the auxiliary base are in this case expediently employed in equimolar amounts. A small excess, e.g. from 1.2 to 1.5 molar equivalents, based on II, of the auxiliary base can be advantageous under certain circumstances.

Suitable auxiliary bases are tertiary alkylamines, pyridine or alkali metal carbonates. The solvents used can be, e.g. methylene chloride, dioxane, diethyl ether, toluene, acetonitrile or ethyl acetate.

During the addition of the acid chloride, the reaction mixture is preferably cooled to from 0 to 10° C., then it is stirred at from 20 to 100° C., in particular 25 to 50° C., until the reaction is complete. working up is carried out in the customary manner, e.g. the reaction mixture is poured into water and the useful product is extracted, e.g. with methylene chloride. After drying the organic phase and removing the solvent, the crude enol ester can be employed without further purification for the rearrangement. Preparation examples for benzoyl enol esters of cyclohexane-1,3-diones are found, for example, EP-A 186 118 or U.S. Pat. No. 4,780,127.

The rearrangement of the enol esters to the compounds of the formula Ia–Ie is expediently carried out at from 20 to 40° C. in a solvent and in the presence of an auxiliary base and also with the aid of a cyano compound as a catalyst.

The solvents used can be, e.g. acetonitrile, methylene chloride, 1,2-dichloroethane, ethyl acetate or toluene. A preferred solvent is acetonitrile. Suitable auxiliary bases are tertiary alkylamines, pyridine or alkali metal carbonates, which are preferably employed in equimolar amounts or up to a four-fold excess, based on the benzoyl enol ester. A preferred auxiliary base is triethylamine in twice the amount.

Suitable catalysts are potassium cyanide, acetone cyanohydrin and trimethylsilyl cyanide, preferably in an amount of from 1 to 50 mol percent, based on the enol ester. Preferably, acetone cyanohydrin is added, e.g. in the amounts from 5 to 15, in particular 10 mol percent. Examples of the cyanide-catalyzed rearrangement of enol esters are found, for example, in EP-A 186118 or U.S. Pat. No. 4,780,127.

Working up is carried out in a manner known per se, e.g. the reaction mixture is acidified with dilute mineral acids such as 5% strength hydrochloric acid or sulfuric acid and extracted with an organic solvent such as methylene chloride or ethyl acetate. For purification, the extract is extracted with cold 5 to 10% strength alkali metal carbonate solution, the final product passing into the aqueous phase. By acidifying the aqueous solution, the product of the formula Ia–Ie is precipitated or extracted again with methylene chloride or ethyl acetate, dried and then freed from the solvent.

The 1,3-diketones of the formula II used as a starting material are known and can be prepared by processes known per se, such as are described, for example, in EP-A 71707, EP-A 142741, EP-A 243313, U.S. Pat. No. 4,249,937 and WO 92/13821. Cyclohexanedione and imedone are commercially available compounds.

Benzoic acids of the formula III can be prepared as follows:

Benzoyl halides, for example benzoyl chlorides of the formula III (T=Cl), are prepared in a known manner by reacting the benzoic acids of the formula III (T=OH) with thionyl chloride.

The benzoic acids of the formula III (T=OH) can be prepared in a known manner by acidic or basic hydrolysis of the corresponding esters of the formula III (T=$C_1$–$C_4$-alkoxy).

The intermediates of the formula III are known in some cases or can be prepared by processes known from the literature.

Scheme 2

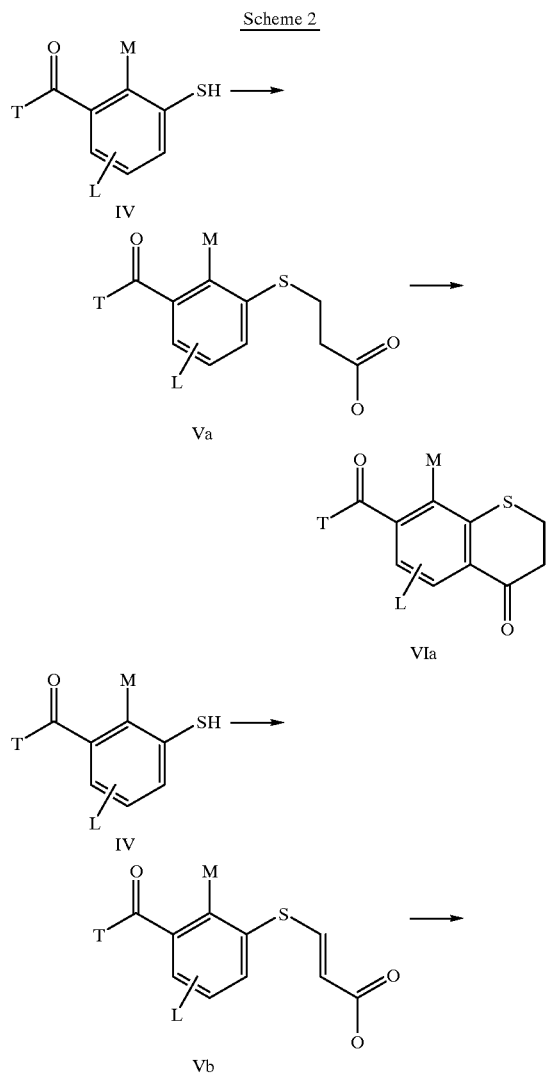

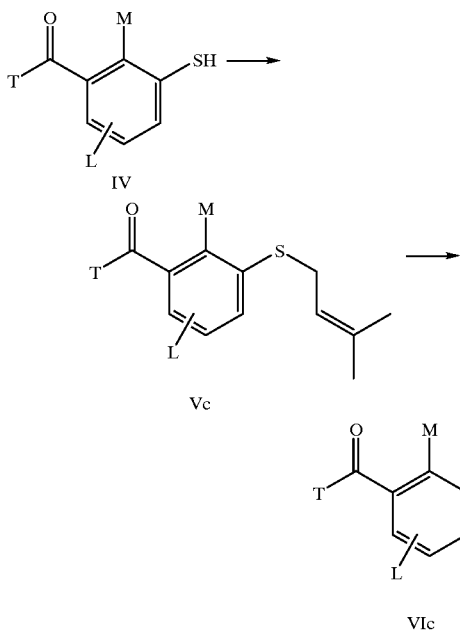

After this, for example, arylthio compounds IV as shown in scheme 2 can be reacted with substituted haloalkenyl as described in J. Med. Chem. 1984, 27, 1516, substituted alkynylcarboxylic acids as described in J. Org. Chem. 1980, 45, 4611 or J. Am. Chem. Soc. 1983, 105, 883, substituted haloalkylcarboxylic acids as desribed in Chem. Ber. 1925, 58, 1612 in the presence of a base such as alkali metal hydroxide, alkali metal hydride or alkali metal carbonate. The resulting compounds V are cyclized to VI under Friedel-Crafts conditions with addition of a Lewis acid 45 or a protic acid. Preferred Lewis acids are $AlCl_3$ or $SnCl_4$ and preferred protic acids are polyphoshoric acid and sulfuric acid as described in Can. J. Chem. 1981, 59, 199; Chem. Ber. 1925, 58, 1625; Chem. Ber. 1926, 59, 1074; Phosp. and Sulf. 1984, 19, 31.

Thiochromenone acids can furthermore be prepared by, for example, elimination of hydrogen halide from 3-halothiochromanone acids or, for example, by reaction of the substituted thiophenol acids with substituted α-alkylacetic esters in the presence of phosphorus pentoxide as described in Ann. Chem. 1964, 680, 40.

The arylthio compounds IV can be obtained, for example, by Sandmeyer reaction from corresponding anilines, which for their part are synthesized by reduction of suitable nitro compounds as described in Organicum 19th Edition 1992, 552 ff.

In the case where, for example, X is equal to (—$CR^{12}R^{13}$—) or (—$CR^{12}R^{13}CR^{21}R^{22}$—), Y is equal to C=O and T is equal to $C_1$–$C_4$-alkoxy, the thiochromonone ester or dihydrobenzothiophene ester as described in scheme 2 can be prepared by alkylation of the arylthio compound IV with halopropionic acid or haloacetic acid in solvent or water in the presence of one of the abovementioned bases and cyclized to VI.

The reactants and the base are in this case expediently employed in equimolar amounts. The reaction mixture is preferably stirred at 20–100° C., in particular at 20–40° C. Working-up is carried out, for example, in such a way that the reaction mixture is poured onto water, the aqueous phase is rendered acidic using mineral acids such as hydrochloric acid or sulfuric acid and the useful product is filtered off with suction or extracted by extraction with methylene chloride or ethyl acetate, and the extract is dried and freed from the solvent. The ester can be reacted without further purification.

By stirring V in, for example, polyphosphoric acid at 40–140° C., in particular at 70–100° C., or by activating the carboxylic acid by conversion into the acid chloride and stirring with 2–6, in particular 3.5 to 4.5, mol equivalents of a Lewis acid such as $AlCl_3$ or $SnCl_4$ in a solvent or by stirring with or in sulfuric acid, an intermediate of the formula III is obtained by working up in a manner known per se, ie. adding ice water and filtering off the useful product with suction or extracting the aqueous phase with ethyl acetate or methylene chloride, drying and removing the solvent.

In the case where, for example, X is equal to an ethylene group ($—CR^{12}=CR^{13}—$), Y is equal to C=O and T is equal to $C_1$–$C_4$-alkoxy, the thiochromenone ester can be converted by, for example, reaction of an arylthio compound with an acetylenecarboxylic acid derivative in water or solvent at 0–140° C. Working up is carried out in a manner known per se by adding water and dilute mineral acid, e.g. hydrochloric acid. The useful product is either filtered off with suction or obtained by extraction with methylene chloride or ethyl acetate, then drying and removing the solvent.

The intermediates of the formula III can be further functionalized by reactions known from the literature, such as reduction as described in Jerry March, Advanced Organic Chemistry, Fourth Ed., e.g. p.910ff, oximation as described in Jerry March, Advanced Organic Chemistry, Fourth Ed., e.g. p. 934, 935, 1039, 1226, 405ff, conversion into imines and amines as described in Jerry March, Advanced Organic Chemistry, Fourth Ed., ketalization, alkylation, halogenation, elimination and oxidation as described in Jerry March, Advanced Organic Chemistry, Fourth Ed.

The acids of the 3-alkoxy-1,2-benzisothiazole-1,1-dioxides or 3-alkoxy-1,2-benzisothiazoles can be obtained starting from corresponding saccharin derivatives or 1,2-benzisothiazoles by, for example, reaction with $PCl_5$, $POCl_3$ or chlorine and alcohol, if appropriate in the presence of an auxiliary base such as triethylamine, which is described, for example, in U.S. Pat. No. 4,571,429, Arch. Pharm. 1984, 317, 807, U.S. Pat. Nos. 4,461,901, 450,916, J. Med. Chem. 1986, 29, 359. Saccharincarboxylic acids can be obtained by processes known from the literature as described in Ann. Chem. 427, 231, 1922, Chem. Ber. 13, 1554, 1980, Chem. Ber. 25, 1740, 1892, German Offenlegungsschrift 3607343, German Patent Application P 44 27 995.7.

The derivatives of the benzo-1,4-oxathiin acids are known in some cases, e.g. from J. Org. Chem. 1968, 33, 456 or can be synthesized, for example, by reaction from the corresponding phenol derivatives as described in Chem. Comm., 1975, 451, J. Org. Chem. 1974, 39, 1811, J. Am. Chem. Soc. 1954, 76, 1068 or by combination of, for example, substitution reactions of halogen-substituted thiophenol derivatives and secondary reactions such as oxidation, reduction or addition as described in J. Het. Chem. 1983, 20, 867.

The benzoic acids of the formula III can also be obtained by reacting the corresponding bromo- or iodo-substituted compound of the formula VII

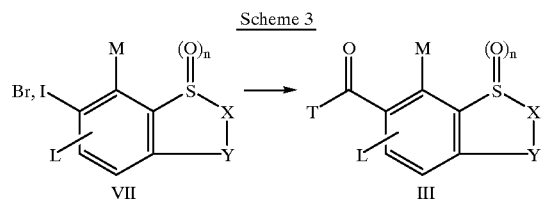

Scheme 3

T is OH, $C_1$–$C_4$-alkoxy
Y,L,M,X, have the meanings described above
with carbon monoxide and water at elevated pressure in the presence of a palladium, nickel, cobalt or rhodium transition metal catalyst and a base.

The catalysts nickel, cobalt, rhodium and in particular palladium can be present in metallic form or in the form of customary salts, such as in the form of halogen compounds, e.g. $PdCl_2$, $RhCl_3 \cdot H_2O$, acetates, e.g. $Pd(OAc)_2$, cyanides etc., in the known valency states. Metal complexes with tertiary phosphines, metal alkylcarbonyls, metal carbonyls, e.g. $CO_2(CO)_8$, $Ni(CO)_4$, metal carbonyl complexes with tertiary phosphines, e.g. $(PPh_3)_2Ni(CO)_2$, or transition metal salts complexed with tertiary phosphines can further be present. The last-mentioned embodiment is preferred, in particular, in the case of palladium as a catalyst. The nature of the phosphine ligands here is widely variable. For example, they can be represented by the following formulae:

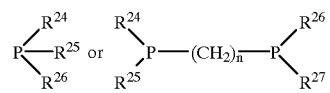

where n is the numbers 1, 2, 3 or 4 and the radicals $R^{24}$ to $R^{27}$ are low molecular weight alkyl, e.g. $C_1$–$C_6$-alkyl, aryl, $C_1$–$C_4$-alkylaryl, e.g. benzyl, phenethyl or aryloxy. Aryl is, for example, naphthyl, anthryl and preferably unsubstituted or substituted phenyl, where with respect to the substituents attention only has to be paid to their inertness to the carboxylation reaction, otherwise they can be widely varied and include all inert C-organic radicals such as $C_1$–$C_6$-alkyl radicals, e.g. methyl, carboxyl radicals such as COOH, COOM (M is, for example, an alkali metal, alkaline earth metal or ammonium salt or C-organic radicals bonded via oxygen, such as $C_1$–$C_6$-alkoxy radicals.

The phosphine complexes can be prepared in a manner known per se, e.g. as described in the documents mentioned at the outset. For example, the starting materials used are customary commercially available metal salts such as $PdCl_2$ or $Pd(OCOCH_3)_2$ and the phosphine for example $P(C_6H_5)_3$, $P(n-C_4H_9)_3$, $PCH_3(C_6H_5)_2$, 1,2-bis(diphenylphosphino) ethane is added.

The amount of phosphine, based on the transition metal, is customarily from 0 to 20, in particular 0.1 to 10, mol equivalents, particularly preferably 1 to 5 mol equivalents.

The amount of transition metal is not critical. Of course, for cost reasons, rather a small amount, e.g. from 0.1 to 10 mol %, in particular from 1 to 5 mol %, based on the starting substance II or III, is used.

For the preparation of the benzoic acids III (T=OH), the reaction is carried out with carbon monoxide and at least equimolar amounts of water, based on the starting substances VI. The reaction component water can simultaneously be used also as a solvent, ie. the maximum amount is not critical.

However, depending on the starting substances and the catalysts used, it can also be advantageous instead of the reaction component to use as the solvent another inert solvent or the base used for the carboxylation.

Suitable inert solvents are solvents customary for carboxylation reactions, such as hydrocarbons, e.g. toluene, xylene, hexane, pentane, cyclohexane, ethers, e.g. methyl tert-butyl ether, tetrahydrofuran, dioxane, dimethoxyethane, substituted amides such as dimethylformamide, persubstituted ureas such as tetra-$C_1$–$C_4$-alkylureas, or nitriles such as benzonitrile or acetonitrile.

In a preferred embodiment of the process, one of the reaction components, in particular the base, is used in an excess so that no additional solvent is necessary.

Bases suitable for the process are all inert bases which are able to bind the hydrogen iodide or hydrogen bromide liberated in the reaction. Examples which may be mentioned here are tertiary amines such as tert-alkylamines, e.g. trialkylamines such as triethylamine, cyclic amines such as N-methylpiperidine or N,N'-dimethylpiperazine, pyridine, alkali metal carbonates or hydrogen carbonates, or tetraalkyl-substituted urea derivatives such as tetra-$C_1$–$C_4$-alkylurea, e.g. tetramethylurea.

The amount of base is not critical, customarily from 1 to 10, in particular from 1 to 5, mol are used. When the base is simultaneously used as a solvent, the amount is generally proportioned such that the reaction components are dissolved, unnecessarily high excesses being avoided for practicability reasons, in order to save costs, to be able to employ small reaction vessels and to guarantee maximum contact of the reaction components.

During the reaction, the carbon monoxide pressure is adjusted such that an excess of CO, based on VI, is always present. Preferably, the carbon monoxide pressure at room temperature is from 1 to 250 bar, in particular from 5 to 150 bar of CO.

The carbonylation is generally carried out continuously or batchwise at from 20 to 250° C., in particular 30 to 150° C. In the case of batchwise operation, carbon monoxide is expediently injected into the reaction mixture continuously to maintain a constant pressure.

The arylhalogen compounds VII used as starting compounds are known or can easily be prepared by suitable combination of known syntheses and by reaction sequences described above.

With respect to the intended use of the benzoyl derivatives of the general formula I, suitable substituents are the following radicals:

L and M are hydrogen, $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl or 1-ethyl-2-methylpropyl, in particular methyl, ethyl, 1-methylethyl, 1-methylpropyl, 2-methylpropyl, 1, 1-dimethylethyl and 1, 1-dimethylpropyl;

$C_2$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2$–$C_6$-alkynyl such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-l-methyl-2-propynyl;

$C_1$–$C_4$-alkoxy such as methoxy, ethoxy, n-propoxy, 1-methylethoxy, n-butoxy, 1-methylpropoxy, 2-methylpropoxy and 1,1-dimethylethoxy, in particular $C_1$–$C_3$-alkoxy such as methoxy, ethoxy or i-propoxy, where these groups can be unsubstituted or substituted by one to five halogen atoms such as fluorine, chlorine, bromine and iodine, preferably fluorine and chlorine or $C_1$–$C_4$-alkoxy as mentioned above.

The group —$(A)_m$—$S(O)_n R^1$ defined above is, for example $C_1$–$C_4$-alkylthio such as methylthio, ethylthio, n-propylthio, 1-methylethylthio, n-butylthio, 1-methylpropylthio, 2-methylpropylthio and 1,1-dimethylethylthio, in particular methylthio;

$C_1$–$C_4$-alkylsulfinyl such as methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl, in particular methylsulfinyl;

$C_1$–$C_4$-alkylsulfonyl such as methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, in particular methylsulfonyl;

$C_1$–$C_4$-alkoxysulfonyl such as methoxysulfonyl, ethoxysulfonyl, n-propoxysulfonyl, 1-methylethoxysulfonyl, n-butoxysulfonyl, 1-methylpropoxysulfonyl, 2-methylpropoxysulfonyl and 1,1-dimethylethoxysulfonyl, in particular methoxysulfonyl;

N-$C_1$–$C_4$-alkylsulfamoyl such as N-methylsulfamoyl, N-ethylsulfamoyl, N-n-propylsulfamoyl, N-1-methylethylsulfamoyl, N-n-butylsulfamoyl, N-1,1-methylpropylsulfamoyl, N-2-methylpropylsulfamoyl and N-1,1-dimethylethylsulfamoyl, in particular N-methylsulfamoyl;

N-C₁–C₄-alkylsulfinamoyl such as N-methylsulfinamoyl, N-ethylsulfinamoyl, N-n-propylsulfinamoyl, N-1-methylethylsulfinamoyl, N-n-butylsulfinamoyl, N-1-methylpropylsulfinamoyl, N-2-methylpropylsulfinamoyl and N-1,1-dimethylethylsulfinamoyl, in particular N-methylsulfinamoyl;

di-C₁–C₄-alkylsulfamoyl such as dimethylsulfamoyl, diethylsulfamoyl, dipropylsulfamoyl, dibutylsulfamoyl, N-methyl-N-ethylsulfamoyl, N-methyl-N-propylsulfamoyl, N-methyl-N-1-methylethylsulfamoyl, N-methyl-N--C₁,1-dimethylethylsulfamoyl, di-1-methylethylsulfamoyl, N-ethyl-N-1-methylethylsulfamoyl and N-ethyl-N-1-dimethylethylsulfamoyl; in particular dimethylsulfamoyl;

di-C₁–C₄-alkylsulfinamoyl such as dimethylsulfinamoyl, diethylsulfinamoyl, dipropylsulfinamoyl, dibutylsulfinamoyl, N-methyl-N-ethylsulfinamoyl, N-methyl-N-propylsulfinamoyl, N-methyl-N-1-methylethylsulfinamoyl, N-methyl-N-1,1-dimethylethylsulfinamoyl, di-1-methylethylsulfinamoyl, N-ethyl-N-1-methylethylsulfinamoyl and N-ethyl-N-1,1-dimethylethylsulfinamoyl; in particular dimethylsulfinamoyl, C₁–C₄-alkylsulfinyloxy such as methylsulfinyloxy, ethylsulfinyloxy, n-propylsulfinyloxy, 1-methylethylsulfinyloxy, n-butylsulfinyloxy, 1-methylpropylsulfinyloxy, 2-methylpropylsulfinyloxy and 1,1-dimethylethylsulfinyloxy, in particular methylsulfinyloxy;

C₁–C₄-alkylsulfonyloxy such as methylsulfonyloxy, ethylsulfonyloxy, n-propylsulfonyloxy, 1-methylethylsulfonyloxy, n-butylsulfonyloxy, 1-methylpropylsulfonyloxy, 2-methylpropylsulfonyloxy and 1,1-dimethylethylsulfonyloxy, in particular methylsulfonyloxy;

C₁–C₄-alkylsulfinylamino such as methylsulfinylamino, ethyl sulfinylamino, n-propylsulfinylamino, 1-methylethylsulfinylamino, n-butylsulfinylamino, 1-methylpropylsulfinylamino, 2-methylpropylsulfinylamino and 1,1-dimethylethylsulfinylamino, in particular methylsulfinylamino;

C₁–C₄-alkylsulfonylamino such as methylsulfonylamino, ethylsulfonylamino, n-propylsulfonylamino, 1-methylethylsulfonylamino, n-butylsulfonylamino, 1-methylpropylsulfonylamino, 2-methylpropylsulfonylamino and 1,1-dimethylethylsulfonylamino, in particular methylsulfonylamino;

N-C₁–C₄-alkylsulfinyl-N-methylamino such as N-methylsulfinyl-N-methylamino, N-ethylsulfinyl-N-methylamino, N-n-propylsulfinyl-N-methylamino, N-1-methylethylsulfinyl-N-methylamino, N-n-butylsulfinyl-N-methylamino, N-1-methylpropylsulfinyl-N-methylamino, N-2-methylpropylsulfinyl-N-methylamino and N-1,1-dimethylethylsulfinyl-N-methylamino, in particular N-methylsulfinyl-N-methylamino;

N-C₁–C₄-alkylsulfinyl-N-ethylamino such as N-methylsulfinyl-N-ethylamino, N-ethylsulfinyl-N-ethylamino, N-n-propylsulfinyl-N-ethylamino, N-1-methylethylsulfinyl-N-ethylamino, N-n-butylsulfinyl-N-ethylamino, N-1-methylpropylsulfinyl-N-ethylamino, N-2-methylpropylsulfinyl-N-ethylamino and N-1,1-dimethylethylsulfinyl-N-ethylamino, in particular N-methylsulfinyl-N-ethylamino;

N-C₁–C₄-alkylsulfonyl-N-methylamino such as N-methylsulfonyl-N-methylamino, N-ethylsulfonyl-N-methylamino, N-n-propylsulfonyl-N-methylamino, N-1-methylethylsulfonyl-N-methylamino, N-n-butylsulfonyl-N-methyl-amino, N-1-methylpropylsulfonyl-N-methylamino, N-2-methylpropylsulfonyl-N-methylamino and N-1,1-dimethylethylsulfonyl-N-methylamino, in particular N-methylsulfonyl-N-methylamino;

N-C₁–C₄-alkylsulfonyl-N-ethylamino such as N-methylsulfonyl-N-ethylamino, N-ethylsulfonyl-N-ethylamino, N-n-propylsulfonyl-N-ethylamino, N-1-methylethylsulfonyl-N-ethylamino, N-n-butylsulfonyl-N-ethylamino, N-1-methylpropylsulfonyl-N-ethylamino, N-2-methylpropylsulfonyl-N-ethylamino and N-1,1-dimethylethylsulfonyl-N-ethylamino, in particular N-methylsulfonyl-N-ethylamino;

C₁–C₄-haloalkylthio such as chloromethylthio, dichloromethylthio, trichloromethylthio, fluoromethylthio, difluoromethylthio, trifluoromethylthio, chlorofluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2 fluoroethylthio, 2,2,2-trichloroethylthio and pentafluoroethylthio, in particular trifluoromethylthio.

The group —(A)$_m$—CO—R² defined above is, for example,

C₁–C₄-alkylcarbonyl such as methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl, in particular methylcarbonyl;

C₁–C₄-alkoxycarbonyl such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, in particular methoxycarbonyl;

N-C₁–C₄-alkylcarbamoyl such as N-methylcarbamoyl, N-ethylcarbamoyl, N-n-propylcarbamoyl, N-1-methylethylcarbamoyl, N-n-butylcarbamoyl, N-1-methylpropylcarbamoyl, N-2-methylpropylcarbamoyl and N-1,1-dimethylethylcarbamoyl, in particular N-methylcarbamoyl;

di-C₁–C₄-alkylcarbamoyl such as dimethylcarbamoyl, diethylcarbamoyl, dipropylcarbamoyl, dibutylcarbamoyl, N-methyl-N-ethylcarbamoyl, N-methyl-N-propylcarbamoyl, N-methyl-N-1-methylethylcarbamoyl, N-methyl-N-1,1-dimethylethylcarbamoyl, di-1-methylethylcarbamoyl, N-ethyl-N-1-methylethylcarbamoyl and N-ethyl-N-1,1-dimethylethylcarbamoyl; in particular dimethylcarbamoyl;

C₁–C₄-alkylcarbonyloxy such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy and 1,1-dimethylethylcarbonyloxy, in particular methylcarbonyloxy;

$C_1$–$C_4$-alkylcarbonylamino such as methylcarbonylamino, ethylcarbonylamino, n-propylcarbonylamino, 1-methylethylcarbonylamino, n-butylcarbonylamino, 1-methylpropylcarbonylamino, 2-methylpropylcarbonylamino and 1,1-dimethylethylcarbonylamino, in particular methylcarbonylamino;

N-$C_1$–$C_4$-alkylcarbonyl-N-methylamino such as N-methylcarbonyl-N-methylamino, N-ethylcarbonyl-N-methylamino, N-n-propylcarbonyl-N-methylamino, N-1-methylethylcarbonyl-N-methylamino, N-n-butylcarbonyl-N-methylamino, N-1-methylpropylcarbonyl-N-methylamino, N-2-methylpropylcarbonyl-N-methylamino and N-1,1-dimethylethylcarbonyl-N-methyl-amino, in particular N-methylcarbonyl-N-methylamino.

X is, for example: $CH_2$, $CH(CH_3)$, $C((CH_3)_2)$, $CH(C_2H_5)$, $C((C_2H_5)_2)$, $CH(C_6H_5)$, $CH_2$—$CH_2$, $CH_2$—$CH(CH_3)$, $CH_2$—$C((CH_3)_2)$, $CH(CH_3)$—$CH(CH_3)$, $CH(CH_3)$—$C((CH_3)_2)$, $C((CH_3)_2)$—$C((CH_3)_2)$, $CH_2$—$CH(C_2H_5)$, $CH_2$—$C((C_2H_5)_2)$, $CH(C_2H_5)$—$CH(C_2H_5)$, $CH(C_2H_5)$—$C((C_2H_5)_2)$, $C((C_2H_5)_2)$—$C((C_2H_5)_2)$, $CH_2$—$CH(C_3H_7)$, $CH_2$—$CH(iC_3H_7)$, $CH_2$—$CH(C_4H_9)$, $CH_2$—$CH(iC_4H_9)$, $CH_2$—$CH(Br)$, $CH_2$—$C((Br)_2)$, $CH(Br)$—$CH(Br)$, $C((Br)_2)$—$C((Br)_2)$, $CH_2$—$CH(Cl)$, $CH_2$—$C((Cl)_2)$, $CH(Cl)$—$C((Cl_2)$, $C((Cl)_2)$—$C((Cl)_2)$, $CH_2$—$CH(C_6H_5)$, $CH(C_6H_5)$—$CH(C_6H_5)$, $CH_2$—$CH(p-NO_2C_6H_5)]CH=CH$, $C(CH_3)=CH$, $C(CH_3)=CCH_3$, $CH=CBr$, $CH=CCl$, $CBr=CBr$, $CCl=CCl$, $CH=C(OCH_3)$, $CH=C(C_6H_5)$, $C(C_6H_5)=C(C_6H_5)$, $C(C_2H_5)=CH$, $C(C_2H_5)=C(C_2H_5)$, $CH=C(C_3H_5)$, $CH=C(C_4H_7)$, $CH_2$—$CH=CH$, $CH(CH_3)$—$C=CH$, $C((CH_3)_2)$—$CH=CH$, $CH_2$—$CH=C(CH_3)$, $CH_2$—$C(CH_3)=CH$, $CH_2$—$C(CH_3)=C(CH_3)$, $CH(CH_3)$—$C(CH_3)=C(CH_3)$, $C((CH_3)_2)$—$C(CH_3)=C(CH_3)$, N—H, N—$CH_3$, N—$C_2H_5$, N—$C_3H_7$, N—$C_4H_9$, N-$iCH_3H_7$, N—$OCH_3$, N—$OC_2H_5$, N—$CH_2C_6H_5$, N—$C_6H_5$;

Y is, for example:
C=O, CH—OH, CH—$OCH_3$, CH—$OC_2H_5$, CH—$OC_3H_7$, CH—OiPr, CH—$OC_4H_9$, CH—OiBu, CH—$OC_5H_{11}$, CH—$OC_6H_{13}$, CH—$OC_6H_5$, $C(CH_3)$—$OCH_3$, $C(CH_3)$—$OC_2H_5$, $C(CH_3)$—$OC_3H_7$, $C(CH_3)$—$OC_4H_9$, $C(CH_3)$—OiPr, $C(CH_3)$—OiBu, $C(CH_3)$—OtBu, $C(CH_3)$—OPh, $CH_2$, $CH(CH_3)$, $C((CH_3)_2)$, C=N—$CH_3$, C=N—$C_2H_5$, C=N-$C_3H_7$, C=N-$C_4H_9$, C=N-$iC_4H_9$, C=N-$tC_4H_9$, C=N-iPr, C=N—$OCH_3$, C=N-$OC_2H_5$, C=N—$OC_3H_7$, C=N—$OC_4H_9$, C=N—$OiC_4H_9$, C=N—$OtC_4H_9$, C=N—$OCH_2CH=CH_2$, C=N—$OCH(CH_3)CH=CH_2$, C=N—$OCH_2CH=CHCH_3$, C=N—$OCH_2CH=C(CH_3)_2$, C=N—$OCH_2CH=CHBr$, C=N—$OCH_2CH=CHCl$, C=N—$OCH_2CH=CHC_2H_5$, C=N—$OCH_2C\equiv CH$, C=N—$OCH_2C\equiv CCH_3$, C=N—$OCH_2C_6H_5$, CH—NH($OCH_3$), CH—NH($OC_2H_5$), CH—NH(OiPr), CH—NH(OnPr), CH—NH($OC_6H_5$), CH—$NCH_3$($OCH_3$), CH—$NCH_3$($OC_2H_5$), CH—$NCH_3$(OiPr), CH—$NCH_3$(OnPr), CH—$NCH_3$($OC_6H_5$), CH—NH($CH_3$), CH—NH($C_2H_5$), CH—NH($C_3H_7$), CH—NH($C_4H_9$), CH—NH(iPr), CH—NH(iBu), CH—NH(tBu), CH—NH($C_6H_5$), CH—N($CH_3$)_2, CH—$NCH_3$($C_2H_5$), CH—$NCH_3$($C_3H_7$), CH—$NCH_3$($C_4H_9$), CH—$NCH_3$(iPr), CH—$NCH_3$(iBu), C=N—$NH_2$, C=N—$NHCH_3$, C=N—(($CH_3)_2$), C=N—NH($C_2H_5$), C=N—$NCH_3(C_2H_5)$, C=N—N($(C_2H_5)_2$), CH—$SCH_3$, CH—$SC_2H_5$, CH—$SC_3H_7$, CH—$SC_4H_9$, CH—SPr, CH—SiBu, CH—SH, $C(CH_3)$—$SCH_3$, $C(CH_3)$—$SC_2H_5$, $C(CH_3)$—$SC_3H_7$, 1,3-dioxanyl, 1,3-dioxolanyl, 5,5-dimethyl-1,3-dioxanyl Preferred benzoyl derivatives are those of the formula Ia,

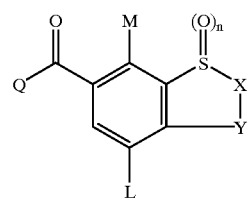

Ia where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkoxy, $C_1$–$C_4$-haloalkylthio, $C_1$–$C_4$-alkylsulfonyl, halogen, nitro or cyano and Q, X, n and Y have the meanings given in claim 1, where in the case where Y=C=O, X is not equal to $NR^{23}$.

Furthermore preferred benzoyl derivatives are those of the formula Ib,

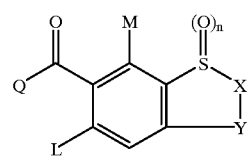

Ib where L is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_{-C1}$–$C_4$-haloalkoxy, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and Q, X, n and Y have the meanings given in claim 1, where in the case where Y=C=O, X is not equal to $NR^{23}$.

Preferred benzoyl derivatives are also those of the formula I as claimed in claim 1, where the radicals L and M are hydrogen, methyl, methoxy, chlorine, cyano, nitro or trifluoromethyl.

Preferred benzoyl derivatives are those of the formula Ic,

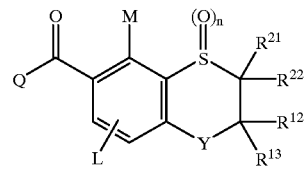

Ic where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and Q, n, Y and also $R^{22}$, $R^{21}$, $R^{12}$ and $R^{13}$ have the meanings given in claim 1.

Likewise preferred benzoyl derivatives are those of the formula Id,

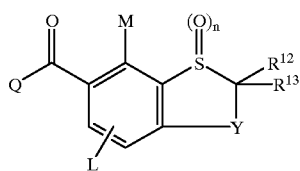

Id

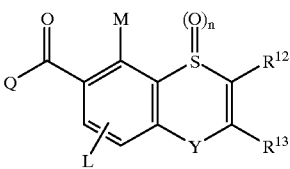

Ie where L is hydrogen, $C_1$–$C_6$-alkyl, $C_2$–$C_6$-alkenyl, $C_2$–$C_6$-alkynyl, $C_1$–$C_4$-alkoxy, $C_1$–$C_1$–$C_4$-haloalkyl, $C_1$–$C_4$-haloalkoxy, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and Q, n, Y and also $R^{12}$ and $R^{13}$ have the meanings given in claim 1.

Also preferred benzoyl derivatives are those of the formula Ie, where L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano and Q, n, Y and also $R^{12}$ and $R^{13}$ have the meanings given in claim 1.

Preferred benzoyl derivatives are likewise those of the formula I as claimed in claim 1, where n is 1 or 2 and Y is $CR^7$—$OR^8$, where $R^7$ and $R^8$ have the meanings given in claim 1.

TABLE 1

Compounds of the formula

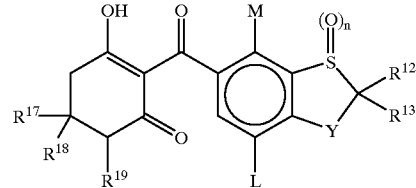

| No. | $R^{17}$ | $R^{18}$ | $R^{19}$ | n | $R^{12}$ | $R^{13}$ | Y | L | M |
|---|---|---|---|---|---|---|---|---|---|
| 1.1 | H | H | H | 0 | H | H | C=O | H | H |
| 1.2 | H | H | H | 2 | H | H | C=O | H | H |
| 1.3 | H | H | H | 0 | H | H | CHOCH$_3$ | H | H |
| 1.4 | H | H | H | 2 | H | H | CHOCH$_3$ | H | H |
| 1.5 | H | H | H | 0 | H | H | CHOC$_2$H$_5$ | H | H |
| 1.6 | H | H | H | 2 | H | H | CHOC$_2$H$_5$ | H | H |
| 1.7 | H | H | H | 0 | H | H | CHOiPr | H | H |
| 1.8 | H | H | H | 2 | H | H | CHOiPr | H | H |
| 1.9 | H | H | H | 0 | H | H | CHOH | H | H |
| 1.10 | H | H | H | 2 | H | H | CHOH | H | H |
| 1.11 | H | H | H | 0 | H | H | C=NOCH$_3$ | H | H |
| 1.12 | H | H | H | 2 | H | H | C=NOCH$_3$ | H | H |
| 1.13 | H | H | H | 0 | H | H | C=NOC$_2$H$_5$ | H | H |
| 1.14 | H | H | H | 2 | H | H | C=NOC$_2$H$_5$ | H | H |
| 1.15 | H | H | H | 0 | H | H | C=NOiPr | H | H |
| 1.16 | H | H | H | 2 | H | H | C=NOiPr | H | H |
| 1.17 | H | H | H | 0 | H | H | C=NOCH$_2$CH=CHCl | H | H |
| 1.18 | H | H | H | 2 | H | H | C=NOCH$_2$CH=CHCl | H | H |
| 1.19 | H | H | H | 0 | H | H | C=NOCH$_2$C$_6$H$_5$ | H | H |
| 1.20 | H | H | H | 2 | H | H | C=NOCH$_2$C$_6$H$_5$ | H | H |
| 1.21 | H | H | H | 0 | H | H | C(CH$_3$)$_2$ | H | H |
| 1.22 | H | H | H | 2 | H | H | C(CH$_3$)$_2$ | H | H |
| 1.23 | CH$_3$ | H | H | 0 | H | H | C=O | H | H |
| 1.24 | CH$_3$ | H | H | 2 | H | H | C=O | H | H |
| 1.25 | CH$_3$ | H | H | 0 | H | H | CHOCH$_3$ | H | H |
| 1.26 | CH$_3$ | H | H | 2 | H | H | CHOCH$_3$ | H | H |
| 1.27 | CH$_3$ | H | H | 0 | H | H | CHOC$_2$H$_5$ | H | H |
| 1.28 | CH$_3$ | H | H | 2 | H | H | CHOC$_2$H$_5$ | H | H |
| 1.29 | CH$_3$ | H | H | 0 | H | H | CHOiPr | H | H |
| 1.30 | CH$_3$ | H | H | 2 | H | H | CHOiPr | H | H |
| 1.31 | CH$_3$ | H | H | 0 | H | H | CHOH | H | H |
| 1.32 | CH$_3$ | H | H | 2 | H | H | CHOH | H | H |
| 1.33 | CH$_3$ | H | H | 0 | H | H | C=NOCH$_3$ | H | H |
| 1.34 | CH$_3$ | H | H | 2 | H | H | C=NOCH$_3$ | H | H |
| 1.35 | CH$_3$ | H | H | 0 | H | H | C=NOC$_2$H$_5$ | H | H |
| 1.36 | CH$_3$ | H | H | 2 | H | H | C=NOC$_2$H$_5$ | H | H |

TABLE 1-continued

Compounds of the formula

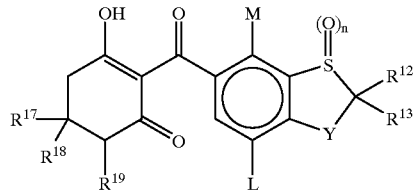

| No. | $R^{17}$ | $R^{18}$ | $R^{19}$ | n | $R^{12}$ | $R^{13}$ | Y | L | M |
|---|---|---|---|---|---|---|---|---|---|
| 1.37 | $CH_3$ | H | H | 0 | H | H | C=NOiPr | H | H |
| 1.38 | $CH_3$ | H | H | 2 | H | H | C=NOiPr | H | H |
| 1.39 | $CH_3$ | H | H | 0 | H | H | C=NOCH$_2$CH=CHCl | H | H |
| 1.40 | $CH_3$ | H | H | 2 | H | H | C=NOCH$_2$CH=CHCl | H | H |
| 1.41 | $CH_3$ | H | H | 0 | H | H | C=NOCH$_2$C$_6$H$_5$ | H | H |
| 1.42 | $CH_3$ | H | H | 2 | H | H | C=NOCH$_2$C$_6$H$_5$ | H | H |
| 1.43 | $CH_3$ | H | H | 0 | H | H | C(CH$_3$)$_2$ | H | H |
| 1.44 | $CH_3$ | H | H | 2 | H | H | C(CH$_3$)$_2$ | H | H |
| 1.45 | $CH_3$ | $CH_3$ | H | 0 | H | H | C=O | H | H |
| 1.46 | $CH_3$ | $CH_3$ | H | 2 | H | H | C=O | H | H |
| 1.47 | $CH_3$ | $CH_3$ | H | 0 | H | H | CHOCH$_3$ | H | H |
| 1.48 | $CH_3$ | $CH_3$ | H | 2 | H | H | CHOCH$_3$ | H | H |
| 1.49 | $CH_3$ | $CH_3$ | H | 0 | H | H | CHOC$_2$H$_5$ | H | H |
| 1.50 | $CH_3$ | $CH_3$ | H | 2 | H | H | CHOC$_2$H$_5$ | H | H |
| 1.51 | $CH_3$ | $CH_3$ | H | 0 | H | H | CHOiPr | H | H |
| 1.52 | $CH_3$ | $CH_3$ | H | 2 | H | H | CHOiPr | H | H |
| 1.53 | $CH_3$ | $CH_3$ | H | 0 | H | H | C=NOCH$_3$ | H | H |
| 1.54 | $CH_3$ | $CH_3$ | H | 2 | H | H | C=NOCH$_3$ | H | H |
| 1.55 | $CH_3$ | $CH_3$ | H | 0 | H | H | C=NOC$_2$H$_5$ | H | H |
| 1.56 | $CH_3$ | $CH_3$ | H | 2 | H | H | C=NOC$_2$H$_5$ | H | H |
| 1.57 | $CH_3$ | $CH_3$ | H | 0 | H | H | C=NOiPr | H | H |
| 1.58 | $CH_3$ | $CH_3$ | H | 2 | H | H | C=NOiPr | H | H |
| 1.59 | $CH_3$ | $CH_3$ | H | 0 | H | H | C=NOCH$_2$CH=CHCl | H | H |
| 1.60 | $CH_3$ | $CH_3$ | H | 2 | H | H | C=NOCH$_2$CH=CHCl | H | H |
| 1.61 | $CH_3$ | $CH_3$ | H | 0 | H | H | C=NOCH$_2$C$_6$H$_5$ | H | H |
| 1.62 | $CH_3$ | $CH_3$ | H | 2 | H | H | C=NOCH$_2$C$_6$H$_5$ | H | H |
| 1.63 | $CH_3$ | $CH_3$ | H | 0 | H | H | C(CH$_3$)$_2$ | H | H |
| 1.64 | $CH_3$ | $CH_3$ | H | 2 | H | H | C(CH$_3$)$_2$ | H | H |
| 1.65 | H | H | H | 0 | H | H | C=O | H | $CH_3$ |
| 1.66 | H | H | H | 2 | H | H | C=O | H | $CH_3$ |
| 1.67 | H | H | H | 0 | H | H | CHOCH$_3$ | H | $CH_3$ |
| 1.68 | H | H | H | 2 | H | H | CHOCH$_3$ | H | $CH_3$ |
| 1.69 | H | H | H | 0 | H | H | CHOC$_2$H$_5$ | H | $CH_3$ |
| 1.70 | H | H | H | 2 | H | H | CHOC$_2$H$_5$ | H | $CH_3$ |
| 1.71 | H | H | H | 0 | H | H | CHOiPr | H | $CH_3$ |
| 1.72 | H | H | H | 2 | H | H | CHOiPr | H | $CH_3$ |
| 1.73 | H | H | H | 0 | H | H | C=NOCH$_3$ | H | $CH_3$ |
| 1.74 | H | H | H | 2 | H | H | C=NOCH$_3$ | H | $CH_3$ |
| 1.75 | H | H | H | 0 | H | H | C=NOC$_2$H$_5$ | H | $CH_3$ |
| 1.76 | H | H | H | 2 | H | H | C=NOC$_2$H$_5$ | H | $CH_3$ |
| 1.77 | H | H | H | 0 | H | H | C=NOiPr | H | $CH_3$ |
| 1.78 | H | H | H | 2 | H | H | C=NOiPr | H | $CH_3$ |
| 1.79 | H | H | H | 0 | H | H | C=NOCH$_2$CH=CHCl | H | $CH_3$ |
| 1.80 | H | H | H | 2 | H | H | C=NOCH$_2$CH=CHCl | H | $CH_3$ |
| 1.81 | H | H | H | 0 | H | H | C=NOCH$_2$C$_6$H$_5$ | H | $CH_3$ |
| 1.82 | H | H | H | 2 | H | H | C=NOCH$_2$C$_6$H$_5$ | H | $CH_3$ |
| 1.83 | H | H | H | 0 | H | H | C(CH$_3$)$_2$ | H | $CH_3$ |
| 1.84 | H | H | H | 2 | H | H | C(CH$_3$)$_2$ | H | $CH_3$ |
| 1.85 | $CH_3$ | H | H | 0 | H | H | C=O | H | $CH_3$ |
| 1.86 | $CH_3$ | H | H | 2 | H | H | C=O | H | $CH_3$ |
| 1.87 | $CH_3$ | H | H | 0 | H | H | CHOCH$_3$ | H | $CH_3$ |
| 1.88 | $CH_3$ | H | H | 2 | H | H | CHOCH$_3$ | H | $CH_3$ |
| 1.89 | $CH_3$ | H | H | 0 | H | H | CHOC$_2$H$_5$ | H | $CH_3$ |
| 1.90 | $CH_3$ | H | H | 2 | H | H | CHOC$_2$H$_5$ | H | $CH_3$ |
| 1.91 | $CH_3$ | H | H | 0 | H | H | CHOiPr | H | $CH_3$ |
| 1.92 | $CH_3$ | H | H | 2 | H | H | CHOiPr | H | $CH_3$ |
| 1.93 | $CH_3$ | H | H | 0 | H | H | C=NOCH$_3$ | H | $CH_3$ |
| 1.94 | $CH_3$ | H | H | 2 | H | H | C=NOCH$_3$ | H | $CH_3$ |
| 1.95 | $CH_3$ | H | H | 0 | H | H | C=NOC$_2$H$_5$ | H | $CH_3$ |
| 1.96 | $CH_3$ | H | H | 2 | H | H | C=NOC$_2$H$_5$ | H | $CH_3$ |
| 1.97 | $CH_3$ | H | H | 0 | H | H | C=NOiPr | H | $CH_3$ |
| 1.98 | $CH_3$ | H | H | 2 | H | H | C=NOiPr | H | $CH_3$ |
| 1.99 | $CH_3$ | H | H | 0 | H | H | C=NOCH$_2$CH=CHCl | H | $CH_3$ |
| 1.100 | $CH_3$ | H | H | 2 | H | H | C=NOCH$_2$CH=CHCl | H | $CH_3$ |

TABLE 1-continued

Compounds of the formula

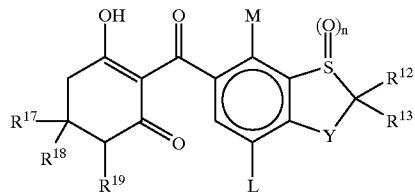

| No. | R17 | R18 | R19 | n | R12 | R13 | Y | L | M |
|---|---|---|---|---|---|---|---|---|---|
| 1.101 | CH3 | H | H | 0 | H | H | C=NOCH2C6H5 | H | CH3 |
| 1.102 | CH3 | H | H | 2 | H | H | C=NOCH2C6H5 | H | CH3 |
| 1.103 | CH3 | H | H | 0 | H | H | C(CH3)2 | H | CH3 |
| 1.104 | CH3 | H | H | 2 | H | H | C(CH3)2 | H | CH3 |
| 1.105 | CH3 | CH3 | H | 0 | H | H | C=O | H | CH3 |
| 1.106 | CH3 | CH3 | H | 2 | H | H | C=O | H | CH3 |
| 1.107 | CH3 | CH3 | H | 0 | H | H | CHOCH3 | H | CH3 |
| 1.108 | CH3 | CH3 | H | 2 | H | H | CHOCH3 | H | CH3 |
| 1.109 | CH3 | CH3 | H | 0 | H | H | CHOC2H5 | H | CH3 |
| 1.110 | CH3 | CH3 | H | 2 | H | H | CHOC2H5 | H | CH3 |
| 1.111 | CH3 | CH3 | H | 0 | H | H | CHOiPr | H | CH3 |
| 1.112 | CH3 | CH3 | H | 2 | H | H | CHOiPr | H | CH3 |
| 1.113 | CH3 | CH3 | H | 0 | H | H | CHOH | H | CH3 |
| 1.114 | CH3 | CH3 | H | 2 | H | H | CHOH | H | CH3 |
| 1.115 | CH3 | CH3 | H | 0 | H | H | C=NOCH3 | H | CH3 |
| 1.116 | CH3 | CH3 | H | 2 | H | H | C=NOCH3 | H | CH3 |
| 1.117 | CH3 | CH3 | H | 0 | H | H | C=NOC2H5 | H | CH3 |
| 1.118 | CH3 | CH3 | H | 2 | H | H | C=NOC2H5 | H | CH3 |
| 1.119 | CH3 | CH3 | H | 0 | H | H | C=NOiPr | H | CH3 |
| 1.120 | CH3 | CH3 | H | 2 | H | H | C=NOiPr | H | CH3 |
| 1.121 | CH3 | CH3 | H | 0 | H | H | C=NOCH2CH=CHCl | H | CH3 |
| 1.122 | CH3 | CH3 | H | 2 | H | H | C=NOCH2CH=CHCl | H | CH3 |
| 1.123 | CH3 | CH3 | H | 0 | H | H | C=NOCH2C6H5 | H | CH3 |
| 1.124 | CH3 | CH3 | H | 2 | H | H | C=NOCH2C6H5 | H | CH3 |
| 1.125 | CH3 | CH3 | H | 0 | H | H | C(CH3)2 | H | CH3 |
| 1.126 | CH3 | CH3 | H | 2 | H | H | C(CH3)2 | H | CH3 |
| 1.127 | H | H | H | 0 | H | H | C=O | H | Cl |
| 1.128 | H | H | H | 2 | H | H | C=O | H | Cl |
| 1.129 | H | H | H | 0 | H | H | CHOCH3 | H | Cl |
| 1.130 | H | H | H | 2 | H | H | CHOCH3 | H | Cl |
| 1.131 | H | H | H | 0 | H | H | CHOC2H5 | H | Cl |
| 1.132 | H | H | H | 2 | H | H | CHOC2H5 | H | Cl |
| 1.133 | H | H | H | 0 | H | H | CHOiPr | H | Cl |
| 1.134 | H | H | H | 2 | H | H | CHOiPr | H | Cl |
| 1.135 | H | H | H | 0 | H | H | C=NOCH3 | H | Cl |
| 1.136 | H | H | H | 2 | H | H | C=NOCH3 | H | Cl |
| 1.137 | H | H | H | 0 | H | H | C=NOC2H5 | H | Cl |
| 1.138 | H | H | H | 2 | H | H | C=NOC2H5 | H | Cl |
| 1.139 | H | H | H | 0 | H | H | C=NOiPr | H | Cl |
| 1.140 | H | H | H | 2 | H | H | C=NOiPr | H | Cl |
| 1.141 | H | H | H | 0 | H | H | C=NOCH2CH=CHCl | H | Cl |
| 1.142 | H | H | H | 2 | H | H | C=NOCH2CH=CHCl | H | Cl |
| 1.143 | H | H | H | 0 | H | H | C=NOCH2C6H5 | H | Cl |
| 1.144 | H | H | H | 2 | H | H | C=NOCH2C6H5 | H | Cl |
| 1.145 | H | H | H | 0 | H | H | C(CH3)2 | H | Cl |
| 1.146 | H | H | H | 2 | H | H | C(CH3)2 | H | Cl |
| 1.147 | CH3 | H | H | 0 | H | H | C=O | H | Cl |
| 1.148 | CH3 | H | H | 2 | H | H | C=O | H | Cl |
| 1.149 | CH3 | H | H | 0 | H | H | CHOCH3 | H | Cl |
| 1.150 | CH3 | H | H | 2 | H | H | CHOCH3 | H | Cl |
| 1.151 | CH3 | H | H | 0 | H | H | CHOC2H5 | H | Cl |
| 1.152 | CH3 | H | H | 2 | H | H | CHOC2H5 | H | Cl |
| 1.153 | CH3 | H | H | 0 | H | H | CHOiPr | H | Cl |
| 1.154 | CH3 | H | H | 2 | H | H | CHOiPr | H | Cl |
| 1.155 | CH3 | H | H | 0 | H | H | C=NOCH3 | H | Cl |
| 1.156 | CH3 | H | H | 2 | H | H | C=NOCH3 | H | Cl |
| 1.157 | CH3 | H | H | 0 | H | H | C=NOC2H5 | H | Cl |
| 1158 | CH3 | H | H | 2 | H | H | C=NOC2H5 | H | Cl |
| 1.159 | CH3 | H | H | 0 | H | H | C=NOiPr | H | Cl |
| 1.160 | CH3 | H | H | 2 | H | H | C=NOiPr | H | Cl |
| 1.161 | CH3 | H | H | 0 | H | H | C=NOCH2CH=CHCl | H | Cl |
| 1.162 | CH3 | H | H | 2 | H | H | C=NOCH2CH=CHCl | H | Cl |
| 1.163 | CH3 | H | H | 0 | H | H | C=NOCH2C6H5 | H | Cl |
| 1.164 | CH3 | H | H | 2 | H | H | C=NOCH2C6H5 | H | Cl |

TABLE 1-continued

Compounds of the formula

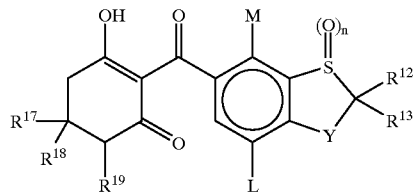

| No. | $R^{17}$ | $R^{18}$ | $R^{19}$ | n | $R^{12}$ | $R^{13}$ | Y | L | M |
|---|---|---|---|---|---|---|---|---|---|
| 1.165 | CH₃ | H | H | 0 | H | H | C(CH₃)₂ | H | Cl |
| 1.166 | CH₃ | H | H | 2 | H | H | C(CH₃)₂ | H | Cl |
| 1.167 | CH₃ | CH₃ | H | 0 | H | H | C=O | H | Cl |
| 1.168 | CH₃ | CH₃ | H | 2 | H | H | C=O | H | Cl |
| 1.169 | CH₃ | CH₃ | H | 0 | H | H | CHOCH₃ | H | Cl |
| 1.170 | CH₃ | CH₃ | H | 2 | H | H | CHOCH₃ | H | Cl |
| 1.171 | CH₃ | CH₃ | H | 0 | H | H | CHOC₂H₅ | H | Cl |
| 1.172 | CH₃ | CH₃ | H | 2 | H | H | CHOC₂H₅ | H | Cl |
| 1.173 | CH₃ | CH₃ | H | 0 | H | H | CHOiPr | H | Cl |
| 1.174 | CH₃ | CH₃ | H | 2 | H | H | CHOiPr | H | Cl |
| 1.175 | CH₃ | CH₃ | H | 0 | H | H | C=NOCH₃ | H | Cl |
| 1.176 | CH₃ | CH₃ | H | 2 | H | H | C=NOCH₃ | H | Cl |
| 1.177 | CH₃ | CH₃ | H | 0 | H | H | C=NOC₂H₅ | H | Cl |
| 1.178 | CH₃ | CH₃ | H | 2 | H | H | C=NOC₂H₅ | H | Cl |
| 1.179 | CH₃ | CH₃ | H | 0 | H | H | C=NOiPr | H | Cl |
| 1.180 | CH₃ | CH₃ | H | 2 | H | H | C=NOiPr | H | Cl |
| 1.181 | CH₃ | CH₃ | H | 0 | H | H | C=NOCH₂CH=CHCl | H | Cl |
| 1.182 | CH₃ | CH₃ | H | 2 | H | H | C=NOCH₂CH=CHCl | H | Cl |
| 1.183 | CH₃ | CH₃ | H | 0 | H | H | C=NOCH₂C₆H₅ | H | Cl |
| 1.184 | CH₃ | CH₃ | H | 2 | H | H | C=NOCH₂C₆H₅ | H | Cl |
| 1.185 | CH₃ | CH₃ | H | 0 | H | H | C(CH₃)₂ | H | Cl |
| 1.186 | CH₃ | CH₃ | H | 2 | H | H | C(CH₃)₂ | H | Cl |

TABLE 2

Compounds of the formula

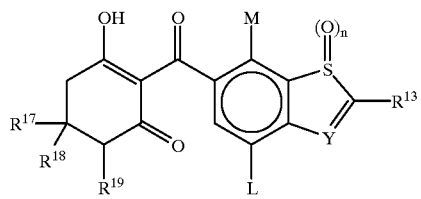

The radicals $R^{12}$ of X and $R^7$ of Y form a bond

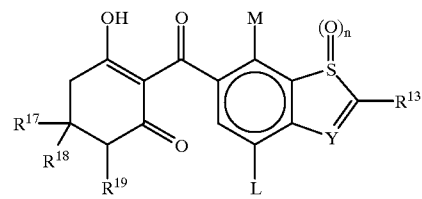

The radicals $R^{12}$ of X and $R^7$ of Y form a bond

| No. | $R^{17}$ | $R^{18}$ | $R^{19}$ | n | $R^{13}$ | Y | L | M | No. | $R^{17}$ | $R^{18}$ | $R^{19}$ | n | $R^{13}$ | Y | L | M |
|---|---|---|---|---|---|---|---|---|---|---|---|---|---|---|---|---|---|
| 2.1 | H | H | H | 0 | H | COCH₃ | H | H | 2.20 | H | H | H | 2 | H | COCH₃ | H | CH₃ |
| 2.2 | H | H | H | 2 | H | COCH₃ | H | H | 2.21 | H | H | H | 0 | H | COC₂H₅ | H | CH₃ |
| 2.3 | H | H | H | 0 | H | COC₂H₅ | H | H | 2.22 | H | H | H | 2 | H | COC₂H₅ | H | CH₃ |
| 2.4 | H | H | H | 2 | H | COC₂H₅ | H | H | 2.23 | H | H | H | 0 | H | COiPr | H | CH₃ |
| 2.5 | H | H | H | 0 | H | COiPr | H | H | 2.24 | H | H | H | 2 | H | COiPr | H | CH₃ |
| 2.6 | H | H | H | 2 | H | COiPr | H | H | 2.25 | CH₃ | H | H | 0 | H | COCH₃ | H | CH₃ |
| 2.7 | CH₃ | H | H | 0 | H | COCH₃ | H | H | 2.26 | CH₃ | H | H | 2 | H | COCH₃ | H | CH₃ |
| 2.8 | CH₃ | H | H | 2 | H | COCH₃ | H | H | 2.27 | CH₃ | H | H | 0 | H | COC₂H₅ | H | CH₃ |
| 2.9 | CH₃ | H | H | 0 | H | COC₂H₅ | H | H | 2.28 | CH₃ | H | H | 2 | H | COC₂H₅ | H | CH₃ |
| 2.10 | CH₃ | H | H | 2 | H | COC₂H₅ | H | H | 2.29 | CH₃ | H | H | 0 | H | COiPr | H | CH₃ |
| 2.11 | CH₃ | H | H | 0 | H | COiPr | H | H | 2.30 | CH₃ | H | H | 2 | H | COiPr | H | CH₃ |
| 2.12 | CH₃ | H | H | 2 | H | COiPr | H | H | 2.31 | CH₃ | CH₃ | H | 0 | H | COCH₃ | H | CH₃ |
| 2.13 | CH₃ | CH₃ | H | 0 | H | COCH₃ | H | H | 2.32 | CH₃ | CH₃ | H | 2 | H | COCH₃ | H | CH₃ |
| 2.14 | CH₃ | CH₃ | H | 2 | H | COCH₃ | H | H | 2.33 | CH₃ | CH₃ | H | 0 | H | COC₂H₅ | H | CH₃ |
| 2.15 | CH₃ | CH₃ | H | 0 | H | COC₂H₅ | H | H | 2.34 | CH₃ | CH₃ | H | 2 | H | COC₂H₅ | H | CH₃ |
| 2.16 | CH₃ | CH₃ | H | 2 | H | COC₂H₅ | H | H | 2.35 | CH₃ | CH₃ | H | 0 | H | COiPr | H | CH₃ |
| 2.17 | CH₃ | CH₃ | H | 0 | H | COiPr | H | H | 2.36 | CH₃ | CH₃ | H | 2 | H | COiPr | H | CH₃ |
| 2.18 | CH₃ | CH₃ | H | 2 | H | COiPr | H | H | 2.37 | H | H | H | 0 | H | COCH₃ | H | Cl |
| 2.19 | H | H | H | 0 | H | COCH₃ | H | CH₃ | 2.38 | H | H | H | 2 | H | COCH₃ | H | Cl |

TABLE 2-continued

Compounds of the formula

The radicals $R^{12}$ of X and $R^7$ of Y form a bond

| No. | $R^{17}$ | $R^{18}$ | $R^{19}$ | n | $R^{13}$ | Y | L | M |
|---|---|---|---|---|---|---|---|---|
| 2.39 | H | H | H | 0 | H | $COC_2H_5$ | H | Cl |
| 2.40 | H | H | H | 2 | H | $COC_2H_5$ | H | Cl |
| 2.41 | H | H | H | 0 | H | COiPr | H | Cl |
| 2.42 | H | H | H | 2 | H | COiPr | H | Cl |
| 2.43 | $CH_3$ | H | H | 0 | H | $COCH_3$ | H | Cl |
| 2.44 | $CH_3$ | H | H | 2 | H | $COCH_3$ | H | Cl |
| 2.45 | $CH_3$ | H | H | 0 | H | $COC_2H_5$ | H | Cl |
| 2.46 | $CH_3$ | H | H | 2 | H | $COC_2H_5$ | H | Cl |
| 2.47 | $CH_3$ | H | H | 0 | H | COiPr | H | Cl |
| 2.48 | $CH_3$ | H | H | 2 | H | COiPr | H | Cl |
| 2.49 | $CH_3$ | $CH_3$ | H | 0 | H | $COCH_3$ | H | Cl |
| 2.50 | $CH_3$ | $CH_3$ | H | 2 | H | $COCH_3$ | H | Cl |
| 2.51 | $CH_3$ | $CH_3$ | H | 0 | H | $COC_2H_5$ | H | Cl |
| 2.52 | $CH_3$ | $CH_3$ | H | 2 | H | $COC_2H_5$ | H | Cl |
| 2.53 | $CH_3$ | $CH_3$ | H | 0 | H | COiPr | H | Cl |
| 2.54 | $CH_3$ | $CH_3$ | H | 2 | H | COiPr | H | Cl |

TABLE 3

Compounds of the formula

| No. | $R^{17}$ | $R^{18}$ | $R^{19}$ | n | $R^{12}$ | $R^{13}$ | Y | L | M |
|---|---|---|---|---|---|---|---|---|---|
| 3.1 | H | H | H | 0 | H | H | C=O | $CH_3$ | H |
| 3.2 | H | H | H | 2 | H | H | C=O | $CH_3$ | H |
| 3.3 | H | H | H | 0 | H | H | $CHOCH_3$ | $CH_3$ | H |
| 3.4 | H | H | H | 2 | H | H | $CHOCH_3$ | $CH_3$ | H |
| 3.5 | H | H | H | 0 | H | H | $CHOC_2H_5$ | $CH_3$ | H |
| 3.6 | H | H | H | 2 | H | H | $CHOC_2H_5$ | $CH_3$ | H |
| 3.7 | H | H | H | 0 | H | H | CHOiPr | $CH_3$ | H |
| 3.8 | H | H | H | 2 | H | H | CHOiPr | $CH_3$ | H |
| 3.9 | H | H | H | 0 | H | H | $C=NOCH_3$ | $CH_3$ | H |
| 3.10 | H | H | H | 2 | H | H | $C=NOCH_3$ | $CH_3$ | H |
| 3.11 | H | H | H | 0 | H | H | $C=NOC_2H_5$ | $CH_3$ | H |
| 3.12 | H | H | H | 2 | H | H | $C=NOC_2H_5$ | $CH_3$ | H |
| 3.13 | H | H | H | D | H | H | C=NOiPr | $CH_3$ | H |
| 3.14 | H | H | H | 2 | H | H | C=NOiPr | $CH_3$ | H |
| 3.15 | H | H | H | 0 | H | H | $C=NOCH_2CH=CHCl$ | $CH_3$ | H |
| 3.16 | H | H | H | 2 | H | H | $C=NOCH_2CH=CHCl$ | $CH_3$ | H |
| 3.17 | H | H | H | 0 | H | H | $C=NOCH_2C_6H_5$ | $CH_3$ | H |
| 3.18 | H | H | H | 2 | H | H | $C=NOCH_2C_6H_5$ | $CH_3$ | H |
| 3.19 | H | H | H | 0 | H | H | $C(CH_3)_2$ | $CH_3$ | H |
| 3.20 | H | H | H | 2 | H | H | $C(CH_3)_2$ | $CH_3$ | H |
| 3.21 | $CH_3$ | H | H | 0 | H | H | C=O | $CH_3$ | H |
| 3.22 | $CH_3$ | H | H | 2 | H | H | C=O | $CH_3$ | H |
| 3.23 | $CH_3$ | H | H | 0 | H | H | $CHOCH_3$ | $CH_3$ | H |
| 3.24 | $CH_3$ | H | H | 2 | H | H | $CHOCH_3$ | $CH_3$ | H |

TABLE 3-continued

Compounds of the formula

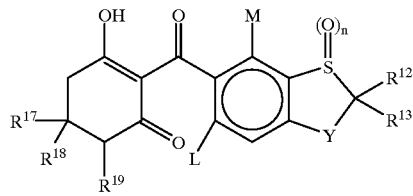

| No. | $R^{17}$ | $R^{18}$ | $R^{19}$ | n | $R^{12}$ | $R^{13}$ | Y | L | M |
|---|---|---|---|---|---|---|---|---|---|
| 3.25 | $CH_3$ | H | H | 0 | H | H | $CHOC_2H_5$ | $CH_3$ | H |
| 3.26 | $CH_3$ | H | H | 2 | H | H | $CHOC_2H_5$ | $CH_3$ | H |
| 3.27 | $CH_3$ | H | H | 0 | H | H | CHOiPr | $CH_3$ | H |
| 3.28 | $CH_3$ | H | H | 2 | H | H | CHOiPr | $CH_3$ | H |
| 3.29 | $CH_3$ | H | H | 0 | H | H | $C=NOCH_3$ | $CH_3$ | H |
| 3.30 | $CH_3$ | H | H | 2 | H | H | $C=NOCH_3$ | $CH_3$ | H |
| 3.31 | $CH_3$ | H | H | 0 | H | H | $C=NOC_2H_5$ | $CH_3$ | H |
| 3.32 | $CH_3$ | H | H | 2 | H | H | $C=NOC_2H_5$ | $CH_3$ | H |
| 3.33 | $CH_3$ | H | H | 0 | H | H | C=NOiPr | $CH_3$ | H |
| 3.34 | $CH_3$ | H | H | 2 | H | H | C=NOiPr | $CH_3$ | H |
| 3.35 | $CH_3$ | H | H | 0 | H | H | $C=NOCH_2CH=CHCl$ | $CH_3$ | H |
| 3.36 | $CH_3$ | H | H | 2 | H | H | $C=NOCH_2CH=CHCl$ | $CH_3$ | H |
| 3.37 | $CH_3$ | H | H | 0 | H | H | $C=NOCH_2C_6H_5$ | $CH_3$ | H |
| 3.38 | $CH_3$ | H | H | 2 | H | H | $C=NOCH_2C_6H_5$ | $CH_3$ | H |
| 3.39 | $CH_3$ | H | H | 0 | H | H | $C(CH_3)_2$ | $CH_3$ | H |
| 3.40 | $CH_3$ | H | H | 2 | H | H | $C(CH_3)_2$ | $CH_3$ | H |
| 3.41 | $CH_3$ | $CH_3$ | H | 0 | H | H | C=O | $CH_3$ | H |
| 3.42 | $CH_3$ | $CH_3$ | H | 2 | H | H | C=O | $CH_3$ | H |
| 3.43 | $CH_3$ | $CH_3$ | H | 0 | H | H | $CHOCH_3$ | $CH_3$ | H |
| 3.44 | $CH_3$ | $CH_3$ | H | 2 | H | H | $CHOCH_3$ | $CH_3$ | H |
| 3.45 | $CH_3$ | $CH_3$ | H | 0 | H | H | $CHOC_2H_5$ | $CH_3$ | H |
| 3.46 | $CH_3$ | $CH_3$ | H | 2 | H | H | $CHOC_2H_5$ | $CH_3$ | H |
| 3.47 | $CH_3$ | $CH_3$ | H | 0 | H | H | CHOiPr | $CH_3$ | H |
| 3.48 | $CH_3$ | $CH_3$ | H | 2 | H | H | CHOiPr | $CH_3$ | H |
| 3.49 | $CH_3$ | $CH_3$ | H | 0 | H | H | $C=NOCH_3$ | $CH_3$ | H |
| 3.50 | $CH_3$ | $CH_3$ | H | 2 | H | H | $C=NOCH_3$ | $CH_3$ | H |
| 3.51 | $CH_3$ | $CH_3$ | H | 0 | H | H | $C=NOC_2H_5$ | $CH_3$ | H |
| 3.52 | $CH_3$ | $CH_3$ | H | 2 | H | H | $C=NOC_2H_5$ | $CH_3$ | H |
| 3.53 | $CH_3$ | $CH_3$ | H | 0 | H | H | C=NOiPr | $CH_3$ | H |
| 3.54 | $CH_3$ | $CH_3$ | H | 2 | H | H | C=NOiPr | $CH_3$ | H |
| 3.55 | $CH_3$ | $CH_3$ | H | 0 | H | H | $C=NOCH_2CH=CHCl$ | $CH_3$ | H |
| 3.56 | $CH_3$ | $CH_3$ | W | 2 | H | H | $C=NOCH_2CH=CHCl$ | $CH_3$ | H |
| 3.57 | $CH_3$ | $CH_3$ | H | 0 | H | H | $C=NOCH_2C_6H_5$ | $CH_3$ | H |
| 3.58 | $CH_3$ | $CH_3$ | H | 2 | H | H | $C=NOCH_2C_6H_5$ | $CH_3$ | H |
| 3.59 | $CH_3$ | $CH_3$ | H | 0 | H | H | $C(CH_3)_2$ | $CH_3$ | H |
| 3.60 | $CH_3$ | $CH_3$ | H | 2 | H | H | $C(CH_3)_2$ | $CH_3$ | H |
| 3.61 | H | H | H | 0 | H | H | C=O | Cl | H |
| 3.62 | H | H | H | 2 | H | H | C=O | Cl | H |
| 3.63 | H | H | H | 0 | H | H | $CHOCH_3$ | Cl | H |
| 3.64 | H | H | H | 2 | H | H | $CHOCH_3$ | Cl | H |
| 3.65 | H | H | H | 0 | H | H | $CHOC_2H_5$ | Cl | H |
| 3.66 | H | H | H | 2 | H | H | $CHOC_2H_5$ | Cl | H |
| 3.67 | H | H | H | 0 | H | H | CHOiPr | Cl | H |
| 3.68 | H | H | H | 2 | H | H | CHOiPr | Cl | H |
| 3.69 | H | H | H | 0 | H | H | $C=NOCH_3$ | Cl | H |
| 3.70 | H | H | H | 2 | H | H | $C=NOCH_3$ | Cl | H |
| 3.71 | H | H | H | 0 | H | H | $C=NOC_2H_5$ | Cl | H |
| 3.72 | H | H | H | 2 | H | H | $C=NOC_2H_5$ | Cl | H |
| 3.73 | H | H | H | 0 | H | H | C=NOiPr | Cl | H |
| 3.74 | H | H | H | 2 | H | H | C=NOiPr | Cl | H |
| 3.75 | H | H | H | 0 | H | H | $C=NOCH_2CH=CHCl$ | Cl | H |
| 3.76 | H | H | H | 2 | H | H | $C=NOCH_2CH=CHCl$ | Cl | H |
| 3 77 | H | H | H | 0 | H | H | $C=NOCH_2C_6H_5$ | Cl | H |
| 3.78 | H | H | H | 2 | H | H | $C=NOCH_2C_6H_5$ | Cl | H |
| 3.79 | H | H | H | 0 | H | H | $C(CH_3)_2$ | Cl | H |
| 3.80 | H | H | H | 2 | H | H | $C(CH_3)_2$ | Cl | H |
| 3.81 | $CH_3$ | H | H | 0 | H | H | C=O | Cl | H |
| 3.82 | $CH_3$ | H | H | 2 | H | H | C=O | Cl | H |
| 3.83 | $CH_3$ | H | H | 0 | H | H | $CHOCH_3$ | Cl | H |
| 3.84 | $CH_3$ | H | H | 2 | H | H | $CHOCH_3$ | Cl | H |
| 3.85 | $CH_3$ | H | H | 0 | H | H | $CHOC_2H_5$ | Cl | H |
| 3.86 | $CH_3$ | H | H | 2 | H | H | $CHOC_2H_5$ | Cl | H |
| 3.87 | $CH_3$ | H | H | 0 | H | H | CHOiPr | Cl | H |
| 3.88 | $CH_3$ | H | H | 2 | H | H | CHOiPr | Cl | H |

TABLE 3-continued

Compounds of the formula

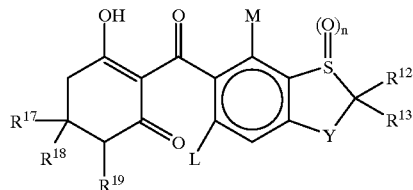

| No. | $R^{17}$ | $R^{18}$ | $R^{19}$ | n | $R^{12}$ | $R^{13}$ | Y | L | M |
|---|---|---|---|---|---|---|---|---|---|
| 3.89 | CH₃ | H | H | 0 | H | H | C=NOCH₃ | Cl | H |
| 3.90 | CH₃ | H | H | 2 | H | H | C=NOCH₃ | Cl | H |
| 3.91 | CH₃ | H | H | 0 | H | H | C=NOC₂H₅ | Cl | H |
| 3.92 | CH₃ | H | H | 2 | H | H | C=NOC₂H₅ | Cl | H |
| 3.93 | CH₃ | H | H | 0 | H | H | C=NOiPr | Cl | H |
| 3.94 | CH₃ | H | H | 2 | H | H | C=NOiPr | Cl | H |
| 3.95 | CH₃ | H | H | 0 | H | H | C=NOCH₂CH=CHCl | Cl | H |
| 3.96 | CH₃ | H | H | 2 | H | H | C=NOCH₂CH=CHCl | Cl | H |
| 3.97 | CH₃ | H | H | 0 | H | H | C=NOCH₂C₆H₅ | Cl | H |
| 3.98 | CH₃ | H | H | 2 | H | H | C=NOCH₂C₆H₅ | Cl | H |
| 3.99 | CH₃ | H | H | 0 | H | H | C(CH₃)₂ | Cl | H |
| 3.100 | CH₃ | H | H | 2 | H | H | C(CH₃)₂ | Cl | H |
| 3.101 | CH₃ | CH₃ | H | 0 | H | H | C=O | Cl | H |
| 3.102 | CH₃ | CH₃ | H | 2 | H | H | C=O | Cl | H |
| 3.103 | CH₃ | CH₃ | H | 0 | H | H | CHOCH₃ | Cl | H |
| 3.104 | CH₃ | CH₃ | H | 2 | H | H | CHOCH₃ | Cl | H |
| 3.105 | CH₃ | CH₃ | H | 0 | H | H | CHOC₂H₅ | Cl | H |
| 3.106 | CH₃ | CH₃ | H | 2 | H | H | CHOC₂H₅ | Cl | H |
| 3.107 | CH₃ | CH₃ | H | 0 | H | H | CHOiPr | Cl | H |
| 3.108 | CH₃ | CH₃ | H | 2 | H | H | CHOiPr | Cl | H |
| 3.109 | CH₃ | CH₃ | H | 0 | H | H | C=N—OCH₃ | Cl | H |
| 3.110 | CH₃ | CH₃ | H | 2 | H | H | C=NOCH₃ | Cl | H |
| 3.111 | CH₃ | CH₃ | H | 0 | H | H | C=NOC₂H₅ | Cl | H |
| 3.112 | CH₃ | CH₃ | H | 2 | H | H | C=NOC₂H₅ | Cl | H |
| 3.113 | CH₃ | CH₃ | H | 0 | H | H | C=NOiPr | Cl | H |
| 3.114 | CH₃ | CH₃ | H | 2 | H | H | C=NOiPr | Cl | H |
| 3.115 | CH₃ | CH₃ | H | 0 | H | H | C=NOCH₂CH=CHCl | Cl | H |
| 3.116 | CH₃ | CH₃ | H | 2 | H | H | C=NOCH₂CH=CHCl | Cl | H |
| 3.117 | CH₃ | CH₃ | H | 0 | H | H | C=NOCH₂C₆H₅ | Cl | H |
| 3.118 | CH₃ | CH₃ | H | 2 | H | H | C=NOCH₂C₆H₅ | Cl | H |
| 3.119 | CH₃ | CH₃ | H | 0 | H | H | C(CH₃)₂ | Cl | H |
| 3.120 | CH₃ | CH₃ | H | 2 | H | H | C(CH₃)₂ | Cl | H |
| 3.121 | H | H | H | 0 | H | CH₃ | C=O | CH₃ | H |
| 3.122 | H | H | H | 2 | H | CH₃ | C=O | CH₃ | H |
| 3.123 | H | H | H | 0 | H | CH₃ | CHOCH₃ | CH₃ | H |
| 3.124 | H | H | H | 2 | H | CH₃ | CHOCH₃ | CH₃ | H |
| 3.125 | H | H | H | 0 | H | CH₃ | CHOC₂H₅ | CH₃ | H |
| 3.126 | H | H | H | 2 | H | CH₃ | CHOC₂H₅ | CH₃ | H |
| 3.127 | H | H | H | 0 | H | CH₃ | CHOiPr | CH₃ | H |
| 3.128 | H | H | H | 2 | H | CH₃ | CHOiPr | CH₃ | H |
| 3.129 | H | H | H | 0 | H | CH₃ | C=NOCH₃ | CH₃ | H |
| 3.130 | H | H | H | 2 | H | CH₃ | C=NOCH₃ | CH₃ | H |
| 3.131 | H | H | H | 0 | H | CH₃ | C=NOC₂H₅ | CH₃ | H |
| 3.132 | H | H | H | 2 | H | CH₃ | C=NOC₂H₅ | CH₃ | H |
| 3.133 | H | H | H | 0 | H | CH₃ | C=NOiPr | CH₃ | H |
| 3.134 | H | H | H | 2 | H | CH₃ | C=NOiPr | CH₃ | H |
| 3.135 | H | H | H | 0 | H | CH₃ | C=NOCH₂CH=CHCl | CH₃ | H |
| 3.136 | H | H | H | 2 | H | CH₃ | C=NOCH₂CH=CHCl | CH₃ | H |
| 3.137 | H | H | H | 0 | H | CH₃ | C=NOCH₂C₆H₅ | CH₃ | H |
| 3.138 | H | H | H | 2 | H | CH₃ | C=NOCH₂C₆H₅ | CH₃ | H |
| 3.139 | H | H | H | 0 | H | CH₃ | C(CH₃)₂ | CH₃ | H |
| 3.140 | H | H | H | 2 | H | CH₃ | C(CH₃)₂ | CH₃ | H |
| 3.141 | CH₃ | H | H | 0 | H | CH₃ | C=O | CH₃ | H |
| 3.142 | CH₃ | H | H | 2 | H | CH₃ | C=O | CH₃ | H |
| 3.143 | CH₃ | H | H | 0 | H | CH₃ | CHOCH₃ | CH₃ | H |
| 3.144 | CH₃ | H | H | 2 | H | CH₃ | CHOCH₃ | CH₃ | H |
| 3.145 | CH₃ | H | H | 0 | H | CH₃ | CHOC₂H₅ | CH₃ | H |
| 3.146 | CH₃ | H | H | 2 | H | CH₃ | CHOC₂H₅ | CH₃ | H |
| 3.147 | CH₃ | H | H | 0 | H | CH₃ | CHOiPr | CH₃ | H |
| 3.148 | CH₃ | H | H | 2 | H | CH₃ | CHOiPr | CH₃ | H |
| 3.149 | CH₃ | H | H | 0 | H | CH₃ | C=NOCH₃ | CH₃ | H |
| 3.150 | CH₃ | H | H | 2 | H | CH₃ | C=NOCH₃ | CH₃ | H |
| 3.151 | CH₃ | H | H | 0 | H | CH₃ | C=NOC₂H₅ | CH₃ | H |
| 3.152 | CH₃ | H | H | 2 | H | CH₃ | C=NOC₂H₅ | CH₃ | H |

TABLE 3-continued

Compounds of the formula

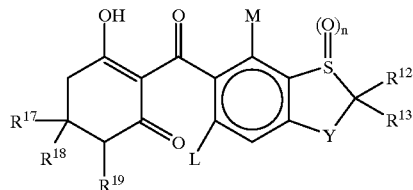

| No. | $R^{17}$ | $R^{18}$ | $R^{19}$ | n | $R^{12}$ | $R^{13}$ | Y | L | M |
|---|---|---|---|---|---|---|---|---|---|
| 3.153 | $CH_3$ | H | H | 0 | H | $CH_3$ | C=NOiPr | $CH_3$ | H |
| 3.154 | $CH_3$ | H | H | 2 | H | $CH_3$ | C=NOiPr | $CH_3$ | H |
| 3.155 | $CH_3$ | H | H | 0 | H | $CH_3$ | C=NOCH$_2$CH=CHCl | $CH_3$ | H |
| 3.156 | $CH_3$ | H | H | 2 | H | $CH_3$ | C=NOCH$_2$CH=CHCl | $CH_3$ | H |
| 3.157 | $CH_3$ | H | H | 0 | H | $CH_3$ | C=NOCH$_2$C$_6$H$_5$ | $CH_3$ | H |
| 3.158 | $CH_3$ | H | H | 2 | H | $CH_3$ | C=NOCH$_2$C$_6$H$_5$ | $CH_3$ | H |
| 3.159 | $CH_3$ | H | H | 0 | H | $CH_3$ | C(CH$_3$)$_2$ | $CH_3$ | H |
| 3.160 | $CH_3$ | H | H | 2 | H | $CH_3$ | C(CH$_3$)$_2$ | $CH_3$ | H |
| 3.161 | $CH_3$ | $CH_3$ | H | 0 | H | $CH_3$ | C=O | $CH_3$ | H |
| 3.162 | $CH_3$ | $CH_3$ | H | 2 | H | $CH_3$ | C=O | $CH_3$ | H |
| 3.163 | $CH_3$ | $CH_3$ | H | 0 | H | $CH_3$ | CHOCH$_3$ | $CH_3$ | H |
| 3.164 | $CH_3$ | $CH_3$ | H | 2 | H | $CH_3$ | CHOCH$_3$ | $CH_3$ | H |
| 3.165 | $CH_3$ | $CH_3$ | H | 0 | H | $CH_3$ | CHOC$_2$H$_5$ | $CH_3$ | H |
| 3.166 | $CH_3$ | $CH_3$ | H | 2 | H | $CH_3$ | CHOC$_2$H$_5$ | $CH_3$ | H |
| 3.167 | $CH_3$ | $CH_3$ | H | 0 | H | $CH_3$ | CHOiPr | $CH_3$ | H |
| 3.168 | $CH_3$ | $CH_3$ | H | 2 | H | $CH_3$ | CHOiPr | $CH_3$ | H |
| 3.169 | $CH_3$ | $CH_3$ | H | 0 | H | $CH_3$ | C=NOCH$_3$ | $CH_3$ | H |
| 3.170 | $CH_3$ | $CH_3$ | H | 2 | H | $CH_3$ | C=NOCH$_3$ | $CH_3$ | H |
| 3.171 | $CH_3$ | $CH_3$ | H | 0 | H | $CH_3$ | C=NOC$_2$H$_5$ | $CH_3$ | H |
| 3.172 | $CH_3$ | $CH_3$ | H | 2 | H | $CH_3$ | C=NOC$_2$H$_5$ | $CH_3$ | H |
| 3.173 | $CH_3$ | $CH_3$ | H | 0 | H | $CH_3$ | C=NOiPr | $CH_3$ | H |
| 3.174 | $CH_3$ | $CH_3$ | H | 2 | H | $CH_3$ | C=NOiPr | $CH_3$ | H |
| 3.175 | $CH_3$ | $CH_3$ | H | 0 | H | $CH_3$ | C=NOCH$_2$CH=CHCl | $CH_3$ | H |
| 3.176 | $CH_3$ | $CH_3$ | H | 2 | H | $CH_3$ | C=NOCH$_2$CH=CHCl | $CH_3$ | H |
| 3.177 | $CH_3$ | $CH_3$ | H | 0 | H | $CH_3$ | C=NOCH$_2$C$_6$H$_5$ | $CH_3$ | H |
| 3.178 | $CH_3$ | $CH_3$ | H | 2 | H | $CH_3$ | C=NOCH$_2$C$_6$H$_5$ | $CH_3$ | H |
| 3.179 | $CH_3$ | $CH_3$ | H | 0 | H | $CH_3$ | C(CH$_3$)$_2$ | $CH_3$ | H |
| 3.180 | $CH_3$ | $CH_3$ | H | 2 | H | $CH_3$ | C(CH$_3$)$_2$ | $CH_3$ | H |
| 3.181 | H | H | H | 0 | H | $CH_3$ | C=O | Cl | H |
| 3.182 | H | H | H | 2 | H | $CH_3$ | C=O | Cl | H |
| 3.183 | H | H | H | 0 | H | $CH_3$ | CHOCH$_3$ | Cl | H |
| 3.184 | H | H | H | 2 | H | $CH_3$ | CHOCH$_3$ | Cl | H |
| 3.185 | H | H | H | 0 | H | $CH_3$ | CHOC$_2$H$_5$ | Cl | H |
| 3.186 | H | H | H | 2 | H | $CH_3$ | CHOC$_2$H$_5$ | Cl | H |
| 3.187 | H | H | H | 0 | H | $CH_3$ | CHOiPr | Cl | H |
| 3.188 | H | H | H | 2 | H | $CH_3$ | CHOiPr | Cl | H |
| 3.189 | H | H | H | 0 | H | $CH_3$ | C=NOCH$_3$ | Cl | H |
| 3.190 | H | H | H | 2 | H | $CH_3$ | C=NOCH$_3$ | Cl | H |
| 3.191 | H | H | H | 0 | H | $CH_3$ | C=NOC$_2$H$_5$ | Cl | H |
| 3.192 | H | H | H | 2 | H | $CH_3$ | C=NOC$_2$H$_5$ | Cl | H |
| 3.193 | H | H | H | 0 | H | $CH_3$ | C=NOiPr | Cl | H |
| 3.194 | H | H | H | 2 | H | $CH_3$ | C=NOiPr | Cl | H |
| 3.195 | H | H | H | 0 | H | $CH_3$ | C=NOCH$_2$CH=CHCl | Cl | H |
| 3.196 | H | H | H | 2 | H | $CH_3$ | C=NOCH$_2$CH=CHCl | Cl | H |
| 3.197 | H | H | H | 0 | H | $CH_3$ | C=NOCH$_2$C$_6$H$_5$ | Cl | H |
| 3.198 | H | H | H | 2 | H | $CH_3$ | C=NOCH$_2$C$_6$H$_5$ | Cl | H |
| 3.199 | H | H | H | 0 | H | $CH_3$ | C(CH$_3$)$_2$ | Cl | H |
| 3.200 | H | H | H | 2 | H | $CH_3$ | C(CH$_3$)$_2$ | Cl | H |
| 3.201 | $CH_3$ | H | H | 0 | H | $CH_3$ | C=O | Cl | H |
| 3.202 | $CH_3$ | H | H | 2 | H | $CH_3$ | C=O | Cl | H |
| 3.203 | $CH_3$ | H | H | 0 | H | $CH_3$ | CHOCH$_3$ | Cl | H |
| 3.204 | $CH_3$ | H | H | 2 | H | $CH_3$ | CHOCH$_3$ | Cl | H |
| 3.205 | $CH_3$ | H | H | 0 | H | $CH_3$ | CHOC$_2$H$_5$ | Cl | H |
| 3.206 | $CH_3$ | H | H | 2 | H | $CH_3$ | CHOC$_2$H$_5$ | Cl | H |
| 3.207 | $CH_3$ | H | H | 0 | H | $CH_3$ | CHOiPr | Cl | H |
| 3.208 | $CH_3$ | H | H | 2 | H | $CH_3$ | CHOiPr | Cl | H |
| 3.209 | $CH_3$ | H | H | 0 | H | $CH_3$ | C=NOCH$_3$ | Cl | H |
| 3.210 | $CH_3$ | H | H | 2 | H | $CH_3$ | C=NOCH$_3$ | Cl | H |
| 3.211 | $CH_3$ | H | H | 0 | H | $CH_3$ | C=NOC$_2$H$_5$ | Cl | H |
| 3.212 | $CH_3$ | H | H | 2 | H | $CH_3$ | C=NOC$_2$H$_5$ | Cl | H |
| 3.213 | $CH_3$ | H | H | 0 | H | $CH_3$ | C=NOiPr | Cl | H |
| 3.214 | $CH_3$ | H | H | 2 | H | $CH_3$ | C=NOiPr | Cl | H |
| 3.215 | $CH_3$ | H | H | 0 | H | $CH_3$ | C=NOCH$_2$CH=CHCl | Cl | H |
| 3.216 | $CH_3$ | H | H | 2 | H | $CH_3$ | C=NOCH$_2$CH=CHCl | Cl | H |

TABLE 3-continued

Compounds of the formula

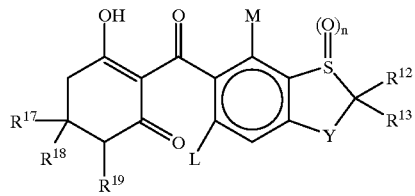

| No. | $R^{17}$ | $R^{18}$ | $R^{19}$ | n | $R^{12}$ | $R^{13}$ | Y | L | M |
|---|---|---|---|---|---|---|---|---|---|
| 3.217 | $CH_3$ | H | H | 0 | H | $CH_3$ | $C=NOCH_2C_6H_5$ | Cl | H |
| 3.218 | $CH_3$ | H | H | 2 | H | $CH_3$ | $C=NOCH_2C_6H_5$ | Cl | H |
| 3.219 | $CH_3$ | H | H | 0 | H | $CH_3$ | $C(CH_3)_2$ | Cl | H |
| 3.220 | $CH_3$ | H | H | 2 | H | $CH_3$ | $C(CH_3)_2$ | Cl | H |
| 3.221 | $CH_3$ | $CH_3$ | H | 0 | H | $CH_3$ | $C=O$ | Cl | H |
| 3.222 | $CH_3$ | $CH_3$ | H | 2 | H | $CH_3$ | $C=O$ | Cl | H |
| 3.223 | $CH_3$ | $CH_3$ | H | 0 | H | $CH_3$ | $CHOCH_3$ | Cl | H |
| 3.224 | $CH_3$ | $CH_3$ | H | 2 | H | $CH_3$ | $CHOCH_3$ | Cl | H |
| 3.225 | $CH_3$ | $CH_3$ | H | 0 | H | $CH_3$ | $CHOC_2H_5$ | Cl | H |
| 3.226 | $CH_3$ | $CH_3$ | H | 2 | H | $CH_3$ | $CHOC_2H_5$ | Cl | H |
| 3.227 | $CH_3$ | $CH_3$ | H | 0 | H | $CH_3$ | $CHOiPr$ | Cl | H |
| 3.228 | $CH_3$ | $CH_3$ | H | 2 | H | $CH_3$ | $CHOiPr$ | Cl | H |
| 3.229 | $CH_3$ | $CH_3$ | H | 0 | H | $CH_3$ | $C=NOCH_3$ | Cl | H |
| 3.230 | $CH_3$ | $CH_3$ | H | 2 | H | $CH_3$ | $C=NOCH_3$ | Cl | H |
| 3.231 | $CH_3$ | $CH_3$ | H | 0 | H | $CH_3$ | $C=NOC_2H_5$ | Cl | H |
| 3.232 | $CH_3$ | $CH_3$ | H | 2 | H | $CH_3$ | $C=NOC_2H_5$ | Cl | H |
| 3.233 | $CH_3$ | $CH_3$ | H | 0 | H | $CH_3$ | $C=NOiPr$ | Cl | H |
| 3.234 | $CH_3$ | $CH_3$ | H | 2 | H | $CH_3$ | $C=NOiPr$ | Cl | H |
| 3.235 | $CH_3$ | $CH_3$ | H | 0 | H | $CH_3$ | $C=NOCH_2CH=CHCl$ | Cl | H |
| 3.236 | $CH_3$ | $CH_3$ | H | 2 | H | $CH_3$ | $C=NOCH_2CH=CHCl$ | Cl | H |
| 3.237 | $CH_3$ | $CH_3$ | H | 0 | H | $CH_3$ | $C=NOCH_2C_6H_5$ | Cl | H |
| 3.238 | $CH_3$ | $CH_3$ | H | 2 | H | $CH_3$ | $C=NOCH_2C_6H_5$ | Cl | H |
| 3.239 | $CH_3$ | $CH_3$ | H | 0 | H | $CH_3$ | $(CH_3)_2$ | Cl | H |
| 3.240 | $CH_3$ | $CH_3$ | H | 2 | H | $CH_3$ | $C(CH_3)_2$ | Cl | H |
| 3.241 | H | H | H | 0 | H | $CH_3$ | $C=O$ | $CH_3$ | $CH_3$ |
| 3.242 | H | H | H | 2 | H | $CH_3$ | $C=O$ | $CH_3$ | $CH_3$ |
| 3.243 | H | H | H | 0 | H | $CH_3$ | $CHOCH_3$ | $CH_3$ | $CH_3$ |
| 3.244 | H | H | H | 2 | H | $CH_3$ | $CHOCH_3$ | $CH_3$ | $CH_3$ |
| 3.245 | H | H | H | 0 | H | $CH_3$ | $CHOC_2H_5$ | $CH_3$ | $CH_3$ |
| 3.246 | H | H | H | 2 | H | $CH_3$ | $CHOC_2H_5$ | $CH_3$ | $CH_3$ |
| 3.247 | H | H | H | 0 | H | $CH_3$ | $CHOiPr$ | $CH_3$ | $CH_3$ |
| 3.248 | H | H | H | 2 | H | $CH_3$ | $CHOiPr$ | $CH_3$ | $CH_3$ |
| 3.249 | H | H | H | 0 | H | $CH_3$ | $COCH_3$ | $CH_3$ | $CH_3$ |
| 3.250 | H | H | H | 2 | H | $CH_3$ | $COCH_3$ | $CH_3$ | $CH_3$ |
| 3.251 | H | H | H | 0 | H | $CH_3$ | $COC_2H_5$ | $CH_3$ | $CH_3$ |
| 3.252 | H | H | H | 2 | H | $CH_3$ | $COC_2H_5$ | $CH_3$ | $CH_3$ |
| 3.253 | H | H | H | 0 | H | $CH_3$ | $C=NOCH_3$ | $CH_3$ | $CH_3$ |
| 3.254 | H | H | H | 2 | H | $CH_3$ | $C=NOCH_3$ | $CH_3$ | $CH_3$ |
| 3.255 | H | H | H | 0 | H | $CH_3$ | $C=NOC_2H_5$ | $CH_3$ | $CH_3$ |
| 3.256 | H | H | H | 2 | H | $CH_3$ | $C=NOC_2H_5$ | $CH_3$ | $CH_3$ |
| 3.257 | H | H | H | 0 | H | $CH_3$ | $C=NOiPr$ | $CH_3$ | $CH_3$ |
| 3.258 | H | H | H | 2 | H | $CH_3$ | $C=NOiPr$ | $CH_3$ | $CH_3$ |
| 3.259 | H | H | H | 0 | H | $CH_3$ | $C=NOCH_2CH=CHCl$ | $CH_3$ | $CH_3$ |
| 3.260 | H | H | H | 2 | H | $CH_3$ | $C=NOCH_2CH=CHCl$ | $CH_3$ | $CH_3$ |
| 3.261 | H | H | H | 0 | H | $CH_3$ | $C=NOCH_2C_6H_5$ | $CH_3$ | $CH_3$ |
| 3.262 | H | H | H | 2 | H | $CH_3$ | $C=NOCH_2C_6H_5$ | $CH_3$ | $CH_3$ |
| 3.263 | H | H | H | 0 | H | $CH_3$ | $C(CH_3)_2$ | $CH_3$ | $CH_3$ |
| 3.264 | H | H | H | 2 | H | $CH_3$ | $C(CH_3)_2$ | $CH_3$ | $CH_3$ |
| 3.265 | $CH_3$ | H | H | 0 | H | $CH_3$ | $C=O$ | $CH_3$ | $CH_3$ |
| 3.266 | $CH_3$ | H | H | 2 | H | $CH_3$ | $C=O$ | $CH_3$ | $CH_3$ |
| 3.267 | $CH_3$ | H | H | 0 | H | $CH_3$ | $CHOCH_3$ | $CH_3$ | $CH_3$ |
| 3.268 | $CH_3$ | H | H | 2 | H | $CH_3$ | $CHOCH_3$ | $CH_3$ | $CH_3$ |
| 3.269 | $CH_3$ | H | H | 0 | H | $CH_3$ | $CHOC_2H_5$ | $CH_3$ | $CH_3$ |
| 3.270 | $CH_3$ | H | H | 2 | H | $CH_3$ | $CHOC_2H_5$ | $CH_3$ | $CH_3$ |
| 3.271 | $CH_3$ | H | H | 0 | H | $CH_3$ | $CHOiPr$ | $CH_3$ | $CH_3$ |
| 3.272 | $CH_3$ | H | H | 2 | H | $CH_3$ | $CHOiPr$ | $CH_3$ | $CH_3$ |
| 3.273 | $CH_3$ | H | H | 0 | H | $CH_3$ | $C=NOCH_3$ | $CH_3$ | $CH_3$ |
| 3.274 | $CH_3$ | H | H | 2 | H | $CH_3$ | $C=NOCH_3$ | $CH_3$ | $CH_3$ |
| 3.275 | $CH_3$ | H | H | 0 | H | $CH_3$ | $C=NOC_2H_5$ | $CH_3$ | $CH_3$ |
| 3.276 | $CH_3$ | H | H | 2 | H | $CH_3$ | $C=NOC_2H_5$ | $CH_3$ | $CH_3$ |
| 3.277 | $CH_3$ | H | H | 0 | H | $CH_3$ | $C=NOiPr$ | $CH_3$ | $CH_3$ |
| 3.278 | $CH_3$ | H | H | 2 | H | $CH_3$ | $C=NOiPr$ | $CH_3$ | $CH_3$ |
| 3.279 | $CH_3$ | H | H | 0 | H | $CH_3$ | $C=NOCH_2CH=CHCl$ | $CH_3$ | $CH_3$ |
| 3.280 | $CH_3$ | H | H | 2 | H | $CH_3$ | $C=NOCH_2CH=CHCl$ | $CH_3$ | $CH_3$ |

TABLE 3-continued

Compounds of the formula

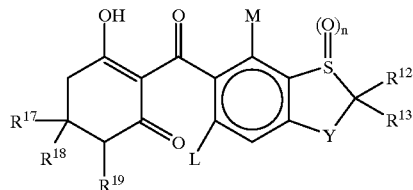

| No. | $R^{17}$ | $R^{18}$ | $R^{19}$ | n | $R^{12}$ | $R^{13}$ | Y | L | M |
|---|---|---|---|---|---|---|---|---|---|
| 3.281 | $CH_3$ | H | H | 0 | H | $CH_3$ | $C=NOCH_2C_6H_5$ | $CH_3$ | $CH_3$ |
| 3.282 | $CH_3$ | H | H | 2 | H | $CH_3$ | $C=NOCH_2C_6H_5$ | $CH_3$ | $CH_3$ |
| 3.283 | $CH_3$ | H | H | 0 | H | $CH_3$ | $C(CH_3)_2$ | $CH_3$ | $CH_3$ |
| 3.284 | $CH_3$ | H | H | 2 | H | $CH_3$ | $C(CH_3)_2$ | $CH_3$ | $CH_3$ |
| 3.285 | $CH_3$ | $CH_3$ | H | 0 | H | $CH_3$ | $C=O$ | $CH_3$ | $CH_3$ |
| 3.286 | $CH_3$ | $CH_3$ | H | 2 | H | $CH_3$ | $C=O$ | $CH_3$ | $CH_3$ |
| 3.287 | $CH_3$ | $CH_3$ | H | 0 | H | $CH_3$ | $CHOCH_3$ | $CH_3$ | $CH_3$ |
| 3.288 | $CH_3$ | $CH_3$ | H | 2 | H | $CH_3$ | $CHOCH_3$ | $CH_3$ | $CH_3$ |
| 3.289 | $CH_3$ | $CH_3$ | H | 0 | H | $CH_3$ | $CHOC_2H_5$ | $CH_3$ | $CH_3$ |
| 3.290 | $CH_3$ | $CH_3$ | H | 2 | H | $CH_3$ | $CHOC_2H_5$ | $CH_3$ | $CH_3$ |
| 3.291 | $CH_3$ | $CH_3$ | H | 0 | H | $CH_3$ | $CHOiPr$ | $CH_3$ | $CH_3$ |
| 3.292 | $CH_3$ | $CH_3$ | H | 2 | H | $CH_3$ | $CHOiPr$ | $CH_3$ | $CH_3$ |
| 3.293 | $CH_3$ | $CH_3$ | H | 0 | H | $CH_3$ | $C=NOCH_3$ | $CH_3$ | $CH_3$ |
| 3.294 | $CH_3$ | $CH_3$ | H | 2 | H | $CH_3$ | $C=NOCH_3$ | $CH_3$ | $CH_3$ |
| 3.295 | $CH_3$ | $CH_3$ | H | 0 | H | $CH_3$ | $C=NOC_2H_5$ | $CH_3$ | $CH_3$ |
| 3.296 | $CH_3$ | $CH_3$ | H | 2 | H | $CH_3$ | $C=NOC_2H_5$ | $CH_3$ | $CH_3$ |
| 3.297 | $CH_3$ | $CH_3$ | H | 0 | H | $CH_3$ | $C=NOiPr$ | $CH_3$ | $CH_3$ |
| 3.298 | $CH_3$ | $CH_3$ | H | 2 | H | $CH_3$ | $C=NOiPr$ | $CH_3$ | $CH_3$ |
| 3.299 | $CH_3$ | $CH_3$ | H | 0 | H | $CH_3$ | $C=NOCH_2CH=CHCl$ | $CH_3$ | $CH_3$ |
| 3.300 | $CH_3$ | $CH_3$ | H | 2 | H | $CH_3$ | $C=NOCH_2CH=CHCl$ | $CH_3$ | $CH_3$ |
| 3.301 | $CH_3$ | $CH_3$ | H | 0 | H | $CH_3$ | $C=NOCH_2C_6H_5$ | $CH_3$ | $CH_3$ |
| 3.302 | $CH_3$ | $CH_3$ | H | 2 | H | $CH_3$ | $C=NOCH_2C_6H_5$ | $CH_3$ | $CH_3$ |
| 3.303 | $CH_3$ | $CH_3$ | H | 0 | H | $CH_3$ | $C(CH_3)_2$ | $CH_3$ | $CH_3$ |
| 3.304 | $CH_3$ | $CH_3$ | H | 2 | H | $CH_3$ | $C(CH_3)_2$ | $CH_3$ | $CH_3$ |

TABLE 4

Compounds of the formula

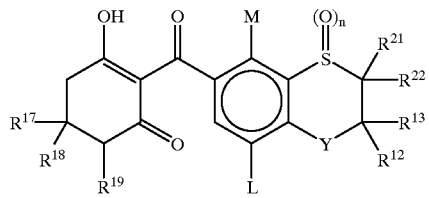

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.1 | H | H | H | 0 | H | H | H | H | $C=O$ | H | H |
| 4.2 | H | H | H | 1 | H | H | H | H | $C=O$ | H | H |
| 4.3 | H | H | H | 2 | H | H | H | H | $C=O$ | H | H |
| 4.4 | H | H | H | 0 | H | H | H | H | $CHOH$ | H | H |
| 4.5 | H | H | H | 1 | H | H | H | H | $CHOH$ | H | H |
| 4.6 | H | H | H | 2 | H | H | H | H | $CHOH$ | H | H |
| 4.7 | H | H | H | 0 | H | H | H | H | $CHOCH_3$ | H | H |
| 4.8 | H | H | H | 1 | H | H | H | H | $CHOCH_3$ | H | H |
| 4.9 | H | H | H | 2 | H | H | H | H | $CHOCH_3$ | H | H |
| 4.10 | H | H | H | 0 | H | H | H | H | $CHOC_2H_5$ | H | H |
| 4.11 | H | H | H | 1 | H | H | H | H | $CHOC_2H_5$ | H | H |
| 4.12 | H | H | H | 2 | H | H | H | H | $CHOC_2H_5$ | H | H |
| 4.13 | H | H | H | 0 | H | H | H | H | $CHOiPr$ | H | H |
| 4.14 | H | H | H | 1 | H | H | H | H | $CHOiPr$ | H | H |
| 4.15 | H | H | H | 2 | H | H | H | H | $CHOiPr$ | H | H |
| 4.16 | H | H | H | 0 | H | H | H | H | $C=NOCH_3$ | H | H |
| 4.17 | H | H | H | 1 | H | H | H | H | $C=NOCH_3$ | H | H |
| 4.18 | H | H | H | 2 | H | H | H | H | $C=NOCH_3$ | H | H |
| 4.19 | H | H | H | 0 | H | H | H | H | $C=NOC_2H_5$ | H | H |
| 4.20 | H | H | H | 1 | H | H | H | H | $C=NOC_2H_5$ | H | H |

TABLE 4-continued

Compounds of the formula

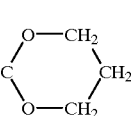

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.21 | H | H | H | 2 | H | H | H | H | C=NOC$_2$H$_5$ | H | H |
| 4.22 | H | H | H | 0 | H | H | H | H | C=NOiPr | H | H |
| 4.23 | H | H | H | 1 | H | H | H | H | C=NOiPr | H | H |
| 4.24 | H | H | H | 2 | H | H | H | H | C=NOiPr | H | H |
| 4.25 | H | H | H | 0 | H | H | H | H | C=NOCH$_2$CH=CHCl | H | H |
| 4.26 | H | H | H | 1 | H | H | H | H | C=NOCH$_2$CH=CHCl | H | H |
| 4.27 | H | H | H | 2 | H | H | H | H | C=NOCH$_2$CH=CHCl | H | H |
| 4.28 | H | H | H | 0 | H | H | H | H | C=NOCH$_2$C$_6$H$_5$ | H | H |
| 4.29 | H | H | H | 1 | H | H | H | H | C=NOCH$_2$C$_6$H$_5$ | H | H |
| 4.30 | H | H | H | 2 | H | H | H | H | C=NOCH$_2$C$_6$H$_5$ | H | H |
| 4.31 | H | H | H | 0 | H | H | H | H | C(CH$_3$)$_2$ | H | H |
| 4.32 | H | H | H | 1 | H | H | H | H | C(CH$_3$)$_2$ | H | H |
| 4.33 | H | H | H | 2 | H | H | H | H | C(CH$_3$)$_2$ | H | H |
| 4.34 | H | H | H | 0 | H | H | H | H | 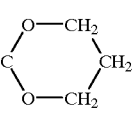 | H | H |
| 4.35 | H | H | H | 1 | H | H | H | H | 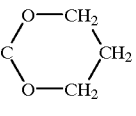 | H | H |
| 4.36 | H | H | H | 2 | H | H | H | H | 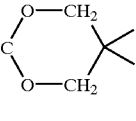 | H | H |
| 4.37 | H | H | H | 0 | H | H | H | H | 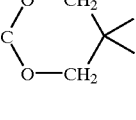 | H | H |
| 4.38 | H | H | H | 1 | H | H | H | H | 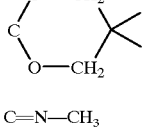 | H | H |
| 4.39 | H | H | H | 2 | H | H | H | H |  | H | H |
| 4.40 | H | H | H | 0 | H | H | H | H | C=N—CH$_3$ | H | H |
| 4.41 | H | H | H | 1 | H | H | H | H | C=N—CH$_3$ | H | H |
| 4.42 | H | H | H | 2 | H | H | H | H | C=N—CH$_3$ | H | H |
| 4.43 | H | H | H | 0 | H | H | H | H | C=NC$_2$H$_5$ | H | H |
| 4.44 | H | H | H | 1 | H | H | H | H | C=NC$_2$H$_5$ | H | H |
| 4.45 | H | H | H | 2 | H | H | H | H | C=NC$_2$H$_5$ | H | H |
| 4.46 | H | H | H | 0 | H | H | H | H | CH—NHCH$_3$ | H | H |
| 4.47 | H | H | H | 1 | H | H | H | H | CH—NHCH$_3$ | H | H |
| 4.48 | H | H | H | 2 | H | H | H | H | CH—NHCH$_3$ | H | H |
| 4.49 | H | H | H | 0 | H | H | H | H | CH—NHC$_2$H$_5$ | H | H |
| 4.50 | H | H | H | 1 | H | H | H | H | CH—NHC$_2$H$_5$ | H | H |
| 4.51 | H | H | H | 2 | H | H | H | H | CH—NHC$_2$H$_5$ | H | H |
| 4.52 | H | H | H | 0 | H | H | H | H | CH—N(CH$_3$)$_2$ | H | H |
| 4.53 | H | H | H | 1 | H | H | H | H | CH—N(CH$_3$)$_2$ | H | H |

TABLE 4-continued

Compounds of the formula

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.54 | H | H | H | 2 | H | H | H | H | CH—N(CH$_3$)$_2$ | H | H |
| 4.55 | H | H | H | 0 | H | H | H | H | CH—NHOC$_2$H$_5$ | H | H |
| 4.56 | H | H | H | 1 | H | H | H | H | CH—NHOC$_2$H$_5$ | H | H |
| 4.57 | H | H | H | 2 | H | H | H | H | CH—NHOC$_2$H$_5$ | H | H |
| 4.58 | H | H | H | 0 | H | H | H | H | CH—N(CH$_3$)OC$_2$H$_5$ | H | H |
| 4.59 | H | H | H | 1 | H | H | H | H | CH—N(CH$_3$)OC$_2$H$_5$ | H | H |
| 4.60 | H | H | H | 2 | H | H | H | H | CH—N(CH$_3$)OC$_2$H$_5$ | H | H |
| 4.61 | H | H | H | 0 | H | H | H | H | C=N—NH$_2$ | H | H |
| 4.62 | H | H | H | 1 | H | H | H | H | C=N—NH$_2$ | H | H |
| 4.63 | H | H | H | 2 | H | H | H | H | C=N—NH$_2$ | H | H |
| 4.64 | H | H | H | 0 | H | H | H | H | C=N—N(CH$_3$)$_2$ | H | H |
| 4.65 | H | H | H | 1 | H | H | H | H | C=N—N(CH$_3$)$_2$ | H | H |
| 4.66 | H | H | H | 2 | H | H | H | H | C=N—N(CH$_3$)$_2$ | H | H |
| 4.67 | H | H | H | 0 | H | H | H | H | CH—N(CH$_3$)OCH$_2$C$_6$H$_5$ | H | H |
| 4.68 | H | H | H | 1 | H | H | H | H | CH—N(CH$_3$)OCH$_2$C$_6$H$_5$ | H | H |
| 4.69 | H | H | H | 2 | H | H | H | H | CH—N(CH$_3$)OCH$_2$C$_6$H$_5$ | H | H |
| 4.70 | H | H | H | 0 | H | H | H | H | C(CH$_3$)—OCH$_3$ | H | H |
| 4.71 | H | H | H | 1 | H | H | H | H | C(CH$_3$)—OCH$_3$ | H | H |
| 4.72 | H | H | H | 2 | H | H | H | H | C(CH$_3$)—OCH$_3$ | H | H |
| 4.73 | H | H | H | 0 | H | H | H | H | O | H | H |
| 4.74 | H | H | H | 1 | H | H | H | H | O | H | H |
| 4.75 | H | H | H | 2 | H | H | H | H | O | H | H |
| 4.76 | CH$_3$ | H | H | 0 | H | H | H | H | C=O | H | H |
| 4.77 | CH$_3$ | H | H | 1 | H | H | H | H | C=O | H | H |
| 4.78 | CH$_3$ | H | H | 2 | H | H | H | H | C=O | H | H |
| 4.79 | CH$_3$ | H | H | 0 | H | H | H | H | CHOH | H | H |
| 4.80 | CH$_3$ | H | H | 1 | H | H | H | H | CHOH | H | H |
| 4.81 | CH$_3$ | H | H | 2 | H | H | H | H | CHOH | H | H |
| 4.82 | CH$_3$ | H | H | 0 | H | H | H | H | CHOCH$_3$ | H | H |
| 4.83 | CH$_3$ | H | H | 1 | H | H | H | H | CHOCH$_3$ | H | H |
| 4.84 | CH$_3$ | H | H | 2 | H | H | H | H | CHOCH$_3$ | H | H |
| 4.85 | CH$_3$ | H | H | 0 | H | H | H | H | CHOC$_2$H$_5$ | H | H |
| 4.86 | CH$_3$ | H | H | 1 | H | H | H | H | CHOC$_2$H$_5$ | H | H |
| 4.87 | CH$_3$ | H | H | 2 | H | H | H | H | CHOC$_2$H$_5$ | H | H |
| 4.88 | CH$_3$ | H | H | 0 | H | H | H | H | CHOiPr | H | H |
| 4.89 | CH$_3$ | H | H | 1 | H | H | H | H | CHOiPr | H | H |
| 4.90 | CH$_3$ | H | H | 2 | H | H | H | H | CHOiPr | H | H |
| 4.91 | CH$_3$ | H | H | 0 | H | H | H | H | C=NOCH$_3$ | H | H |
| 4.92 | CH$_3$ | H | H | 1 | H | H | H | H | C=NOCH$_3$ | H | H |
| 4.93 | CH$_3$ | H | H | 2 | H | H | H | H | C=NOCH$_3$ | H | H |
| 4.94 | CH$_3$ | H | H | 0 | H | H | H | H | C=NOC$_2$H$_5$ | H | H |
| 4.95 | CH$_3$ | H | H | 1 | H | H | H | H | C=NOC$_2$H$_5$ | H | H |
| 4.96 | CH$_3$ | H | H | 2 | H | H | H | H | C=NOC$_2$H$_5$ | H | H |
| 4.97 | CH$_3$ | H | H | 0 | H | H | H | H | C=NOiPr | H | H |
| 4.98 | CH$_3$ | H | H | 1 | H | H | H | H | C=NOiPr | H | H |
| 4.99 | CH$_3$ | H | H | 2 | H | H | H | H | C=NOiPr | H | H |
| 4.100 | CH$_3$ | H | H | 0 | H | H | H | H | C=NOCH$_2$CH=CHCl | H | H |
| 4.101 | CH$_3$ | H | H | 1 | H | H | H | H | C=NOCH$_2$CH=CHCl | H | H |
| 4.102 | CH$_3$ | H | H | 2 | H | H | H | H | C=NOCH$_2$CH=CHCl | H | H |
| 4.103 | CH$_3$ | H | H | 0 | H | H | H | H | C=NOCH$_2$C$_6$H$_5$ | H | H |
| 4.104 | CH$_3$ | H | H | 1 | H | H | H | H | C=NOCH$_2$C$_6$H$_5$ | H | H |
| 4.105 | CH$_3$ | H | H | 2 | H | H | H | H | C=NOCH$_2$C$_6$H$_5$ | H | H |
| 4.106 | CH$_3$ | H | H | 0 | H | H | H | H | C(CH$_3$)$_2$ | H | H |
| 4.107 | CH$_3$ | H | H | 1 | H | H | H | H | C(CH$_3$)$_2$ | H | H |
| 4.108 | CH$_3$ | H | H | 2 | H | H | H | H | C(CH$_3$)$_2$ | H | H |
| 4.109 | CH$_3$ | H | H | 0 | H | H | H | H | C(OCH$_2$CH$_2$CH$_2$O) (cyclic) | H | H |

TABLE 4-continued

Compounds of the formula

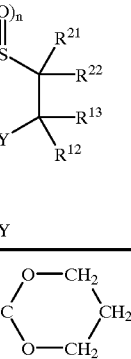

| No. | R¹⁷ | R¹⁸ | R¹⁹ | n | R¹² | R¹³ | R²¹ | R²² | Y | L | M |
|---|---|---|---|---|---|---|---|---|---|---|---|
| 4.110 | $CH_3$ | H | H | 1 | H | H | H | H | 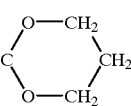 | H | H |
| 4.111 | $CH_3$ | H | H | 2 | H | H | H | H | 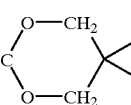 | H | H |
| 4.112 | $CH_3$ | H | H | 0 | H | H | H | H | 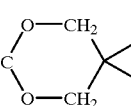 | H | H |
| 4.113 | $CH_3$ | H | H | 1 | H | H | H | H | 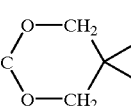 | H | H |
| 4.114 | $CH_3$ | H | H | 2 | H | H | H | H | (same as above) | H | H |
| 4.115 | $CH_3$ | H | H | 0 | H | H | H | H | C=N—$CH_3$ | H | H |
| 4.116 | $CH_3$ | H | H | 1 | H | H | H | H | C=N—$CH_3$ | H | H |
| 4.117 | $CH_3$ | H | H | 2 | H | H | H | H | C=N—$CH_3$ | H | H |
| 4.118 | $CH_3$ | H | H | 0 | H | H | H | H | C=N$C_2H_5$ | H | H |
| 4.119 | $CH_3$ | H | H | 1 | H | H | H | H | C=N$C_2H_5$ | H | H |
| 4.120 | $CH_3$ | H | H | 2 | H | H | H | H | C=N$C_2H_5$ | H | H |
| 4.121 | $CH_3$ | H | H | 0 | H | H | H | H | CH—$NHCH_3$ | H | H |
| 4.122 | $CH_3$ | H | H | 1 | H | H | H | H | CH—$NHCH_3$ | H | H |
| 4.123 | $CH_3$ | H | H | 2 | H | H | H | H | CH—$NHCH_3$ | H | H |
| 4.124 | $CH_3$ | H | H | 0 | H | H | H | H | CH—$NHC_2H_5$ | H | H |
| 4.125 | $CH_3$ | H | H | 1 | H | H | H | H | CH—$NHC_2H_5$ | H | H |
| 4.126 | $CH_3$ | H | H | 2 | H | H | H | H | CH—$NHC_2H_5$ | H | H |
| 4.127 | $CH_3$ | H | H | 0 | H | H | H | H | CH—$N(CH_3)_2$ | H | H |
| 4.128 | $CH_3$ | H | H | 1 | H | H | H | H | CH—$N(CH_3)_2$ | H | H |
| 4.129 | $CH_3$ | H | H | 2 | H | H | H | H | CH—$N(CH_3)_2$ | H | H |
| 4.130 | $CH_3$ | H | H | 0 | H | H | H | H | CH—$NHOC_2H_5$ | H | H |
| 4.131 | $CH_3$ | H | H | 1 | H | H | H | H | CH—$NHOC_2H_5$ | H | H |
| 4.132 | $CH_3$ | H | H | 2 | H | H | H | H | CH—$NHOC_2H_5$ | H | H |
| 4.133 | $CH_3$ | H | H | 0 | H | H | H | H | CH—$N(CH_3)OC_2H_5$ | H | H |
| 4.134 | $CH_3$ | H | H | 1 | H | H | H | H | CH—$N(CH_3)OC_2H_5$ | H | H |
| 4.135 | $CH_3$ | H | H | 2 | H | H | H | H | CH—$N(CH_3)OC_2H_5$ | H | H |
| 4.136 | $CH_3$ | H | H | 0 | H | H | H | H | C=N—$NH_2$ | H | H |
| 4.137 | $CH_3$ | H | H | 1 | H | H | H | H | C=N—$NH_2$ | H | H |
| 4.138 | $CH_3$ | H | H | 2 | H | H | H | H | C=N—$NH_2$ | H | H |
| 4.139 | $CH_3$ | H | H | 0 | H | H | H | H | C=N—$N(CH_3)_2$ | H | H |
| 4.140 | $CH_3$ | H | H | 1 | H | H | H | H | C=N—$N(CH_3)_2$ | H | H |
| 4.141 | $CH_3$ | H | H | 2 | H | H | H | H | C=N—$N(CH_3)_2$ | H | H |
| 4.142 | $CH_3$ | H | H | 0 | H | H | H | H | CH—$N(CH_3)OCH_2C_6H_5$ | H | H |
| 4.143 | $CH_3$ | H | H | 1 | H | H | H | H | CH—$N(CH_3)OCH_2C_6H_5$ | H | H |
| 4.144 | $CH_3$ | H | H | 2 | H | H | H | H | CH—$N(CH_3)OCH_2C_6H_5$ | H | H |
| 4.145 | $CH_3$ | H | H | 0 | H | H | H | H | $C(CH_3)$—$OCH_3$ | H | H |
| 4.146 | $CH_3$ | H | H | 1 | H | H | H | H | $C(CH_3)$—$OCH_3$ | H | H |
| 4.147 | $CH_3$ | H | H | 2 | H | H | H | H | $C(CH_3)$—$OCH_3$ | H | H |
| 4.148 | $CH_3$ | H | H | 0 | H | H | H | H | O | H | H |

TABLE 4-continued

Compounds of the formula

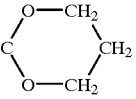

| No. | R17 | R18 | R19 | n | R12 | R13 | R21 | R22 | Y | L | M |
|---|---|---|---|---|---|---|---|---|---|---|---|
| 4.149 | CH₃ | H | H | 1 | H | H | H | H | O | H | H |
| 4.150 | CH₃ | H | H | 2 | H | H | H | H | O | H | H |
| 4.151 | CH₃ | CH₃ | H | 0 | H | H | H | H | C=O | H | H |
| 4.152 | CH₃ | CH₃ | H | 1 | H | H | H | H | C=O | H | H |
| 4.153 | CH₃ | CH₃ | H | 2 | H | H | H | H | C=O | H | H |
| 4.154 | CH₃ | CH₃ | H | 0 | H | H | H | H | CHOH | H | H |
| 4.155 | CH₃ | CH₃ | H | 1 | H | H | H | H | CHOH | H | H |
| 4.156 | CH₃ | CH₃ | H | 2 | H | H | H | H | CHOH | H | H |
| 4.157 | CH₃ | CH₃ | H | 0 | H | H | H | H | CHOCH₃ | H | H |
| 4.158 | CH₃ | CH₃ | H | 1 | H | H | H | H | CHOCH₃ | H | H |
| 4.159 | CH₃ | CH₃ | H | 2 | H | H | H | H | CHOCH₃ | H | H |
| 4.160 | CH₃ | CH₃ | H | 0 | H | H | H | H | CHOC₂H₅ | H | H |
| 4.161 | CH₃ | CH₃ | H | 1 | H | H | H | H | CHOC₂H₅ | H | H |
| 4.162 | CH₃ | CH₃ | H | 2 | H | H | H | H | CHOC₂H₅ | H | H |
| 4.163 | CH₃ | CH₃ | H | 0 | H | H | H | H | CHOiPr | H | H |
| 4.164 | CH₃ | CH₃ | H | 1 | H | H | H | H | CHOiPr | H | H |
| 4.165 | CH₃ | CH₃ | H | 2 | H | H | H | H | CHOiPr | H | H |
| 4.166 | CH₃ | CH₃ | H | 0 | H | H | H | H | C=NOCH₃ | H | H |
| 4.167 | CH₃ | CH₃ | H | 1 | H | H | H | H | C=NOCH₃ | H | H |
| 4.168 | CH₃ | CH₃ | H | 2 | H | H | H | H | C=NOCH₃ | H | H |
| 4.169 | CH₃ | CH₃ | H | 0 | H | H | H | H | C=NOC₂H₅ | H | H |
| 4.170 | CH₃ | CH₃ | H | 1 | H | H | H | H | C=NOC₂H₅ | H | H |
| 4.171 | CH₃ | CH₃ | H | 2 | H | H | H | H | C=NOC₂H₅ | H | H |
| 4.172 | CH₃ | CH₃ | H | 0 | H | H | H | H | C=NOiPr | H | H |
| 4.173 | CH₃ | CH₃ | H | 1 | H | H | H | H | C=NOiPr | H | H |
| 4.174 | CH₃ | CH₃ | H | 2 | H | H | H | H | C=NOiPr | H | H |
| 4.175 | CH₃ | CH₃ | H | 0 | H | H | H | H | C=NOCH₂CH=CHCl | H | H |
| 4.176 | CH₃ | CH₃ | H | 1 | H | H | H | H | C=NOCH₂CH=CHCl | H | H |
| 4.177 | CH₃ | CH₃ | H | 2 | H | H | H | H | C=NOCH₂CH=CHCl | H | H |
| 4.178 | CH₃ | CH₃ | H | 0 | H | H | H | H | C=NOCH₂C₆H₅ | H | H |
| 4.179 | CH₃ | CH₃ | H | 1 | H | H | H | H | C=NOCH₂C₆H₅ | H | H |
| 4.180 | CH₃ | CH₃ | H | 2 | H | H | H | H | C=NOCH₂C₆H₅ | H | H |
| 4.181 | CH₃ | CH₃ | H | 0 | H | H | H | H | C(CH₃)₂ | H | H |
| 4.182 | CH₃ | CH₃ | H | 1 | H | H | H | H | C(CH₃)₂ | H | H |
| 4.183 | CH₃ | CH₃ | H | 2 | H | H | H | H | C(CH₃)₂ | H | H |
| 4.184 | CH₃ | CH₃ | H | 0 | H | H | H | H | 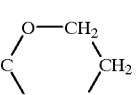 | H | H |
| 4.185 | CH₃ | CH₃ | H | 1 | H | H | H | H | 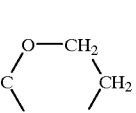 | H | H |
| 4.186 | CH₃ | CH₃ | H | 2 | H | H | H | H | 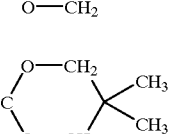 | H | H |
| 4.187 | CH₃ | CH₃ | H | 0 | H | H | H | H |  | H | H |

TABLE 4-continued

Compounds of the formula

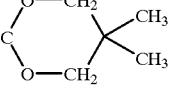

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.188 | $CH_3$ | $CH_3$ | H | 1 | H | H | H | H | 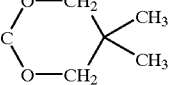 | H | H |
| 4.189 | $CH_3$ | $CH_3$ | H | 2 | H | H | H | H | (same dioxane group) | H | H |
| 4.190 | $CH_3$ | $CH_3$ | H | 0 | H | H | H | H | C=N—$CH_3$ | H | H |
| 4.191 | $CH_3$ | $CH_3$ | H | 1 | H | H | H | H | C=N—$CH_3$ | H | H |
| 4.192 | $CH_3$ | $CH_3$ | H | 2 | H | H | H | H | C=N—$CH_3$ | H | H |
| 4.193 | $CH_3$ | $CH_3$ | H | 0 | H | H | H | H | C=$NC_2H_5$ | H | H |
| 4.194 | $CH_3$ | $CH_3$ | H | 1 | H | H | H | H | C=$NC_2H_5$ | H | H |
| 4.195 | $CH_3$ | $CH_3$ | H | 2 | H | H | H | H | C=$NC_2H_5$ | H | H |
| 4.196 | $CH_3$ | $CH_3$ | H | 0 | H | H | H | H | CH—$NHCH_3$ | H | H |
| 4.197 | $CH_3$ | $CH_3$ | H | 1 | H | H | H | H | CH—$NHCH_3$ | H | H |
| 4.198 | $CH_3$ | $CH_3$ | H | 2 | H | H | H | H | CH—$NHCH_3$ | H | H |
| 4.199 | $CH_3$ | $CH_3$ | H | 0 | H | H | H | H | CH—$NHC_2H_5$ | H | H |
| 4.200 | $CH_3$ | $CH_3$ | H | 1 | H | H | H | H | CH—$NHC_2H_5$ | H | H |
| 4.201 | $CH_3$ | $CH_3$ | H | 2 | H | H | H | H | CH—$NHC_2H_5$ | H | H |
| 4.202 | $CH_3$ | $CH_3$ | H | 0 | H | H | H | H | CH—$N(CH_3)_2$ | H | H |
| 4.203 | $CH_3$ | $CH_3$ | H | 1 | H | H | H | H | CH—$N(CH_3)_2$ | H | H |
| 4.204 | $CH_3$ | $CH_3$ | H | 2 | H | H | H | H | CH—$N(CH_3)_2$ | H | H |
| 4.205 | $CH_3$ | $CH_3$ | H | 0 | H | H | H | H | CH—$NHOC_2H_5$ | H | H |
| 4.206 | $CH_3$ | $CH_3$ | H | 1 | H | H | H | H | CH—$NHOC_2H_5$ | H | H |
| 4.207 | $CH_3$ | $CH_3$ | H | 2 | H | H | H | H | CH—$NHOC_2H_5$ | H | H |
| 4.208 | $CH_3$ | $CH_3$ | H | 0 | H | H | H | H | CH—$N(CH_3)OC_2H_5$ | H | H |
| 4.209 | $CH_3$ | $CH_3$ | H | 1 | H | H | H | H | CH—$N(CH_3)OC_2H_5$ | H | H |
| 4.210 | $CH_3$ | $CH_3$ | H | 2 | H | H | H | H | CH—$N(CH_3)OC_2H_5$ | H | H |
| 4.211 | $CH_3$ | $CH_3$ | H | 0 | H | H | H | H | C=N—$NH_2$ | H | H |
| 4.212 | $CH_3$ | $CH_3$ | H | 1 | H | H | H | H | C=N—$NH_2$ | H | H |
| 4.213 | $CH_3$ | $CH_3$ | H | 2 | H | H | H | H | C=N—$NH_2$ | H | H |
| 4.214 | $CH_3$ | $CH_3$ | H | 0 | H | H | H | H | C=N—$N(CH_3)_2$ | H | H |
| 4.215 | $CH_3$ | $CH_3$ | H | 1 | H | H | H | H | C=N—$N(CH_3)_2$ | H | H |
| 4.216 | $CH_3$ | $CH_3$ | H | 2 | H | H | H | H | C=N—$N(CH_3)_2$ | H | H |
| 4.217 | $CH_3$ | $CH_3$ | H | 0 | H | H | H | H | CH—$N(CH_3)OCH_2C_6H_5$ | H | H |
| 4.218 | $CH_3$ | $CH_3$ | H | 1 | H | H | H | H | CH—$N(CH_3)OCH_2C_6H_5$ | H | H |
| 4.219 | $CH_3$ | $CH_3$ | H | 2 | H | H | H | H | CH—$N(CH_3)OCH_2C_6H_5$ | H | H |
| 4.220 | $CH_3$ | $CH_3$ | H | 0 | H | H | H | H | C($CH_3$)—$OCH_3$ | H | H |
| 4.221 | $CH_3$ | $CH_3$ | H | 1 | H | H | H | H | C($CH_3$)—$OCH_3$ | H | H |
| 4.222 | $CH_3$ | $CH_3$ | H | 2 | H | H | H | H | C($CH_3$)—$OCH_3$ | H | H |
| 4.223 | $CH_3$ | $CH_3$ | H | 0 | H | H | H | H | O | H | H |
| 4.224 | $CH_3$ | $CH_3$ | H | 1 | H | H | H | H | O | H | H |
| 4.225 | $CH_3$ | $CH_3$ | H | 2 | H | H | H | H | O | H | H |
| 4.226 | H | H | H | 0 | H | H | H | H | C=O | H | $CH_3$ |
| 4.227 | H | H | H | 1 | H | H | H | H | C=O | H | $CH_3$ |
| 4.228 | H | H | H | 2 | H | H | H | H | C=O | H | $CH_3$ |
| 4.229 | H | H | H | 0 | H | H | H | H | CHOH | H | $CH_3$ |
| 4.230 | H | H | H | 1 | H | H | H | H | CHOH | H | $CH_3$ |
| 4.231 | H | H | H | 2 | H | H | H | H | CHOH | H | $CH_3$ |
| 4.232 | H | H | H | 0 | H | H | H | H | $CHOCH_3$ | H | $CH_3$ |
| 4.233 | H | H | H | 1 | H | H | H | H | $CHOCH_3$ | H | $CH_3$ |
| 4.234 | H | H | H | 2 | H | H | H | H | $CHOCH_3$ | H | $CH_3$ |
| 4.235 | H | H | H | 0 | H | H | H | H | $CHOC_2H_5$ | H | $CH_3$ |
| 4.236 | H | H | H | 1 | H | H | H | H | $CHOC_2H_5$ | H | $CH_3$ |
| 4.237 | H | H | H | 2 | H | H | H | H | $CHOC_2H_5$ | H | $CH_3$ |
| 4.238 | H | H | H | 0 | H | H | H | H | CHOiPr | H | $CH_3$ |
| 4.239 | H | H | H | 1 | H | H | H | H | CHOiPr | H | $CH_3$ |
| 4.240 | H | H | H | 2 | H | H | H | H | CHOiPr | H | $CH_3$ |
| 4.241 | H | H | H | 0 | H | H | H | H | C=$NOCH_3$ | H | $CH_3$ |

TABLE 4-continued

Compounds of the formula

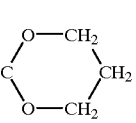

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.242 | H | H | H | 1 | H | H | H | H | C=NOCH$_3$ | H | CH$_3$ |
| 4.243 | H | H | H | 2 | H | H | H | H | C=NOCH$_3$ | H | CH$_3$ |
| 4.244 | H | H | H | 0 | H | H | H | H | C=NOC$_2$H$_5$ | H | CH$_3$ |
| 4.245 | H | H | H | 1 | H | H | H | H | C=NOC$_2$H$_5$ | H | CH$_3$ |
| 4.246 | H | H | H | 2 | H | H | H | H | C=NOC$_2$H$_5$ | H | CH$_3$ |
| 4.247 | H | H | H | 0 | H | H | H | H | C=NOiPr | H | CH$_3$ |
| 4.248 | H | H | H | 1 | H | H | H | H | C=NOiPr | H | CH$_3$ |
| 4.249 | H | H | H | 2 | H | H | H | H | C=NOiPr | H | CH$_3$ |
| 4.250 | H | H | H | 0 | H | H | H | H | C=NOCH$_2$CH=CHCl | H | CH$_3$ |
| 4.251 | H | H | H | 1 | H | H | H | H | C=NOCH$_2$CH=CHCl | H | CH$_3$ |
| 4.252 | H | H | H | 2 | H | H | H | H | C=NOCH$_2$CH=CHCl | H | CH$_3$ |
| 4.253 | H | H | H | 0 | H | H | H | H | C=NOCH$_2$C$_6$H$_5$ | H | CH$_3$ |
| 4.254 | H | H | H | 1 | H | H | H | H | C=NOCH$_2$C$_6$H$_5$ | H | CH$_3$ |
| 4.255 | H | H | H | 2 | H | H | H | H | C=NOCH$_2$C$_6$H$_5$ | H | CH$_3$ |
| 4.256 | H | H | H | 0 | H | H | H | H | C(CH$_3$)$_2$ | H | CH$_3$ |
| 4.257 | H | H | H | 1 | H | H | H | H | C(CH$_3$)$_2$ | H | CH$_3$ |
| 4.258 | H | H | H | 2 | H | H | H | H | C(CH$_3$)$_2$ | H | CH$_3$ |
| 4.259 | H | H | H | 0 | H | H | H | H | 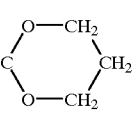 | H | CH$_3$ |
| 4.260 | H | H | H | 1 | H | H | H | H | 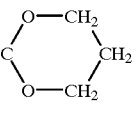 | H | CH$_3$ |
| 4.261 | H | H | H | 2 | H | H | H | H | 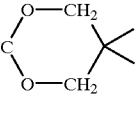 | H | CH$_3$ |
| 4.262 | H | H | H | 0 | H | H | H | H | 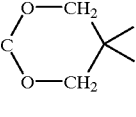 | H | CH$_3$ |
| 4.263 | H | H | H | 1 | H | H | H | H | 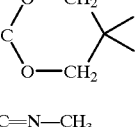 | H | CH$_3$ |
| 4.264 | H | H | H | 2 | H | H | H | H |  | H | CH$_3$ |
| 4.265 | H | H | H | 0 | H | H | H | H | C=N—CH$_3$ | H | CH$_3$ |
| 4.266 | H | H | H | 1 | H | H | H | H | C=N—CH$_3$ | H | CH$_3$ |
| 4.267 | H | H | H | 2 | H | H | H | H | C=N—CH$_3$ | H | CH$_3$ |
| 4.268 | H | H | H | 0 | H | H | H | H | C=NC$_2$H$_5$ | H | CH$_3$ |
| 4.269 | H | H | H | 1 | H | H | H | H | C=NC$_2$H$_5$ | H | CH$_3$ |
| 4.270 | H | H | H | 2 | H | H | H | H | C=NC$_2$H$_5$ | H | CH$_3$ |
| 4.271 | H | H | H | 0 | H | H | H | H | CH—NHCH$_3$ | H | CH$_3$ |
| 4.272 | H | H | H | 1 | H | H | H | H | CH—NHCH$_3$ | H | CH$_3$ |
| 4.273 | H | H | H | 2 | H | H | H | H | CH—NHCH$_3$ | H | CH$_3$ |
| 4.274 | H | H | H | 0 | H | H | H | H | CH—NHC$_2$H$_5$ | H | CH$_3$ |

TABLE 4-continued

Compounds of the formula

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.275 | H | H | H | 1 | H | H | H | H | CH—NHC$_2$H$_5$ | H | CH$_3$ |
| 4.276 | H | H | H | 2 | H | H | H | H | CH—NHC$_2$H$_5$ | H | CH$_3$ |
| 4.277 | H | H | H | 0 | H | H | H | H | CH—N(CH$_3$)$_2$ | H | CH$_3$ |
| 4.278 | H | H | H | 1 | H | H | H | H | CH—N(CH$_3$)$_2$ | H | CH$_3$ |
| 4.279 | H | H | H | 2 | H | H | H | H | CH—N(CH$_3$)$_2$ | H | CH$_3$ |
| 4.280 | H | H | H | 0 | H | H | H | H | CH—NHOC$_2$H$_5$ | H | CH$_3$ |
| 4.281 | H | H | H | 1 | H | H | H | H | CH—NHOC$_2$H$_5$ | H | CH$_3$ |
| 4.282 | H | H | H | 2 | H | H | H | H | CH—NHOC$_2$H$_5$ | H | CH$_3$ |
| 4.283 | H | H | H | 0 | H | H | H | H | CH—N(CH$_3$)OC$_2$H$_5$ | H | CH$_3$ |
| 4.284 | H | H | H | 1 | H | H | H | H | CH—N(CH$_3$)OC$_2$H$_5$ | H | CH$_3$ |
| 4.285 | H | H | H | 2 | H | H | H | H | CH—N(CH$_3$)OC$_2$H$_5$ | H | CH$_3$ |
| 4.286 | H | H | H | 0 | H | H | H | H | C=N—NH$_2$ | H | CH$_3$ |
| 4.287 | H | H | H | 1 | H | H | H | H | C=N—NH$_2$ | H | CH$_3$ |
| 4.288 | H | H | H | 2 | H | H | H | H | C=N—NH$_2$ | H | CH$_3$ |
| 4.289 | H | H | H | 0 | H | H | H | H | C=N—N(CH$_3$)$_2$ | H | CH$_3$ |
| 4.290 | H | H | H | 1 | H | H | H | H | C=N—N(CH$_3$)$_2$ | H | CH$_3$ |
| 4.291 | H | H | H | 2 | H | H | H | H | C=N—N(CH$_3$)$_2$ | H | CH$_3$ |
| 4.292 | H | H | H | 0 | H | H | H | H | CH—N(CH$_3$)OCH$_2$C$_6$H$_5$ | H | CH$_3$ |
| 4.293 | H | H | H | 1 | H | H | H | H | CH—N(CH$_3$)OCH$_2$C$_6$H$_5$ | H | CH$_3$ |
| 4.294 | H | H | H | 2 | H | H | H | H | CH—N(CH$_3$)OCH$_2$C$_6$H$_5$ | H | CH$_3$ |
| 4.295 | H | H | H | 0 | H | H | H | H | C(CH$_3$)—OCH$_3$ | H | CH$_3$ |
| 4.296 | H | H | H | 1 | H | H | H | H | C(CH$_3$)—OCH$_3$ | H | CH$_3$ |
| 4.297 | H | H | H | 2 | H | H | H | H | C(CH$_3$)—OCH$_3$ | H | CH$_3$ |
| 4.298 | H | H | H | 0 | H | H | H | H | O | H | CH$_3$ |
| 4.299 | H | H | H | 1 | H | H | H | H | O | H | CH$_3$ |
| 4.300 | H | H | H | 2 | H | H | H | H | O | H | CH$_3$ |
| 4.301 | CH$_3$ | H | H | 0 | H | H | H | H | C=O | H | CH$_3$ |
| 4.302 | CH$_3$ | H | H | 1 | H | H | H | H | C=O | H | CH$_3$ |
| 4.303 | CH$_3$ | H | H | 2 | H | H | H | H | C=O | H | CH$_3$ |
| 4.304 | CH$_3$ | H | H | 0 | H | H | H | H | CHOH | H | CH$_3$ |
| 4.305 | CH$_3$ | H | H | 1 | H | H | H | H | CHOH | H | CH$_3$ |
| 4.306 | CH$_3$ | H | H | 2 | H | H | H | H | CHOH | H | CH$_3$ |
| 4.307 | CH$_3$ | H | H | 0 | H | H | H | H | CHOCH$_3$ | H | CH$_3$ |
| 4.308 | CH$_3$ | H | H | 1 | H | H | H | H | CHOCH$_3$ | H | CH$_3$ |
| 4.309 | CH$_3$ | H | H | 2 | H | H | H | H | CHOCH$_3$ | H | CH$_3$ |
| 4.310 | CH$_3$ | H | H | 0 | H | H | H | H | CHOC$_2$H$_5$ | H | CH$_3$ |
| 4.311 | CH$_3$ | H | H | 1 | H | H | H | H | CHOC$_2$H$_5$ | H | CH$_3$ |
| 4.312 | CH$_3$ | H | H | 2 | H | H | H | H | CHOC$_2$H$_5$ | H | CH$_3$ |
| 4.313 | CH$_3$ | H | H | 0 | H | H | H | H | CHOiPr | H | CH$_3$ |
| 4.314 | CH$_3$ | H | H | 1 | H | H | H | H | CHOiPr | H | CH$_3$ |
| 4.315 | CH$_3$ | H | H | 2 | H | H | H | H | CHOiPr | H | CH$_3$ |
| 4.316 | CH$_3$ | H | H | 0 | H | H | H | H | C=NOCH$_3$ | H | CH$_3$ |
| 4.317 | CH$_3$ | H | H | 1 | H | H | H | H | C=NOCH$_3$ | H | CH$_3$ |
| 4.318 | CH$_3$ | H | H | 2 | H | H | H | H | C=NOCH$_3$ | H | CH$_3$ |
| 4.319 | CH$_3$ | H | H | 0 | H | H | H | H | C=NOC$_2$H$_5$ | H | CH$_3$ |
| 4.320 | CH$_3$ | H | H | 1 | H | H | H | H | C=NOC$_2$H$_5$ | H | CH$_3$ |
| 4.321 | CH$_3$ | H | H | 2 | H | H | H | H | C=NOC$_2$H$_5$ | H | CH$_3$ |
| 4.322 | CH$_3$ | H | H | 0 | H | H | H | H | C=NOiPr | H | CH$_3$ |
| 4.323 | CH$_3$ | H | H | 1 | H | H | H | H | C=NOiPr | H | CH$_3$ |
| 4.324 | CH$_3$ | H | H | 2 | H | H | H | H | C=NOiPr | H | CH$_3$ |
| 4.325 | CH$_3$ | H | H | 0 | H | H | H | H | C=NOCH$_2$CH=CHCl | H | CH$_3$ |
| 4.326 | CH$_3$ | H | H | 1 | H | H | H | H | C=NOCH$_2$CH=CHCl | H | CH$_3$ |
| 4.327 | CH$_3$ | H | H | 2 | H | H | H | H | C=NOCH$_2$CH=CHCl | H | CH$_3$ |
| 4.328 | CH$_3$ | H | H | 0 | H | H | H | H | C=NOCH$_2$C$_6$H$_5$ | H | CH$_3$ |
| 4.329 | CH$_3$ | H | H | 1 | H | H | H | H | C=NOCH$_2$C$_6$H$_5$ | H | CH$_3$ |
| 4.330 | CH$_3$ | H | H | 2 | H | H | H | H | C=NOCH$_2$C$_6$H$_5$ | H | CH$_3$ |
| 4.331 | CH$_3$ | H | H | 0 | H | H | H | H | C(CH$_3$)$_2$ | H | CH$_3$ |
| 4.332 | CH$_3$ | H | H | 1 | H | H | H | H | C(CH$_3$)$_2$ | H | CH$_3$ |
| 4.333 | CH$_3$ | H | H | 2 | H | H | H | H | C(CH$_3$)$_2$ | H | CH$_3$ |

TABLE 4-continued

Compounds of the formula

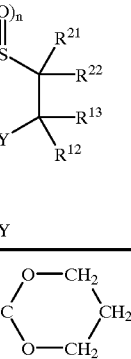

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.334 | CH$_3$ | H | H | 0 | H | H | H | H | 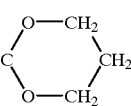 | H | CH$_3$ |
| 4.335 | CH$_3$ | H | H | 1 | H | H | H | H | 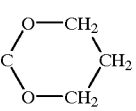 | H | CH$_3$ |
| 4.336 | CH$_3$ | H | H | 2 | H | H | H | H | 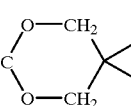 | H | CH$_3$ |
| 4.337 | CH$_3$ | H | H | 0 | H | H | H | H | 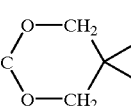 | H | CH$_3$ |
| 4.338 | CH$_3$ | H | H | 1 | H | H | H | H | 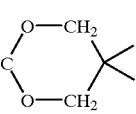 | H | CH$_3$ |
| 4.339 | CH$_3$ | H | H | 2 | H | H | H | H |  | H | CH$_3$ |
| 4.340 | CH$_3$ | H | H | 0 | H | H | H | H | C=N—CH$_3$ | H | CH$_3$ |
| 4.341 | CH$_3$ | H | H | 1 | H | H | H | H | C=N—CH$_3$ | H | CH$_3$ |
| 4.342 | CH$_3$ | H | H | 2 | H | H | H | H | C=N—CH$_3$ | H | CH$_3$ |
| 4.343 | CH$_3$ | H | H | 0 | H | H | H | H | C=NC$_2$H$_5$ | H | CH$_3$ |
| 4.344 | CH$_3$ | H | H | 1 | H | H | H | H | C=NC$_2$H$_5$ | H | CH$_3$ |
| 4.345 | CH$_3$ | H | H | 2 | H | H | H | H | C=NC$_2$H$_5$ | H | CH$_3$ |
| 4.346 | CH$_3$ | H | H | 0 | H | H | H | H | CH—NHCH$_3$ | H | CH$_3$ |
| 4.347 | CH$_3$ | H | H | 1 | H | H | H | H | CH—NHCH$_3$ | H | CH$_3$ |
| 4.348 | CH$_3$ | H | H | 2 | H | H | H | H | CH—NHCH$_3$ | H | CH$_3$ |
| 4.349 | CH$_3$ | H | H | 0 | H | H | H | H | CH—NHC$_2$H$_5$ | H | CH$_3$ |
| 4.350 | CH$_3$ | H | H | 1 | H | H | H | H | CH—NHC$_2$H$_5$ | H | CH$_3$ |
| 4.351 | CH$_3$ | H | H | 2 | H | H | H | H | CH—NHC$_2$H$_5$ | H | CH$_3$ |
| 4.352 | CH$_3$ | H | H | 0 | H | H | H | H | CH—N(CH$_3$)$_2$ | H | CH$_3$ |
| 4.353 | CH$_3$ | H | H | 1 | H | H | H | H | CH—N(CH$_3$)$_2$ | H | CH$_3$ |
| 4.354 | CH$_3$ | H | H | 2 | H | H | H | H | CH—N(CH$_3$)$_2$ | H | CH$_3$ |
| 4.355 | CH$_3$ | H | H | 0 | H | H | H | H | CH—NHOC$_2$H$_5$ | H | CH$_3$ |
| 4.356 | CH$_3$ | H | H | 1 | H | H | H | H | CH—NHOC$_2$H$_5$ | H | CH$_3$ |
| 4.357 | CH$_3$ | H | H | 2 | H | H | H | H | CH—NHOC$_2$H$_5$ | H | CH$_3$ |
| 4.358 | CH$_3$ | H | H | 0 | H | H | H | H | CH—N(CH$_3$)OC$_2$H$_5$ | H | CH$_3$ |
| 4.359 | CH$_3$ | H | H | 1 | H | H | H | H | CH—N(CH$_3$)OC$_2$H$_5$ | H | CH$_3$ |
| 4.360 | CH$_3$ | H | H | 2 | H | H | H | H | CH—N(CH$_3$)OC$_2$H$_5$ | H | CH$_3$ |
| 4.361 | CH$_3$ | H | H | 0 | H | H | H | H | C=N—NH$_2$ | H | CH$_3$ |
| 4.362 | CH$_3$ | H | H | 1 | H | H | H | H | C=N—NH$_2$ | H | CH$_3$ |
| 4.363 | CH$_3$ | H | H | 2 | H | H | H | H | C=N—NH$_2$ | H | CH$_3$ |
| 4.364 | CH$_3$ | H | H | 0 | H | H | H | H | C=N—N(CH$_3$)$_2$ | H | CH$_3$ |
| 4.365 | CH$_3$ | H | H | 1 | H | H | H | H | C=N—N(CH$_3$)$_2$ | H | CH$_3$ |
| 4.366 | CH$_3$ | H | H | 2 | H | H | H | H | C=N—N(CH$_3$)$_2$ | H | CH$_3$ |
| 4.367 | CH$_3$ | H | H | 0 | H | H | H | H | CH—N(CH$_3$)OCH$_2$C$_6$H$_5$ | H | CH$_3$ |

TABLE 4-continued

Compounds of the formula

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.368 | $CH_3$ | H | H | 1 | H | H | H | H | CH—N($CH_3$)$OCH_2C_6H_5$ | H | $CH_3$ |
| 4.369 | $CH_3$ | H | H | 2 | H | H | H | H | CH—N($CH_3$)$OCH_2C_6H_5$ | H | $CH_3$ |
| 4.370 | $CH_3$ | H | H | 0 | H | H | H | H | C($CH_3$)—$OCH_3$ | H | $CH_3$ |
| 4.371 | $CH_3$ | H | H | 1 | H | H | H | H | C($CH_3$)—$OCH_3$ | H | $CH_3$ |
| 4.372 | $CH_3$ | H | H | 2 | H | H | H | H | C($CH_3$)—$OCH_3$ | H | $CH_3$ |
| 4.373 | $CH_3$ | H | H | 0 | H | H | H | H | O | H | $CH_3$ |
| 4.374 | $CH_3$ | H | H | 1 | H | H | H | H | O | H | $CH_3$ |
| 4.375 | $CH_3$ | H | H | 2 | H | H | H | H | O | H | $CH_3$ |
| 4.376 | $CH_3$ | $CH_3$ | H | 0 | H | H | H | H | C=O | H | $CH_3$ |
| 4.377 | $CH_3$ | $CH_3$ | H | 1 | H | H | H | H | C=O | H | $CH_3$ |
| 4.378 | $CH_3$ | $CH_3$ | H | 2 | H | H | H | H | C=O | H | $CH_3$ |
| 4.379 | $CH_3$ | $CH_3$ | H | 0 | H | H | H | H | CHOH | H | $CH_3$ |
| 4.380 | $CH_3$ | $CH_3$ | H | 1 | H | H | H | H | CHOH | H | $CH_3$ |
| 4.381 | $CH_3$ | $CH_3$ | H | 2 | H | H | H | H | CHOH | H | $CH_3$ |
| 4.382 | $CH_3$ | $CH_3$ | H | 0 | H | H | H | H | $CHOCH_3$ | H | $CH_3$ |
| 4.383 | $CH_3$ | $CH_3$ | H | 1 | H | H | H | H | $CHOCH_3$ | H | $CH_3$ |
| 4.384 | $CH_3$ | $CH_3$ | H | 2 | H | H | H | H | $CHOCH_3$ | H | $CH_3$ |
| 4.385 | $CH_3$ | $CH_3$ | H | 0 | H | H | H | H | $CHOC_2H_5$ | H | $CH_3$ |
| 4.386 | $CH_3$ | $CH_3$ | H | 1 | H | H | H | H | $CHOC_2H_5$ | H | $CH_3$ |
| 4.387 | $CH_3$ | $CH_3$ | H | 2 | H | H | H | H | $CHOC_2H_5$ | H | $CH_3$ |
| 4.388 | $CH_3$ | $CH_3$ | H | 0 | H | H | H | H | CHOiPr | H | $CH_3$ |
| 4.389 | $CH_3$ | $CH_3$ | H | 1 | H | H | H | H | CHOiPr | H | $CH_3$ |
| 4.390 | $CH_3$ | $CH_3$ | H | 2 | H | H | H | H | CHOiPr | H | $CH_3$ |
| 4.391 | $CH_3$ | $CH_3$ | H | 0 | H | H | H | H | C=$NOCH_3$ | H | $CH_3$ |
| 4.392 | $CH_3$ | $CH_3$ | H | 1 | H | H | H | H | C=$NOCH_3$ | H | $CH_3$ |
| 4.393 | $CH_3$ | $CH_3$ | H | 2 | H | H | H | H | C=$NOCH_3$ | H | $CH_3$ |
| 4.394 | $CH_3$ | $CH_3$ | H | 0 | H | H | H | H | C=$NOC_2H_5$ | H | $CH_3$ |
| 4.395 | $CH_3$ | $CH_3$ | H | 1 | H | H | H | H | C=$NOC_2H_5$ | H | $CH_3$ |
| 4.396 | $CH_3$ | $CH_3$ | H | 2 | H | H | H | H | C=$NOC_2H_5$ | H | $CH_3$ |
| 4.397 | $CH_3$ | $CH_3$ | H | 0 | H | H | H | H | C=NOiPr | H | $CH_3$ |
| 4.398 | $CH_3$ | $CH_3$ | H | 1 | H | H | H | H | C=NOiPr | H | $CH_3$ |
| 4.399 | $CH_3$ | $CH_3$ | H | 2 | H | H | H | H | C=NOiPr | H | $CH_3$ |
| 4.400 | $CH_3$ | $CH_3$ | H | 0 | H | H | H | H | C=$NOCH_2$CH=CHCl | H | $CH_3$ |
| 4.401 | $CH_3$ | $CH_3$ | H | 1 | H | H | H | H | C=$NOCH_2$CH=CHCl | H | $CH_3$ |
| 4.402 | $CH_3$ | $CH_3$ | H | 2 | H | H | H | H | C=$NOCH_2$CH=CHCl | H | $CH_3$ |
| 4.403 | $CH_3$ | $CH_3$ | H | 0 | H | H | H | H | C=$NOCH_2C_6H_5$ | H | $CH_3$ |
| 4.404 | $CH_3$ | $CH_3$ | H | 1 | H | H | H | H | C=$NOCH_2C_6H_5$ | H | $CH_3$ |
| 4.405 | $CH_3$ | $CH_3$ | H | 2 | H | H | H | H | C=$NOCH_2C_6H_5$ | H | $CH_3$ |
| 4.406 | $CH_3$ | $CH_3$ | H | 0 | H | H | H | H | C($CH_3$)$_2$ | H | $CH_3$ |
| 4.407 | $CH_3$ | $CH_3$ | H | 1 | H | H | H | H | C($CH_3$)$_2$ | H | $CH_3$ |
| 4.408 | $CH_3$ | $CH_3$ | H | 2 | H | H | H | H | C($CH_3$)$_2$ | H | $CH_3$ |
| 4.409 | $CH_3$ | $CH_3$ | H | 0 | H | H | H | H | 1,3-dioxane-2-yl | H | $CH_3$ |
| 4.410 | $CH_3$ | $CH_3$ | H | 1 | H | H | H | H | 1,3-dioxane-2-yl | H | $CH_3$ |
| 4.411 | $CH_3$ | $CH_3$ | H | 2 | H | H | H | H | 1,3-dioxane-2-yl | H | $CH_3$ |

TABLE 4-continued

Compounds of the formula

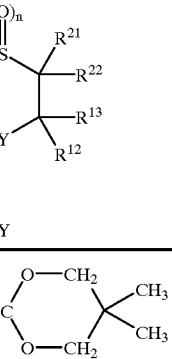

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.412 | $CH_3$ | $CH_3$ | H | 0 | H | H | H | H | 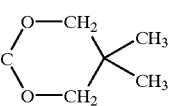 | H | $CH_3$ |
| 4.413 | $CH_3$ | $CH_3$ | H | 1 | H | H | H | H | 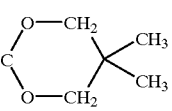 | H | $CH_3$ |
| 4.414 | $CH_3$ | $CH_3$ | H | 2 | H | H | H | H | (same as above) | H | $CH_3$ |
| 4.415 | $CH_3$ | $CH_3$ | H | 0 | H | H | H | H | C=N—$CH_3$ | H | $CH_3$ |
| 4.416 | $CH_3$ | $CH_3$ | H | 1 | H | H | H | H | C=N—$CH_3$ | H | $CH_3$ |
| 4.417 | $CH_3$ | $CH_3$ | H | 2 | H | H | H | H | C=N—$CH_3$ | H | $CH_3$ |
| 4.418 | $CH_3$ | $CH_3$ | H | 0 | H | H | H | H | C=N$C_2H_5$ | H | $CH_3$ |
| 4.419 | $CH_3$ | $CH_3$ | H | 1 | H | H | H | H | C=N$C_2H_5$ | H | $CH_3$ |
| 4.420 | $CH_3$ | $CH_3$ | H | 2 | H | H | H | H | C=N$C_2H_5$ | H | $CH_3$ |
| 4.421 | $CH_3$ | $CH_3$ | H | 0 | H | H | H | H | CH—$NHCH_3$ | H | $CH_3$ |
| 4.422 | $CH_3$ | $CH_3$ | H | 1 | H | H | H | H | CH—$NHCH_3$ | H | $CH_3$ |
| 4.423 | $CH_3$ | $CH_3$ | H | 2 | H | H | H | H | CH—$NHCH_3$ | H | $CH_3$ |
| 4.424 | $CH_3$ | $CH_3$ | H | 0 | H | H | H | H | CH—$NHC_2H_5$ | H | $CH_3$ |
| 4.425 | $CH_3$ | $CH_3$ | H | 1 | H | H | H | H | CH—$NHC_2H_5$ | H | $CH_3$ |
| 4.426 | $CH_3$ | $CH_3$ | H | 2 | H | H | H | H | CH—$NHC_2H_5$ | H | $CH_3$ |
| 4.427 | $CH_3$ | $CH_3$ | H | 0 | H | H | H | H | CH—$N(CH_3)_2$ | H | $CH_3$ |
| 4.428 | $CH_3$ | $CH_3$ | H | 1 | H | H | H | H | CH—$N(CH_3)_2$ | H | $CH_3$ |
| 4.429 | $CH_3$ | $CH_3$ | H | 2 | H | H | H | H | CH—$N(CH_3)_2$ | H | $CH_3$ |
| 4.430 | $CH_3$ | $CH_3$ | H | 0 | H | H | H | H | CH—$NHOC_2H_5$ | H | $CH_3$ |
| 4.431 | $CH_3$ | $CH_3$ | H | 1 | H | H | H | H | CH—$NHOC_2H_5$ | H | $CH_3$ |
| 4.432 | $CH_3$ | $CH_3$ | H | 2 | H | H | H | H | CH—$NHOC_2H_5$ | H | $CH_3$ |
| 4.433 | $CH_3$ | $CH_3$ | H | 0 | H | H | H | H | CH—$N(CH_3)OC_2H_5$ | H | $CH_3$ |
| 4.434 | $CH_3$ | $CH_3$ | H | 1 | H | H | H | H | CH—$N(CH_3)OC_2H_5$ | H | $CH_3$ |
| 4.435 | $CH_3$ | $CH_3$ | H | 2 | H | H | H | H | CH—$N(CH_3)OC_2H_5$ | H | $CH_3$ |
| 4.436 | $CH_3$ | $CH_3$ | H | 0 | H | H | H | H | C=N—$NH_2$ | H | $CH_3$ |
| 4.437 | $CH_3$ | $CH_3$ | H | 1 | H | H | H | H | C=N—$NH_2$ | H | $CH_3$ |
| 4.438 | $CH_3$ | $CH_3$ | H | 2 | H | H | H | H | C=N—$NH_2$ | H | $CH_3$ |
| 4.439 | $CH_3$ | $CH_3$ | H | 0 | H | H | H | H | C=N—$N(CH_3)_2$ | H | $CH_3$ |
| 4.440 | $CH_3$ | $CH_3$ | H | 1 | H | H | H | H | C=N—$N(CH_3)_2$ | H | $CH_3$ |
| 4.441 | $CH_3$ | $CH_3$ | H | 2 | H | H | H | H | C=N—$N(CH_3)_2$ | H | $CH_3$ |
| 4.442 | $CH_3$ | $CH_3$ | H | 0 | H | H | H | H | CH—$N(CH_3)OCH_2C_6H_5$ | H | $CH_3$ |
| 4.443 | $CH_3$ | $CH_3$ | H | 1 | H | H | H | H | CH—$N(CH_3)OCH_2C_6H_5$ | H | $CH_3$ |
| 4.444 | $CH_3$ | $CH_3$ | H | 2 | H | H | H | H | CH—$N(CH_3)OCH_2C_6H_5$ | H | $CH_3$ |
| 4.445 | $CH_3$ | $CH_3$ | H | 0 | H | H | H | H | $C(CH_3)$—$OCH_3$ | H | $CH_3$ |
| 4.446 | $CH_3$ | $CH_3$ | H | 1 | H | H | H | H | $C(CH_3)$—$OCH_3$ | H | $CH_3$ |
| 4.447 | $CH_3$ | $CH_3$ | H | 2 | H | H | H | H | $C(CH_3)$—$OCH_3$ | H | $CH_3$ |
| 4.448 | $CH_3$ | $CH_3$ | H | 0 | H | H | H | H | O | H | $CH_3$ |
| 4.449 | $CH_3$ | $CH_3$ | H | 1 | H | H | H | H | O | H | $CH_3$ |
| 4.450 | $CH_3$ | $CH_3$ | H | 2 | H | H | H | H | O | H | $CH_3$ |
| 4.451 | H | H | H | 0 | H | H | H | H | C=O | H | Cl |
| 4.452 | H | H | H | 1 | H | H | H | H | C=O | H | Cl |
| 4.453 | H | H | H | 2 | H | H | H | H | C=O | H | Cl |
| 4.454 | H | H | H | 0 | H | H | H | H | CHOH | H | Cl |
| 4.455 | H | H | H | 1 | H | H | H | H | CHOH | H | Cl |
| 4.456 | H | H | H | 2 | H | H | H | H | CHOH | H | Cl |
| 4.457 | H | H | H | 0 | H | H | H | H | $CHOCH_3$ | H | Cl |
| 4.458 | H | H | H | 1 | H | H | H | H | $CHOCH_3$ | H | Cl |
| 4.459 | H | H | H | 2 | H | H | H | H | $CHOCH_3$ | H | Cl |
| 4.460 | H | H | H | 0 | H | H | H | H | $CHOC_2H_5$ | H | Cl |

TABLE 4-continued

Compounds of the formula

[Structure: cyclohexanedione-hydroxy-ketone connected to benzene ring bearing M, L substituents fused with S(O)n-R21,R22-R13,R12-Y containing thiazine-type ring; cyclohexane bears R17, R18, R19]

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.461 | H | H | H | 1 | H | H | H | H | $CHOC_2H_5$ | H | Cl |
| 4.462 | H | H | H | 2 | H | H | H | H | $CHOC_2H_5$ | H | Cl |
| 4.463 | H | H | H | 0 | H | H | H | H | CHOiPr | H | Cl |
| 4.464 | H | H | H | 1 | H | H | H | H | CHOiPr | H | Cl |
| 4.465 | H | H | H | 2 | H | H | H | H | CHOiPr | H | Cl |
| 4.466 | H | H | H | 0 | H | H | H | H | $C=NOCH_3$ | H | Cl |
| 4.467 | H | H | H | 1 | H | H | H | H | $C=NOCH_3$ | H | Cl |
| 4.468 | H | H | H | 2 | H | H | H | H | $C=NOCH_3$ | H | Cl |
| 4.469 | H | H | H | 0 | H | H | H | H | $C=NOC_2H_5$ | H | Cl |
| 4.470 | H | H | H | 1 | H | H | H | H | $C=NOC_2H_5$ | H | Cl |
| 4.471 | H | H | H | 2 | H | H | H | H | $C=NOC_2H_5$ | H | Cl |
| 4.472 | H | H | H | 0 | H | H | H | H | C=NOiPr | H | Cl |
| 4.473 | H | H | H | 1 | H | H | H | H | C=NOiPr | H | Cl |
| 4.474 | H | H | H | 2 | H | H | H | H | C=NOiPr | H | Cl |
| 4.475 | H | H | H | 0 | H | H | H | H | $C=NOCH_2CH=CHCl$ | H | Cl |
| 4.476 | H | H | H | 1 | H | H | H | H | $C=NOCH_2CH=CHCl$ | H | Cl |
| 4.477 | H | H | H | 2 | H | H | H | H | $C=NOCH_2CH=CHCl$ | H | Cl |
| 4.478 | H | H | H | 0 | H | H | H | H | $C=NOCH_2C_6H_5$ | H | Cl |
| 4.479 | H | H | H | 1 | H | H | H | H | $C=NOCH_2C_6H_5$ | H | Cl |
| 4.480 | H | H | H | 2 | H | H | H | H | $C=NOCH_2C_6H_5$ | H | Cl |
| 4.481 | H | H | H | 0 | H | H | H | H | $C(CH_3)_2$ | H | Cl |
| 4.482 | H | H | H | 1 | H | H | H | H | $C(CH_3)_2$ | H | Cl |
| 4.483 | H | H | H | 2 | H | H | H | H | $C(CH_3)_2$ | H | Cl |
| 4.484 | H | H | H | 0 | H | H | H | H | [1,3-dioxane spiro, C(OCH₂CH₂OCH₂)] | H | Cl |
| 4.485 | H | H | H | 1 | H | H | H | H | [1,3-dioxane spiro, C(OCH₂CH₂OCH₂)] | H | Cl |
| 4.486 | H | H | H | 2 | H | H | H | H | [1,3-dioxane spiro, C(OCH₂CH₂OCH₂)] | H | Cl |
| 4.487 | H | H | H | 0 | H | H | H | H | [dimethyl-1,3-dioxane spiro, C(OCH₂C(CH₃)₂CH₂O)] | H | Cl |
| 4.488 | H | H | H | 1 | H | H | H | H | [dimethyl-1,3-dioxane spiro, C(OCH₂C(CH₃)₂CH₂O)] | H | Cl |
| 4.489 | H | H | H | 2 | H | H | H | H | [dimethyl-1,3-dioxane spiro, C(OCH₂C(CH₃)₂CH₂O)] | H | Cl |
| 4.490 | H | H | H | 0 | H | H | H | H | $C=N-CH_3$ | H | Cl |
| 4.491 | H | H | H | 1 | H | H | H | H | $C=N-CH_3$ | H | Cl |
| 4.492 | H | H | H | 2 | H | H | H | H | $C=N-CH_3$ | H | Cl |
| 4.493 | H | H | H | 0 | H | H | H | H | $C=NC_2H_5$ | H | Cl |

TABLE 4-continued

Compounds of the formula

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.494 | H | H | H | 1 | H | H | H | H | C=NC$_2$H$_5$ | H | Cl |
| 4.495 | H | H | H | 2 | H | H | H | H | C=NC$_2$H$_5$ | H | Cl |
| 4.496 | H | H | H | 0 | H | H | H | H | CH—NHCH$_3$ | H | Cl |
| 4.497 | H | H | H | 1 | H | H | H | H | CH—NHCH$_3$ | H | Cl |
| 4.498 | H | H | H | 2 | H | H | H | H | CH—NHCH$_3$ | H | Cl |
| 4.499 | H | H | H | 0 | H | H | H | H | CH—NHC$_2$H$_5$ | H | Cl |
| 4.500 | H | H | H | 1 | H | H | H | H | CH—NHC$_2$H$_5$ | H | Cl |
| 4.501 | H | H | H | 2 | H | H | H | H | CH—NHC$_2$H$_5$ | H | Cl |
| 4.502 | H | H | H | 0 | H | H | H | H | CH—N(CH$_3$)$_2$ | H | Cl |
| 4.503 | H | H | H | 1 | H | H | H | H | CH—N(CH$_3$)$_2$ | H | Cl |
| 4.504 | H | H | H | 2 | H | H | H | H | CH—N(CH$_3$)$_2$ | H | Cl |
| 4.505 | H | H | H | 0 | H | H | H | H | CH—NHOC$_2$H$_5$ | H | Cl |
| 4.506 | H | H | H | 1 | H | H | H | H | CH—NHOC$_2$H$_5$ | H | Cl |
| 4.507 | H | H | H | 2 | H | H | H | H | CH—NHOC$_2$H$_5$ | H | Cl |
| 4.508 | H | H | H | 0 | H | H | H | H | CH—N(CH$_3$)OC$_2$H$_5$ | H | Cl |
| 4.509 | H | H | H | 1 | H | H | H | H | CH—N(CH$_3$)OC$_2$H$_5$ | H | Cl |
| 4.510 | H | H | H | 2 | H | H | H | H | CH—N(CH$_3$)OC$_2$H$_5$ | H | Cl |
| 4.511 | H | H | H | 0 | H | H | H | H | C=N—NH$_2$ | H | Cl |
| 4.512 | H | H | H | 1 | H | H | H | H | C=N—NH$_2$ | H | Cl |
| 4.513 | H | H | H | 2 | H | H | H | H | C=N—NH$_2$ | H | Cl |
| 4.514 | H | H | H | 0 | H | H | H | H | C=N—N(CH$_3$)$_2$ | H | Cl |
| 4.515 | H | H | H | 1 | H | H | H | H | C=N—N(CH$_3$)$_2$ | H | Cl |
| 4.516 | H | H | H | 2 | H | H | H | H | C=N—N(CH$_3$)$_2$ | H | Cl |
| 4.517 | H | H | H | 0 | H | H | H | H | CH—N(CH$_3$)OCH$_2$C$_6$H$_5$ | H | Cl |
| 4.518 | H | H | H | 1 | H | H | H | H | CH—N(CH$_3$)OCH$_2$C$_6$H$_5$ | H | Cl |
| 4.519 | H | H | H | 2 | H | H | H | H | CH—N(CH$_3$)OCH$_2$C$_6$H$_5$ | H | Cl |
| 4.520 | H | H | H | 0 | H | H | H | H | C(CH$_3$)—OCH$_3$ | H | Cl |
| 4.521 | H | H | H | 1 | H | H | H | H | C(CH$_3$)—OCH$_3$ | H | Cl |
| 4.522 | H | H | H | 2 | H | H | H | H | C(CH$_3$)—OCH$_3$ | H | Cl |
| 4.523 | H | H | H | 0 | H | H | H | H | O | H | Cl |
| 4.524 | H | H | H | 1 | H | H | H | H | O | H | Cl |
| 4.525 | H | H | H | 2 | H | H | H | H | O | H | Cl |
| 4.526 | CH$_3$ | H | H | 0 | H | H | H | H | C=O | H | Cl |
| 4.527 | CH$_3$ | H | H | 1 | H | H | H | H | C=O | H | Cl |
| 4.528 | CH$_3$ | H | H | 2 | H | H | H | H | C=O | H | Cl |
| 4.529 | CH$_3$ | H | H | 0 | H | H | H | H | CHOH | H | Cl |
| 4.530 | CH$_3$ | H | H | 1 | H | H | H | H | CHOH | H | Cl |
| 4.531 | CH$_3$ | H | H | 2 | H | H | H | H | CHOH | H | Cl |
| 4.532 | CH$_3$ | H | H | 0 | H | H | H | H | CHOCH$_3$ | H | Cl |
| 4.533 | CH$_3$ | H | H | 1 | H | H | H | H | CHOCH$_3$ | H | Cl |
| 4.534 | CH$_3$ | H | H | 2 | H | H | H | H | CHOCH$_3$ | H | Cl |
| 4.535 | CH$_3$ | H | H | 0 | H | H | H | H | CHOC$_2$H$_5$ | H | Cl |
| 4.536 | CH$_3$ | H | H | 1 | H | H | H | H | CHOC$_2$H$_5$ | H | Cl |
| 4.537 | CH$_3$ | H | H | 2 | H | H | H | H | CHOC$_2$H$_5$ | H | Cl |
| 4.538 | CH$_3$ | H | H | 0 | H | H | H | H | CHOiPr | H | Cl |
| 4.539 | CH$_3$ | H | H | 1 | H | H | H | H | CHOiPr | H | Cl |
| 4.540 | CH$_3$ | H | H | 2 | H | H | H | H | CHOiPr | H | Cl |
| 4.541 | CH$_3$ | H | H | 0 | H | H | H | H | C=NOCH$_3$ | H | Cl |
| 4.542 | CH$_3$ | H | H | 1 | H | H | H | H | C=NOCH$_3$ | H | Cl |
| 4.543 | CH$_3$ | H | H | 2 | H | H | H | H | C=NOCH$_3$ | H | Cl |
| 4.544 | CH$_3$ | H | H | 0 | H | H | H | H | C=NOC$_2$H$_5$ | H | Cl |
| 4.545 | CH$_3$ | H | H | 1 | H | H | H | H | C=NOC$_2$H$_5$ | H | Cl |
| 4.546 | CH$_3$ | H | H | 2 | H | H | H | H | C=NOC$_2$H$_5$ | H | Cl |
| 4.547 | CH$_3$ | H | H | 0 | H | H | H | H | C=NOiPr | H | Cl |
| 4.548 | CH$_3$ | H | H | 1 | H | H | H | H | C=NOiPr | H | Cl |
| 4.549 | CH$_3$ | H | H | 2 | H | H | H | H | C=NOiPr | H | Cl |
| 4.550 | CH$_3$ | H | H | 0 | H | H | H | H | C=NOCH$_2$CH=CHCl | H | Cl |
| 4.551 | CH$_3$ | H | H | 1 | H | H | H | H | C=NOCH$_2$CH=CHCl | H | Cl |
| 4.552 | CH$_3$ | H | H | 2 | H | H | H | H | C=NOCH$_2$CH=CHCl | H | Cl |
| 4.553 | CH$_3$ | H | H | 0 | H | H | H | H | C=NOCH$_2$C$_6$H$_5$ | H | Cl |
| 4.554 | CH$_3$ | H | H | 1 | H | H | H | H | C=NOCH$_2$C$_6$H$_5$ | H | Cl |
| 4.555 | CH$_3$ | H | H | 2 | H | H | H | H | C=NOCH$_2$C$_6$H$_5$ | H | Cl |
| 4.556 | CH$_3$ | H | H | 0 | H | H | H | H | C(CH$_3$)$_2$ | H | Cl |
| 4.557 | CH$_3$ | H | H | 1 | H | H | H | H | C(CH$_3$)$_2$ | H | Cl |

TABLE 4-continued

Compounds of the formula

[Structure: cyclohexanedione with OH, connected via C=O to a benzene ring fused with a sulfur-containing ring bearing $R^{21}$, $R^{22}$, $R^{13}$, $R^{12}$, Y, with substituents $R^{17}$, $R^{18}$, $R^{19}$ on the cyclohexanedione, and L, M on the benzene; $(O)_n$ on S]

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.558 | $CH_3$ | H | H | 2 | H | H | H | H | $C(CH_3)_2$ | H | Cl |
| 4.559 | $CH_3$ | H | H | 0 | H | H | H | H | [dioxane-CH₂CH₂ bridge] | H | Cl |
| 4.560 | $CH_3$ | H | H | 1 | H | H | H | H | [dioxane-CH₂CH₂ bridge] | H | Cl |
| 4.561 | $CH_3$ | H | H | 2 | H | H | H | H | [dioxane-CH₂CH₂ bridge] | H | Cl |
| 4.562 | $CH_3$ | H | H | 0 | H | H | H | H | [dioxane with C(CH₃)₂ bridge] | H | Cl |
| 4.563 | $CH_3$ | H | H | 1 | H | H | H | H | [dioxane with C(CH₃)₂ bridge] | H | Cl |
| 4.564 | $CH_3$ | H | H | 2 | H | H | H | H | [dioxane with C(CH₃)₂ bridge] | H | Cl |
| 4.565 | $CH_3$ | H | H | 0 | H | H | H | H | $C=N-CH_3$ | H | Cl |
| 4.566 | $CH_3$ | H | H | 1 | H | H | H | H | $C=N-CH_3$ | H | Cl |
| 4.567 | $CH_3$ | H | H | 2 | H | H | H | H | $C=N-CH_3$ | H | Cl |
| 4.568 | $CH_3$ | H | H | 0 | H | H | H | H | $C=NC_2H_5$ | H | Cl |
| 4.569 | $CH_3$ | H | H | 1 | H | H | H | H | $C=NC_2H_5$ | H | Cl |
| 4.570 | $CH_3$ | H | H | 2 | H | H | H | H | $C=NC_2H_5$ | H | Cl |
| 4.571 | $CH_3$ | H | H | 0 | H | H | H | H | $CH-NHCH_3$ | H | Cl |
| 4.572 | $CH_3$ | H | H | 1 | H | H | H | H | $CH-NHCH_3$ | H | Cl |
| 4.573 | $CH_3$ | H | H | 2 | H | H | H | H | $CH-NHCH_3$ | H | Cl |
| 4.574 | $CH_3$ | H | H | 0 | H | H | H | H | $CH-NHC_2H_5$ | H | Cl |
| 4.575 | $CH_3$ | H | H | 1 | H | H | H | H | $CH-NHC_2H_5$ | H | Cl |
| 4.576 | $CH_3$ | H | H | 2 | H | H | H | H | $CH-NHC_2H_5$ | H | Cl |
| 4.577 | $CH_3$ | H | H | 0 | H | H | H | H | $CH-N(CH_3)_2$ | H | Cl |
| 4.578 | $CH_3$ | H | H | 1 | H | H | H | H | $CH-N(CH_3)_2$ | H | Cl |
| 4.579 | $CH_3$ | H | H | 2 | H | H | H | H | $CH-N(CH_3)_2$ | H | Cl |
| 4.580 | $CH_3$ | H | H | 0 | H | H | H | H | $CH-NHOC_2H_5$ | H | Cl |
| 4.581 | $CH_3$ | H | H | 1 | H | H | H | H | $CH-NHOC_2H_5$ | H | Cl |
| 4.582 | $CH_3$ | H | H | 2 | H | H | H | H | $CH-NHOC_2H_5$ | H | Cl |
| 4.583 | $CH_3$ | H | H | 0 | H | H | H | H | $CH-N(CH_3)OC_2H_5$ | H | Cl |
| 4.584 | $CH_3$ | H | H | 1 | H | H | H | H | $CH-N(CH_3)OC_2H_5$ | H | Cl |
| 4.585 | $CH_3$ | H | H | 2 | H | H | H | H | $CH-N(CH_3)OC_2H_5$ | H | Cl |
| 4.586 | $CH_3$ | H | H | 0 | H | H | H | H | $C=N-NH_2$ | H | Cl |
| 4.587 | $CH_3$ | H | H | 1 | H | H | H | H | $C=N-NH_2$ | H | Cl |
| 4.588 | $CH_3$ | H | H | 2 | H | H | H | H | $C=N-NH_2$ | H | Cl |
| 4.589 | $CH_3$ | H | H | 0 | H | H | H | H | $C=N-N(CH_3)_2$ | H | Cl |
| 4.590 | $CH_3$ | H | H | 1 | H | H | H | H | $C=N-N(CH_3)_2$ | H | Cl |

TABLE 4-continued

Compounds of the formula

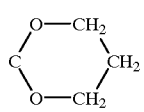

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.591 | $CH_3$ | H | H | 2 | H | H | H | H | $C=N-N(CH_3)_2$ | H | Cl |
| 4.592 | $CH_3$ | H | H | 0 | H | H | H | H | $CH-N(CH_3)OCH_2C_6H_5$ | H | Cl |
| 4.593 | $CH_3$ | H | H | 1 | H | H | H | H | $CH-N(CH_3)OCH_2C_6H_5$ | H | Cl |
| 4.594 | $CH_3$ | H | H | 2 | H | H | H | H | $CH-N(CH_3)OCH_2C_6H_5$ | H | Cl |
| 4.595 | $CH_3$ | H | H | 0 | H | H | H | H | $C(CH_3)-OCH_3$ | H | Cl |
| 4.596 | $CH_3$ | H | H | 1 | H | H | H | H | $C(CH_3)-OCH_3$ | H | Cl |
| 4.597 | $CH_3$ | H | H | 2 | H | H | H | H | $C(CH_3)-OCH_3$ | H | Cl |
| 4.598 | $CH_3$ | H | H | 0 | H | H | H | H | O | H | Cl |
| 4.599 | $CH_3$ | H | H | 1 | H | H | H | H | O | H | Cl |
| 4.600 | $CH_3$ | H | H | 2 | H | H | H | H | O | H | Cl |
| 4.601 | $CH_3$ | $CH_3$ | H | 0 | H | H | H | H | $C=O$ | H | Cl |
| 4.602 | $CH_3$ | $CH_3$ | H | 1 | H | H | H | H | $C=O$ | H | Cl |
| 4.603 | $CH_3$ | $CH_3$ | H | 2 | H | H | H | H | $C=O$ | H | Cl |
| 4.604 | $CH_3$ | $CH_3$ | H | 0 | H | H | H | H | CHOH | H | Cl |
| 4.605 | $CH_3$ | $CH_3$ | H | 1 | H | H | H | H | CHOH | H | Cl |
| 4.606 | $CH_3$ | $CH_3C$ | H | 2 | H | H | H | H | CHOH | H | Cl |
| 4.607 | $CH_3$ | $CH_3$ | H | 0 | H | H | H | H | $CHOCH_3$ | H | Cl |
| 4.608 | $CH_3$ | $CH_3$ | H | 1 | H | H | H | H | $CHOCH_3$ | H | Cl |
| 4.609 | $CH_3$ | $CH_3$ | H | 2 | H | H | H | H | $CHOCH_3$ | H | Cl |
| 4.610 | $CH_3$ | $CH_3$ | H | 0 | H | H | H | H | $CHOC_2H_5$ | H | Cl |
| 4.611 | $CH_3$ | $CH_3$ | H | 1 | H | H | H | H | $CHOC_2H_5$ | H | Cl |
| 4.612 | $CH_3$ | $CH_3$ | H | 2 | H | H | H | H | $CHOC_2H_5$ | H | Cl |
| 4.613 | $CH_3$ | $CH_3$ | H | 0 | H | H | H | H | CHOiPr | H | Cl |
| 4.614 | $CH_3$ | $CH_3$ | H | 1 | H | H | H | H | CHOiPr | H | Cl |
| 4.615 | $CH_3$ | $CH_3$ | H | 2 | H | H | H | H | CHOiPr | H | Cl |
| 4.616 | $CH_3$ | $CH_3$ | H | 0 | H | H | H | H | $C=NOCH_3$ | H | Cl |
| 4.617 | $CH_3$ | $CH_3$ | H | 1 | H | H | H | H | $C=NOCH_3$ | H | Cl |
| 4.618 | $CH_3$ | $CH_3$ | H | 2 | H | H | H | H | $C=NOCH_3$ | H | Cl |
| 4.619 | $CH_3$ | $CH_3$ | H | 0 | H | H | H | H | $C=NOC_2H_5$ | H | Cl |
| 4.620 | $CH_3$ | $CH_3$ | H | 1 | H | H | H | H | $C=NOC_2H_5$ | H | Cl |
| 4.621 | $CH_3$ | $CH_3$ | H | 2 | H | H | H | H | $C=NOC_2H_5$ | H | Cl |
| 4.622 | $CH_3$ | $CH_3$ | H | 0 | H | H | H | H | $C=NOiPr$ | H | Cl |
| 4.623 | $CH_3$ | $CH_3$ | H | 1 | H | H | H | H | $C=NOiPr$ | H | Cl |
| 4.624 | $CH_3$ | $CH_3$ | H | 2 | H | H | H | H | $C=NOiPr$ | H | Cl |
| 4.625 | $CH_3$ | $CH_3$ | H | 0 | H | H | H | H | $C=NOCH_2CH=CHCl$ | H | Cl |
| 4.626 | $CH_3$ | $CH_3$ | H | 1 | H | H | H | H | $C=NOCH_2CH=CHCl$ | H | Cl |
| 4.627 | $CH_3$ | $CH_3$ | H | 2 | H | H | H | H | $C=NOCH_2CH=CHCl$ | H | Cl |
| 4.628 | $CH_3$ | $CH_3$ | H | 0 | H | H | H | H | $C=NOCH_2C_6H_5$ | H | Cl |
| 4.629 | $CH_3$ | $CH_3$ | H | 1 | H | H | H | H | $C=NOCH_2C_6H_5$ | H | Cl |
| 4.630 | $CH_3$ | $CH_3$ | H | 2 | H | H | H | H | $C=NOCH_2C_6H_5$ | H | Cl |
| 4.631 | $CH_3$ | $CH_3$ | H | 0 | H | H | H | H | $C(CH_3)_2$ | H | Cl |
| 4.632 | $CH_3$ | $CH_3$ | H | 1 | H | H | H | H | $C(CH_3)_2$ | H | Cl |
| 4.633 | $CH_3$ | $CH_3$ | H | 2 | H | H | H | H | $C(CH_3)_2$ | H | Cl |
| 4.634 | $CH_3$ | $CH_3$ | H | 0 | H | H | H | H | 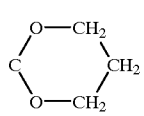 | H | Cl |
| 4.635 | $CH_3$ | $CH_3$ | H | 1 | H | H | H | H | 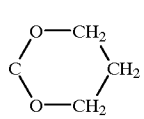 | H | Cl |
| 4.636 | $CH_3$ | $CH_3$ | H | 2 | H | H | H | H | 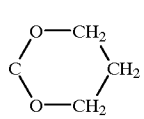 | H | Cl |

TABLE 4-continued

Compounds of the formula

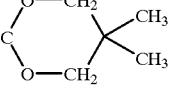

| No. | R17 | R18 | R19 | n | R12 | R13 | R21 | R22 | Y | L | M |
|---|---|---|---|---|---|---|---|---|---|---|---|
| 4.637 | CH₃ | CH₃ | H | 0 | H | H | H | H | 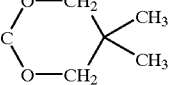 | H | Cl |
| 4.638 | CH₃ | CH₃ | H | 1 | H | H | H | H | 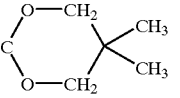 | H | Cl |
| 4.639 | CH₃ | CH₃ | H | 2 | H | H | H | H | (same dioxane group) | H | Cl |
| 4.640 | CH₃ | CH₃ | H | 0 | H | H | H | H | C=N—CH₃ | H | Cl |
| 4.641 | CH₃ | CH₃ | H | 1 | H | H | H | H | C=N—CH₃ | H | Cl |
| 4.642 | CH₃ | CH₃ | H | 2 | H | H | H | H | C=N—CH₃ | H | Cl |
| 4.643 | CH₃ | CH₃ | H | 0 | H | H | H | H | C=NC₂H₅ | H | Cl |
| 4.644 | CH₃ | CH₃ | H | 1 | H | H | H | H | C=NC₂H₅ | H | Cl |
| 4.645 | CH₃ | CH₃ | H | 2 | H | H | H | H | C=NC₂H₅ | H | Cl |
| 4.646 | CH₃ | CH₃ | H | 0 | H | H | H | H | CH—NHCH₃ | H | Cl |
| 4.647 | CH₃ | CH₃ | H | 1 | H | H | H | H | CH—NHCH₃ | H | Cl |
| 4.648 | CH₃ | CH₃ | H | 2 | H | H | H | H | CH—NHCH₃ | H | Cl |
| 4.649 | CH₃ | CH₃ | H | 0 | H | H | H | H | CH—NHC₂H₅ | H | Cl |
| 4.650 | CH₃ | CH₃ | H | 1 | H | H | H | H | CH—NHC₂H₅ | H | Cl |
| 4.651 | CH₃ | CH₃ | H | 2 | H | H | H | H | CH—NHC₂H₅ | H | Cl |
| 4.652 | CH₃ | CH₃ | H | 0 | H | H | H | H | CH—N(CH₃)₂ | H | Cl |
| 4.653 | CH₃ | CH₃ | H | 1 | H | H | H | H | CH—N(CH₃)₂ | H | Cl |
| 4.654 | CH₃ | CH₃ | H | 2 | H | H | H | H | CH—N(CH₃)₂ | H | Cl |
| 4.655 | CH₃ | CH₃ | H | 0 | H | H | H | H | CH—NHOC₂H₅ | H | Cl |
| 4.656 | CH₃ | CH₃ | H | 1 | H | H | H | H | CH—NHOC₂H₅ | H | Cl |
| 4.657 | CH₃ | CH₃ | H | 2 | H | H | H | H | CH—NHOC₂H₅ | H | Cl |
| 4.658 | CH₃ | CH₃ | H | 0 | H | H | H | H | CH—N(CH₃)OC₂H₅ | H | Cl |
| 4.659 | CH₃ | CH₃ | H | 1 | H | H | H | H | CH—N(CH₃)OC₂H₅ | H | Cl |
| 4.660 | CH₃ | CH₃ | H | 2 | H | H | H | H | CH—N(CH₃)OC₂H₅ | H | Cl |
| 4.661 | CH₃ | CH₃ | H | 0 | H | H | H | H | C=N—NH₂ | H | Cl |
| 4.662 | CH₃ | CH₃ | H | 1 | H | H | H | H | C=N—NH₂ | H | Cl |
| 4.663 | CH₃ | CH₃ | H | 2 | H | H | H | H | C=N—NH₂ | H | Cl |
| 4.664 | CH₃ | CH₃ | H | 0 | H | H | H | H | C=N—N(CH₃)₂ | H | Cl |
| 4.665 | CH₃ | CH₃ | H | 1 | H | H | H | H | C=N—N(CH₃)₂ | H | Cl |
| 4.666 | CH₃ | CH₃ | H | 2 | H | H | H | H | C=N—N(CH₃)₂ | H | Cl |
| 4.667 | CH₃ | CH₃ | H | 0 | H | H | H | H | CH—N(CH₃)OCH₂C₆H₅ | H | Cl |
| 4.668 | CH₃ | CH₃ | H | 1 | H | H | H | H | CH—N(CH₃)OCH₂C₆H₅ | H | Cl |
| 4.669 | CH₃ | CH₃ | H | 2 | H | H | H | H | CH—N(CH₃)OCH₂C₆H₅ | H | Cl |
| 4.670 | CH₃ | CH₃ | H | 0 | H | H | H | H | C(CH₃)—OCH₃ | H | Cl |
| 4.671 | CH₃ | CH₃ | H | 1 | H | H | H | H | C(CH₃)—OCH₃ | H | Cl |
| 4.672 | CH₃ | CH₃ | H | 2 | H | H | H | H | C(CH₃)—OCH₃ | H | Cl |
| 4.673 | CH₃ | CH₃ | H | 0 | H | H | H | H | O | H | Cl |
| 4.674 | CH₃ | CH₃ | H | 1 | H | H | H | H | O | H | Cl |
| 4.675 | CH₃ | CH₃ | H | 2 | H | H | H | H | O | H | Cl |
| 4.676 | H | H | H | 0 | H | H | H | H | C=O | H | NO₂ |
| 4.677 | H | H | H | 1 | H | H | H | H | C=O | H | NO₂ |
| 4.678 | H | H | H | 2 | H | H | H | H | C=O | H | NO₂ |
| 4.679 | H | H | H | 0 | H | H | H | H | CHOCH₃ | H | NO₂ |
| 4.680 | H | H | H | 1 | H | H | H | H | CHOCH₃ | H | NO₂ |
| 4.681 | H | H | H | 2 | H | H | H | H | CHOCH₃ | H | NO₂ |
| 4.682 | H | H | H | 0 | H | H | H | H | CHOC₂H₅ | H | NO₂ |
| 4.683 | H | H | H | 1 | H | H | H | H | CHOC₂H₅ | H | NO₂ |
| 4.684 | H | H | H | 2 | H | H | H | H | CHOC₂H₅ | H | NO₂ |
| 4.685 | H | H | H | 0 | H | H | H | H | CHOiPr | H | NO₂ |

TABLE 4-continued

Compounds of the formula

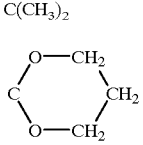

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.686 | H | H | H | 1 | H | H | H | H | CHOiPr | H | $NO_2$ |
| 4.687 | H | H | H | 2 | H | H | H | H | CHOiPr | H | $NO_2$ |
| 4.688 | H | H | H | 0 | H | H | H | H | C=$NOCH_3$ | H | $NO_2$ |
| 4.689 | H | H | H | 1 | H | H | H | H | C=$NOCH_3$ | H | $NO_2$ |
| 4.690 | H | H | H | 2 | H | H | H | H | C=$NOCH_3$ | H | $NO_2$ |
| 4.691 | H | H | H | 0 | H | H | H | H | C=$NOC_2H_5$ | H | $NO_2$ |
| 4.692 | H | H | H | 1 | H | H | H | H | C=$NOC_2H_5$ | H | $NO_2$ |
| 4.693 | H | H | H | 2 | H | H | H | H | C=$NOC_2H_5$ | H | $NO_2$ |
| 4.694 | H | H | H | 0 | H | H | H | H | C=NOiPr | H | $NO_2$ |
| 4.695 | H | H | H | 1 | H | H | H | H | C=NOiPr | H | $NO_2$ |
| 4.696 | H | H | H | 2 | H | H | H | H | C=NOiPr | H | $NO_2$ |
| 4.697 | H | H | H | 0 | H | H | H | H | C=$NOCH_2$CH=CHCl | H | $NO_2$ |
| 4.698 | H | H | H | 1 | H | H | H | H | C=$NOCH_2$CH=CHCl | H | $NO_2$ |
| 4.699 | H | H | H | 2 | H | H | H | H | C=$NOCH_2$CH=CHCl | H | $NO_2$ |
| 4.700 | H | H | H | 0 | H | H | H | H | C=$NOCH_2C_6H_5$ | H | $NO_2$ |
| 4.701 | H | H | H | 1 | H | H | H | H | C=$NOCH_2C_6H_5$ | H | $NO_2$ |
| 4.702 | H | H | H | 2 | H | H | H | H | C=$NOCH_2C_6H_5$ | H | $NO_2$ |
| 4.703 | H | H | H | 0 | H | H | H | H | $C(CH_3)_2$ | H | $NO_2$ |
| 4.704 | H | H | H | 1 | H | H | H | H | $C(CH_3)_2$ | H | $NO_2$ |
| 4.705 | H | H | H | 2 | H | H | H | H | $C(CH_3)_2$ | H | $NO_2$ |
| 4.706 | H | H | H | 0 | H | H | H | H | 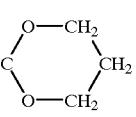 | H | $NO_2$ |
| 4.707 | H | H | H | 1 | H | H | H | H | 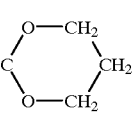 | H | $NO_2$ |
| 4.708 | H | H | H | 2 | H | H | H | H | 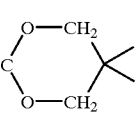 | H | $NO_2$ |
| 4.709 | H | H | H | 0 | H | H | H | H | 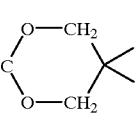 | H | $NO_2$ |
| 4.710 | H | H | H | 1 | H | H | H | H | 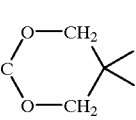 | H | $NO_2$ |
| 4.711 | H | H | H | 2 | H | H | H | H |  | H | $NO_2$ |
| 4.712 | H | H | H | 0 | H | H | H | H | C=N—$CH_3$ | H | $NO_2$ |
| 4.713 | H | H | H | 1 | H | H | H | H | C=N—$CH_3$ | H | $NO_2$ |
| 4.714 | H | H | H | 2 | H | H | H | H | C=N—$CH_3$ | H | $NO_2$ |
| 4.715 | H | H | H | 0 | H | H | H | H | C=$NC_2H_5$ | H | $NO_2$ |
| 4.716 | H | H | H | 1 | H | H | H | H | C=$NC_2H_5$ | H | $NO_2$ |
| 4.717 | H | H | H | 2 | H | H | H | H | C=$NC_2H_5$ | H | $NO_2$ |
| 4.718 | H | H | H | 0 | H | H | H | H | CH—$NHCH_3$ | H | $NO_2$ |

TABLE 4-continued

Compounds of the formula

[Structure: cyclohexenone with OH, connected via C=O to benzene ring bearing M substituent, fused to thiazine ring with S(O)$_n$, R$^{21}$, R$^{22}$, Y, R$^{13}$, R$^{12}$; cyclohexenone bears R$^{17}$, R$^{18}$, R$^{19}$; benzene bears L]

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.719 | H | H | H | 1 | H | H | H | H | CH—NHCH$_3$ | H | NO$_2$ |
| 4.720 | H | H | H | 2 | H | H | H | H | CH—NHCH$_3$ | H | NO$_2$ |
| 4.721 | H | H | H | 0 | H | H | H | H | CH—NHC$_2$H$_5$ | H | NO$_2$ |
| 4.722 | H | H | H | 1 | H | H | H | H | CH—NHC$_2$H$_5$ | H | NO$_2$ |
| 4.723 | H | H | H | 2 | H | H | H | H | CH—NHC$_2$H$_5$ | H | NO$_2$ |
| 4.724 | H | H | H | 0 | H | H | H | H | CH—N(CH$_3$)$_2$ | H | NO$_2$ |
| 4.725 | H | H | H | 1 | H | H | H | H | CH—N(CH$_3$)$_2$ | H | NO$_2$ |
| 4.726 | H | H | H | 2 | H | H | H | H | CH—N(CH$_3$)$_2$ | H | NO$_2$ |
| 4.727 | H | H | H | 0 | H | H | H | H | CH—NHOC$_2$H$_5$ | H | NO$_2$ |
| 4.728 | H | H | H | 1 | H | H | H | H | CH—NHOC$_2$H$_5$ | H | NO$_2$ |
| 4.729 | H | H | H | 2 | H | H | H | H | CH—NHOC$_2$H$_5$ | H | NO$_2$ |
| 4.730 | H | H | H | 0 | H | H | H | H | CH—N(CH$_3$)OC$_2$H$_5$ | H | NO$_2$ |
| 4.731 | H | H | H | 1 | H | H | H | H | CH—N(CH$_3$)OC$_2$H$_5$ | H | NO$_2$ |
| 4.732 | H | H | H | 2 | H | H | H | H | CH—N(CH$_3$)OC$_2$H$_5$ | H | NO$_2$ |
| 4.733 | H | H | H | 0 | H | H | H | H | C=N—NH$_2$ | H | NO$_2$ |
| 4.734 | H | H | H | 1 | H | H | H | H | C=N—NH$_2$ | H | NO$_2$ |
| 4.735 | H | H | H | 2 | H | H | H | H | C=N—NH$_2$ | H | NO$_2$ |
| 4.736 | H | H | H | 0 | H | H | H | H | C=N—N(CH$_3$)$_2$ | H | NO$_2$ |
| 4.737 | H | H | H | 1 | H | H | H | H | C=N—N(CH$_3$)$_2$ | H | NO$_2$ |
| 4.738 | H | H | H | 2 | H | H | H | H | C=N—N(CH$_3$)$_2$ | H | NO$_2$ |
| 4.739 | H | H | H | 0 | H | H | H | H | CH—N(CH$_3$)OCH$_2$C$_6$H$_5$ | H | NO$_2$ |
| 4.740 | H | H | H | 1 | H | H | H | H | CH—N(CH$_3$)OCH$_2$C$_6$H$_5$ | H | NO$_2$ |
| 4.741 | H | H | H | 2 | H | H | H | H | CH—N(CH$_3$)OCH$_2$C$_6$H$_5$ | H | NO$_2$ |
| 4.742 | H | H | H | 0 | H | H | H | H | C(CH$_3$)—OCH$_3$ | H | NO$_2$ |
| 4.743 | H | H | H | 1 | H | H | H | H | C(CH$_3$)—OCH$_3$ | H | NO$_2$ |
| 4.744 | H | H | H | 2 | H | H | H | H | C(CH$_3$)—OCH$_3$ | H | NO$_2$ |
| 4.745 | H | H | H | 0 | H | H | H | H | O | H | NO$_2$ |
| 4.746 | H | H | H | 1 | H | H | H | H | O | H | NO$_2$ |
| 4.747 | H | H | H | 2 | H | H | H | H | O | H | NO$_2$ |
| 4.748 | CH$_3$ | H | H | 0 | H | H | H | H | C=O | H | NO$_2$ |
| 4.749 | CH$_3$ | H | H | 1 | H | H | H | H | C=O | H | NO$_2$ |
| 4.750 | CH$_3$ | H | H | 2 | H | H | H | H | C=O | H | NO$_2$ |
| 4.751 | CH$_3$ | H | H | 0 | H | H | H | H | CHOCH$_3$ | H | NO$_2$ |
| 4.752 | CH$_3$ | H | H | 1 | H | H | H | H | CHOCH$_3$ | H | NO$_2$ |
| 4.753 | CH$_3$ | H | H | 2 | H | H | H | H | CHOCH$_3$ | H | NO$_2$ |
| 4.754 | CH$_3$ | H | H | 0 | H | H | H | H | CHOC$_2$H$_5$ | H | NO$_2$ |
| 4.755 | CH$_3$ | H | H | 1 | H | H | H | H | CHOC$_2$H$_5$ | H | NO$_2$ |
| 4.756 | CH$_3$ | H | H | 2 | H | H | H | H | CHOC$_2$H$_5$ | H | NO$_2$ |
| 4.757 | CH$_3$ | H | H | 0 | H | H | H | H | CHOiPr | H | NO$_2$ |
| 4.758 | CH$_3$ | H | H | 1 | H | H | H | H | CHOiPr | H | NO$_2$ |
| 4.759 | CH$_3$ | H | H | 2 | H | H | H | H | CHOiPr | H | NO$_2$ |
| 4.760 | CH$_3$ | H | H | 0 | H | H | H | H | C=NOCH$_3$ | H | NO$_2$ |
| 4.761 | CH$_3$ | H | H | 1 | H | H | H | H | C=NOCH$_3$ | H | NO$_2$ |
| 4.762 | CH$_3$ | H | H | 2 | H | H | H | H | C=NOCH$_3$ | H | NO$_2$ |
| 4.763 | CH$_3$ | H | H | 0 | H | H | H | H | C=NOC$_2$H$_5$ | H | NO$_2$ |
| 4.764 | CH$_3$ | H | H | 1 | H | H | H | H | C=NOC$_2$H$_5$ | H | NO$_2$ |
| 4.765 | CH$_3$ | H | H | 2 | H | H | H | H | C=NOC$_2$H$_5$ | H | NO$_2$ |
| 4.766 | CH$_3$ | H | H | 0 | H | H | H | H | C=NOiPr | H | NO$_2$ |
| 4.767 | CH$_3$ | H | H | 1 | H | H | H | H | C=NOiPr | H | NO$_2$ |
| 4.768 | CH$_3$ | H | H | 2 | H | H | H | H | C=NOiPr | H | NO$_2$ |
| 4.769 | CH$_3$ | H | H | 0 | H | H | H | H | C=NOCH$_2$CH=CHCl | H | NO$_2$ |
| 4.770 | CH$_3$ | H | H | 1 | H | H | H | H | C=NOCH$_2$CH=CHCl | H | NO$_2$ |
| 4.771 | CH$_3$ | H | H | 2 | H | H | H | H | C=NOCH$_2$CH=CHCl | H | NO$_2$ |
| 4.772 | CH$_3$ | H | H | 0 | H | H | H | H | C=NOCH$_2$C$_6$H$_5$ | H | NO$_2$ |
| 4.773 | CH$_3$ | H | H | 1 | H | H | H | H | C=NOCH$_2$C$_6$H$_5$ | H | NO$_2$ |
| 4.774 | CH$_3$ | H | H | 2 | H | H | H | H | C=NOCH$_2$C$_6$H$_5$ | H | NO$_2$ |
| 4.775 | CH$_3$ | H | H | 0 | H | H | H | H | C(CH$_3$)$_2$ | H | NO$_2$ |
| 4.776 | CH$_3$ | H | H | 1 | H | H | H | H | C(CH$_3$)$_2$ | H | NO$_2$ |
| 4.777 | CH$_3$ | H | H | 2 | H | H | H | H | C(CH$_3$)$_2$ | H | NO$_2$ |

TABLE 4-continued

Compounds of the formula

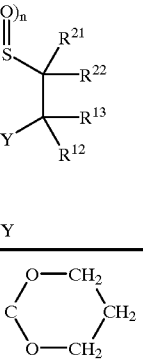

| No. | R17 | R18 | R19 | n | R12 | R13 | R21 | R22 | Y | L | M |
|---|---|---|---|---|---|---|---|---|---|---|---|
| 4.778 | CH$_3$ | H | H | 0 | H | H | H | H | 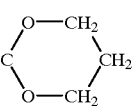 | H | NO$_2$ |
| 4.779 | CH$_3$ | H | H | 1 | H | H | H | H | 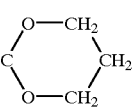 | H | NO$_2$ |
| 4.780 | CH$_3$ | H | H | 2 | H | H | H | H | 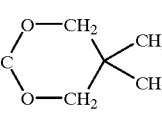 | H | NO$_2$ |
| 4.781 | CH$_3$ | H | H | 0 | H | H | H | H | 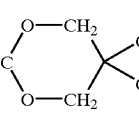 | H | NO$_2$ |
| 4.782 | CH$_3$ | H | H | 1 | H | H | H | H | 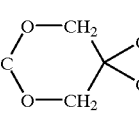 | H | NO$_2$ |
| 4.783 | CH$_3$ | H | H | 2 | H | H | H | H |  | H | NO$_2$ |
| 4.784 | CH$_3$ | H | H | 0 | H | H | H | H | C=N—CH$_3$ | H | NO$_2$ |
| 4.785 | CH$_3$ | H | H | 1 | H | H | H | H | C=N—CH$_3$ | H | NO$_2$ |
| 4.786 | CH$_3$ | H | H | 2 | H | H | H | H | C=N—CH$_3$ | H | NO$_2$ |
| 4.787 | CH$_3$ | H | H | 0 | H | H | H | H | C=NC$_2$H$_5$ | H | NO$_2$ |
| 4.788 | CH$_3$ | H | H | 1 | H | H | H | H | C=NC$_2$H$_5$ | H | NO$_2$ |
| 4.789 | CH$_3$ | H | H | 2 | H | H | H | H | C=NC$_2$H$_5$ | H | NO$_2$ |
| 4.790 | CH$_3$ | H | H | 0 | H | H | H | H | CH—NHCH$_3$ | H | NO$_2$ |
| 4.791 | CH$_3$ | H | H | 1 | H | H | H | H | CH—NHCH$_3$ | H | NO$_2$ |
| 4.792 | CH$_3$ | H | H | 2 | H | H | H | H | CH—NHCH$_3$ | H | NO$_2$ |
| 4.793 | CH$_3$ | H | H | 0 | H | H | H | H | CH—NHC$_2$H$_5$ | H | NO$_2$ |
| 4.794 | CH$_3$ | H | H | 1 | H | H | H | H | CH—NHC$_2$H$_5$ | H | NO$_2$ |
| 4.795 | CH$_3$ | H | H | 2 | H | H | H | H | CH—NHC$_2$H$_5$ | H | NO$_2$ |
| 4.796 | CH$_3$ | H | H | 0 | H | H | H | H | CH—N(CH$_3$)$_2$ | H | NO$_2$ |
| 4.797 | CH$_3$ | H | H | 1 | H | H | H | H | CH—N(CH$_3$)$_2$ | H | NO$_2$ |
| 4.798 | CH$_3$ | H | H | 2 | H | H | H | H | CH—N(CH$_3$)$_2$ | H | NO$_2$ |
| 4.799 | CH$_3$ | H | H | 0 | H | H | H | H | CH—NHOC$_2$H$_5$ | H | NO$_2$ |
| 4.800 | CH$_3$ | H | H | 1 | H | H | H | H | CH—NHOC$_2$H$_5$ | H | NO$_2$ |
| 4.801 | CH$_3$ | H | H | 2 | H | H | H | H | CH—NHOC$_2$H$_5$ | H | NO$_2$ |
| 4.802 | CH$_3$ | H | H | 0 | H | H | H | H | CH—N(CH$_3$)OC$_2$H$_5$ | H | NO$_2$ |
| 4.803 | CH$_3$ | H | H | 1 | H | H | H | H | CH—N(CH$_3$)OC$_2$H$_5$ | H | NO$_2$ |
| 4.804 | CH$_3$ | H | H | 2 | H | H | H | H | CH—N(CH$_3$)OC$_2$H$_5$ | H | NO$_2$ |
| 4.805 | CH$_3$ | H | H | 0 | H | H | H | H | C=N—NH$_2$ | H | NO$_2$ |
| 4.806 | CH$_3$ | H | H | 1 | H | H | H | H | C=N—NH$_2$ | H | NO$_2$ |
| 4.807 | CH$_3$ | H | H | 2 | H | H | H | H | C=N—NH$_2$ | H | NO$_2$ |
| 4.808 | CH$_3$ | H | H | 0 | H | H | H | H | C=N—N(CH$_3$)$_2$ | H | NO$_2$ |
| 4.809 | CH$_3$ | H | H | 1 | H | H | H | H | C=N—N(CH$_3$)$_2$ | H | NO$_2$ |
| 4.810 | CH$_3$ | H | H | 2 | H | H | H | H | C=N—N(CH$_3$)$_2$ | H | NO$_2$ |
| 4.811 | CH$_3$ | H | H | 0 | H | H | H | H | CH—N(CH$_3$)OCH$_2$C$_6$H$_5$ | H | NO$_2$ |

TABLE 4-continued

Compounds of the formula

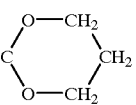

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.812 | $CH_3$ | H | H | 1 | H | H | H | H | CH—N($CH_3$)$OCH_2C_6H_5$ | H | $NO_2$ |
| 4.813 | $CH_3$ | H | H | 2 | H | H | H | H | CH—N($CH_3$)$OCH_2C_6H_5$ | H | $NO_2$ |
| 4.814 | $CH_3$ | H | H | 0 | H | H | H | H | C($CH_3$)—$OCH_3$ | H | $NO_2$ |
| 4.815 | $CH_3$ | H | H | 1 | H | H | H | H | C($CH_3$)—$OCH_3$ | H | $NO_2$ |
| 4.816 | $CH_3$ | H | H | 2 | H | H | H | H | C($CH_3$)—$OCH_3$ | H | $NO_2$ |
| 4.817 | $CH_3$ | H | H | 0 | H | H | H | H | O | H | $NO_2$ |
| 4.818 | $CH_3$ | H | H | 1 | H | H | H | H | O | H | $NO_2$ |
| 4.819 | $CH_3$ | H | H | 2 | H | H | H | H | O | H | $NO_2$ |
| 4.820 | $CH_3$ | $CH_3$ | H | 0 | H | H | H | H | C=O | H | $NO_2$ |
| 4.821 | $CH_3$ | $CH_3$ | H | 1 | H | H | H | H | C=O | H | $NO_2$ |
| 4.822 | $CH_3$ | $CH_3$ | H | 2 | H | H | H | H | C=O | H | $NO_2$ |
| 4.823 | $CH_3$ | $CH_3$ | H | 0 | H | H | H | H | $CHOCH_3$ | H | $NO_2$ |
| 4.824 | $CH_3$ | $CH_3$ | H | 1 | H | H | H | H | $CHOCH_3$ | H | $NO_2$ |
| 4.825 | $CH_3$ | $CH_3$ | H | 2 | H | H | H | H | $CHOCH_3$ | H | $NO_2$ |
| 4.826 | $CH_3$ | $CH_3$ | H | 0 | H | H | H | H | $CHOC_2H_5$ | H | $NO_2$ |
| 4.827 | $CH_3$ | $CH_3$ | H | 1 | H | H | H | H | $CHOC_2H_5$ | H | $NO_2$ |
| 4.828 | $CH_3$ | $CH_3$ | H | 2 | H | H | H | H | $CHOC_2H_5$ | H | $NO_2$ |
| 4.829 | $CH_3$ | $CH_3$ | H | 0 | H | H | H | H | CHOiPr | H | $NO_2$ |
| 4.830 | $CH_3$ | $CH_3$ | H | 1 | H | H | H | H | CHOiPr | H | $NO_2$ |
| 4.831 | $CH_3$ | $CH_3$ | H | 2 | H | H | H | H | CHOiPr | H | $NO_2$ |
| 4.832 | $CH_3$ | $CH_3$ | H | 0 | H | H | H | H | C=$NOCH_3$ | H | $NO_2$ |
| 4.833 | $CH_3$ | $CH_3$ | H | 1 | H | H | H | H | C=$NOCH_3$ | H | $NO_2$ |
| 4.834 | $CH_3$ | $CH_3$ | H | 2 | H | H | H | H | C=$NOCH_3$ | H | $NO_2$ |
| 4.835 | $CH_3$ | $CH_3$ | H | 0 | H | H | H | H | C=$NOC_2H_5$ | H | $NO_2$ |
| 4.836 | $CH_3$ | $CH_3$ | H | 1 | H | H | H | H | C=$NOC_2H_5$ | H | $NO_2$ |
| 4.837 | $CH_3$ | $CH_3$ | H | 2 | H | H | H | H | C=$NOC_2H_5$ | H | $NO_2$ |
| 4.838 | $CH_3$ | $CH_3$ | H | 0 | H | H | H | H | C=NOiPr | H | $NO_2$ |
| 4.839 | $CH_3$ | $CH_3$ | H | 1 | H | H | H | H | C=NOiPr | H | $NO_2$ |
| 4.840 | $CH_3$ | $CH_3$ | H | 2 | H | H | H | H | C=NOiPr | H | $NO_2$ |
| 4.841 | $CH_3$ | $CH_3$ | H | 0 | H | H | H | H | C=$NOCH_2CH$=CHCl | H | $NO_2$ |
| 4.842 | $CH_3$ | $CH_3$ | H | 1 | H | H | H | H | C=$NOCH_2CH$=CHCl | H | $NO_2$ |
| 4.843 | $CH_3$ | $CH_3$ | H | 2 | H | H | H | H | C=$NOCH_2CH$=CHCl | H | $NO_2$ |
| 4.844 | $CH_3$ | $CH_3$ | H | 0 | H | H | H | H | C=$NOCH_2C_6H_5$ | H | $NO_2$ |
| 4.845 | $CH_3$ | $CH_3$ | H | 1 | H | H | H | H | C=$NOCH_2C_6H_5$ | H | $NO_2$ |
| 4.846 | $CH_3$ | $CH_3$ | H | 2 | H | H | H | H | C=$NOCH_2C_6H_5$ | H | $NO_2$ |
| 4.847 | $CH_3$ | $CH_3$ | H | 0 | H | H | H | H | C($CH_3$)$_2$ | H | $NO_2$ |
| 4.848 | $CH_3$ | $CH_3$ | H | 1 | H | H | H | H | C($CH_3$)$_2$ | H | $NO_2$ |
| 4.849 | $CH_3$ | $CH_3$ | H | 2 | H | H | H | H | C($CH_3$)$_2$ | H | $NO_2$ |
| 4.850 | $CH_3$ | $CH_3$ | H | 0 | H | H | H | H | 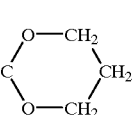 | H | $NO_2$ |
| 4.851 | $CH_3$ | $CH_3$ | H | 1 | H | H | H | H | 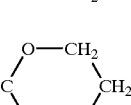 | H | $NO_2$ |
| 4.852 | $CH_3$ | $CH_3$ | H | 2 | H | H | H | H | 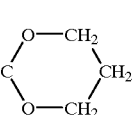 | H | $NO_2$ |
| 4.853 | $CH_3$ | $CH_3$ | H | 0 | H | H | H | H | 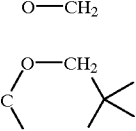 | H | $NO_2$ |

TABLE 4-continued

Compounds of the formula

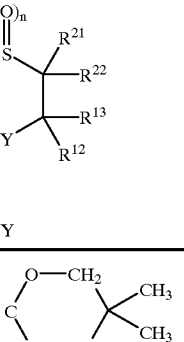

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.854 | $CH_3$ | $CH_3$ | H | 1 | H | H | H | H | 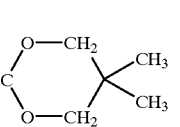 | H | $NO_2$ |
| 4.855 | $CH_3$ | $CH_3$ | H | 2 | H | H | H | H |  | H | $NO_2$ |
| 4.856 | $CH_3$ | $CH_3$ | H | 0 | H | H | H | H | C=N—$CH_3$ | H | $NO_2$ |
| 4.857 | $CH_3$ | $CH_3$ | H | 1 | H | H | H | H | C=N—$CH_3$ | H | $NO_2$ |
| 4.858 | $CH_3$ | $CH_3$ | H | 2 | H | H | H | H | C=N—$CH_3$ | H | $NO_2$ |
| 4.859 | $CH_3$ | $CH_3$ | H | 0 | H | H | H | H | C=N$C_2H_5$ | H | $NO_2$ |
| 4.860 | $CH_3$ | $CH_3$ | H | 1 | H | H | H | H | C=N$C_2H_5$ | H | $NO_2$ |
| 4.861 | $CH_3$ | $CH_3$ | H | 2 | H | H | H | H | C=N$C_2H_5$ | H | $NO_2$ |
| 4.862 | $CH_3$ | $CH_3$ | H | 0 | H | H | H | H | CH—$NHCH_3$ | H | $NO_2$ |
| 4.863 | $CH_3$ | $CH_3$ | H | 1 | H | H | H | H | CH—$NHCH_3$ | H | $NO_2$ |
| 4.864 | $CH_3$ | $CH_3$ | H | 2 | H | H | H | H | CH—$NHCH_3$ | H | $NO_2$ |
| 4.865 | $CH_3$ | $CH_3$ | H | 0 | H | H | H | H | CH—$NHC_2H_5$ | H | $NO_2$ |
| 4.866 | $CH_3$ | $CH_3$ | H | 1 | H | H | H | H | CH—$NHC_2H_5$ | H | $NO_2$ |
| 4.867 | $CH_3$ | $CH_3$ | H | 2 | H | H | H | H | CH—$NHC_2H_5$ | H | $NO_2$ |
| 4.868 | $CH_3$ | $CH_3$ | H | 0 | H | H | H | H | CH—$N(CH_3)_2$ | H | $NO_2$ |
| 4.869 | $CH_3$ | $CH_3$ | H | 1 | H | H | H | H | CH—$N(CH_3)_2$ | H | $NO_2$ |
| 4.870 | $CH_3$ | $CH_3$ | H | 2 | H | H | H | H | CH—$N(CH_3)_2$ | H | $NO_2$ |
| 4.871 | $CH_3$ | $CH_3$ | H | 0 | H | H | H | H | CH—$NHOC_2H_5$ | H | $NO_2$ |
| 4.872 | $CH_3$ | $CH_3$ | H | 1 | H | H | H | H | CH—$NHOC_2H_5$ | H | $NO_2$ |
| 4.873 | $CH_3$ | $CH_3$ | H | 2 | H | H | H | H | CH—$NHOC_2H_5$ | H | $NO_2$ |
| 4.874 | $CH_3$ | $CH_3$ | H | 0 | H | H | H | H | CH—$N(CH_3)OC_2H_5$ | H | $NO_2$ |
| 4.875 | $CH_3$ | $CH_3$ | H | 1 | H | H | H | H | CH—$N(CH_3)OC_2H_5$ | H | $NO_2$ |
| 4.876 | $CH_3$ | $CH_3$ | H | 2 | H | H | H | H | CH—$N(CH_3)OC_2H_5$ | H | $NO_2$ |
| 4.877 | $CH_3$ | $CH_3$ | H | 0 | H | H | H | H | C=N—$NH_2$ | H | $NO_2$ |
| 4.878 | $CH_3$ | $CH_3$ | H | 1 | H | H | H | H | C=N—$NH_2$ | H | $NO_2$ |
| 4.879 | $CH_3$ | $CH_3$ | H | 2 | H | H | H | H | C=N—$NH_2$ | H | $NO_2$ |
| 4.880 | $CH_3$ | $CH_3$ | H | 0 | H | H | H | H | C=N—$N(CH_3)_2$ | H | $NO_2$ |
| 4.881 | $CH_3$ | $CH_3$ | H | 1 | H | H | H | H | C=N—$N(CH_3)_2$ | H | $NO_2$ |
| 4.882 | $CH_3$ | $CH_3$ | H | 2 | H | H | H | H | C=N—$N(CH_3)_2$ | H | $NO_2$ |
| 4.883 | $CH_3$ | $CH_3$ | H | 0 | H | H | H | H | CH—$N(CH_3)OCH_2C_6H_5$ | H | $NO_2$ |
| 4.884 | $CH_3$ | $CH_3$ | H | 1 | H | H | H | H | CH—$N(CH_3)OCH_2C_6H_5$ | H | $NO_2$ |
| 4.885 | $CH_3$ | $CH_3$ | H | 2 | H | H | H | H | CH—$N(CH_3)OCH_2C_6H_5$ | H | $NO_2$ |
| 4.886 | $CH_3$ | $CH_3$ | H | 0 | H | H | H | H | $C(CH_3)$—$OCH_3$ | H | $NO_2$ |
| 4.887 | $CH_3$ | $CH_3$ | H | 1 | H | H | H | H | $C(CH_3)$—$OCH_3$ | H | $NO_2$ |
| 4.888 | $CH_3$ | $CH_3$ | H | 2 | H | H | H | H | $C(CH_3)$—$OCH_3$ | H | $NO_2$ |
| 4.889 | $CH_3$ | $CH_3$ | H | 0 | H | H | H | H | O | H | $NO_2$ |
| 4.890 | $CH_3$ | $CH_3$ | H | 1 | H | H | H | H | O | H | $NO_2$ |
| 4.891 | $CH_3$ | $CH_3$ | H | 2 | H | H | H | H | O | H | $NO_2$ |
| 4.892 | H | H | H | 0 | H | H | H | H | C=O | $CH_3$ | $CH_3$ |
| 4.893 | H | H | H | 1 | H | H | H | H | C=O | $CH_3$ | $CH_3$ |
| 4.894 | H | H | H | 2 | H | H | H | H | C=O | $CH_3$ | $CH_3$ |
| 4.895 | H | H | H | 0 | H | H | H | H | $CHOCH_3$ | $CH_3$ | $CH_3$ |
| 4.896 | H | H | H | 1 | H | H | H | H | $CHOCH_3$ | $CH_3$ | $CH_3$ |
| 4.897 | H | H | H | 2 | H | H | H | H | $CHOCH_3$ | $CH_3$ | $CH_3$ |
| 4.898 | H | H | H | 0 | H | H | H | H | $CHOC_2H_5$ | $CH_3$ | $CH_3$ |
| 4.899 | H | H | H | 1 | H | H | H | H | $CHOC_2H_5$ | $CH_3$ | $CH_3$ |
| 4.900 | H | H | H | 2 | H | H | H | H | $CHOC_2H_5$ | $CH_3$ | $CH_3$ |
| 4.901 | H | H | H | 0 | H | H | H | H | CHOiPr | $CH_3$ | $CH_3$ |
| 4.902 | H | H | H | 1 | H | H | H | H | CHOiPr | $CH_3$ | $CH_3$ |
| 4.903 | H | H | H | 2 | H | H | H | H | CHOiPr | $CH_3$ | $CH_3$ |
| 4.904 | H | H | H | 0 | H | H | H | H | C=$NOCH_3$ | $CH_3$ | $CH_3$ |
| 4.905 | H | H | H | 1 | H | H | H | H | C=$NOCH_3$ | $CH_3$ | $CH_3$ |
| 4.906 | H | H | H | 2 | H | H | H | H | C=$NOCH_3$ | $CH_3$ | $CH_3$ |
| 4.907 | H | H | H | 0 | H | H | H | H | C=$NOC_2H_5$ | $CH_3$ | $CH_3$ |

TABLE 4-continued

Compounds of the formula

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.908 | H | H | H | 1 | H | H | H | H | C=NOC$_2$H$_5$ | CH$_3$ | CH$_3$ |
| 4.909 | H | H | H | 2 | H | H | H | H | C=NOC$_2$H$_5$ | CH$_3$ | CH$_3$ |
| 4.910 | H | H | H | 0 | H | H | H | H | C=NOiPr | CH$_3$ | CH$_3$ |
| 4.911 | H | H | H | 1 | H | H | H | H | C=NOiPr | CH$_3$ | CH$_3$ |
| 4.912 | H | H | H | 2 | H | H | H | H | C=NOiPr | CH$_3$ | CH$_3$ |
| 4.913 | H | H | H | 0 | H | H | H | H | C=NOCH$_2$CH=CHCl | CH$_3$ | CH$_3$ |
| 4.914 | H | H | H | 1 | H | H | H | H | C=NOCH$_2$CH=CHCl | CH$_3$ | CH$_3$ |
| 4.915 | H | H | H | 2 | H | H | H | H | C=NOCH$_2$CH=CHCl | CH$_3$ | CH$_3$ |
| 4.916 | H | H | H | 0 | H | H | H | H | C=NOCH$_2$C$_6$H$_5$ | CH$_3$ | CH$_3$ |
| 4.917 | H | H | H | 1 | H | H | H | H | C=NOCH$_2$C$_6$H$_5$ | CH$_3$ | CH$_3$ |
| 4.918 | H | H | H | 2 | H | H | H | H | C=NOCH$_2$C$_6$H$_5$ | CH$_3$ | CH$_3$ |
| 4.919 | H | H | H | 0 | H | H | H | H | C(CH$_3$)$_2$ | CH$_3$ | CH$_3$ |
| 4.920 | H | H | H | 1 | H | H | H | H | C(CH$_3$)$_2$ | CH$_3$ | CH$_3$ |
| 4.921 | H | H | H | 2 | H | H | H | H | C(CH$_3$)$_2$ | CH$_3$ | CH$_3$ |
| 4.922 | H | H | H | 0 | H | H | H | H | dioxane-spiro | CH$_3$ | CH$_3$ |
| 4.923 | H | H | H | 1 | H | H | H | H | dioxane-spiro | CH$_3$ | CH$_3$ |
| 4.924 | H | H | H | 2 | H | H | H | H | dioxane-spiro | CH$_3$ | CH$_3$ |
| 4.925 | H | H | H | 0 | H | H | H | H | dimethyl-dioxane-spiro | CH$_3$ | CH$_3$ |
| 4.926 | H | H | H | 1 | H | H | H | H | dimethyl-dioxane-spiro | CH$_3$ | CH$_3$ |
| 4.927 | H | H | H | 2 | H | H | H | H | dimethyl-dioxane-spiro | CH$_3$ | CH$_3$ |
| 4.928 | H | H | H | 0 | H | H | H | H | C=N—CH$_3$ | CH$_3$ | CH$_3$ |
| 4.929 | H | H | H | 1 | H | H | H | H | C=N—CH$_3$ | CH$_3$ | CH$_3$ |
| 4.930 | H | H | H | 2 | H | H | H | H | C=N—CH$_3$ | CH$_3$ | CH$_3$ |
| 4.931 | H | H | H | 0 | H | H | H | H | C=NC$_2$H$_5$ | CH$_3$ | CH$_3$ |
| 4.932 | H | H | H | 1 | H | H | H | H | C=NC$_2$H$_5$ | CH$_3$ | CH$_3$ |
| 4.933 | H | H | H | 2 | H | H | H | H | C=NC$_2$H$_5$ | CH$_3$ | CH$_3$ |
| 4.934 | H | H | H | 0 | H | H | H | H | CH—NHCH$_3$ | CH$_3$ | CH$_3$ |
| 4.935 | H | H | H | 1 | H | H | H | H | CH—NHCH$_3$ | CH$_3$ | CH$_3$ |
| 4.936 | H | H | H | 2 | H | H | H | H | CH—NHCH$_3$ | CH$_3$ | CH$_3$ |
| 4.937 | H | H | H | 0 | H | H | H | H | CH—NHC$_2$H$_5$ | CH$_3$ | CH$_3$ |
| 4.938 | H | H | H | 1 | H | H | H | H | CH—NHC$_2$H$_5$ | CH$_3$ | CH$_3$ |
| 4.939 | H | H | H | 2 | H | H | H | H | CH—NHC$_2$H$_5$ | CH$_3$ | CH$_3$ |
| 4.940 | H | H | H | 0 | H | H | H | H | CH—N(CH$_3$)$_2$ | CH$_3$ | CH$_3$ |

TABLE 4-continued

Compounds of the formula

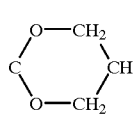

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.941 | H | H | H | 1 | H | H | H | H | CH—N(CH$_3$)$_2$ | CH$_3$ | CH$_3$ |
| 4.942 | H | H | H | 2 | H | H | H | H | CH—N(CH$_3$)$_2$ | CH$_3$ | CH$_3$ |
| 4.943 | H | H | H | 0 | H | H | H | H | CH—NHOC$_2$H$_5$ | CH$_3$ | CH$_3$ |
| 4.944 | H | H | H | 1 | H | H | H | H | CH—NHOC$_2$H$_5$ | CH$_3$ | CH$_3$ |
| 4.945 | H | H | H | 2 | H | H | H | H | CH—NHOC$_2$H$_5$ | CH$_3$ | CH$_3$ |
| 4.946 | H | H | H | 0 | H | H | H | H | CH—N(CH$_3$)OC$_2$H$_5$ | CH$_3$ | CH$_3$ |
| 4.947 | H | H | H | 1 | H | H | H | H | CH—N(CH$_3$)OC$_2$H$_5$ | CH$_3$ | CH$_3$ |
| 4.948 | H | H | H | 2 | H | H | H | H | CH—N(CH$_3$)OC$_2$H$_5$ | CH$_3$ | CH$_3$ |
| 4.949 | H | H | H | 0 | H | H | H | H | C═N—NH$_2$ | CH$_3$ | CH$_3$ |
| 4.950 | H | H | H | 1 | H | H | H | H | C═N—NH$_2$ | CH$_3$ | CH$_3$ |
| 4.951 | H | H | H | 2 | H | H | H | H | C═N—NH$_2$ | CH$_3$ | CH$_3$ |
| 4.952 | H | H | H | 0 | H | H | H | H | C═N—N(CH$_3$)$_2$ | CH$_3$ | CH$_3$ |
| 4.953 | H | H | H | 1 | H | H | H | H | C═N—N(CH$_3$)$_2$ | CH$_3$ | CH$_3$ |
| 4.954 | H | H | H | 2 | H | H | H | H | C═N—N(CH$_3$)$_2$ | CH$_3$ | CH$_3$ |
| 4.955 | H | H | H | 0 | H | H | H | H | CH—N(CH$_3$)OCH$_2$C$_6$H$_5$ | CH$_3$ | CH$_3$ |
| 4.956 | H | H | H | 1 | H | H | H | H | CH—N(CH$_3$)OCH$_2$C$_6$H$_5$ | CH$_3$ | CH$_3$ |
| 4.957 | H | H | H | 2 | H | H | H | H | CH—N(CH$_3$)OCH$_2$C$_6$H$_5$ | CH$_3$ | CH$_3$ |
| 4.958 | H | H | H | 0 | H | H | H | H | C(CH$_3$)—OCH$_3$ | CH$_3$ | CH$_3$ |
| 4.959 | H | H | H | 1 | H | H | H | H | C(CH$_3$)—OCH$_3$ | CH$_3$ | CH$_3$ |
| 4.960 | H | H | H | 2 | H | H | H | H | C(CH$_3$)—OCH$_3$ | CH$_3$ | CH$_3$ |
| 4.961 | H | H | H | 0 | H | H | H | H | O | CH$_3$ | CH$_3$ |
| 4.962 | H | H | H | 1 | H | H | H | H | O | CH$_3$ | CH$_3$ |
| 4.963 | H | H | H | 2 | H | H | H | H | O | CH$_3$ | CH$_3$ |
| 4.964 | CH$_3$ | H | H | 0 | H | H | H | H | C═O | CH$_3$ | CH$_3$ |
| 4.965 | CH$_3$ | H | H | 1 | H | H | H | H | C═O | CH$_3$ | CH$_3$ |
| 4.966 | CH$_3$ | H | H | 2 | H | H | H | H | C═O | CH$_3$ | CH$_3$ |
| 4.967 | CH$_3$ | H | H | 0 | H | H | H | H | CHOCH$_3$ | CH$_3$ | CH$_3$ |
| 4.968 | CH$_3$ | H | H | 1 | H | H | H | H | CHOCH$_3$ | CH$_3$ | CH$_3$ |
| 4.969 | CH$_3$ | H | H | 2 | H | H | H | H | CHOCH$_3$ | CH$_3$ | CH$_3$ |
| 4.970 | CH$_3$ | H | H | 0 | H | H | H | H | CHOC$_2$H$_5$ | CH$_3$ | CH$_3$ |
| 4.971 | CH$_3$ | H | H | 1 | H | H | H | H | CHOC$_2$H$_5$ | CH$_3$ | CH$_3$ |
| 4.972 | CH$_3$ | H | H | 2 | H | H | H | H | CHOC$_2$H$_5$ | CH$_3$ | CH$_3$ |
| 4.973 | CH$_3$ | H | H | 0 | H | H | H | H | CHOiPr | CH$_3$ | CH$_3$ |
| 4.974 | CH$_3$ | H | H | 1 | H | H | H | H | CHOiPr | CH$_3$ | CH$_3$ |
| 4.975 | CH$_3$ | H | H | 2 | H | H | H | H | CHOiPr | CH$_3$ | CH$_3$ |
| 4.976 | CH$_3$ | H | H | 0 | H | H | H | H | C═NOCH$_3$ | CH$_3$ | CH$_3$ |
| 4.977 | CH$_3$ | H | H | 1 | H | H | H | H | C═NOCH$_3$ | CH$_3$ | CH$_3$ |
| 4.978 | CH$_3$ | H | H | 2 | H | H | H | H | C═NOCH$_3$ | CH$_3$ | CH$_3$ |
| 4.979 | CH$_3$ | H | H | 0 | H | H | H | H | C═NOC$_2$H$_5$ | CH$_3$ | CH$_3$ |
| 4.980 | CH$_3$ | H | H | 1 | H | H | H | H | C═NOC$_2$H$_5$ | CH$_3$ | CH$_3$ |
| 4.981 | CH$_3$ | H | H | 2 | H | H | H | H | C═NOC$_2$H$_5$ | CH$_3$ | CH$_3$ |
| 4.982 | CH$_3$ | H | H | 0 | H | H | H | H | C═NOiPr | CH$_3$ | CH$_3$ |
| 4.983 | CH$_3$ | H | H | 1 | H | H | H | H | C═NOiPr | CH$_3$ | CH$_3$ |
| 4.984 | CH$_3$ | H | H | 2 | H | H | H | H | C═NOiPr | CH$_3$ | CH$_3$ |
| 4.985 | CH$_3$ | H | H | 0 | H | H | H | H | C═NOCH$_2$CH═CHCl | CH$_3$ | CH$_3$ |
| 4.986 | CH$_3$ | H | H | 1 | H | H | H | H | C═NOCH$_2$CH═CHCl | CH$_3$ | CH$_3$ |
| 4.987 | CH$_3$ | H | H | 2 | H | H | H | H | C═NOCH$_2$CH═CHCl | CH$_3$ | CH$_3$ |
| 4.988 | CH$_3$ | H | H | 0 | H | H | H | H | C═NOCH$_2$C$_6$H$_5$ | CH$_3$ | CH$_3$ |
| 4.989 | CH$_3$ | H | H | 1 | H | H | H | H | C═NOCH$_2$C$_6$H$_5$ | CH$_3$ | CH$_3$ |
| 4.990 | CH$_3$ | H | H | 2 | H | H | H | H | C═NOCH$_2$C$_6$H$_5$ | CH$_3$ | CH$_3$ |
| 4.991 | CH$_3$ | H | H | 0 | H | H | H | H | C(CH$_3$)$_2$ | CH$_3$ | CH$_3$ |
| 4.992 | CH$_3$ | H | H | 1 | H | H | H | H | C(CH$_3$)$_2$ | CH$_3$ | CH$_3$ |
| 4.993 | CH$_3$ | H | H | 2 | H | H | H | H | C(CH$_3$)$_2$ | CH$_3$ | CH$_3$ |
| 4.994 | CH$_3$ | H | H | 0 | H | H | H | H | (dioxane ring) | CH$_3$ | CH$_3$ |

TABLE 4-continued

Compounds of the formula

[Structure: cyclohexanedione with OH, carbonyl linker to benzene bearing M, L substituents and fused thiazine-type ring containing S(O)$_n$, R$^{21}$, R$^{22}$, R$^{13}$, R$^{12}$, Y]

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.995 | CH$_3$ | H | H | 1 | H | H | H | H | 1,3-dioxane-2,2-diyl (O—CH$_2$—CH$_2$—CH$_2$—O) | CH$_3$ | CH$_3$ |
| 4.996 | CH$_3$ | H | H | 2 | H | H | H | H | 1,3-dioxane-2,2-diyl | CH$_3$ | CH$_3$ |
| 4.997 | CH$_3$ | H | H | 0 | H | H | H | H | 5,5-dimethyl-1,3-dioxane-2,2-diyl | CH$_3$ | CH$_3$ |
| 4.998 | CH$_3$ | H | H | 1 | H | H | H | H | 5,5-dimethyl-1,3-dioxane-2,2-diyl | CH$_3$ | CH$_3$ |
| 4.999 | CH$_3$ | H | H | 2 | H | H | H | H | 5,5-dimethyl-1,3-dioxane-2,2-diyl | CH$_3$ | CH$_3$ |
| 4.1000 | CH$_3$ | H | H | 0 | H | H | H | H | C=N—CH$_3$ | CH$_3$ | CH$_3$ |
| 4.1001 | CH$_3$ | H | H | 1 | H | H | H | H | C=N—CH$_3$ | CH$_3$ | CH$_3$ |
| 4.1002 | CH$_3$ | H | H | 2 | H | H | H | H | C=N—CH$_3$ | CH$_3$ | CH$_3$ |
| 4.1003 | CH$_3$ | H | H | 0 | H | H | H | H | C=NC$_2$H$_5$ | CH$_3$ | CH$_3$ |
| 4.1004 | CH$_3$ | H | H | 1 | H | H | H | H | C=NC$_2$H$_5$ | CH$_3$ | CH$_3$ |
| 4.1005 | CH$_3$ | H | H | 2 | H | H | H | H | C=NC$_2$H$_5$ | CH$_3$ | CH$_3$ |
| 4.1006 | CH$_3$ | H | H | 0 | H | H | H | H | CH—NHCH$_3$ | CH$_3$ | CH$_3$ |
| 4.1007 | CH$_3$ | H | H | 1 | H | H | H | H | CH—NHCH$_3$ | CH$_3$ | CH$_3$ |
| 4.1008 | CH$_3$ | H | H | 2 | H | H | H | H | CH—NHCH$_3$ | CH$_3$ | CH$_3$ |
| 4.1009 | CH$_3$ | H | H | 0 | H | H | H | H | CH—NHC$_2$H$_5$ | CH$_3$ | CH$_3$ |
| 4.1010 | CH$_3$ | H | H | 1 | H | H | H | H | CH—NHC$_2$H$_5$ | CH$_3$ | CH$_3$ |
| 4.1011 | CH$_3$ | H | H | 2 | H | H | H | H | CH—NHC$_2$H$_5$ | CH$_3$ | CH$_3$ |
| 4.1012 | CH$_3$ | H | H | 0 | H | H | H | H | CH—N(CH$_3$)$_2$ | CH$_3$ | CH$_3$ |
| 4.1013 | CH$_3$ | H | H | 1 | H | H | H | H | CH—N(CH$_3$)$_2$ | CH$_3$ | CH$_3$ |
| 4.1014 | CH$_3$ | H | H | 2 | H | H | H | H | CH—N(CH$_3$)$_2$ | CH$_3$ | CH$_3$ |
| 4.1015 | CH$_3$ | H | H | 0 | H | H | H | H | CH—NHOC$_2$H$_5$ | CH$_3$ | CH$_3$ |
| 4.1016 | CH$_3$ | H | H | 1 | H | H | H | H | CH—NHOC$_2$H$_5$ | CH$_3$ | CH$_3$ |
| 4.1017 | CH$_3$ | H | H | 2 | H | H | H | H | CH—NHOC$_2$H$_5$ | CH$_3$ | CH$_3$ |
| 4.1018 | CH$_3$ | H | H | 0 | H | H | H | H | CH—N(CH$_3$)OC$_2$H$_5$ | CH$_3$ | CH$_3$ |
| 4.1019 | CH$_3$ | H | H | 1 | H | H | H | H | CH—N(CH$_3$)OC$_2$H$_5$ | CH$_3$ | CH$_3$ |
| 4.1020 | CH$_3$ | H | H | 2 | H | H | H | H | CH—N(CH$_3$)OC$_2$H$_5$ | CH$_3$ | CH$_3$ |
| 4.1021 | CH$_3$ | H | H | 0 | H | H | H | H | C=N—NH$_2$ | CH$_3$ | CH$_3$ |
| 4.1022 | CH$_3$ | H | H | 1 | H | H | H | H | C=N—NH$_2$ | CH$_3$ | CH$_3$ |
| 4.1023 | CH$_3$ | H | H | 2 | H | H | H | H | C=N—NH$_2$ | CH$_3$ | CH$_3$ |
| 4.1024 | CH$_3$ | H | H | 0 | H | H | H | H | C=N—N(CH$_3$)$_2$ | CH$_3$ | CH$_3$ |
| 4.1025 | CH$_3$ | H | H | 1 | H | H | H | H | C=N—N(CH$_3$)$_2$ | CH$_3$ | CH$_3$ |
| 4.1026 | CH$_3$ | H | H | 2 | H | H | H | H | C=N—N(CH$_3$)$_2$ | CH$_3$ | CH$_3$ |
| 4.1027 | CH$_3$ | H | H | 0 | H | H | H | H | CH—N(CH$_3$)OCH$_2$C$_6$H$_5$ | CH$_3$ | CH$_3$ |
| 4.1028 | CH$_3$ | H | H | 1 | H | H | H | H | CH—N(CH$_3$)OCH$_2$C$_6$H$_5$ | CH$_3$ | CH$_3$ |
| 4.1029 | CH$_3$ | H | H | 2 | H | H | H | H | CH—N(CH$_3$)OCH$_2$C$_6$H$_5$ | CH$_3$ | CH$_3$ |
| 4.1030 | CH$_3$ | H | H | 0 | H | H | H | H | C(CH$_3$)—OCH$_3$ | CH$_3$ | CH$_3$ |
| 4.1031 | CH$_3$ | H | H | 1 | H | H | H | H | C(CH$_3$)—OCH$_3$ | CH$_3$ | CH$_3$ |
| 4.1032 | CH$_3$ | H | H | 2 | H | H | H | H | C(CH$_3$)—OCH$_3$ | CH$_3$ | CH$_3$ |
| 4.1033 | CH$_3$ | H | H | 0 | H | H | H | H | O | CH$_3$ | CH$_3$ |

TABLE 4-continued

Compounds of the formula

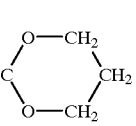

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.1034 | $CH_3$ | H | H | 1 | H | H | H | H | O | $CH_3$ | $CH_3$ |
| 4.1035 | $CH_3$ | H | H | 2 | H | H | H | H | O | $CH_3$ | $CH_3$ |
| 4.1036 | $CH_3$ | $CH_3$ | H | 0 | H | H | H | H | C=O | $CH_3$ | $CH_3$ |
| 4.1037 | $CH_3$ | $CH_3$ | H | 1 | H | H | H | H | C=O | $CH_3$ | $CH_3$ |
| 4.1038 | $CH_3$ | $CH_3$ | H | 2 | H | H | H | H | C=O | $CH_3$ | $CH_3$ |
| 4.1039 | $CH_3$ | $CH_3$ | H | 0 | H | H | H | H | $CHOCH_3$ | $CH_3$ | $CH_3$ |
| 4.1040 | $CH_3$ | $CH_3$ | H | 1 | H | H | H | H | $CHOCH_3$ | $CH_3$ | $CH_3$ |
| 4.1041 | $CH_3$ | $CH_3$ | H | 2 | H | H | H | H | $CHOCH_3$ | $CH_3$ | $CH_3$ |
| 4.1042 | $CH_3$ | $CH_3$ | H | 0 | H | H | H | H | $CHOC_2H_5$ | $CH_3$ | $CH_3$ |
| 4.1043 | $CH_3$ | $CH_3$ | H | 1 | H | H | H | H | $CHOC_2H_5$ | $CH_3$ | $CH_3$ |
| 4.1044 | $CH_3$ | $CH_3$ | H | 2 | H | H | H | H | $CHOC_2H_5$ | $CH_3$ | $CH_3$ |
| 4.1045 | $CH_3$ | $CH_3$ | H | 0 | H | H | H | H | CHOiPr | $CH_3$ | $CH_3$ |
| 4.1046 | $CH_3$ | $CH_3$ | H | 1 | H | H | H | H | CHOiPr | $CH_3$ | $CH_3$ |
| 4.1047 | $CH_3$ | $CH_3$ | H | 2 | H | H | H | H | CHOiPr | $CH_3$ | $CH_3$ |
| 4.1048 | $CH_3$ | $CH_3$ | H | 0 | H | H | H | H | $C=NOCH_3$ | $CH_3$ | $CH_3$ |
| 4.1049 | $CH_3$ | $CH_3$ | H | 1 | H | H | H | H | $C=NOCH_3$ | $CH_3$ | $CH_3$ |
| 4.1050 | $CH_3$ | $CH_3$ | H | 2 | H | H | H | H | $C=NOCH_3$ | $CH_3$ | $CH_3$ |
| 4.1051 | $CH_3$ | $CH_3$ | H | 0 | H | H | H | H | $C=NOC_2H_5$ | $CH_3$ | $CH_3$ |
| 4.1052 | $CH_3$ | $CH_3$ | H | 1 | H | H | H | H | $C=NOC_2H_5$ | $CH_3$ | $CH_3$ |
| 4.1053 | $CH_3$ | $CH_3$ | H | 2 | H | H | H | H | $C=NOC_2H_5$ | $CH_3$ | $CH_3$ |
| 4.1054 | $CH_3$ | $CH_3$ | H | 0 | H | H | H | H | C=NOiPr | $CH_3$ | $CH_3$ |
| 4.1055 | $CH_3$ | $CH_3$ | H | 1 | H | H | H | H | C=NOiPr | $CH_3$ | $CH_3$ |
| 4.1056 | $CH_3$ | $CH_3$ | H | 2 | H | H | H | H | C=NOiPr | $CH_3$ | $CH_3$ |
| 4.1057 | $CH_3$ | $CH_3$ | H | 0 | H | H | H | H | $C=NOCH_2CH=CHCl$ | $CH_3$ | $CH_3$ |
| 4.1058 | $CH_3$ | $CH_3$ | H | 1 | H | H | H | H | $C=NOCH_2CH=CHCl$ | $CH_3$ | $CH_3$ |
| 4.1059 | $CH_3$ | $CH_3$ | H | 2 | H | H | H | H | $C=NOCH_2CH=CHCl$ | $CH_3$ | $CH_3$ |
| 4.1060 | $CH_3$ | $CH_3$ | H | 1 | H | H | H | H | $C=NOCH_2C_6H_5$ | $CH_3$ | $CH_3$ |
| 4.1061 | $CH_3$ | $CH_3$ | H | 0 | H | H | H | H | $C=NOCH_2C_6H_5$ | $CH_3$ | $CH_3$ |
| 4.1062 | $CH_3$ | $CH_3$ | H | 1 | H | H | H | H | $C=NOCH_2C_6H_5$ | $CH_3$ | $CH_3$ |
| 4.1063 | $CH_3$ | $CH_3$ | H | 0 | H | H | H | H | $C(CH_3)_2$ | $CH_3$ | $CH_3$ |
| 4.1064 | $CH_3$ | $CH_3$ | H | 1 | H | H | H | H | $C(CH_3)_2$ | $CH_3$ | $CH_3$ |
| 4.1065 | $CH_3$ | $CH_3$ | H | 2 | H | H | H | H | $C(CH_3)_2$ | $CH_3$ | $CH_3$ |
| 4.1066 | $CH_3$ | $CH_3$ | H | 0 | H | H | H | H | 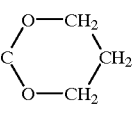 | $CH_3$ | $CH_3$ |
| 4.1067 | $CH_3$ | $CH_3$ | H | 1 | H | H | H | H | 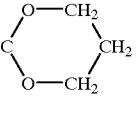 | $CH_3$ | $CH_3$ |
| 4.1068 | $CH_3$ | $CH_3$ | H | 2 | H | H | H | H | 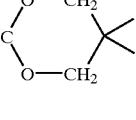 | $CH_3$ | $CH_3$ |
| 4.1069 | $CH_3$ | $CH_3$ | H | 0 | H | H | H | H | 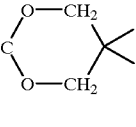 | $CH_3$ | $CH_3$ |
| 4.1070 | $CH_3$ | $CH_3$ | H | 1 | H | H | H | H | 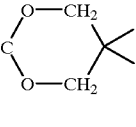 | $CH_3$ | $CH_3$ |

TABLE 4-continued

Compounds of the formula

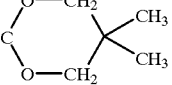

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.1071 | $CH_3$ | $CH_3$ | H | 2 | H | H | H | H | (dioxane-CH₃,CH₃ group) | $CH_3$ | $CH_3$ |
| 4.1072 | $CH_3$ | $CH_3$ | H | 0 | H | H | H | H | C=N—$CH_3$ | $CH_3$ | $CH_3$ |
| 4.1073 | $CH_3$ | $CH_3$ | H | 1 | H | H | H | H | C=N—$CH_3$ | $CH_3$ | $CH_3$ |
| 4.1074 | $CH_3$ | $CH_3$ | H | 2 | H | H | H | H | C=N—$CH_3$ | $CH_3$ | $CH_3$ |
| 4.1075 | $CH_3$ | $CH_3$ | H | 0 | H | H | H | H | C=N$C_2H_5$ | $CH_3$ | $CH_3$ |
| 4.1076 | $CH_3$ | $CH_3$ | H | 1 | H | H | H | H | C=N$C_2H_5$ | $CH_3$ | $CH_3$ |
| 4.1077 | $CH_3$ | $CH_3$ | H | 2 | H | H | H | H | C=N$C_2H_5$ | $CH_3$ | $CH_3$ |
| 4.1078 | $CH_3$ | $CH_3$ | H | 0 | H | H | H | H | CH—NH$CH_3$ | $CH_3$ | $CH_3$ |
| 4.1079 | $CH_3$ | $CH_3$ | H | 1 | H | H | H | H | CH—NH$CH_3$ | $CH_3$ | $CH_3$ |
| 4.1080 | $CH_3$ | $CH_3$ | H | 2 | H | H | H | H | CH—NH$CH_3$ | $CH_3$ | $CH_3$ |
| 4.1081 | $CH_3$ | $CH_3$ | H | 0 | H | H | H | H | CH—NH$C_2H_5$ | $CH_3$ | $CH_3$ |
| 4.1082 | $CH_3$ | $CH_3$ | H | 1 | H | H | H | H | CH—NH$C_2H_5$ | $CH_3$ | $CH_3$ |
| 4.1083 | $CH_3$ | $CH_3$ | H | 2 | H | H | H | H | CH—NH$C_2H_5$ | $CH_3$ | $CH_3$ |
| 4.1084 | $CH_3$ | $CH_3$ | H | 0 | H | H | H | H | CH—N$(CH_3)_2$ | $CH_3$ | $CH_3$ |
| 4.1085 | $CH_3$ | $CH_3$ | H | 1 | H | H | H | H | CH—N$(CH_3)_2$ | $CH_3$ | $CH_3$ |
| 4.1086 | $CH_3$ | $CH_3$ | H | 2 | H | H | H | H | CH—N$(CH_3)_2$ | $CH_3$ | $CH_3$ |
| 4.1087 | $CH_3$ | $CH_3$ | H | 0 | H | H | H | H | CH—NHO$C_2H_5$ | $CH_3$ | $CH_3$ |
| 4.1088 | $CH_3$ | $CH_3$ | H | 1 | H | H | H | H | CH—NHO$C_2H_5$ | $CH_3$ | $CH_3$ |
| 4.1089 | $CH_3$ | $CH_3$ | H | 2 | H | H | H | H | CH—NHO$C_2H_5$ | $CH_3$ | $CH_3$ |
| 4.1090 | $CH_3$ | $CH_3$ | H | 0 | H | H | H | H | CH—N$(CH_3)$O$C_2H_5$ | $CH_3$ | $CH_3$ |
| 4.1091 | $CH_3$ | $CH_3$ | H | 1 | H | H | H | H | CH—N$(CH_3)$O$C_2H_5$ | $CH_3$ | $CH_3$ |
| 4.1092 | $CH_3$ | $CH_3$ | H | 2 | H | H | H | H | CH—N$(CH_3)$O$C_2H_5$ | $CH_3$ | $CH_3$ |
| 4.1093 | $CH_3$ | $CH_3$ | H | 0 | H | H | H | H | C=N—$NH_2$ | $CH_3$ | $CH_3$ |
| 4.1094 | $CH_3$ | $CH_3$ | H | 1 | H | H | H | H | C=N—$NH_2$ | $CH_3$ | $CH_3$ |
| 4.1095 | $CH_3$ | $CH_3$ | H | 2 | H | H | H | H | C=N—$NH_2$ | $CH_3$ | $CH_3$ |
| 4.1096 | $CH_3$ | $CH_3$ | H | 0 | H | H | H | H | C=N—N$(CH_3)_2$ | $CH_3$ | $CH_3$ |
| 4.1097 | $CH_3$ | $CH_3$ | H | 1 | H | H | H | H | C=N—N$(CH_3)_2$ | $CH_3$ | $CH_3$ |
| 4.1098 | $CH_3$ | $CH_3$ | H | 2 | H | H | H | H | C=N—N$(CH_3)_2$ | $CH_3$ | $CH_3$ |
| 4.1099 | $CH_3$ | $CH_3$ | H | 0 | H | H | H | H | CH—N$(CH_3)$OCH$_2C_6H_5$ | $CH_3$ | $CH_3$ |
| 4.1100 | $CH_3$ | $CH_3$ | H | 1 | H | H | H | H | CH—N$(CH_3)$OCH$_2C_6H_5$ | $CH_3$ | $CH_3$ |
| 4.1101 | $CH_3$ | $CH_3$ | H | 2 | H | H | H | H | CH—N$(CH_3)$OCH$_2C_6H_5$ | $CH_3$ | $CH_3$ |
| 4.1102 | $CH_3$ | $CH_3$ | H | 0 | H | H | H | H | C$(CH_3)$—O$CH_3$ | $CH_3$ | $CH_3$ |
| 4.1103 | $CH_3$ | $CH_3$ | H | 1 | H | H | H | H | C$(CH_3)$—O$CH_3$ | $CH_3$ | $CH_3$ |
| 4.1104 | $CH_3$ | $CH_3$ | H | 2 | H | H | H | H | C$(CH_3)$—O$CH_3$ | $CH_3$ | $CH_3$ |
| 4.1105 | $CH_3$ | $CH_3$ | H | 0 | H | H | H | H | O | $CH_3$ | $CH_3$ |
| 4.1106 | $CH_3$ | $CH_3$ | H | 1 | H | H | H | H | O | $CH_3$ | $CH_3$ |
| 4.1107 | $CH_3$ | $CH_3$ | H | 2 | H | H | H | H | O | $CH_3$ | $CH_3$ |
| 4.1108 | H | H | H | 0 | H | H | H | H | C=O | Cl | Cl |
| 4.1109 | H | H | H | 1 | H | H | H | H | C=O | Cl | Cl |
| 4.1110 | H | H | H | 2 | H | H | H | H | C=O | Cl | Cl |
| 4.1111 | H | H | H | 0 | H | H | H | H | CHO$CH_3$ | Cl | Cl |
| 4.1112 | H | H | H | 1 | H | H | H | H | CHO$CH_3$ | Cl | Cl |
| 4.1113 | H | H | H | 2 | H | H | H | H | CHO$CH_3$ | Cl | Cl |
| 4.1114 | H | H | H | 0 | H | H | H | H | CHO$C_2H_5$ | Cl | Cl |
| 4.1115 | H | H | H | 1 | H | H | H | H | CHO$C_2H_5$ | Cl | Cl |
| 4.1116 | H | H | H | 2 | H | H | H | H | CHO$C_2H_5$ | Cl | Cl |
| 4.1117 | H | H | H | 0 | H | H | H | H | CHOiPr | Cl | Cl |
| 4.1118 | H | H | H | 1 | H | H | H | H | CHOiPr | Cl | Cl |
| 4.1119 | H | H | H | 2 | H | H | H | H | CHOiPr | Cl | Cl |
| 4.1120 | H | H | H | 0 | H | H | H | H | C=NO$CH_3$ | Cl | Cl |
| 4.1121 | H | H | H | 1 | H | H | H | H | C=NO$CH_3$ | Cl | Cl |
| 4.1122 | H | H | H | 2 | H | H | H | H | C=NO$CH_3$ | Cl | Cl |
| 4.1123 | H | H | H | 0 | H | H | H | H | C=NO$C_2H_5$ | Cl | Cl |
| 4.1124 | H | H | H | 1 | H | H | H | H | C=NO$C_2H_5$ | Cl | Cl |
| 4.1125 | H | H | H | 2 | H | H | H | H | C=NO$C_2H_5$ | Cl | Cl |
| 4.1126 | H | H | H | 0 | H | H | H | H | C=NOiPr | Cl | Cl |
| 4.1127 | H | H | H | 1 | H | H | H | H | C=NOiPr | Cl | Cl |
| 4.1128 | H | H | H | 2 | H | H | H | H | C=NOiPr | Cl | Cl |
| 4.1129 | H | H | H | 0 | H | H | H | H | C=NOCH$_2$CH=CHCl | Cl | Cl |

TABLE 4-continued

Compounds of the formula

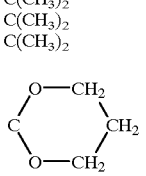

| No. | R^17 | R^18 | R^19 | n | R^12 | R^13 | R^21 | R^22 | Y | L | M |
|---|---|---|---|---|---|---|---|---|---|---|---|
| 4.1130 | H | H | H | 1 | H | H | H | H | C=NOCH$_2$CH=CHCl | Cl | Cl |
| 4.1131 | H | H | H | 2 | H | H | H | H | C=NOCH$_2$CH=CHCl | Cl | Cl |
| 4.1132 | H | H | H | 0 | H | H | H | H | C=NOCH$_2$C$_6$H$_5$ | Cl | Cl |
| 4.1133 | H | H | H | 1 | H | H | H | H | C=NOCH$_2$C$_6$H$_5$ | Cl | Cl |
| 4.1134 | H | H | H | 2 | H | H | H | H | C=NOCH$_2$C$_6$H$_5$ | Cl | Cl |
| 4.1135 | H | H | H | 0 | H | H | H | H | C(CH$_3$)$_2$ | Cl | Cl |
| 4.1136 | H | H | H | 1 | H | H | H | H | C(CH$_3$)$_2$ | Cl | Cl |
| 4.1137 | H | H | H | 2 | H | H | H | H | C(CH$_3$)$_2$ | Cl | Cl |
| 4.1138 | H | H | H | 0 | H | H | H | H | 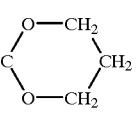 | Cl | Cl |
| 4.1139 | H | H | H | 1 | H | H | H | H | 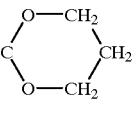 | Cl | Cl |
| 4.1140 | H | H | H | 2 | H | H | H | H | 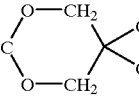 | Cl | Cl |
| 4.1141 | H | H | H | 0 | H | H | H | H | 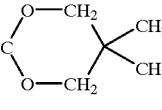 | Cl | Cl |
| 4.1142 | H | H | H | 1 | H | H | H | H | 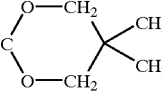 | Cl | Cl |
| 4.1143 | H | H | H | 2 | H | H | H | H |  | Cl | Cl |
| 4.1144 | H | H | H | 0 | H | H | H | H | C=N—CH$_3$ | Cl | Cl |
| 4.1145 | H | H | H | 1 | H | H | H | H | C=N—CH$_3$ | Cl | Cl |
| 4.1146 | H | H | H | 2 | H | H | H | H | C=N—CH$_3$ | Cl | Cl |
| 4.1147 | H | H | H | 0 | H | H | H | H | C=NC$_2$H$_5$ | Cl | Cl |
| 4.1148 | H | H | H | 1 | H | H | H | H | C=NC$_2$H$_5$ | Cl | Cl |
| 4.1149 | H | H | H | 2 | H | H | H | H | C=NC$_2$H$_5$ | Cl | Cl |
| 4.1150 | H | H | H | 0 | H | H | H | H | CH—NHCH$_3$ | Cl | Cl |
| 4.1151 | H | H | H | 1 | H | H | H | H | CH—NHCH$_3$ | Cl | Cl |
| 4.1152 | H | H | H | 2 | H | H | H | H | CH—NHCH$_3$ | Cl | Cl |
| 4.1153 | H | H | H | 0 | H | H | H | H | CH—NHC$_2$H$_5$ | Cl | Cl |
| 4.1154 | H | H | H | 1 | H | H | H | H | CH—NHC$_2$H$_5$ | Cl | Cl |
| 4.1155 | H | H | H | 2 | H | H | H | H | CH—NHC$_2$H$_5$ | Cl | Cl |
| 4.1156 | H | H | H | 0 | H | H | H | H | CH—N(CH$_3$)$_2$ | Cl | Cl |
| 4.1157 | H | H | H | 1 | H | H | H | H | CH—N(CH$_3$)$_2$ | Cl | Cl |
| 4.1158 | H | H | H | 2 | H | H | H | H | CH—N(CH$_3$)$_2$ | Cl | Cl |
| 4.1159 | H | H | H | 0 | H | H | H | H | CH—NHOC$_2$H$_5$ | Cl | Cl |
| 4.1160 | H | H | H | 1 | H | H | H | H | CH—NHOC$_2$H$_5$ | Cl | Cl |
| 4.1161 | H | H | H | 2 | H | H | H | H | CH—NHOC$_2$H$_5$ | Cl | Cl |
| 4.1162 | H | H | H | 0 | H | H | H | H | CH—N(CH$_3$)OC$_2$H$_5$ | Cl | Cl |

TABLE 4-continued

Compounds of the formula

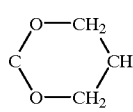

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.1163 | H | H | H | 1 | H | H | H | H | CH—N(CH$_3$)OC$_2$H$_5$ | Cl | Cl |
| 4.1164 | H | H | H | 2 | H | H | H | H | CH—N(CH$_3$)OC$_2$H$_5$ | Cl | Cl |
| 4.1165 | H | H | H | 0 | H | H | H | H | C=N—NH$_2$ | Cl | Cl |
| 4.1166 | H | H | H | 1 | H | H | H | H | C=N—NH$_2$ | Cl | Cl |
| 4.1167 | H | H | H | 2 | H | H | H | H | C=N—NH$_2$ | Cl | Cl |
| 4.1168 | H | H | H | 0 | H | H | H | H | C=N—N(CH$_3$)$_2$ | Cl | Cl |
| 4.1169 | H | H | H | 1 | H | H | H | H | C=N—N(CH$_3$)$_2$ | Cl | Cl |
| 4.1170 | H | H | H | 2 | H | H | H | H | C=N—N(CH$_3$)$_2$ | Cl | Cl |
| 4.1171 | H | H | H | 0 | H | H | H | H | CH—N(CH$_3$)OCH$_2$C$_6$H$_5$ | Cl | Cl |
| 4.1172 | H | H | H | 1 | H | H | H | H | CH—N(CH$_3$)OCH$_2$C$_6$H$_5$ | Cl | Cl |
| 4.1173 | H | H | H | 2 | H | H | H | H | CH—N(CH$_3$)OCH$_2$C$_6$H$_5$ | Cl | Cl |
| 4.1174 | H | H | H | 0 | H | H | H | H | C(CH$_3$)—OCH$_3$ | Cl | Cl |
| 4.1175 | H | H | H | 1 | H | H | H | H | C(CH$_3$)—OCH$_3$ | Cl | Cl |
| 4.1176 | H | H | H | 2 | H | H | H | H | C(CH$_3$)—OCH$_3$ | Cl | Cl |
| 4.1177 | H | H | H | 0 | H | H | H | H | O | Cl | Cl |
| 4.1178 | H | H | H | 1 | H | H | H | H | O | Cl | Cl |
| 4.1179 | H | H | H | 2 | H | H | H | H | O | Cl | Cl |
| 4.1180 | CH$_3$ | H | H | 0 | H | H | H | H | C=O | Cl | Cl |
| 4.1181 | CH$_3$ | H | H | 1 | H | H | H | H | C=O | Cl | Cl |
| 4.1182 | CH$_3$ | H | H | 2 | H | H | H | H | C=O | Cl | Cl |
| 4.1183 | CH$_3$ | H | H | 0 | H | H | H | H | CHOCH$_3$ | Cl | Cl |
| 4.1184 | CH$_3$ | H | H | 1 | H | H | H | H | CHOCH$_3$ | Cl | Cl |
| 4.1185 | CH$_3$ | H | H | 2 | H | H | H | H | CHOCH$_3$ | Cl | Cl |
| 4.1186 | CH$_3$ | H | H | 0 | H | H | H | H | CHOC$_2$H$_5$ | Cl | Cl |
| 4.1187 | CH$_3$ | H | H | 1 | H | H | H | H | CHOC$_2$H$_5$ | Cl | Cl |
| 4.1188 | CH$_3$ | H | H | 2 | H | H | H | H | CHOC$_2$H$_5$ | Cl | Cl |
| 4.1189 | CH$_3$ | H | H | 0 | H | H | H | H | CHOiPr | Cl | Cl |
| 4.1190 | CH$_3$ | H | H | 1 | H | H | H | H | CHOiPr | Cl | Cl |
| 4.1191 | CH$_3$ | H | H | 2 | H | H | H | H | CHOiPr | Cl | Cl |
| 4.1192 | CH$_3$ | H | H | 0 | H | H | H | H | C=NOCH$_3$ | Cl | Cl |
| 4.1193 | CH$_3$ | H | H | 1 | H | H | H | H | C=NOCH$_3$ | Cl | Cl |
| 4.1194 | CH$_3$ | H | H | 2 | H | H | H | H | C=NOCH$_3$ | Cl | Cl |
| 4.1195 | CH$_3$ | H | H | 0 | H | H | H | H | C=NOC$_2$H$_5$ | Cl | Cl |
| 4.1196 | CH$_3$ | H | H | 1 | H | H | H | H | C=NOC$_2$H$_5$ | Cl | Cl |
| 4.1197 | CH$_3$ | H | H | 2 | H | H | H | H | C=NOC$_2$H$_5$ | Cl | Cl |
| 4.1198 | CH$_3$ | H | H | 0 | H | H | H | H | C=NOiPr | Cl | Cl |
| 4.1199 | CH$_3$ | H | H | 1 | H | H | H | H | C=NOiPr | Cl | Cl |
| 4.1200 | CH$_3$ | H | H | 2 | H | H | H | H | C=NOiPr | Cl | Cl |
| 4.1201 | CH$_3$ | H | H | 0 | H | H | H | H | C=NOCH$_2$CH=CHCl | Cl | Cl |
| 4.1202 | CH$_3$ | H | H | 1 | H | H | H | H | C=NOCH$_2$CH=CHCl | Cl | Cl |
| 4.1203 | CH$_3$ | H | H | 2 | H | H | H | H | C=NOCH$_2$CH=CHCl | Cl | Cl |
| 4.1204 | CH$_3$ | H | H | 0 | H | H | H | H | C=NOCH$_2$C$_6$H$_5$ | Cl | Cl |
| 4.1205 | CH$_3$ | H | H | 1 | H | H | H | H | C=NOCH$_2$C$_6$H$_5$ | Cl | Cl |
| 4.1206 | CH$_3$ | H | H | 2 | H | H | H | H | C=NOCH$_2$C$_6$H$_5$ | Cl | Cl |
| 4.1207 | CH$_3$ | H | H | 0 | H | H | H | H | C(CH$_3$)$_2$ | Cl | Cl |
| 4.1208 | CH$_3$ | H | H | 1 | H | H | H | H | C(CH$_3$)$_2$ | Cl | Cl |
| 4.1209 | CH$_3$ | H | H | 2 | H | H | H | H | C(CH$_3$)$_2$ | Cl | Cl |
| 4.1210 | CH$_3$ | H | H | 0 | H | H | H | H | 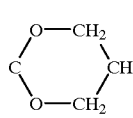 | Cl | Cl |
| 4.1211 | CH$_3$ | H | H | 1 | H | H | H | H | 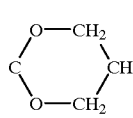 | Cl | Cl |

TABLE 4-continued

Compounds of the formula

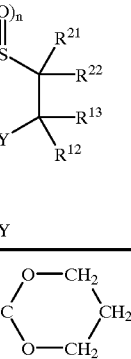

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.1212 | CH$_3$ | H | H | 2 | H | H | H | H | 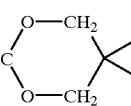 | Cl | Cl |
| 4.1213 | CH$_3$ | H | H | 0 | H | H | H | H | 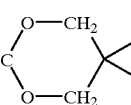 | Cl | Cl |
| 4.1214 | CH$_3$ | H | H | 1 | H | H | H | H | 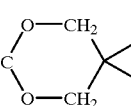 | Cl | Cl |
| 4.1215 | CH$_3$ | H | H | 2 | H | H | H | H | (same as above) | Cl | Cl |
| 4.1216 | CH$_3$ | H | H | 0 | H | H | H | H | C=N—CH$_3$ | Cl | Cl |
| 4.1217 | CH$_3$ | H | H | 1 | H | H | H | H | C=N—CH$_3$ | Cl | Cl |
| 4.1218 | CH$_3$ | H | H | 2 | H | H | H | H | C=N—CH$_3$ | Cl | Cl |
| 4.1219 | CH$_3$ | H | H | 0 | H | H | H | H | C=NC$_2$H$_5$ | Cl | Cl |
| 4.1220 | CH$_3$ | H | H | 1 | H | H | H | H | C=NC$_2$H$_5$ | Cl | Cl |
| 4.1221 | CH$_3$ | H | H | 2 | H | H | H | H | C=NC$_2$H$_5$ | Cl | Cl |
| 4.1222 | CH$_3$ | H | H | 0 | H | H | H | H | CH—NHCH$_3$ | Cl | Cl |
| 4.1223 | CH$_3$ | H | H | 1 | H | H | H | H | CH—NHCH$_3$ | Cl | Cl |
| 4.1224 | CH$_3$ | H | H | 2 | H | H | H | H | CH—NHCH$_3$ | Cl | Cl |
| 4.1225 | CH$_3$ | H | H | 0 | H | H | H | H | CH—NHC$_2$H$_5$ | Cl | Cl |
| 4.1226 | CH$_3$ | H | H | 1 | H | H | H | H | CH—NHC$_2$H$_5$ | Cl | Cl |
| 4.1227 | CH$_3$ | H | H | 2 | H | H | H | H | CH—NHC$_2$H$_5$ | Cl | Cl |
| 4.1228 | CH$_3$ | H | H | 0 | H | H | H | H | CH—N(CH$_3$)$_2$ | Cl | Cl |
| 4.1229 | CH$_3$ | H | H | 1 | H | H | H | H | CH—N(CH$_3$)$_2$ | Cl | Cl |
| 4.1230 | CH$_3$ | H | H | 2 | H | H | H | H | CH—N(CH$_3$)$_2$ | Cl | Cl |
| 4.1231 | CH$_3$ | H | H | 0 | H | H | H | H | CH—NHOC$_2$H$_5$ | Cl | Cl |
| 4.1232 | CH$_3$ | H | H | 1 | H | H | H | H | CH—NHOC$_2$H$_5$ | Cl | Cl |
| 4.1233 | CH$_3$ | H | H | 2 | H | H | H | H | CH—NHOC$_2$H$_5$ | Cl | Cl |
| 4.1234 | CH$_3$ | H | H | 0 | H | H | H | H | CH—N(CH$_3$)OC$_2$H$_5$ | Cl | Cl |
| 4.1235 | CH$_3$ | H | H | 1 | H | H | H | H | CH—N(CH$_3$)OC$_2$H$_5$ | Cl | Cl |
| 4.1236 | CH$_3$ | H | H | 2 | H | H | H | H | CH—N(CH$_3$)OC$_2$H$_5$ | Cl | Cl |
| 4.1237 | CH$_3$ | H | H | 0 | H | H | H | H | C=N—NH$_2$ | Cl | Cl |
| 4.1238 | CH$_3$ | H | H | 1 | H | H | H | H | C=N—NH$_2$ | Cl | Cl |
| 4.1239 | CH$_3$ | H | H | 2 | H | H | H | H | C=N—NH$_2$ | Cl | Cl |
| 4.1240 | CH$_3$ | H | H | 0 | H | H | H | H | C=N—N(CH$_3$)$_2$ | Cl | Cl |
| 4.1241 | CH$_3$ | H | H | 1 | H | H | H | H | C=N—N(CH$_3$)$_2$ | Cl | Cl |
| 4.1242 | CH$_3$ | H | H | 2 | H | H | H | H | C=N—N(CH$_3$)$_2$ | Cl | Cl |
| 4.1243 | CH$_3$ | H | H | 0 | H | H | H | H | CH—N(CH$_3$)OCH$_2$C$_6$H$_5$ | Cl | Cl |
| 4.1244 | CH$_3$ | H | H | 1 | H | H | H | H | CH—N(CH$_3$)OCH$_2$C$_6$H$_5$ | Cl | Cl |
| 4.1245 | CH$_3$ | H | H | 2 | H | H | H | H | CH—N(CH$_3$)OCH$_2$C$_6$H$_5$ | Cl | Cl |
| 4.1246 | CH$_3$ | H | H | 0 | H | H | H | H | C(CH$_3$)—OCH$_3$ | Cl | Cl |
| 4.1247 | CH$_3$ | H | H | 1 | H | H | H | H | C(CH$_3$)—OCH$_3$ | Cl | Cl |
| 4.1248 | CH$_3$ | H | H | 2 | H | H | H | H | C(CH$_3$)—OCH$_3$ | Cl | Cl |
| 4.1249 | CH$_3$ | H | H | 0 | H | H | H | H | O | Cl | Cl |
| 4.1250 | CH$_3$ | H | H | 1 | H | H | H | H | O | Cl | Cl |
| 4.1251 | CH$_3$ | H | H | 2 | H | H | H | H | O | Cl | Cl |
| 4.1252 | CH$_3$ | CH$_3$ | H | 0 | H | H | H | H | C=O | Cl | Cl |
| 4.1253 | CH$_3$ | CH$_3$ | H | 1 | H | H | H | H | C=O | Cl | Cl |
| 4.1254 | CH$_3$ | CH$_3$ | H | 2 | H | H | H | H | C=O | Cl | Cl |
| 4.1255 | CH$_3$ | CH$_3$ | H | 0 | H | H | H | H | CHOCH$_3$ | Cl | Cl |

TABLE 4-continued

Compounds of the formula

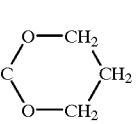

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.1256 | CH$_3$ | CH$_3$ | H | 1 | H | H | H | H | CHOCH$_3$ | Cl | Cl |
| 4.1257 | CH$_3$ | CH$_3$ | H | 2 | H | H | H | H | CHOCH$_3$ | Cl | Cl |
| 4.1258 | CH$_3$ | CH$_3$ | H | 0 | H | H | H | H | CHOC$_2$H$_5$ | Cl | Cl |
| 4.1259 | CH$_3$ | CH$_3$ | H | 1 | H | H | H | H | CHOC$_2$H$_5$ | Cl | Cl |
| 4.1260 | CH$_3$ | CH$_3$ | H | 2 | H | H | H | H | CHOC$_2$H$_5$ | Cl | Cl |
| 4.1261 | CH$_3$ | CH$_3$ | H | 0 | H | H | H | H | CHOiPr | Cl | Cl |
| 4.1262 | CH$_3$ | CH$_3$ | H | 1 | H | H | H | H | CHOiPr | Cl | Cl |
| 4.1263 | CH$_3$ | CH$_3$ | H | 2 | H | H | H | H | CHOiPr | Cl | Cl |
| 4.1264 | CH$_3$ | CH$_3$ | H | 0 | H | H | H | H | C=NOCH$_3$ | Cl | Cl |
| 4.1265 | CH$_3$ | CH$_3$ | H | 1 | H | H | H | H | C=NOCH$_3$ | Cl | Cl |
| 4.1266 | CH$_3$ | CH$_3$ | H | 2 | H | H | H | H | C=NOCH$_3$ | Cl | Cl |
| 4.1267 | CH$_3$ | CH$_3$ | H | 0 | H | H | H | H | C=NOC$_2$H$_5$ | Cl | Cl |
| 4.1268 | CH$_3$ | CH$_3$ | H | 1 | H | H | H | H | C=NOC$_2$H$_5$ | Cl | Cl |
| 4.1269 | CH$_3$ | CH$_3$ | H | 2 | H | H | H | H | C=NOC$_2$H$_5$ | Cl | Cl |
| 4.1270 | CH$_3$ | CH$_3$ | H | 0 | H | H | H | H | C=NOiPr | Cl | Cl |
| 4.1271 | CH$_3$ | CH$_3$ | H | 1 | H | H | H | H | C=NOiPr | Cl | Cl |
| 4.1272 | CH$_3$ | CH$_3$ | H | 2 | H | H | H | H | C=NOiPr | Cl | Cl |
| 4.1273 | CH$_3$ | CH$_3$ | H | 0 | H | H | H | H | C=NOCH$_2$CH=CHCl | Cl | Cl |
| 4.1274 | CH$_3$ | CH$_3$ | H | 1 | H | H | H | H | C=NOCH$_2$CH=CHCl | Cl | Cl |
| 4.1275 | CH$_3$ | CH$_3$ | H | 2 | H | H | H | H | C=NOCH$_2$CH=CHCl | Cl | Cl |
| 4.1276 | CH$_3$ | CH$_3$ | H | 0 | H | H | H | H | C=NOCH$_2$C$_6$H$_5$ | Cl | Cl |
| 4.1277 | CH$_3$ | CH$_3$ | H | 1 | H | H | H | H | C=NOCH$_2$C$_6$H$_5$ | Cl | Cl |
| 4.1278 | CH$_3$ | CH$_3$ | H | 2 | H | H | H | H | C=NOCH$_2$C$_6$H$_5$ | Cl | Cl |
| 4.1279 | CH$_3$ | CH$_3$ | H | 0 | H | H | H | H | C(CH$_3$)$_2$ | Cl | Cl |
| 4.1280 | CH$_3$ | CH$_3$ | H | 1 | H | H | H | H | C(CH$_3$)$_2$ | Cl | Cl |
| 4.1281 | CH$_3$ | CH$_3$ | H | 2 | H | H | H | H | C(CH$_3$)$_2$ | Cl | Cl |
| 4.1282 | CH$_3$ | CH$_3$ | H | 0 | H | H | H | H | 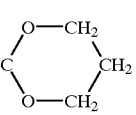 | Cl | Cl |
| 4.1283 | CH$_3$ | CH$_3$ | H | 1 | H | H | H | H | 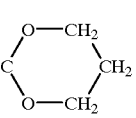 | Cl | Cl |
| 4.1284 | CH$_3$ | CH$_3$ | H | 2 | H | H | H | H | 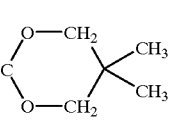 | Cl | Cl |
| 4.1285 | CH$_3$ | CH$_3$ | H | 0 | H | H | H | H | 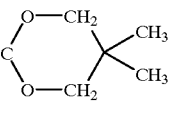 | Cl | Cl |
| 4.1286 | CH$_3$ | CH$_3$ | H | 1 | H | H | H | H | 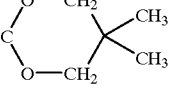 | Cl | Cl |
| 4.1287 | CH$_3$ | CH$_3$ | H | 2 | H | H | H | H |  | Cl | Cl |
| 4.1288 | CH$_3$ | CH$_3$ | H | 0 | H | H | H | H | C=N—CH$_3$ | Cl | Cl |

TABLE 4-continued

Compounds of the formula

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.1289 | $CH_3$ | $CH_3$ | H | 1 | H | H | H | H | C=N—$CH_3$ | Cl | Cl |
| 4.1290 | $CH_3$ | $CH_3$ | H | 2 | H | H | H | H | C=N—$CH_3$ | Cl | Cl |
| 4.1291 | $CH_3$ | $CH_3$ | H | 0 | H | H | H | H | C=N$C_2H_5$ | Cl | Cl |
| 4.1292 | $CH_3$ | $CH_3$ | H | 1 | H | H | H | H | C=N$C_2H_5$ | Cl | Cl |
| 4.1293 | $CH_3$ | $CH_3$ | H | 2 | H | H | H | H | C=N$C_2H_5$ | Cl | Cl |
| 4.1294 | $CH_3$ | $CH_3$ | H | 0 | H | H | H | H | CH—NH$CH_3$ | Cl | Cl |
| 4.1295 | $CH_3$ | $CH_3$ | H | 1 | H | H | H | H | CH—NH$CH_3$ | Cl | Cl |
| 4.1296 | $CH_3$ | $CH_3$ | H | 2 | H | H | H | H | CH—NH$CH_3$ | Cl | Cl |
| 4.1297 | $CH_3$ | $CH_3$ | H | 0 | H | H | H | H | CH—NH$C_2H_5$ | Cl | Cl |
| 4.1298 | $CH_3$ | $CH_3$ | H | 1 | H | H | H | H | CH—NH$C_2H_5$ | Cl | Cl |
| 4.1299 | $CH_3$ | $CH_3$ | H | 2 | H | H | H | H | CH—NH$C_2H_5$ | Cl | Cl |
| 4.1300 | $CH_3$ | $CH_3$ | H | 0 | H | H | H | H | CH—N$(CH_3)_2$ | Cl | Cl |
| 4.1301 | $CH_3$ | $CH_3$ | H | 1 | H | H | H | H | CH—N$(CH_3)_2$ | Cl | Cl |
| 4.1302 | $CH_3$ | $CH_3$ | H | 2 | H | H | H | H | CH—N$(CH_3)_2$ | Cl | Cl |
| 4.1303 | $CH_3$ | $CH_3$ | H | 0 | H | H | H | H | CH—NHO$C_2H_5$ | Cl | Cl |
| 4.1304 | $CH_3$ | $CH_3$ | H | 1 | H | H | H | H | CH—NHO$C_2H_5$ | Cl | Cl |
| 4.1305 | $CH_3$ | $CH_3$ | H | 2 | H | H | H | H | CH—NHO$C_2H_5$ | Cl | Cl |
| 4.1306 | $CH_3$ | $CH_3$ | H | 0 | H | H | H | H | CH—N$(CH_3)$O$C_2H_5$ | Cl | Cl |
| 4.1307 | $CH_3$ | $CH_3$ | H | 1 | H | H | H | H | CH—N$(CH_3)$O$C_2H_5$ | Cl | Cl |
| 4.1308 | $CH_3$ | $CH_3$ | H | 2 | H | H | H | H | CH—N$(CH_3)$O$C_2H_5$ | Cl | Cl |
| 4.1309 | $CH_3$ | $CH_3$ | H | 0 | H | H | H | H | C=N—$NH_2$ | Cl | Cl |
| 4.1310 | $CH_3$ | $CH_3$ | H | 1 | H | H | H | H | C=N—$NH_2$ | Cl | Cl |
| 4.1311 | $CH_3$ | $CH_3$ | H | 2 | H | H | H | H | C=N—$NH_2$ | Cl | Cl |
| 4.1312 | $CH_3$ | $CH_3$ | H | 0 | H | H | H | H | C=N—N$(CH_3)_2$ | Cl | Cl |
| 4.1313 | $CH_3$ | $CH_3$ | H | 1 | H | H | H | H | C=N—N$(CH_3)_2$ | Cl | Cl |
| 4.1314 | $CH_3$ | $CH_3$ | H | 2 | H | H | H | H | C=N—N$(CH_3)_2$ | Cl | Cl |
| 4.1315 | $CH_3$ | $CH_3$ | H | 0 | H | H | H | H | CH—N$(CH_3)$O$CH_2C_6H_5$ | Cl | Cl |
| 4.1316 | $CH_3$ | $CH_3$ | H | 1 | H | H | H | H | CH—N$(CH_3)$O$CH_2C_6H_5$ | Cl | Cl |
| 4.1317 | $CH_3$ | $CH_3$ | H | 2 | H | H | H | H | CH—N$(CH_3)$O$CH_2C_6H_5$ | Cl | Cl |
| 4.1 | $CH_3$ | $CH_3$ | H | 0 | H | H | H | H | C$(CH_3)$—O$CH_3$ | Cl | Cl |
| 4.2 | $CH_3$ | $CH_3$ | H | 1 | H | H | H | H | C$(CH_3)$—O$CH_3$ | Cl | Cl |
| 4.3 | $CH_3$ | $CH_3$ | H | 2 | H | H | H | H | C$(CH_3)$—O$CH_3$ | Cl | Cl |
| 4.4 | $CH_3$ | $CH_3$ | H | 0 | H | H | H | H | O | Cl | Cl |
| 4.5 | $CH_3$ | $CH_3$ | H | 1 | H | H | H | H | O | Cl | Cl |
| 4.6 | $CH_3$ | $CH_3$ | H | 2 | H | H | H | H | O | Cl | Cl |
| 4.7 | H | H | H | 0 | $CH_3$ | $CH_3$ | H | H | C=O | H | $CH_3$ |
| 4.8 | H | H | H | 1 | $CH_3$ | $CH_3$ | H | H | C=O | H | $CH_3$ |
| 4.9 | H | H | H | 2 | $CH_3$ | $CH_3$ | H | H | C=O | H | $CH_3$ |
| 4.10 | H | H | H | 0 | $CH_3$ | $CH_3$ | H | H | CH—O$CH_3$ | H | $CH_3$ |
| 4.11 | H | H | H | 1 | $CH_3$ | $CH_3$ | H | H | CH—O$CH_3$ | H | $CH_3$ |
| 4.12 | H | H | H | 2 | $CH_3$ | $CH_3$ | H | H | CH—O$CH_3$ | H | $CH_3$ |
| 4.13 | H | H | H | 0 | $CH_3$ | $CH_3$ | H | H | CHO$C_2H_5$ | H | $CH_3$ |
| 4.14 | H | H | H | 1 | $CH_3$ | $CH_3$ | H | H | CHO$C_2H_5$ | H | $CH_3$ |
| 4.15 | H | H | H | 2 | $CH_3$ | $CH_3$ | H | H | CHO$C_2H_5$ | H | $CH_3$ |
| 4.16 | H | H | H | 0 | $CH_3$ | $CH_3$ | H | H | CHOiPr | H | $CH_3$ |
| 4.17 | H | H | H | 1 | $CH_3$ | $CH_3$ | H | H | CHOiPr | H | $CH_3$ |
| 4.18 | H | H | H | 2 | $CH_3$ | $CH_3$ | H | H | CHOiPr | H | $CH_3$ |
| 4.19 | H | H | H | 0 | $CH_3$ | $CH_3$ | H | H | C=NO$CH_3$ | H | $CH_3$ |
| 4.20 | H | H | H | 1 | $CH_3$ | $CH_3$ | H | H | C=NO$CH_3$ | H | $CH_3$ |
| 4.21 | H | H | H | 2 | $CH_3$ | $CH_3$ | H | H | C=NO$CH_3$ | H | $CH_3$ |
| 4.22 | H | H | H | 0 | $CH_3$ | $CH_3$ | H | H | C=NO$C_2H_5$ | H | $CH_3$ |
| 4.23 | H | H | H | 1 | $CH_3$ | $CH_3$ | H | H | C=NO$C_2H_5$ | H | $CH_3$ |
| 4.24 | H | H | H | 2 | $CH_3$ | $CH_3$ | H | H | C=NO$C_2H_5$ | H | $CH_3$ |
| 4.25 | H | H | H | 0 | $CH_3$ | $CH_3$ | H | H | C=NOiPr | H | $CH_3$ |
| 4.26 | H | H | H | 1 | $CH_3$ | $CH_3$ | H | H | C=NOiPr | H | $CH_3$ |
| 4.27 | H | H | H | 2 | $CH_3$ | $CH_3$ | H | H | C=NOiPr | H | $CH_3$ |
| 4.28 | H | H | H | 0 | $CH_3$ | $CH_3$ | H | H | C=NO$CH_2$CH=CHCl | H | $CH_3$ |
| 4.29 | H | H | H | 1 | $CH_3$ | $CH_3$ | H | H | C=NO$CH_2$CH=CHCl | H | $CH_3$ |
| 4.30 | H | H | H | 2 | $CH_3$ | $CH_3$ | H | H | C=NO$CH_2$CH=CHCl | H | $CH_3$ |
| 4.31 | H | H | H | 0 | $CH_3$ | $CH_3$ | H | H | C=NO$CH_2C_6H_5$ | H | $CH_3$ |
| 4.32 | H | H | H | 1 | $CH_3$ | $CH_3$ | H | H | C=NO$CH_2C_6H_5$ | H | $CH_3$ |
| 4.33 | H | H | H | 2 | $CH_3$ | $CH_3$ | H | H | C=NO$CH_2C_6H_5$ | H | $CH_3$ |
| 4.34 | H | H | H | 0 | $CH_3$ | $CH_3$ | H | H | C$(CH_3)_2$ | H | $CH_3$ |
| 4.35 | H | H | H | 1 | $CH_3$ | $CH_3$ | H | H | C$(CH_3)_2$ | H | $CH_3$ |

TABLE 4-continued

Compounds of the formula

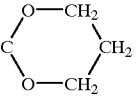

| No. | R¹⁷ | R¹⁸ | R¹⁹ | n | R¹² | R¹³ | R²¹ | R²² | Y | L | M |
|---|---|---|---|---|---|---|---|---|---|---|---|
| 4.36 | H | H | H | 2 | CH₃ | CH₃ | H | H | C(CH₃)₂ | H | CH₃ |
| 4.37 | H | H | H | 0 | CH₃ | CH₃ | H | H | 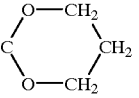 | H | CH₃ |
| 4.38 | H | H | H | 1 | CH₃ | CH₃ | H | H | 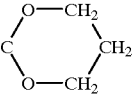 | H | CH₃ |
| 4.39 | H | H | H | 2 | CH₃ | CH₃ | H | H | 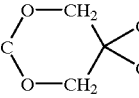 | H | CH₃ |
| 4.40 | H | H | H | 0 | CH₃ | CH₃ | H | H | 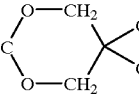 | H | CH₃ |
| 4.41 | H | H | H | 1 | CH₃ | CH₃ | H | H | 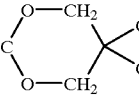 | H | CH₃ |
| 4.42 | H | H | H | 2 | CH₃ | CH₃ | H | H | (same as above) | H | CH₃ |
| 4.43 | H | H | H | 0 | CH₃ | CH₃ | H | H | C=N—CH₃ | H | CH₃ |
| 4.44 | H | H | H | 1 | CH₃ | CH₃ | H | H | C=N—CH₃ | H | CH₃ |
| 4.45 | H | H | H | 2 | CH₃ | CH₃ | H | H | C=N—CH₃ | H | CH₃ |
| 4.46 | H | H | H | 0 | CH₃ | CH₃ | H | H | C=NC₂H₅ | H | CH₃ |
| 4.47 | H | H | H | 1 | CH₃ | CH₃ | H | H | C=NC₂H₅ | H | CH₃ |
| 4.48 | H | H | H | 2 | CH₃ | CH₃ | H | H | C=NC₂H₅ | H | CH₃ |
| 4.49 | H | H | H | 0 | CH₃ | CH₃ | H | H | CH—NHCH₃ | H | CH₃ |
| 4.50 | H | H | H | 1 | CH₃ | CH₃ | H | H | CH—NHCH₃ | H | CH₃ |
| 4.51 | H | H | H | 2 | CH₃ | CH₃ | H | H | CH—NHCH₃ | H | CH₃ |
| 4.52 | H | H | H | 0 | CH₃ | CH₃ | H | H | CH—NHC₂H₅ | H | CH₃ |
| 4.53 | H | H | H | 1 | CH₃ | CH₃ | H | H | CH—NHC₂H₅ | H | CH₃ |
| 4.54 | H | H | H | 2 | CH₃ | CH₃ | H | H | CH—NHC₂H₅ | H | CH₃ |
| 4.55 | H | H | H | 0 | CH₃ | CH₃ | H | H | CH—N(CH₃)₂ | H | CH₃ |
| 4.56 | H | H | H | 1 | CH₃ | CH₃ | H | H | CH—N(CH₃)₂ | H | CH₃ |
| 4.57 | H | H | H | 2 | CH₃ | CH₃ | H | H | CH—N(CH₃)₂ | H | CH₃ |
| 4.58 | H | H | H | 0 | CH₃ | CH₃ | H | H | CH—NHOC₂H₅ | H | CH₃ |
| 4.59 | H | H | H | 1 | CH₃ | CH₃ | H | H | CH—NHOC₂H₅ | H | CH₃ |
| 4.60 | H | H | H | 2 | CH₃ | CH₃ | H | H | CH—NHOC₂H₅ | H | CH₃ |
| 4.61 | H | H | H | 0 | CH₃ | CH₃ | H | H | CH—N(CH₃)OC₂H₅ | H | CH₃ |
| 4.62 | H | H | H | 1 | CH₃ | CH₃ | H | H | CH—N(CH₃)OC₂H₅ | H | CH₃ |
| 4.63 | H | H | H | 2 | CH₃ | CH₃ | H | H | CH—N(CH₃)OC₂H₅ | H | CH₃ |
| 4.64 | H | H | H | 0 | CH₃ | CH₃ | H | H | C=N—NH₂ | H | CH₃ |
| 4.65 | H | H | H | 1 | CH₃ | CH₃ | H | H | C=N—NH₂ | H | CH₃ |
| 4.66 | H | H | H | 2 | CH₃ | CH₃ | H | H | C=N—NH₂ | H | CH₃ |
| 4.67 | H | H | H | 0 | CH₃ | CH₃ | H | H | C=N—N(CH₃)₂ | H | CH₃ |
| 4.68 | H | H | H | 1 | CH₃ | CH₃ | H | H | C=N—N(CH₃)₂ | H | CH₃ |

TABLE 4-continued

Compounds of the formula

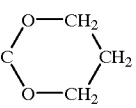

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.69 | H | H | H | 2 | $CH_3$ | $CH_3$ | H | H | C=N—N$(CH_3)_2$ | H | $CH_3$ |
| 4.70 | H | H | H | 0 | $CH_3$ | $CH_3$ | H | H | CH—N$(CH_3)$OCH$_2$C$_6$H$_5$ | H | $CH_3$ |
| 4.71 | H | H | H | 1 | $CH_3$ | $CH_3$ | H | H | CH—N$(CH_3)$OCH$_2$C$_6$H$_5$ | H | $CH_3$ |
| 4.72 | H | H | H | 2 | $CH_3$ | $CH_3$ | H | H | CH—N$(CH_3)$OCH$_2$C$_6$H$_5$ | H | $CH_3$ |
| 4.73 | H | H | H | 0 | $CH_3$ | $CH_3$ | H | H | C$(CH_3)$—OCH$_3$ | H | $CH_3$ |
| 4.74 | H | H | H | 1 | $CH_3$ | $CH_3$ | H | H | C$(CH_3)$—OCH$_3$ | H | $CH_3$ |
| 4.75 | H | H | H | 2 | $CH_3$ | $CH_3$ | H | H | C$(CH_3)$—OCH$_3$ | H | $CH_3$ |
| 4.76 | H | H | H | 0 | $CH_3$ | $CH_3$ | H | H | O | H | $CH_3$ |
| 4.77 | H | H | H | 2 | $CH_3$ | $CH_3$ | H | H | O | H | $CH_3$ |
| 4.78 | $CH_3$ | H | H | 0 | $CH_3$ | $CH_3$ | H | H | C=O | H | $CH_3$ |
| 4.79 | $CH_3$ | H | H | 1 | $CH_3$ | $CH_3$ | H | H | C=O | H | $CH_3$ |
| 4.80 | $CH_3$ | H | H | 2 | $CH_3$ | $CH_3$ | H | H | C=O | H | $CH_3$ |
| 4.81 | $CH_3$ | H | H | 0 | $CH_3$ | $CH_3$ | H | H | CHOCH$_3$ | H | $CH_3$ |
| 4.82 | $CH_3$ | H | H | 1 | $CH_3$ | $CH_3$ | H | H | CHOCH$_3$ | H | $CH_3$ |
| 4.83 | $CH_3$ | H | H | 2 | $CH_3$ | $CH_3$ | H | H | CHOCH$_3$ | H | $CH_3$ |
| 4.84 | $CH_3$ | H | H | 0 | $CH_3$ | $CH_3$ | H | H | CHOC$_2$H$_5$ | H | $CH_3$ |
| 4.85 | $CH_3$ | H | H | 1 | $CH_3$ | $CH_3$ | H | H | CHOC$_2$H$_5$ | H | $CH_3$ |
| 4.86 | $CH_3$ | H | H | 2 | $CH_3$ | $CH_3$ | H | H | CHOC$_2$H$_5$ | H | $CH_3$ |
| 4.87 | $CH_3$ | H | H | 0 | $CH_3$ | $CH_3$ | H | H | CHOiPr | H | $CH_3$ |
| 4.88 | $CH_3$ | H | H | 1 | $CH_3$ | $CH_3$ | H | H | CHOiPr | H | $CH_3$ |
| 4.89 | $CH_3$ | H | H | 2 | $CH_3$ | $CH_3$ | H | H | CHOiPr | H | $CH_3$ |
| 4.90 | $CH_3$ | H | H | 0 | $CH_3$ | $CH_3$ | H | H | C=NOCH$_3$ | H | $CH_3$ |
| 4.91 | $CH_3$ | H | H | 1 | $CH_3$ | $CH_3$ | H | H | C=NOCH$_3$ | H | $CH_3$ |
| 4.92 | $CH_3$ | H | H | 2 | $CH_3$ | $CH_3$ | H | H | C=NOCH$_3$ | H | $CH_3$ |
| 4.93 | $CH_3$ | H | H | 0 | $CH_3$ | $CH_3$ | H | H | C=NOC$_2$H$_5$ | H | $CH_3$ |
| 4.94 | $CH_3$ | H | H | 1 | $CH_3$ | $CH_3$ | H | H | C=NOC$_2$H$_5$ | H | $CH_3$ |
| 4.95 | $CH_3$ | H | H | 2 | $CH_3$ | $CH_3$ | H | H | C=NOC$_2$H$_5$ | H | $CH_3$ |
| 4.96 | $CH_3$ | H | H | 0 | $CH_3$ | $CH_3$ | H | H | C=NOiPr | H | $CH_3$ |
| 4.97 | $CH_3$ | H | H | 1 | $CH_3$ | $CH_3$ | H | H | C=NOiPr | H | $CH_3$ |
| 4.98 | $CH_3$ | H | H | 2 | $CH_3$ | $CH_3$ | H | H | C=NOiPr | H | $CH_3$ |
| 4.99 | $CH_3$ | H | H | 0 | $CH_3$ | $CH_3$ | H | H | C=NOCH$_2$CH=CHCl | H | $CH_3$ |
| 4.100 | $CH_3$ | H | H | 1 | $CH_3$ | $CH_3$ | H | H | C=NOCH$_2$CH=CHCl | H | $CH_3$ |
| 4.101 | $CH_3$ | H | H | 2 | $CH_3$ | $CH_3$ | H | H | C=NOCH$_2$CH=CHCl | H | $CH_3$ |
| 4.102 | $CH_3$ | H | H | 0 | $CH_3$ | $CH_3$ | H | H | C=NOCH$_2$C$_6$H$_5$ | H | $CH_3$ |
| 4.103 | $CH_3$ | H | H | 1 | $CH_3$ | $CH_3$ | H | H | C=NOCH$_2$C$_6$H$_5$ | H | $CH_3$ |
| 4.104 | $CH_3$ | H | H | 2 | $CH_3$ | $CH_3$ | H | H | C=NOCH$_2$C$_6$H$_5$ | H | $CH_3$ |
| 4.105 | $CH_3$ | H | H | 0 | $CH_3$ | $CH_3$ | H | H | C$(CH_3)_2$ | H | $CH_3$ |
| 4.106 | $CH_3$ | H | H | 1 | $CH_3$ | $CH_3$ | H | H | C$(CH_3)_2$ | H | $CH_3$ |
| 4.107 | $CH_3$ | H | H | 2 | $CH_3$ | $CH_3$ | H | H | C$(CH_3)_2$ | H | $CH_3$ |
| 4.108 | $CH_3$ | H | H | 0 | $CH_3$ | $CH_3$ | H | H | 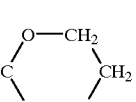 | H | $CH_3$ |
| 4.109 | $CH_3$ | H | H | 1 | $CH_3$ | $CH_3$ | H | H | 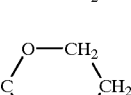 | H | $CH_3$ |
| 4.110 | $CH_3$ | H | H | 2 | $CH_3$ | $CH_3$ | H | H | 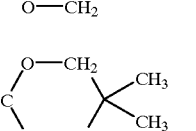 | H | $CH_3$ |
| 4.111 | $CH_3$ | H | H | 0 | $CH_3$ | $CH_3$ | H | H |  | H | $CH_3$ |

TABLE 4-continued

Compounds of the formula

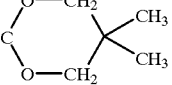

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.112 | $CH_3$ | H | H | 1 | $CH_3$ | $CH_3$ | H | H | 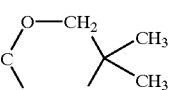 | H | $CH_3$ |
| 4.113 | $CH_3$ | H | H | 2 | $CH_3$ | $CH_3$ | H | H | (same as 4.112) | H | $CH_3$ |
| 4.114 | $CH_3$ | H | H | 0 | $CH_3$ | $CH_3$ | H | H | C=N—$CH_3$ | H | $CH_3$ |
| 4.115 | $CH_3$ | H | H | 1 | $CH_3$ | $CH_3$ | H | H | C=N—$CH_3$ | H | $CH_3$ |
| 4.116 | $CH_3$ | H | H | 2 | $CH_3$ | $CH_3$ | H | H | C=N—$CH_3$ | H | $CH_3$ |
| 4.117 | $CH_3$ | H | H | 0 | $CH_3$ | $CH_3$ | H | H | C=N$C_2H_5$ | H | $CH_3$ |
| 4.118 | $CH_3$ | H | H | 1 | $CH_3$ | $CH_3$ | H | H | C=N$C_2H_5$ | H | $CH_3$ |
| 4.119 | $CH_3$ | H | H | 2 | $CH_3$ | $CH_3$ | H | H | C=N$C_2H_5$ | H | $CH_3$ |
| 4.120 | $CH_3$ | H | H | 0 | $CH_3$ | $CH_3$ | H | H | CH—NH$CH_3$ | H | $CH_3$ |
| 4.121 | $CH_3$ | H | H | 1 | $CH_3$ | $CH_3$ | H | H | CH—NH$CH_3$ | H | $CH_3$ |
| 4.122 | $CH_3$ | H | H | 2 | $CH_3$ | $CH_3$ | H | H | CH—NH$CH_3$ | H | $CH_3$ |
| 4.123 | $CH_3$ | H | H | 0 | $CH_3$ | $CH_3$ | H | H | CH—NH$C_2H_5$ | H | $CH_3$ |
| 4.124 | $CH_3$ | H | H | 1 | $CH_3$ | $CH_3$ | H | H | CH—NH$C_2H_5$ | H | $CH_3$ |
| 4.125 | $CH_3$ | H | H | 2 | $CH_3$ | $CH_3$ | H | H | CH—NH$C_2H_5$ | H | $CH_3$ |
| 4.126 | $CH_3$ | H | H | 0 | $CH_3$ | $CH_3$ | H | H | CH—N$(CH_3)_2$ | H | $CH_3$ |
| 4.127 | $CH_3$ | H | H | 1 | $CH_3$ | $CH_3$ | H | H | CH—N$(CH_3)_2$ | H | $CH_3$ |
| 4.128 | $CH_3$ | H | H | 2 | $CH_3$ | $CH_3$ | H | H | CH—N$(CH_3)_2$ | H | $CH_3$ |
| 4.129 | $CH_3$ | H | H | 0 | $CH_3$ | $CH_3$ | H | H | CH—NHO$C_2H_5$ | H | $CH_3$ |
| 4.130 | $CH_3$ | H | H | 1 | $CH_3$ | $CH_3$ | H | H | CH—NHO$C_2H_5$ | H | $CH_3$ |
| 4.131 | $CH_3$ | H | H | 2 | $CH_3$ | $CH_3$ | H | H | CH—NHO$C_2H_5$ | H | $CH_3$ |
| 4.132 | $CH_3$ | H | H | 0 | $CH_3$ | $CH_3$ | H | H | CH—N$(CH_3)$O$C_2H_5$ | H | $CH_3$ |
| 4.133 | $CH_3$ | H | H | 1 | $CH_3$ | $CH_3$ | H | H | CH—N$(CH_3)$O$C_2H_5$ | H | $CH_3$ |
| 4.134 | $CH_3$ | H | H | 2 | $CH_3$ | $CH_3$ | H | H | CH—N$(CH_3)$O$C_2H_5$ | H | $CH_3$ |
| 4.135 | $CH_3$ | H | H | 0 | $CH_3$ | $CH_3$ | H | H | C=N—$NH_2$ | H | $CH_3$ |
| 4.136 | $CH_3$ | H | H | 1 | $CH_3$ | $CH_3$ | H | H | C=N—$NH_2$ | H | $CH_3$ |
| 4.137 | $CH_3$ | H | H | 2 | $CH_3$ | $CH_3$ | H | H | C=N—$NH_2$ | H | $CH_3$ |
| 4.138 | $CH_3$ | H | H | 0 | $CH_3$ | $CH_3$ | H | H | C=N—N$(CH_3)_2$ | H | $CH_3$ |
| 4.139 | $CH_3$ | H | H | 1 | $CH_3$ | $CH_3$ | H | H | C=N—N$(CH_3)_2$ | H | $CH_3$ |
| 4.140 | $CH_3$ | H | H | 2 | $CH_3$ | $CH_3$ | H | H | C=N—N$(CH_3)_2$ | H | $CH_3$ |
| 4.141 | $CH_3$ | H | H | 0 | $CH_3$ | $CH_3$ | H | H | CH—N$(CH_3)$OCH$_2$C$_6$H$_5$ | H | $CH_3$ |
| 4.142 | $CH_3$ | H | H | 1 | $CH_3$ | $CH_3$ | H | H | CH—N$(CH_3)$OCH$_2$C$_6$H$_5$ | H | $CH_3$ |
| 4.143 | $CH_3$ | H | H | 2 | $CH_3$ | $CH_3$ | H | H | CH—N$(CH_3)$OCH$_2$C$_6$H$_5$ | H | $CH_3$ |
| 4.144 | $CH_3$ | H | H | 0 | $CH_3$ | $CH_3$ | H | H | C$(CH_3)$—O$CH_3$ | H | $CH_3$ |
| 4.145 | $CH_3$ | H | H | 1 | $CH_3$ | $CH_3$ | H | H | C$(CH_3)$—O$CH_3$ | H | $CH_3$ |
| 4.146 | $CH_3$ | H | H | 2 | $CH_3$ | $CH_3$ | H | H | C$(CH_3)$—O$CH_3$ | H | $CH_3$ |
| 4.147 | $CH_3$ | H | H | 0 | $CH_3$ | $CH_3$ | H | H | O | H | $CH_3$ |
| 4.148 | $CH_3$ | H | H | 2 | $CH_3$ | $CH_3$ | H | H | O | H | $CH_3$ |
| 4.149 | $CH_3$ | $CH_3$ | H | 0 | $CH_3$ | $CH_3$ | H | H | C=O | H | $CH_3$ |
| 4.150 | $CH_3$ | $CH_3$ | H | 1 | $CH_3$ | $CH_3$ | H | H | C=O | H | $CH_3$ |
| 4.151 | $CH_3$ | $CH_3$ | H | 2 | $CH_3$ | $CH_3$ | H | H | C=O | H | $CH_3$ |
| 4.152 | $CH_3$ | $CH_3$ | H | 0 | $CH_3$ | $CH_3$ | H | H | CHO$CH_3$ | H | $CH_3$ |
| 4.153 | $CH_3$ | $CH_3$ | H | 1 | $CH_3$ | $CH_3$ | H | H | CHO$CH_3$ | H | $CH_3$ |
| 4.154 | $CH_3$ | $CH_3$ | H | 2 | $CH_3$ | $CH_3$ | H | H | CHO$CH_3$ | H | $CH_3$ |
| 4.155 | $CH_3$ | $CH_3$ | H | 0 | $CH_3$ | $CH_3$ | H | H | CHO$C_2H_5$ | H | $CH_3$ |
| 4.156 | $CH_3$ | $CH_3$ | H | 1 | $CH_3$ | $CH_3$ | H | H | CHO$C_2H_5$ | H | $CH_3$ |
| 4.157 | $CH_3$ | $CH_3$ | H | 2 | $CH_3$ | $CH_3$ | H | H | CHO$C_2H_5$ | H | $CH_3$ |
| 4.158 | $CH_3$ | $CH_3$ | H | 0 | $CH_3$ | $CH_3$ | H | H | CHOiPr | H | $CH_3$ |
| 4.159 | $CH_3$ | $CH_3$ | H | 1 | $CH_3$ | $CH_3$ | H | H | CHOiPr | H | $CH_3$ |
| 4.160 | $CH_3$ | $CH_3$ | H | 2 | $CH_3$ | $CH_3$ | H | H | CHOiPr | H | $CH_3$ |
| 4.161 | $CH_3$ | $CH_3$ | H | 0 | $CH_3$ | $CH_3$ | H | H | C=NO$CH_3$ | H | $CH_3$ |
| 4.162 | $CH_3$ | $CH_3$ | H | 1 | $CH_3$ | $CH_3$ | H | H | C=NO$CH_3$ | H | $CH_3$ |
| 4.163 | $CH_3$ | $CH_3$ | H | 2 | $CH_3$ | $CH_3$ | H | H | C=NO$CH_3$ | H | $CH_3$ |
| 4.164 | $CH_3$ | $CH_3$ | H | 0 | $CH_3$ | $CH_3$ | H | H | C=NO$C_2H_5$ | H | $CH_3$ |
| 4.165 | $CH_3$ | $CH_3$ | H | 1 | $CH_3$ | $CH_3$ | H | H | C=NO$C_2H_5$ | H | $CH_3$ |

TABLE 4-continued

Compounds of the formula

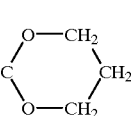

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.166 | $CH_3$ | $CH_3$ | H | 2 | $CH_3$ | $CH_3$ | H | H | C=$NOC_2H_5$ | H | $CH_3$ |
| 4.167 | $CH_3$ | $CH_3$ | H | 0 | $CH_3$ | $CH_3$ | H | H | C=NOiPr | H | $CH_3$ |
| 4.168 | $CH_3$ | $CH_3$ | H | 1 | $CH_3$ | $CH_3$ | H | H | C=NOiPr | H | $CH_3$ |
| 4.169 | $CH_3$ | $CH_3$ | H | 2 | $CH_3$ | $CH_3$ | H | H | C=NOiPr | H | $CH_3$ |
| 4.170 | $CH_3$ | $CH_3$ | H | 0 | $CH_3$ | $CH_3$ | H | H | C=$NOCH_2CH$=CHCl | H | $CH_3$ |
| 4.171 | $CH_3$ | $CH_3$ | H | 1 | $CH_3$ | $CH_3$ | H | H | C=$NOCH_2CH$=CHCl | H | $CH_3$ |
| 4.172 | $CH_3$ | $CH_3$ | H | 2 | $CH_3$ | $CH_3$ | H | H | C=$NOCH_2CH$=CHCl | H | $CH_3$ |
| 4.173 | $CH_3$ | $CH_3$ | H | 0 | $CH_3$ | $CH_3$ | H | H | C=$NOCH_2C_6H_5$ | H | $CH_3$ |
| 4.174 | $CH_3$ | $CH_3$ | H | 1 | $CH_3$ | $CH_3$ | H | H | C=$NOCH_2C_6H_5$ | H | $CH_3$ |
| 4.175 | $CH_3$ | $CH_3$ | H | 2 | $CH_3$ | $CH_3$ | H | H | C=$NOCH_2C_6H_5$ | H | $CH_3$ |
| 4.176 | $CH_3$ | $CH_3$ | H | 0 | $CH_3$ | $CH_3$ | H | H | $C(CH_3)_2$ | H | $CH_3$ |
| 4.177 | $CH_3$ | $CH_3$ | H | 1 | $CH_3$ | $CH_3$ | H | H | $C(CH_3)_2$ | H | $CH_3$ |
| 4.178 | $CH_3$ | $CH_3$ | H | 2 | $CH_3$ | $CH_3$ | H | H | $C(CH_3)_2$ | H | $CH_3$ |
| 4.179 | $CH_3$ | $CH_3$ | H | 0 | $CH_3$ | $CH_3$ | H | H | 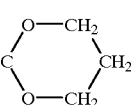 | H | $CH_3$ |
| 4.180 | $CH_3$ | $CH_3$ | H | 1 | $CH_3$ | $CH_3$ | H | H | 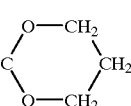 | H | $CH_3$ |
| 4.181 | $CH_3$ | $CH_3$ | H | 2 | $CH_3$ | $CH_3$ | H | H | 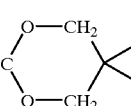 | H | $CH_3$ |
| 4.182 | $CH_3$ | $CH_3$ | H | 0 | $CH_3$ | $CH_3$ | H | H | 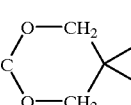 | H | $CH_3$ |
| 4.183 | $CH_3$ | $CH_3$ | H | 1 | $CH_3$ | $CH_3$ | H | H | 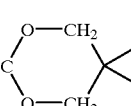 | H | $CH_3$ |
| 4.184 | $CH_3$ | $CH_3$ | H | 2 | $CH_3$ | $CH_3$ | H | H |  | H | $CH_3$ |
| 4.185 | $CH_3$ | $CH_3$ | H | 0 | $CH_3$ | $CH_3$ | H | H | C=N—$CH_3$ | H | $CH_3$ |
| 4.186 | $CH_3$ | $CH_3$ | H | 1 | $CH_3$ | $CH_3$ | H | H | C=N—$CH_3$ | H | $CH_3$ |
| 4.187 | $CH_3$ | $CH_3$ | H | 2 | $CH_3$ | $CH_3$ | H | H | C=N—$CH_3$ | H | $CH_3$ |
| 4.188 | $CH_3$ | $CH_3$ | H | 0 | $CH_3$ | $CH_3$ | H | H | C=$NC_2H_5$ | H | $CH_3$ |
| 4.189 | $CH_3$ | $CH_3$ | H | 1 | $CH_3$ | $CH_3$ | H | H | C=$NC_2H_5$ | H | $CH_3$ |
| 4.190 | $CH_3$ | $CH_3$ | H | 2 | $CH_3$ | $CH_3$ | H | H | C=$NC_2H_5$ | H | $CH_3$ |
| 4.191 | $CH_3$ | $CH_3$ | H | 0 | $CH_3$ | $CH_3$ | H | H | CH—$NHCH_3$ | H | $CH_3$ |
| 4.192 | $CH_3$ | $CH_3$ | H | 1 | $CH_3$ | $CH_3$ | H | H | CH—$NHCH_3$ | H | $CH_3$ |
| 4.193 | $CH_3$ | $CH_3$ | H | 2 | $CH_3$ | $CH_3$ | H | H | CH—$NHCH_3$ | H | $CH_3$ |
| 4.194 | $CH_3$ | $CH_3$ | H | 0 | $CH_3$ | $CH_3$ | H | H | CH—$NHC_2H_5$ | H | $CH_3$ |
| 4.195 | $CH_3$ | $CH_3$ | H | 1 | $CH_3$ | $CH_3$ | H | H | CH—$NHC_2H_5$ | H | $CH_3$ |
| 4.196 | $CH_3$ | $CH_3$ | H | 2 | $CH_3$ | $CH_3$ | H | H | CH—$NHC_2H_5$ | H | $CH_3$ |
| 4.197 | $CH_3$ | $CH_3$ | H | 0 | $CH_3$ | $CH_3$ | H | H | CH—$N(CH_3)_2$ | H | $CH_3$ |
| 4.198 | $CH_3$ | $CH_3$ | H | 1 | $CH_3$ | $CH_3$ | H | H | CH—$N(CH_3)_2$ | H | $CH_3$ |

TABLE 4-continued

Compounds of the formula

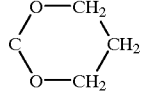

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.199 | $CH_3$ | $CH_3$ | H | 2 | $CH_3$ | $CH_3$ | H | H | CH—N(CH$_3$)$_2$ | H | $CH_3$ |
| 4.200 | $CH_3$ | $CH_3$ | H | 0 | $CH_3$ | $CH_3$ | H | H | CH—NHOC$_2$H$_5$ | H | $CH_3$ |
| 4.201 | $CH_3$ | $CH_3$ | H | 1 | $CH_3$ | $CH_3$ | H | H | CH—NHOC$_2$H$_5$ | H | $CH_3$ |
| 4.202 | $CH_3$ | $CH_3$ | H | 2 | $CH_3$ | $CH_3$ | H | H | CH—NHOC$_2$H$_5$ | H | $CH_3$ |
| 4.203 | $CH_3$ | $CH_3$ | H | 0 | $CH_3$ | $CH_3$ | H | H | CH—N(CH$_3$)OC$_2$H$_5$ | H | $CH_3$ |
| 4.204 | $CH_3$ | $CH_3$ | H | 1 | $CH_3$ | $CH_3$ | H | H | CH—N(CH$_3$)OC$_2$H$_5$ | H | $CH_3$ |
| 4.205 | $CH_3$ | $CH_3$ | H | 2 | $CH_3$ | $CH_3$ | H | H | CH—N(CH$_3$)OC$_2$H$_5$ | H | $CH_3$ |
| 4.206 | $CH_3$ | $CH_3$ | H | 0 | $CH_3$ | $CH_3$ | H | H | C=N—NH$_2$ | H | $CH_3$ |
| 4.207 | $CH_3$ | $CH_3$ | H | 1 | $CH_3$ | $CH_3$ | H | H | C=N—NH$_2$ | H | $CH_3$ |
| 4.208 | $CH_3$ | $CH_3$ | H | 2 | $CH_3$ | $CH_3$ | H | H | C=N—NH$_2$ | H | $CH_3$ |
| 4.209 | $CH_3$ | $CH_3$ | H | 0 | $CH_3$ | $CH_3$ | H | H | C=N—N(CH$_3$)$_2$ | H | $CH_3$ |
| 4.210 | $CH_3$ | $CH_3$ | H | 1 | $CH_3$ | $CH_3$ | H | H | C=N—N(CH$_3$)$_2$ | H | $CH_3$ |
| 4.211 | $CH_3$ | $CH_3$ | H | 2 | $CH_3$ | $CH_3$ | H | H | C=N—N(CH$_3$)$_2$ | H | $CH_3$ |
| 4.212 | $CH_3$ | $CH_3$ | H | 0 | $CH_3$ | $CH_3$ | H | H | CH—N(CH$_3$)OCH$_2$C$_6$H$_5$ | H | $CH_3$ |
| 4.213 | $CH_3$ | $CH_3$ | H | 1 | $CH_3$ | $CH_3$ | H | H | CH—N(CH$_3$)OCH$_2$C$_6$H$_5$ | H | $CH_3$ |
| 4.214 | $CH_3$ | $CH_3$ | H | 2 | $CH_3$ | $CH_3$ | H | H | CH—N(CH$_3$)OCH$_2$C$_6$H$_5$ | H | $CH_3$ |
| 4.215 | $CH_3$ | $CH_3$ | H | 0 | $CH_3$ | $CH_3$ | H | H | C(CH$_3$)—OCH$_3$ | H | $CH_3$ |
| 4.216 | $CH_3$ | $CH_3$ | H | 1 | $CH_3$ | $CH_3$ | H | H | C(CH$_3$)—OCH$_3$ | H | $CH_3$ |
| 4.217 | $CH_3$ | $CH_3$ | H | 2 | $CH_3$ | $CH_3$ | H | H | C(CH$_3$)—OCH$_3$ | H | $CH_3$ |
| 4.218 | $CH_3$ | $CH_3$ | H | 0 | $CH_3$ | $CH_3$ | H | H | O | H | $CH_3$ |
| 4.219 | $CH_3$ | $CH_3$ | H | 2 | $CH_3$ | $CH_3$ | H | H | O | H | $CH_3$ |
| 4.220 | H | H | H | 0 | $CH_3$ | H | H | H | C=O | H | Cl |
| 4.221 | H | H | H | 1 | $CH_3$ | H | H | H | C=O | H | Cl |
| 4.222 | H | H | H | 2 | $CH_3$ | H | H | H | C=O | H | Cl |
| 4.223 | H | H | H | 0 | $CH_3$ | H | H | H | CHOCH$_3$ | H | Cl |
| 4.224 | H | H | H | 1 | $CH_3$ | H | H | H | CHOCH$_3$ | H | Cl |
| 4.225 | H | H | H | 2 | $CH_3$ | H | H | H | CHOCH$_3$ | H | Cl |
| 4.226 | H | H | H | 0 | $CH_3$ | H | H | H | CHOC$_2$H$_5$ | H | Cl |
| 4.227 | H | H | H | 1 | $CH_3$ | H | H | H | CHOC$_2$H$_5$ | H | Cl |
| 4.228 | H | H | H | 2 | $CH_3$ | H | H | H | CHOC$_2$H$_5$ | H | Cl |
| 4.229 | H | H | H | 0 | $CH_3$ | H | H | H | CHOiPr | H | Cl |
| 4.230 | H | H | H | 1 | $CH_3$ | H | H | H | CHOiPr | H | Cl |
| 4.231 | H | H | H | 2 | $CH_3$ | H | H | H | CHOiPr | H | Cl |
| 4.232 | H | H | H | 0 | $CH_3$ | H | H | H | C=NOCH$_3$ | H | Cl |
| 4.233 | H | H | H | 1 | $CH_3$ | H | H | H | C=NOCH$_3$ | H | Cl |
| 4.234 | H | H | H | 2 | $CH_3$ | H | H | H | C=NOCH$_3$ | H | Cl |
| 4.235 | H | H | H | 0 | $CH_3$ | H | H | H | C=NOC$_2$H$_5$ | H | Cl |
| 4.236 | H | H | H | 1 | $CH_3$ | H | H | H | C=NOC$_2$H$_5$ | H | Cl |
| 4.237 | H | H | H | 2 | $CH_3$ | H | H | H | C=NOC$_2$H$_5$ | H | Cl |
| 4.238 | H | H | H | 0 | $CH_3$ | H | H | H | C=NOiPr | H | Cl |
| 4.239 | H | H | H | 1 | $CH_3$ | H | H | H | C=NOiPr | H | Cl |
| 4.240 | H | H | H | 2 | $CH_3$ | H | H | H | C=NOiPr | H | Cl |
| 4.241 | H | H | H | 0 | $CH_3$ | H | H | H | C=NOCH$_2$CH=CHCl | H | Cl |
| 4.242 | H | H | H | 1 | $CH_3$ | H | H | H | C=NOCH$_2$CH=CHCl | H | Cl |
| 4.243 | H | H | H | 2 | $CH_3$ | H | H | H | C=NOCH$_2$CH=CHCl | H | Cl |
| 4.244 | H | H | H | 0 | $CH_3$ | H | H | H | C=NOCH$_2$C$_6$H$_5$ | H | Cl |
| 4.245 | H | H | H | 1 | $CH_3$ | H | H | H | C=NOCH$_2$C$_6$H$_5$ | H | Cl |
| 4.246 | H | H | H | 2 | $CH_3$ | H | H | H | C=NOCH$_2$C$_6$H$_5$ | H | Cl |
| 4.247 | H | H | H | 0 | $CH_3$ | H | H | H | C(CH$_3$)$_2$ | H | Cl |
| 4.248 | H | H | H | 1 | $CH_3$ | H | H | H | C(CH$_3$)$_2$ | H | Cl |
| 4.249 | H | H | H | 2 | $CH_3$ | H | H | H | C(CH$_3$)$_2$ | H | Cl |
| 4.250 | H | H | H | 0 | $CH_3$ | H | H | H | 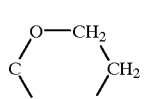 | H | Cl |
| 4.251 | H | H | H | 1 | $CH_3$ | H | H | H | | H | Cl |

TABLE 4-continued

Compounds of the formula

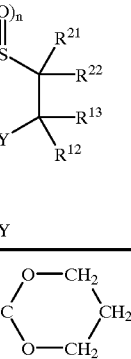

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.252 | H | H | H | 2 | CH$_3$ | H | H | H | 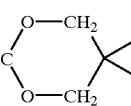 | H | Cl |
| 4.253 | H | H | H | 0 | CH$_3$ | H | H | H | 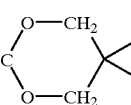 | H | Cl |
| 4.254 | H | H | H | 1 | CH$_3$ | H | H | H | | H | Cl |
| 4.255 | H | H | H | 2 | CH$_3$ | H | H | H | 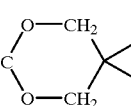 | H | Cl |
| 4.256 | H | H | H | 0 | CH$_3$ | H | H | H | C=N—CH$_3$ | H | Cl |
| 4.257 | H | H | H | 1 | CH$_3$ | H | H | H | C=N—CH$_3$ | H | Cl |
| 4.258 | H | H | H | 2 | CH$_3$ | H | H | H | C=N—CH$_3$ | H | Cl |
| 4.259 | H | H | H | 0 | CH$_3$ | H | H | H | C=NC$_2$H$_5$ | H | Cl |
| 4.260 | H | H | H | 1 | CH$_3$ | H | H | H | C=NC$_2$H$_5$ | H | Cl |
| 4.261 | H | H | H | 2 | CH$_3$ | H | H | H | C=NC$_2$H$_5$ | H | Cl |
| 4.262 | H | H | H | 0 | CH$_3$ | H | H | H | CH—NHCH$_3$ | H | Cl |
| 4.263 | H | H | H | 1 | CH$_3$ | H | H | H | CH—NHCH$_3$ | H | Cl |
| 4.264 | H | H | H | 2 | CH$_3$ | H | H | H | CH—NHCH$_3$ | H | Cl |
| 4.265 | H | H | H | 0 | CH$_3$ | H | H | H | CH—NHC$_2$H$_5$ | H | Cl |
| 4.266 | H | H | H | 1 | CH$_3$ | H | H | H | CH—NHC$_2$H$_5$ | H | Cl |
| 4.267 | H | H | H | 2 | CH$_3$ | H | H | H | CH—NHC$_2$H$_5$ | H | Cl |
| 4.268 | H | H | H | 0 | CH$_3$ | H | H | H | CH—N(CH$_3$)$_2$ | H | Cl |
| 4.269 | H | H | H | 1 | CH$_3$ | H | H | H | CH—N(CH$_3$)$_2$ | H | Cl |
| 4.270 | H | H | H | 2 | CH$_3$ | H | H | H | CH—N(CH$_3$)$_2$ | H | Cl |
| 4.271 | H | H | H | 0 | CH$_3$ | H | H | H | CH—NHOC$_2$H$_5$ | H | Cl |
| 4.272 | H | H | H | 1 | CH$_3$ | H | H | H | CH—NHOC$_2$H$_5$ | H | Cl |
| 4.273 | H | H | H | 2 | CH$_3$ | H | H | H | CH—NHOC$_2$H$_5$ | H | Cl |
| 4.274 | H | H | H | 0 | CH$_3$ | H | H | H | CH—N(CH$_3$)OC$_2$H$_5$ | H | Cl |
| 4.275 | H | H | H | 1 | CH$_3$ | H | H | H | CH—N(CH$_3$)OC$_2$H$_5$ | H | Cl |
| 4.276 | H | H | H | 2 | CH$_3$ | H | H | H | CH—N(CH$_3$)OC$_2$H$_5$ | H | Cl |
| 4.277 | H | H | H | 0 | CH$_3$ | H | H | H | C=N—NH$_2$ | H | Cl |
| 4.278 | H | H | H | 1 | CH$_3$ | H | H | H | C=N—NH$_2$ | H | Cl |
| 4.279 | H | H | H | 2 | CH$_3$ | H | H | H | C=N—NH$_2$ | H | Cl |
| 4.280 | H | H | H | 0 | CH$_3$ | H | H | H | C=N—N(CH$_3$)$_2$ | H | Cl |
| 4.281 | H | H | H | 1 | CH$_3$ | H | H | H | C=N—N(CH$_3$)$_2$ | H | Cl |
| 4.282 | H | H | H | 2 | CH$_3$ | H | H | H | C=N—N(CH$_3$)$_2$ | H | Cl |
| 4.283 | H | H | H | 0 | CH$_3$ | H | H | H | CH—N(CH$_3$)OCH$_2$C$_6$H$_5$ | H | Cl |
| 4.284 | H | H | H | 1 | CH$_3$ | H | H | H | CH—N(CH$_3$)OCH$_2$C$_6$H$_5$ | H | Cl |
| 4.285 | H | H | H | 2 | CH$_3$ | H | H | H | CH—N(CH$_3$)OCH$_2$C$_6$H$_5$ | H | Cl |
| 4.286 | H | H | H | 0 | CH$_3$ | H | H | H | C(CH$_3$)—OCH$_3$ | H | Cl |
| 4.287 | H | H | H | 1 | CH$_3$ | H | H | H | C(CH$_3$)—OCH$_3$ | H | Cl |
| 4.288 | H | H | H | 2 | CH$_3$ | H | H | H | C(CH$_3$)—OCH$_3$ | H | Cl |
| 4.289 | H | H | H | 0 | CH$_3$ | H | H | H | O | H | Cl |
| 4.290 | H | H | H | 2 | CH$_3$ | H | H | H | O | H | Cl |
| 4.291 | CH$_3$ | H | H | 0 | CH$_3$ | H | H | H | C=O | H | Cl |
| 4.292 | CH$_3$ | H | H | 1 | CH$_3$ | H | H | H | C=O | H | Cl |
| 4.293 | CH$_3$ | H | H | 2 | CH$_3$ | H | H | H | C=O | H | Cl |
| 4.294 | CH$_3$ | H | H | 0 | CH$_3$ | H | H | H | CHOCH$_3$ | H | Cl |
| 4.295 | CH$_3$ | H | H | 1 | CH$_3$ | H | H | H | CHOCH$_3$ | H | Cl |

TABLE 4-continued

Compounds of the formula

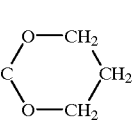

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.296 | $CH_3$ | H | H | 2 | $CH_3$ | H | H | H | $CHOCH_3$ | H | Cl |
| 4.297 | $CH_3$ | H | H | 0 | $CH_3$ | H | H | H | $CHOC_2H_5$ | H | Cl |
| 4.298 | $CH_3$ | H | H | 1 | $CH_3$ | H | H | H | $CHOC_2H_5$ | H | Cl |
| 4.299 | $CH_3$ | H | H | 2 | $CH_3$ | H | H | H | $CHOC_2H_5$ | H | Cl |
| 4.300 | $CH_3$ | H | H | 0 | $CH_3$ | H | H | H | CHOiPr | H | Cl |
| 4.301 | $CH_3$ | H | H | 1 | $CH_3$ | H | H | H | CHOiPr | H | Cl |
| 4.302 | $CH_3$ | H | H | 2 | $CH_3$ | H | H | H | CHOiPr | H | Cl |
| 4.303 | $CH_3$ | H | H | 0 | $CH_3$ | H | H | H | $C=NOCH_3$ | H | Cl |
| 4.304 | $CH_3$ | H | H | 1 | $CH_3$ | H | H | H | $C=NOCH_3$ | H | Cl |
| 4.305 | $CH_3$ | H | H | 2 | $CH_3$ | H | H | H | $C=NOCH_3$ | H | Cl |
| 4.306 | $CH_3$ | H | H | 0 | $CH_3$ | H | H | H | $C=NOC_2H_5$ | H | Cl |
| 4.307 | $CH_3$ | H | H | 1 | $CH_3$ | H | H | H | $C=NOC_2H_5$ | H | Cl |
| 4.308 | $CH_3$ | H | H | 2 | $CH_3$ | H | H | H | $C=NOC_2H_5$ | H | Cl |
| 4.309 | $CH_3$ | H | H | 0 | $CH_3$ | H | H | H | C=NOiPr | H | Cl |
| 4.310 | $CH_3$ | H | H | 1 | $CH_3$ | H | H | H | C=NOiPr | H | Cl |
| 4.311 | $CH_3$ | H | H | 2 | $CH_3$ | H | H | H | C=NOiPr | H | Cl |
| 4.312 | $CH_3$ | H | H | 0 | $CH_3$ | H | H | H | $C=NOCH_2CH=CHCl$ | H | Cl |
| 4.313 | $CH_3$ | H | H | 1 | $CH_3$ | H | H | H | $C=NOCH_2CH=CHCl$ | H | Cl |
| 4.314 | $CH_3$ | H | H | 2 | $CH_3$ | H | H | H | $C=NOCH_2CH=CHCl$ | H | Cl |
| 4.315 | $CH_3$ | H | H | 0 | $CH_3$ | H | H | H | $C=NOCH_2C_6H_5$ | H | Cl |
| 4.316 | $CH_3$ | H | H | 1 | $CH_3$ | H | H | H | $C=NOCH_2C_6H_5$ | H | Cl |
| 4.317 | $CH_3$ | H | H | 2 | $CH_3$ | H | H | H | $C=NOCH_2C_6H_5$ | H | Cl |
| 4.318 | $CH_3$ | H | H | 0 | $CH_3$ | H | H | H | $C(CH_3)_2$ | H | Cl |
| 4.319 | $CH_3$ | H | H | 1 | $CH_3$ | H | H | H | $C(CH_3)_2$ | H | Cl |
| 4.320 | $CH_3$ | H | H | 2 | $CH_3$ | H | H | H | $C(CH_3)_2$ | H | Cl |
| 4.321 | $CH_3$ | H | H | 0 | $CH_3$ | H | H | H | 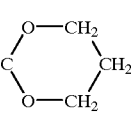 | H | Cl |
| 4.322 | $CH_3$ | H | H | 1 | $CH_3$ | H | H | H | 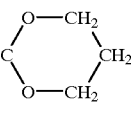 | H | Cl |
| 4.323 | $CH_3$ | H | H | 2 | $CH_3$ | H | H | H | 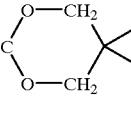 | H | Cl |
| 4.324 | $CH_3$ | H | H | 0 | $CH_3$ | H | H | H | 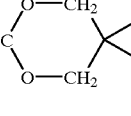 | H | Cl |
| 4.325 | $CH_3$ | H | H | 1 | $CH_3$ | H | H | H | 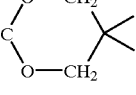 | H | Cl |
| 4.326 | $CH_3$ | H | H | 2 | $CH_3$ | H | H | H |  | H | Cl |
| 4.327 | $CH_3$ | H | H | 0 | $CH_3$ | H | H | H | $C=N-CH_3$ | H | Cl |
| 4.328 | $CH_3$ | H | H | 1 | $CH_3$ | H | H | H | $C=N-CH_3$ | H | Cl |

TABLE 4-continued

Compounds of the formula

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.329 | $CH_3$ | H | H | 2 | $CH_3$ | H | H | H | C=N—$CH_3$ | H | Cl |
| 4.330 | $CH_3$ | H | H | 0 | $CH_3$ | H | H | H | C=N$C_2H_5$ | H | Cl |
| 4.331 | $CH_3$ | H | H | 1 | $CH_3$ | H | H | H | C=N$C_2H_5$ | H | Cl |
| 4.332 | $CH_3$ | H | H | 2 | $CH_3$ | H | H | H | C=N$C_2H_5$ | H | Cl |
| 4.333 | $CH_3$ | H | H | 0 | $CH_3$ | H | H | H | CH—NH$CH_3$ | H | Cl |
| 4.334 | $CH_3$ | H | H | 1 | $CH_3$ | H | H | H | CH—NH$CH_3$ | H | Cl |
| 4.335 | $CH_3$ | H | H | 2 | $CH_3$ | H | H | H | CH—NH$CH_3$ | H | Cl |
| 4.336 | $CH_3$ | H | H | 0 | $CH_3$ | H | H | H | CH—NH$C_2H_5$ | H | Cl |
| 4.337 | $CH_3$ | H | H | 1 | $CH_3$ | H | H | H | CH—NH$C_2H_5$ | H | Cl |
| 4.338 | $CH_3$ | H | H | 2 | $CH_3$ | H | H | H | CH—NH$C_2H_5$ | H | Cl |
| 4.339 | $CH_3$ | H | H | 0 | $CH_3$ | H | H | H | CH—N$(CH_3)_2$ | H | Cl |
| 4.340 | $CH_3$ | H | H | 1 | $CH_3$ | H | H | H | CH—N$(CH_3)_2$ | H | Cl |
| 4.341 | $CH_3$ | H | H | 2 | $CH_3$ | H | H | H | CH—N$(CH_3)_2$ | H | Cl |
| 4.342 | $CH_3$ | H | H | 0 | $CH_3$ | H | H | H | CH—NHO$C_2H_5$ | H | Cl |
| 4.343 | $CH_3$ | H | H | 1 | $CH_3$ | H | H | H | CH—NHO$C_2H_5$ | H | Cl |
| 4.344 | $CH_3$ | H | H | 2 | $CH_3$ | H | H | H | CH—NHO$C_2H_5$ | H | Cl |
| 4.345 | $CH_3$ | H | H | 0 | $CH_3$ | H | H | H | CH—N($CH_3$)O$C_2H_5$ | H | Cl |
| 4.346 | $CH_3$ | H | H | 1 | $CH_3$ | H | H | H | CH—N($CH_3$)O$C_2H_5$ | H | Cl |
| 4.347 | $CH_3$ | H | H | 2 | $CH_3$ | H | H | H | CH—N($CH_3$)O$C_2H_5$ | H | Cl |
| 4.348 | $CH_3$ | H | H | 0 | $CH_3$ | H | H | H | C=N—$NH_2$ | H | Cl |
| 4.349 | $CH_3$ | H | H | 1 | $CH_3$ | H | H | H | C=N—$NH_2$ | H | Cl |
| 4.350 | $CH_3$ | H | H | 2 | $CH_3$ | H | H | H | C=N—$NH_2$ | H | Cl |
| 4.351 | $CH_3$ | H | H | 0 | $CH_3$ | H | H | H | C=N—N$(CH_3)_2$ | H | Cl |
| 4.352 | $CH_3$ | H | H | 1 | $CH_3$ | H | H | H | C=N—N$(CH_3)_2$ | H | Cl |
| 4.353 | $CH_3$ | H | H | 2 | $CH_3$ | H | H | H | C=N—N$(CH_3)_2$ | H | Cl |
| 4.354 | $CH_3$ | H | H | 0 | $CH_3$ | H | H | H | CH—N($CH_3$)O$CH_2C_6H_5$ | H | Cl |
| 4.355 | $CH_3$ | H | H | 1 | $CH_3$ | H | H | H | CH—N($CH_3$)O$CH_2C_6H_5$ | H | Cl |
| 4.356 | $CH_3$ | H | H | 2 | $CH_3$ | H | H | H | CH—N($CH_3$)O$CH_2C_6H_5$ | H | Cl |
| 4.357 | $CH_3$ | H | H | 0 | $CH_3$ | H | H | H | C($CH_3$)—O$CH_3$ | H | Cl |
| 4.358 | $CH_3$ | H | H | 1 | $CH_3$ | H | H | H | C($CH_3$)—O$CH_3$ | H | Cl |
| 4.359 | $CH_3$ | H | H | 2 | $CH_3$ | H | H | H | C($CH_3$)—O$CH_3$ | H | Cl |
| 4.360 | $CH_3$ | H | H | 0 | $CH_3$ | H | H | H | O | H | Cl |
| 4.361 | $CH_3$ | H | H | 2 | $CH_3$ | H | H | H | O | H | Cl |
| 4.362 | $CH_3$ | $CH_3$ | H | 0 | $CH_3$ | H | H | H | C=O | H | Cl |
| 4.363 | $CH_3$ | $CH_3$ | H | 1 | $CH_3$ | H | H | H | C=O | H | Cl |
| 4.364 | $CH_3$ | $CH_3$ | H | 2 | $CH_3$ | H | H | H | C=O | H | Cl |
| 4.365 | $CH_3$ | $CH_3$ | H | 0 | $CH_3$ | H | H | H | CHO$CH_3$ | H | Cl |
| 4.366 | $CH_3$ | $CH_3$ | H | 1 | $CH_3$ | H | H | H | CHO$CH_3$ | H | Cl |
| 4.367 | $CH_3$ | $CH_3$ | H | 2 | $CH_3$ | H | H | H | CHO$CH_3$ | H | Cl |
| 4.368 | $CH_3$ | $CH_3$ | H | 0 | $CH_3$ | H | H | H | CHO$C_2H_5$ | H | Cl |
| 4.369 | $CH_3$ | $CH_3$ | H | 1 | $CH_3$ | H | H | H | CHO$C_2H_5$ | H | Cl |
| 4.370 | $CH_3$ | $CH_3$ | H | 2 | $CH_3$ | H | H | H | CHO$C_2H_5$ | H | Cl |
| 4.371 | $CH_3$ | $CH_3$ | H | 0 | $CH_3$ | H | H | H | CHOiPr | H | Cl |
| 4.372 | $CH_3$ | $CH_3$ | H | 1 | $CH_3$ | H | H | H | CHOiPr | H | Cl |
| 4.373 | $CH_3$ | $CH_3$ | H | 2 | $CH_3$ | H | H | H | CHOiPr | H | Cl |
| 4.374 | $CH_3$ | $CH_3$ | H | 0 | $CH_3$ | H | H | H | C=NO$CH_3$ | H | Cl |
| 4.375 | $CH_3$ | $CH_3$ | H | 1 | $CH_3$ | H | H | H | C=NO$CH_3$ | H | Cl |
| 4.376 | $CH_3$ | $CH_3$ | H | 2 | $CH_3$ | H | H | H | C=NO$CH_3$ | H | Cl |
| 4.377 | $CH_3$ | $CH_3$ | H | 0 | $CH_3$ | H | H | H | C=NO$C_2H_5$ | H | Cl |
| 4.378 | $CH_3$ | $CH_3$ | H | 1 | $CH_3$ | H | H | H | C=NO$C_2H_5$ | H | Cl |
| 4.379 | $CH_3$ | $CH_3$ | H | 2 | $CH_3$ | H | H | H | C=NO$C_2H_5$ | H | Cl |
| 4.380 | $CH_3$ | $CH_3$ | H | 0 | $CH_3$ | H | H | H | C=NOiPr | H | Cl |
| 4.381 | $CH_3$ | $CH_3$ | H | 1 | $CH_3$ | H | H | H | C=NOiPr | H | Cl |
| 4.382 | $CH_3$ | $CH_3$ | H | 2 | $CH_3$ | H | H | H | C=NOiPr | H | Cl |
| 4.383 | $CH_3$ | $CH_3$ | H | 0 | $CH_3$ | H | H | H | C=NO$CH_2$CH=CHCl | H | Cl |
| 4.384 | $CH_3$ | $CH_3$ | H | 1 | $CH_3$ | H | H | H | C=NO$CH_2$CH=CHCl | H | Cl |
| 4.385 | $CH_3$ | $CH_3$ | H | 2 | $CH_3$ | H | H | H | C=NO$CH_2$CH=CHCl | H | Cl |
| 4.386 | $CH_3$ | $CH_3$ | H | 0 | $CH_3$ | H | H | H | C=NO$CH_2C_6H_5$ | H | Cl |
| 4.387 | $CH_3$ | $CH_3$ | H | 1 | $CH_3$ | H | H | H | C=NO$CH_2C_6H_5$ | H | Cl |
| 4.388 | $CH_3$ | $CH_3$ | H | 2 | $CH_3$ | H | H | H | C=NO$CH_2C_6H_5$ | H | Cl |
| 4.389 | $CH_3$ | $CH_3$ | H | 0 | $CH_3$ | H | H | H | C$(CH_3)_2$ | H | Cl |
| 4.390 | $CH_3$ | $CH_3$ | H | 1 | $CH_3$ | H | H | H | C$(CH_3)_2$ | H | Cl |
| 4.391 | $CH_3$ | $CH_3$ | H | 2 | $CH_3$ | H | H | H | C$(CH_3)_2$ | H | Cl |

TABLE 4-continued

Compounds of the formula

| No. | R17 | R18 | R19 | n | R12 | R13 | R21 | R22 | Y | L | M |
|---|---|---|---|---|---|---|---|---|---|---|---|
| 4.392 | CH3 | CH3 | H | 0 | CH3 | H | H | H | (1,3-dioxane-2,2-diyl-bis-methyleneoxy ring) | H | Cl |
| 4.393 | CH3 | CH3 | H | 1 | CH3 | H | H | H | (1,3-dioxane-2,2-diyl-bis-methyleneoxy ring) | H | Cl |
| 4.394 | CH3 | CH3 | H | 2 | CH3 | H | H | H | (1,3-dioxane-2,2-diyl-bis-methyleneoxy ring) | H | Cl |
| 4.395 | CH3 | CH3 | H | 0 | CH3 | H | H | H | (5,5-dimethyl-1,3-dioxane ring) | H | Cl |
| 4.396 | CH3 | CH3 | H | 1 | CH3 | H | H | H | (5,5-dimethyl-1,3-dioxane ring) | H | Cl |
| 4.397 | CH3 | CH3 | H | 2 | CH3 | H | H | H | (5,5-dimethyl-1,3-dioxane ring) | H | Cl |
| 4.398 | CH3 | CH3 | H | 0 | CH3 | H | H | H | C=N—CH3 | H | Cl |
| 4.399 | CH3 | CH3 | H | 1 | CH3 | H | H | H | C=N—CH3 | H | Cl |
| 4.400 | CH3 | CH3 | H | 2 | CH3 | H | H | H | C=N—CH3 | H | Cl |
| 4.401 | CH3 | CH3 | H | 0 | CH3 | H | H | H | C=NC2H5 | H | Cl |
| 4.402 | CH3 | CH3 | H | 1 | CH3 | H | H | H | C=NC2H5 | H | Cl |
| 4.403 | CH3 | CH3 | H | 2 | CH3 | H | H | H | C=NC2H5 | H | Cl |
| 4.404 | CH3 | CH3 | H | 0 | CH3 | H | H | H | CH—NHCH3 | H | Cl |
| 4.405 | CH3 | CH3 | H | 1 | CH3 | H | H | H | CH—NHCH3 | H | Cl |
| 4.406 | CH3 | CH3 | H | 2 | CH3 | H | H | H | CH—NHCH3 | H | Cl |
| 4.407 | CH3 | CH3 | H | 0 | CH3 | H | H | H | CH—NHC2H5 | H | Cl |
| 4.408 | CH3 | CH3 | H | 1 | CH3 | H | H | H | CH—NHC2H5 | H | Cl |
| 4.409 | CH3 | CH3 | H | 2 | CH3 | H | H | H | CH—NHC2H5 | H | Cl |
| 4.410 | CH3 | CH3 | H | 0 | CH3 | H | H | H | CH—N(CH3)2 | H | Cl |
| 4.411 | CH3 | CH3 | H | 1 | CH3 | H | H | H | CH—N(CH3)2 | H | Cl |
| 4.412 | CH3 | CH3 | H | 2 | CH3 | H | H | H | CH—N(CH3)2 | H | Cl |
| 4.413 | CH3 | CH3 | H | 0 | CH3 | H | H | H | CH—NHOC2H5 | H | Cl |
| 4.414 | CH3 | CH3 | H | 1 | CH3 | H | H | H | CH—NHOC2H5 | H | Cl |
| 4.415 | CH3 | CH3 | H | 2 | CH3 | H | H | H | CH—NHOC2H5 | H | Cl |
| 4.416 | CH3 | CH3 | H | 0 | CH3 | H | H | H | CH—N(CH3)OC2H5 | H | Cl |
| 4.417 | CH3 | CH3 | H | 1 | CH3 | H | H | H | CH—N(CH3)OC2H5 | H | Cl |
| 4.418 | CH3 | CH3 | H | 2 | CH3 | H | H | H | CH—N(CH3)OC2H5 | H | Cl |
| 4.419 | CH3 | CH3 | H | 0 | CH3 | H | H | H | C=N—NH2 | H | Cl |
| 4.420 | CH3 | CH3 | H | 1 | CH3 | H | H | H | C=N—NH2 | H | Cl |
| 4.421 | CH3 | CH3 | H | 2 | CH3 | H | H | H | C=N—NH2 | H | Cl |
| 4.422 | CH3 | CH3 | H | 0 | CH3 | H | H | H | C=N—N(CH3)2 | H | Cl |
| 4.423 | CH3 | CH3 | H | 1 | CH3 | H | H | H | C=N—N(CH3)2 | H | Cl |
| 4.424 | CH3 | CH3 | H | 2 | CH3 | H | H | H | C=N—N(CH3)2 | H | Cl |
| 4.425 | CH3 | CH3 | H | 0 | CH3 | H | H | H | CH—N(CH3)OCH2C6H5 | H | Cl |

TABLE 4-continued

Compounds of the formula

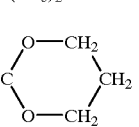

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.426 | $CH_3$ | $CH_3$ | H | 1 | $CH_3$ | H | H | H | CH—N($CH_3$)$OCH_2C_6H_5$ | H | Cl |
| 4.427 | $CH_3$ | $CH_3$ | H | 2 | $CH_3$ | H | H | H | CH—N($CH_3$)$OCH_2C_6H_5$ | H | Cl |
| 4.428 | $CH_3$ | $CH_3$ | H | 0 | $CH_3$ | H | H | H | C($CH_3$)—$OCH_3$ | H | Cl |
| 4.429 | $CH_3$ | $CH_3$ | H | 1 | $CH_3$ | H | H | H | C($CH_3$)—$OCH_3$ | H | Cl |
| 4.430 | $CH_3$ | $CH_3$ | H | 2 | $CH_3$ | H | H | H | C($CH_3$)—$OCH_3$ | H | Cl |
| 4.431 | $CH_3$ | $CH_3$ | H | 0 | $CH_3$ | H | H | H | O | H | Cl |
| 4.432 | $CH_3$ | $CH_3$ | H | 2 | $CH_3$ | H | H | H | O | H | Cl |
| 4.433 | H | H | H | 0 | $CH_3$ | H | $CH_3$ | H | C=O | H | $CH_3$ |
| 4.434 | H | H | H | 1 | $CH_3$ | H | $CH_3$ | H | C=O | H | $CH_3$ |
| 4.435 | H | H | H | 2 | $CH_3$ | H | $CH_3$ | H | C=O | H | $CH_3$ |
| 4.436 | H | H | H | 0 | $CH_3$ | H | $CH_3$ | H | CH—$OCH_3$ | H | $CH_3$ |
| 4.437 | H | H | H | 1 | $CH_3$ | H | $CH_3$ | H | CH—$OCH_3$ | H | $CH_3$ |
| 4.438 | H | H | H | 2 | $CH_3$ | H | $CH_3$ | H | CH—$OCH_3$ | H | $CH_3$ |
| 4.439 | H | H | H | 0 | $CH_3$ | H | $CH_3$ | H | $CHOC_2H_5$ | H | $CH_3$ |
| 4.440 | H | H | H | 1 | $CH_3$ | H | $CH_3$ | H | $CHOC_2H_5$ | H | $CH_3$ |
| 4.441 | H | H | H | 2 | $CH_3$ | H | $CH_3$ | H | $CHOC_2H_5$ | H | $CH_3$ |
| 4.442 | H | H | H | 0 | $CH_3$ | H | $CH_3$ | H | CHOiPr | H | $CH_3$ |
| 4.443 | H | H | H | 1 | $CH_3$ | H | $CH_3$ | H | CHOiPr | H | $CH_3$ |
| 4.444 | H | H | H | 2 | $CH_3$ | H | $CH_3$ | H | CHOiPr | H | $CH_3$ |
| 4.445 | H | H | H | 0 | $CH_3$ | H | $CH_3$ | H | C=$NOCH_3$ | H | $CH_3$ |
| 4.446 | H | H | H | 1 | $CH_3$ | H | $CH_3$ | H | C=$NOCH_3$ | H | $CH_3$ |
| 4.447 | H | H | H | 2 | $CH_3$ | H | $CH_3$ | H | C=$NOCH_3$ | H | $CH_3$ |
| 4.448 | H | H | H | 0 | $CH_3$ | H | $CH_3$ | H | C=$NOC_2H_5$ | H | $CH_3$ |
| 4.449 | H | H | H | 1 | $CH_3$ | H | $CH_3$ | H | C=$NOC_2H_5$ | H | $CH_3$ |
| 4.450 | H | H | H | 2 | $CH_3$ | H | $CH_3$ | H | C=$NOC_2H_5$ | H | $CH_3$ |
| 4.451 | H | H | H | 0 | $CH_3$ | H | $CH_3$ | H | C=NOiPr | H | $CH_3$ |
| 4.452 | H | H | H | 1 | $CH_3$ | H | $CH_3$ | H | C=$NOC_2H_5$ | H | $CH_3$ |
| 4.453 | H | H | H | 2 | $CH_3$ | H | $CH_3$ | H | C=NOiPr | H | $CH_3$ |
| 4.454 | H | H | H | 0 | $CH_3$ | H | $CH_3$ | H | C=$NOCH_2$CH=CHCl | H | $CH_3$ |
| 4.455 | H | H | H | 1 | $CH_3$ | H | $CH_3$ | H | C=$NOCH_2$CH=CHCl | H | $CH_3$ |
| 4.456 | H | H | H | 2 | $CH_3$ | H | $CH_3$ | H | C=$NOCH_2$CH=CHCl | H | $CH_3$ |
| 4.457 | H | H | H | 0 | $CH_3$ | H | $CH_3$ | H | C=$NOCH_2C_6H_5$ | H | $CH_3$ |
| 4.458 | H | H | H | 1 | $CH_3$ | H | $CH_3$ | H | C=$NOCH_2C_6H_5$ | H | $CH_3$ |
| 4.459 | H | H | H | 2 | $CH_3$ | H | $CH_3$ | H | C=$NOCH_2C_6H_5$ | H | $CH_3$ |
| 4.460 | H | H | H | 0 | $CH_3$ | H | $CH_3$ | H | C($CH_3$)$_2$ | H | $CH_3$ |
| 4.461 | H | H | H | 1 | $CH_3$ | H | $CH_3$ | H | C($CH_3$)$_2$ | H | $CH_3$ |
| 4.462 | H | H | H | 2 | $CH_3$ | H | $CH_3$ | H | C($CH_3$)$_2$ | H | $CH_3$ |
| 4.463 | H | H | H | 0 | $CH_3$ | H | | H | 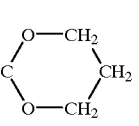 | H | $CH_3$ |
| 4.464 | H | H | H | 1 | $CH_3$ | H | H | H | 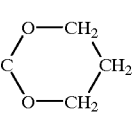 | H | $CH_3$ |
| 4.465 | H | H | H | 2 | $CH_3$ | H | H | H | 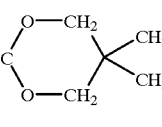 | H | $CH_3$ |
| 4.466 | H | H | H | 0 | $CH_3$ | H | H | H |  | H | $CH_3$ |

TABLE 4-continued

Compounds of the formula

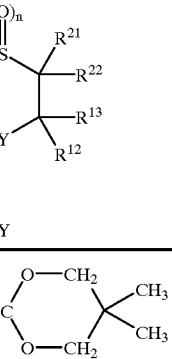

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.467 | H | H | H | 1 | $CH_3$ | H | H | H | 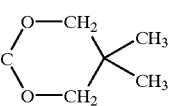 | H | $CH_3$ |
| 4.468 | H | H | H | 2 | $CH_3$ | H | H | H | (same dioxane group) | H | $CH_3$ |
| 4.469 | H | H | H | 0 | $CH_3$ | H | H | H | C=N—$CH_3$ | H | $CH_3$ |
| 4.470 | H | H | H | 1 | $CH_3$ | H | H | H | C=N—$CH_3$ | H | $CH_3$ |
| 4.471 | H | H | H | 2 | $CH_3$ | H | H | H | C=N—$CH_3$ | H | $CH_3$ |
| 4.472 | H | H | H | 0 | $CH_3$ | H | H | H | C=N$C_2H_5$ | H | $CH_3$ |
| 4.473 | H | H | H | 1 | $CH_3$ | H | H | H | C=N$C_2H_5$ | H | $CH_3$ |
| 4.474 | H | H | H | 2 | $CH_3$ | H | H | H | C=N$C_2H_5$ | H | $CH_3$ |
| 4.475 | H | H | H | 0 | $CH_3$ | H | $CH_3$ | H | CH—NH$CH_3$ | H | $CH_3$ |
| 4.476 | H | H | H | 1 | $CH_3$ | H | $CH_3$ | H | CH—NH$CH_3$ | H | $CH_3$ |
| 4.477 | H | H | H | 2 | $CH_3$ | H | $CH_3$ | H | CH—NH$CH_3$ | H | $CH_3$ |
| 4.478 | H | H | H | 0 | $CH_3$ | H | $CH_3$ | H | CH—NH$C_2H_5$ | H | $CH_3$ |
| 4.479 | H | H | H | 1 | $CH_3$ | H | $CH_3$ | H | CH—NH$C_2H_5$ | H | $CH_3$ |
| 4.480 | H | H | H | 2 | $CH_3$ | H | $CH_3$ | H | CH—NH$C_2H_5$ | H | $CH_3$ |
| 4.481 | H | H | H | 0 | $CH_3$ | H | $CH_3$ | H | CH—N($CH_3$)$_2$ | H | $CH_3$ |
| 4.482 | H | H | H | 1 | $CH_3$ | H | $CH_3$ | H | CH—N($CH_3$)$_2$ | H | $CH_3$ |
| 4.483 | H | H | H | 2 | $CH_3$ | H | $CH_3$ | H | CH—N($CH_3$)$_2$ | H | $CH_3$ |
| 4.484 | H | H | H | 0 | $CH_3$ | H | $CH_3$ | H | CH—NHO$C_2H_5$ | H | $CH_3$ |
| 4.485 | H | H | H | 1 | $CH_3$ | H | $CH_3$ | H | CH—NHO$C_2H_5$ | H | $CH_3$ |
| 4.486 | H | H | H | 2 | $CH_3$ | H | $CH_3$ | H | CH—NHO$C_2H_5$ | H | $CH_3$ |
| 4.487 | H | H | H | 0 | $CH_3$ | H | $CH_3$ | H | CH—N($CH_3$)O$C_2H_5$ | H | $CH_3$ |
| 4.488 | H | H | H | 1 | $CH_3$ | H | $CH_3$ | H | CH—N($CH_3$)O$C_2H_5$ | H | $CH_3$ |
| 4.489 | H | H | H | 2 | $CH_3$ | H | $CH_3$ | H | CH—N($CH_3$)O$C_2H_5$ | H | $CH_3$ |
| 4.490 | H | H | H | 0 | $CH_3$ | H | $CH_3$ | H | C=N—$NH_2$ | H | $CH_3$ |
| 4.491 | H | H | H | 1 | $CH_3$ | H | $CH_3$ | H | C=N—$NH_2$ | H | $CH_3$ |
| 4.492 | H | H | H | 2 | $CH_3$ | H | $CH_3$ | H | C=N—$NH_2$ | H | $CH_3$ |
| 4.493 | H | H | H | 0 | $CH_3$ | H | $CH_3$ | H | C=N—N($CH_3$)$_2$ | H | $CH_3$ |
| 4.494 | H | H | H | 1 | $CH_3$ | H | $CH_3$ | H | C=N—N($CH_3$)$_2$ | H | $CH_3$ |
| 4.495 | H | H | H | 2 | $CH_3$ | H | $CH_3$ | H | C=N—N($CH_3$)$_2$ | H | $CH_3$ |
| 4.496 | H | H | H | 0 | $CH_3$ | H | $CH_3$ | H | CH—N($CH_3$)OCH$_2$C$_6$H$_5$ | H | $CH_3$ |
| 4.497 | H | H | H | 1 | $CH_3$ | H | $CH_3$ | H | CH—N($CH_3$)OCH$_2$C$_6$H$_5$ | H | $CH_3$ |
| 4.498 | H | H | H | 2 | $CH_3$ | H | $CH_3$ | H | CH—N($CH_3$)OCH$_2$C$_6$H$_5$ | H | $CH_3$ |
| 4.499 | H | H | H | 0 | $CH_3$ | H | $CH_3$ | H | C($CH_3$)—O$CH_3$ | H | $CH_3$ |
| 4.500 | H | H | H | 1 | $CH_3$ | H | $CH_3$ | H | C($CH_3$)—O$CH_3$ | H | $CH_3$ |
| 4.501 | H | H | H | 2 | $CH_3$ | H | $CH_3$ | H | C($CH_3$)—O$CH_3$ | H | $CH_3$ |
| 4.502 | H | H | H | 0 | $CH_3$ | H | $CH_3$ | H | O | H | $CH_3$ |
| 4.503 | H | H | H | 2 | $CH_3$ | H | $CH_3$ | H | O | H | $CH_3$ |
| 4.504 | $CH_3$ | H | H | 0 | $CH_3$ | H | $CH_3$ | H | C=O | H | $CH_3$ |
| 4.505 | $CH_3$ | H | H | 1 | $CH_3$ | H | $CH_3$ | H | C=O | H | $CH_3$ |
| 4.506 | $CH_3$ | H | H | 2 | $CH_3$ | H | $CH_3$ | H | C=O | H | $CH_3$ |
| 4.507 | $CH_3$ | H | H | 0 | $CH_3$ | H | $CH_3$ | H | CHO$CH_3$ | H | $CH_3$ |
| 4.508 | $CH_3$ | H | H | 1 | $CH_3$ | H | $CH_3$ | H | CHO$CH_3$ | H | $CH_3$ |
| 4.509 | $CH_3$ | H | H | 2 | $CH_3$ | H | $CH_3$ | H | CHO$CH_3$ | H | $CH_3$ |
| 4.510 | $CH_3$ | H | H | 0 | $CH_3$ | H | $CH_3$ | H | CHO$C_2H_5$ | H | $CH_3$ |
| 4.511 | $CH_3$ | H | H | 1 | $CH_3$ | H | $CH_3$ | H | CHO$C_2H_5$ | H | $CH_3$ |
| 4.512 | $CH_3$ | H | H | 2 | $CH_3$ | H | $CH_3$ | H | CHO$C_2H_5$ | H | $CH_3$ |
| 4.513 | $CH_3$ | H | H | 0 | $CH_3$ | H | $CH_3$ | H | CHOiPr | H | $CH_3$ |
| 4.514 | $CH_3$ | H | H | 1 | $CH_3$ | H | $CH_3$ | H | CHOiPr | H | $CH_3$ |
| 4.515 | $CH_3$ | H | H | 2 | $CH_3$ | H | $CH_3$ | H | CHOiPr | H | $CH_3$ |
| 4.516 | $CH_3$ | H | H | 0 | $CH_3$ | H | $CH_3$ | H | C=NO$CH_3$ | H | $CH_3$ |
| 4.517 | $CH_3$ | H | H | 1 | $CH_3$ | H | $CH_3$ | H | C=NO$CH_3$ | H | $CH_3$ |
| 4.518 | $CH_3$ | H | H | 2 | $CH_3$ | H | $CH_3$ | H | C=NO$CH_3$ | H | $CH_3$ |
| 4.519 | $CH_3$ | H | H | 0 | $CH_3$ | H | $CH_3$ | H | C=NO$C_2H_5$ | H | $CH_3$ |
| 4.520 | $CH_3$ | H | H | 1 | $CH_3$ | H | $CH_3$ | H | C=NO$C_2H_5$ | H | $CH_3$ |

TABLE 4-continued

Compounds of the formula

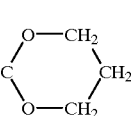

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.521 | $CH_3$ | H | H | 2 | $CH_3$ | H | $CH_3$ | H | C=$NOC_2H_5$ | H | $CH_3$ |
| 4.522 | $CH_3$ | H | H | 0 | $CH_3$ | H | $CH_3$ | H | C=NOiPr | H | $CH_3$ |
| 4.523 | $CH_3$ | H | H | 1 | $CH_3$ | H | $CH_3$ | H | C=NOiPr | H | $CH_3$ |
| 4.524 | $CH_3$ | H | H | 2 | $CH_3$ | H | $CH_3$ | H | C=NOiPr | H | $CH_3$ |
| 4.525 | $CH_3$ | H | H | 0 | $CH_3$ | H | $CH_3$ | H | C=$NOCH_2CH$=CHCl | H | $CH_3$ |
| 4.526 | $CH_3$ | H | H | 1 | $CH_3$ | H | $CH_3$ | H | C=$NOCH_2CH$=CHCl | H | $CH_3$ |
| 4.527 | $CH_3$ | H | H | 2 | $CH_3$ | H | $CH_3$ | H | C=$NOCH_2CH$=CHCl | H | $CH_3$ |
| 4.528 | $CH_3$ | H | H | 0 | $CH_3$ | H | $CH_3$ | H | C=$NOCH_2C_6H_5$ | H | $CH_3$ |
| 4.529 | $CH_3$ | H | H | 1 | $CH_3$ | H | $CH_3$ | H | C=$NOCH_2C_6H_5$ | H | $CH_3$ |
| 4.530 | $CH_3$ | H | H | 2 | $CH_3$ | H | $CH_3$ | H | C=$NOCH_2C_6H_5$ | H | $CH_3$ |
| 4.531 | $CH_3$ | H | H | 0 | $CH_3$ | H | $CH_3$ | H | $C(CH_3)_2$ | H | $CH_3$ |
| 4.532 | $CH_3$ | H | H | 1 | $CH_3$ | H | $CH_3$ | H | $C(CH_3)_2$ | H | $CH_3$ |
| 4.533 | $CH_3$ | H | H | 2 | $CH_3$ | H | $CH_3$ | H | $C(CH_3)_2$ | H | $CH_3$ |
| 4.534 | $CH_3$ | H | H | 0 | $CH_3$ | H | $CH_3$ | H | 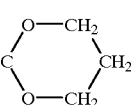 | H | $CH_3$ |
| 4.535 | $CH_3$ | H | H | 1 | $CH_3$ | H | $CH_3$ | H | 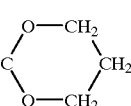 | H | $CH_3$ |
| 4.536 | $CH_3$ | H | H | 2 | $CH_3$ | H | $CH_3$ | H | 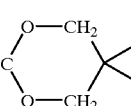 | H | $CH_3$ |
| 4.537 | $CH_3$ | H | H | 0 | $CH_3$ | H | $CH_3$ | H | 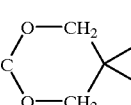 | H | $CH_3$ |
| 4.538 | $CH_3$ | H | H | 1 | $CH_3$ | H | $CH_3$ | H | 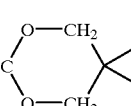 | H | $CH_3$ |
| 4.539 | $CH_3$ | H | H | 2 | $CH_3$ | H | $CH_3$ | H |  | H | $CH_3$ |
| 4.540 | $CH_3$ | H | H | 0 | $CH_3$ | H | $CH_3$ | H | C=N—$CH_3$ | H | $CH_3$ |
| 4.541 | $CH_3$ | H | H | 1 | $CH_3$ | H | $CH_3$ | H | C=N—$CH_3$ | H | $CH_3$ |
| 4.542 | $CH_3$ | H | H | 2 | $CH_3$ | H | $CH_3$ | H | C=N—$CH_3$ | H | $CH_3$ |
| 4.543 | $CH_3$ | H | H | 0 | $CH_3$ | H | $CH_3$ | H | C=$NC_2H_5$ | H | $CH_3$ |
| 4.544 | $CH_3$ | H | H | 1 | $CH_3$ | H | $CH_3$ | H | C=$NC_2H_5$ | H | $CH_3$ |
| 4.545 | $CH_3$ | H | H | 2 | $CH_3$ | H | $CH_3$ | H | C=$NC_2H_5$ | H | $CH_3$ |
| 4.546 | $CH_3$ | H | H | 0 | $CH_3$ | H | $CH_3$ | H | CH—$NHCH_3$ | H | $CH_3$ |
| 4.547 | $CH_3$ | H | H | 1 | $CH_3$ | H | $CH_3$ | H | CH—$NHCH_3$ | H | $CH_3$ |
| 4.548 | $CH_3$ | H | H | 2 | $CH_3$ | H | $CH_3$ | H | CH—$NHCH_3$ | H | $CH_3$ |
| 4.549 | $CH_3$ | H | H | 0 | $CH_3$ | H | $CH_3$ | H | CH—$NHC_2H_5$ | H | $CH_3$ |
| 4.550 | $CH_3$ | H | H | 1 | $CH_3$ | H | $CH_3$ | H | CH—$NHC_2H_5$ | H | $CH_3$ |
| 4.551 | $CH_3$ | H | H | 2 | $CH_3$ | H | $CH_3$ | H | CH—$NHC_2H_5$ | H | $CH_3$ |
| 4.552 | $CH_3$ | H | H | 0 | $CH_3$ | H | $CH_3$ | H | CH—$N(CH_3)_2$ | H | $CH_3$ |
| 4.553 | $CH_3$ | H | H | 1 | $CH_3$ | H | $CH_3$ | H | CH—$N(CH_3)_2$ | H | $CH_3$ |

TABLE 4-continued

Compounds of the formula $$\text{structure with OH, O, M, (O)}_n, R^{21}, R^{22}, R^{13}, R^{12}, R^{17}, R^{18}, R^{19}, Y, L$$

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.554 | $CH_3$ | H | H | 2 | $CH_3$ | H | $CH_3$ | H | CH—N($CH_3$)$_2$ | H | $CH_3$ |
| 4.555 | $CH_3$ | H | H | 0 | $CH_3$ | H | $CH_3$ | H | CH—NHOC$_2$H$_5$ | H | $CH_3$ |
| 4.556 | $CH_3$ | H | H | 1 | $CH_3$ | H | $CH_3$ | H | CH—NHOC$_2$H$_5$ | H | $CH_3$ |
| 4.557 | $CH_3$ | H | H | 2 | $CH_3$ | H | $CH_3$ | H | CH—NHOC$_2$H$_5$ | H | $CH_3$ |
| 4.558 | $CH_3$ | H | H | 0 | $CH_3$ | H | $CH_3$ | H | CH—N($CH_3$)OC$_2$H$_5$ | H | $CH_3$ |
| 4.559 | $CH_3$ | H | H | 1 | $CH_3$ | H | $CH_3$ | H | CH—N($CH_3$)OC$_2$H$_5$ | H | $CH_3$ |
| 4.560 | $CH_3$ | H | H | 2 | $CH_3$ | H | $CH_3$ | H | CH—N($CH_3$)OC$_2$H$_5$ | H | $CH_3$ |
| 4.561 | $CH_3$ | H | H | 0 | $CH_3$ | H | $CH_3$ | H | C=N—NH$_2$ | H | $CH_3$ |
| 4.562 | $CH_3$ | H | H | 1 | $CH_3$ | H | $CH_3$ | H | C=N—NH$_2$ | H | $CH_3$ |
| 4.563 | $CH_3$ | H | H | 2 | $CH_3$ | H | $CH_3$ | H | C=N—NH$_2$ | H | $CH_3$ |
| 4.564 | $CH_3$ | H | H | 0 | $CH_3$ | H | $CH_3$ | H | C=N—N($CH_3$)$_2$ | H | $CH_3$ |
| 4.565 | $CH_3$ | H | H | 1 | $CH_3$ | H | $CH_3$ | H | C=N—N($CH_3$)$_2$ | H | $CH_3$ |
| 4.566 | $CH_3$ | H | H | 2 | $CH_3$ | H | $CH_3$ | H | C=N—N($CH_3$)$_2$ | H | $CH_3$ |
| 4.567 | $CH_3$ | H | H | 0 | $CH_3$ | H | $CH_3$ | H | CH—N($CH_3$)OCH$_2$C$_6$H$_5$ | H | $CH_3$ |
| 4.568 | $CH_3$ | H | H | 1 | $CH_3$ | H | $CH_3$ | H | CH—N($CH_3$)OCH$_2$C$_6$H$_5$ | H | $CH_3$ |
| 4.569 | $CH_3$ | H | H | 2 | $CH_3$ | H | $CH_3$ | H | CH—N($CH_3$)OCH$_2$C$_6$H$_5$ | H | $CH_3$ |
| 4.570 | $CH_3$ | H | H | 0 | $CH_3$ | H | $CH_3$ | H | C($CH_3$)—OCH$_3$ | H | $CH_3$ |
| 4.571 | $CH_3$ | H | H | 1 | $CH_3$ | H | $CH_3$ | H | C($CH_3$)—OCH$_3$ | H | $CH_3$ |
| 4.572 | $CH_3$ | H | H | 2 | $CH_3$ | H | $CH_3$ | H | C($CH_3$)—OCH$_3$ | H | $CH_3$ |
| 4.573 | $CH_3$ | H | H | 0 | $CH_3$ | H | $CH_3$ | H | O | H | $CH_3$ |
| 4.574 | $CH_3$ | H | H | 2 | $CH_3$ | H | $CH_3$ | H | O | H | $CH_3$ |
| 4.575 | $CH_3$ | $CH_3$ | H | 0 | $CH_3$ | H | $CH_3$ | H | C=O | H | $CH_3$ |
| 4.576 | $CH_3$ | $CH_3$ | H | 1 | $CH_3$ | H | $CH_3$ | H | C=O | H | $CH_3$ |
| 4.577 | $CH_3$ | $CH_3$ | H | 2 | $CH_3$ | H | $CH_3$ | H | C=O | H | $CH_3$ |
| 4.578 | $CH_3$ | $CH_3$ | H | 0 | $CH_3$ | H | $CH_3$ | H | CHOCH$_3$ | H | $CH_3$ |
| 4.579 | $CH_3$ | $CH_3$ | H | 1 | $CH_3$ | H | $CH_3$ | H | CHOCH$_3$ | H | $CH_3$ |
| 4.580 | $CH_3$ | $CH_3$ | H | 2 | $CH_3$ | H | $CH_3$ | H | CHOCH$_3$ | H | $CH_3$ |
| 4.581 | $CH_3$ | $CH_3$ | H | 0 | $CH_3$ | H | $CH_3$ | H | CHOC$_2$H$_5$ | H | $CH_3$ |
| 4.582 | $CH_3$ | $CH_3$ | H | 1 | $CH_3$ | H | $CH_3$ | H | CHOC$_2$H$_5$ | H | $CH_3$ |
| 4.583 | $CH_3$ | $CH_3$ | H | 2 | $CH_3$ | H | $CH_3$ | H | CHOC$_2$H$_5$ | H | $CH_3$ |
| 4.584 | $CH_3$ | $CH_3$ | H | 0 | $CH_3$ | H | $CH_3$ | H | CHOiPr | H | $CH_3$ |
| 4.585 | $CH_3$ | $CH_3$ | H | 1 | $CH_3$ | H | $CH_3$ | H | CHOiPr | H | $CH_3$ |
| 4.586 | $CH_3$ | $CH_3$ | H | 2 | $CH_3$ | H | $CH_3$ | H | CHOiPr | H | $CH_3$ |
| 4.587 | $CH_3$ | $CH_3$ | H | 0 | $CH_3$ | H | $CH_3$ | H | C=NOCH$_3$ | H | $CH_3$ |
| 4.588 | $CH_3$ | $CH_3$ | H | 1 | $CH_3$ | H | $CH_3$ | H | C=NOCH$_3$ | H | $CH_3$ |
| 4.589 | $CH_3$ | $CH_3$ | H | 2 | $CH_3$ | H | $CH_3$ | H | C=NOCH$_3$ | H | $CH_3$ |
| 4.590 | $CH_3$ | $CH_3$ | H | 0 | $CH_3$ | H | $CH_3$ | H | C=NOC$_2$H$_5$ | H | $CH_3$ |
| 4.591 | $CH_3$ | $CH_3$ | H | 1 | $CH_3$ | H | $CH_3$ | H | C=NOC$_2$H$_5$ | H | $CH_3$ |
| 4.592 | $CH_3$ | $CH_3$ | H | 2 | $CH_3$ | H | $CH_3$ | H | C=NOC$_2$H$_5$ | H | $CH_3$ |
| 4.593 | $CH_3$ | $CH_3$ | H | 0 | $CH_3$ | H | $CH_3$ | H | C=NOiPr | H | $CH_3$ |
| 4.594 | $CH_3$ | $CH_3$ | H | 1 | $CH_3$ | H | $CH_3$ | H | C=NOiPr | H | $CH_3$ |
| 4.595 | $CH_3$ | $CH_3$ | H | 2 | $CH_3$ | H | $CH_3$ | H | C=NOiPr | H | $CH_3$ |
| 4.596 | $CH_3$ | $CH_3$ | H | 0 | $CH_3$ | H | $CH_3$ | H | C=NOCH$_2$CH=CHCl | H | $CH_3$ |
| 4.597 | $CH_3$ | $CH_3$ | H | 1 | $CH_3$ | H | $CH_3$ | H | C=NOCH$_2$CH=CHCl | H | $CH_3$ |
| 4.598 | $CH_3$ | $CH_3$ | H | 2 | $CH_3$ | H | $CH_3$ | H | C=NOCH$_2$CH=CHCl | H | $CH_3$ |
| 4.599 | $CH_3$ | $CH_3$ | H | 0 | $CH_3$ | H | $CH_3$ | H | C=NOCH$_2$C$_6$H$_5$ | H | $CH_3$ |
| 4.600 | $CH_3$ | $CH_3$ | H | 1 | $CH_3$ | H | $CH_3$ | H | C=NOCH$_2$C$_6$H$_5$ | H | $CH_3$ |
| 4.601 | $CH_3$ | $CH_3$ | H | 2 | $CH_3$ | H | $CH_3$ | H | C=NOCH$_2$C$_6$H$_5$ | H | $CH_3$ |
| 4.602 | $CH_3$ | $CH_3$ | H | 0 | $CH_3$ | H | $CH_3$ | H | C($CH_3$)$_2$ | H | $CH_3$ |
| 4.603 | $CH_3$ | $CH_3$ | H | 1 | $CH_3$ | H | $CH_3$ | H | C($CH_3$)$_2$ | H | $CH_3$ |
| 4.604 | $CH_3$ | $CH_3$ | H | 2 | $CH_3$ | H | $CH_3$ | H | C($CH_3$)$_2$ | H | $CH_3$ |
| 4.605 | $CH_3$ | $CH_3$ | H | 0 | $CH_3$ | H | $CH_3$ | H | dioxane ring (C with O—CH$_2$—CH$_2$—CH$_2$—O) | H | $CH_3$ |
| 4.606 | $CH_3$ | $CH_3$C | H | 1 | $CH_3$ | H | $CH_3$ | H | dioxane ring (C with O—CH$_2$—CH$_2$—CH$_2$—O) | H | $CH_3$ |

TABLE 4-continued

Compounds of the formula

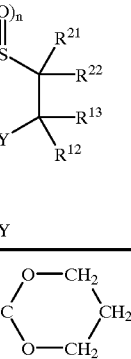

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.607 | $CH_3$ | $CH_3$ | H | 2 | $CH_3$ | H | $CH_3$ | H | 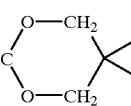 | H | $CH_3$ |
| 4.608 | $CH_3$ | $CH_3$ | H | 0 | $CH_3$ | H | $CH_3$ | H | 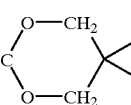 | H | $CH_3$ |
| 4.609 | $CH_3$ | $CH_3$ | H | 1 | $CH_3$ | H | $CH_3$ | H |  | H | $CH_3$ |
| 4.610 | $CH_3$ | $CH_3$ | H | 2 | $CH_3$ | H | $CH_3$ | H | 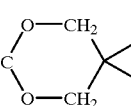 | H | $CH_3$ |
| 4.611 | $CH_3$ | $CH_3$ | H | 0 | $CH_3$ | H | $CH_3$ | H | C=N—$CH_3$ | H | $CH_3$ |
| 4.612 | $CH_3$ | $CH_3$ | H | 1 | $CH_3$ | H | $CH_3$ | H | C=N—$CH_3$ | H | $CH_3$ |
| 4.613 | $CH_3$ | $CH_3$ | H | 2 | $CH_3$ | H | $CH_3$ | H | C=N—$CH_3$ | H | $CH_3$ |
| 4.614 | $CH_3$ | $CH_3$ | H | 0 | $CH_3$ | H | $CH_3$ | H | C=N$C_2H_5$ | H | $CH_3$ |
| 4.615 | $CH_3$ | $CH_3$ | H | 1 | $CH_3$ | H | $CH_3$ | H | C=N$C_2H_5$ | H | $CH_3$ |
| 4.616 | $CH_3$ | $CH_3$ | H | 2 | $CH_3$ | H | $CH_3$ | H | C=N$C_2H_5$ | H | $CH_3$ |
| 4.617 | $CH_3$ | $CH_3$ | H | 0 | $CH_3$ | H | $CH_3$ | H | CH—NH$CH_3$ | H | $CH_3$ |
| 4.618 | $CH_3$ | $CH_3$ | H | 1 | $CH_3$ | H | $CH_3$ | H | CH—NH$CH_3$ | H | $CH_3$ |
| 4.619 | $CH_3$ | $CH_3$ | H | 2 | $CH_3$ | H | $CH_3$ | H | CH—NH$CH_3$ | H | $CH_3$ |
| 4.620 | $CH_3$ | $CH_3$ | H | 0 | $CH_3$ | H | $CH_3$ | H | CH—NH$C_2H_5$ | H | $CH_3$ |
| 4.621 | $CH_3$ | $CH_3$ | H | 1 | $CH_3$ | H | $CH_3$ | H | CH—NH$C_2H_5$ | H | $CH_3$ |
| 4.622 | $CH_3$ | $CH_3$ | H | 2 | $CH_3$ | H | $CH_3$ | H | CH—NH$C_2H_5$ | H | $CH_3$ |
| 4.623 | $CH_3$ | $CH_3$ | H | 0 | $CH_3$ | H | $CH_3$ | H | CH—N($CH_3$)$_2$ | H | $CH_3$ |
| 4.624 | $CH_3$ | $CH_3$ | H | 1 | $CH_3$ | H | $CH_3$ | H | CH—N($CH_3$)$_2$ | H | $CH_3$ |
| 4.625 | $CH_3$ | $CH_3$ | H | 2 | $CH_3$ | H | $CH_3$ | H | CH—N($CH_3$)$_2$ | H | $CH_3$ |
| 4.626 | $CH_3$ | $CH_3$ | H | 0 | $CH_3$ | H | $CH_3$ | H | CH—NHO$C_2H_5$ | H | $CH_3$ |
| 4.627 | $CH_3$ | $CH_3$ | H | 1 | $CH_3$ | H | $CH_3$ | H | CH—NHO$C_2H_5$ | H | $CH_3$ |
| 4.628 | $CH_3$ | $CH_3$ | H | 2 | $CH_3$ | H | $CH_3$ | H | CH—NHO$C_2H_5$ | H | $CH_3$ |
| 4.629 | $CH_3$ | $CH_3$ | H | 0 | $CH_3$ | H | $CH_3$ | H | CH—N($CH_3$)O$C_2H_5$ | H | $CH_3$ |
| 4.630 | $CH_3$ | $CH_3$ | H | 1 | $CH_3$ | H | $CH_3$ | H | CH—N($CH_3$)O$C_2H_5$ | H | $CH_3$ |
| 4.631 | $CH_3$ | $CH_3$ | H | 2 | $CH_3$ | H | $CH_3$ | H | CH—N($CH_3$)O$C_2H_5$ | H | $CH_3$ |
| 4.632 | $CH_3$ | $CH_3$ | H | 0 | $CH_3$ | H | $CH_3$ | H | C=N—$NH_2$ | H | $CH_3$ |
| 4.633 | $CH_3$ | $CH_3$ | H | 1 | $CH_3$ | H | $CH_3$ | H | C=N—$NH_2$ | H | $CH_3$ |
| 4.634 | $CH_3$ | $CH_3$ | H | 2 | $CH_3$ | H | $CH_3$ | H | C=N—$NH_2$ | H | $CH_3$ |
| 4.635 | $CH_3$ | $CH_3$ | H | 0 | $CH_3$ | H | $CH_3$ | H | C=N—N($CH_3$)$_2$ | H | $CH_3$ |
| 4.636 | $CH_3$ | $CH_3$ | H | 1 | $CH_3$ | H | $CH_3$ | H | C=N—N($CH_3$)$_2$ | H | $CH_3$ |
| 4.637 | $CH_3$ | $CH_3$ | H | 2 | $CH_3$ | H | $CH_3$ | H | C=N—N($CH_3$)$_2$ | H | $CH_3$ |
| 4.638 | $CH_3$ | $CH_3$ | H | 0 | $CH_3$ | H | $CH_3$ | H | CH—N($CH_3$)OCH$_2$C$_6$H$_5$ | H | $CH_3$ |
| 4.639 | $CH_3$ | $CH_3$ | H | 1 | $CH_3$ | H | $CH_3$ | H | CH—N($CH_3$)OCH$_2$C$_6$H$_5$ | H | $CH_3$ |
| 4.640 | $CH_3$ | $CH_3$ | H | 2 | $CH_3$ | H | $CH_3$ | H | CH—N($CH_3$)OCH$_2$C$_6$H$_5$ | H | $CH_3$ |
| 4.641 | $CH_3$ | $CH_3$ | H | 0 | $CH_3$ | H | $CH_3$ | H | C($CH_3$)—O$CH_3$ | H | $CH_3$ |
| 4.642 | $CH_3$ | $CH_3$ | H | 1 | $CH_3$ | H | $CH_3$ | H | C($CH_3$)—O$CH_3$ | H | $CH_3$ |
| 4.643 | $CH_3$ | $CH_3$ | H | 2 | $CH_3$ | H | $CH_3$ | H | C($CH_3$)—O$CH_3$ | H | $CH_3$ |
| 4.644 | $CH_3$ | $CH_3$ | H | 0 | $CH_3$ | H | $CH_3$ | H | O | H | $CH_3$ |
| 4.645 | $CH_3$ | $CH_3$ | H | 2 | $CH_3$ | H | $CH_3$ | H | O | H | $CH_3$ |
| 4.646 | H | H | H | 0 | $CH_3$ | H | $CH_3$ | H | C=O | H | Cl |
| 4.647 | H | H | H | 1 | $CH_3$ | H | $CH_3$ | H | C=O | H | Cl |
| 4.648 | H | H | H | 2 | $CH_3$ | H | $CH_3$ | H | C=O | H | Cl |
| 4.649 | H | H | H | 0 | $CH_3$ | H | $CH_3$ | H | CHO$CH_3$ | H | Cl |
| 4.650 | H | H | H | 1 | $CH_3$ | H | $CH_3$ | H | CHO$CH_3$ | H | Cl |

TABLE 4-continued

Compounds of the formula

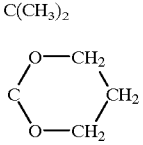

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.651 | H | H | H | 2 | $CH_3$ | H | $CH_3$ | H | $CHOCH_3$ | H | Cl |
| 4.652 | H | H | H | 0 | $CH_3$ | H | $CH_3$ | H | $CHOC_2H_5$ | H | Cl |
| 4.653 | H | H | H | 1 | $CH_3$ | H | $CH_3$ | H | $CHOC_2H_5$ | H | Cl |
| 4.654 | H | H | H | 2 | $CH_3$ | H | $CH_3$ | H | $CHOC_2H_5$ | H | Cl |
| 4.655 | H | H | H | 0 | $CH_3$ | H | $CH_3$ | H | CHOiPr | H | Cl |
| 4.656 | H | H | H | 1 | $CH_3$ | H | $CH_3$ | H | CHOiPr | H | Cl |
| 4.657 | H | H | H | 2 | $CH_3$ | H | $CH_3$ | H | CHOiPr | H | Cl |
| 4.658 | H | H | H | 0 | $CH_3$ | H | $CH_3$ | H | $C=NOCH_3$ | H | Cl |
| 4.659 | H | H | H | 1 | $CH_3$ | H | $CH_3$ | H | $C=NOCH_3$ | H | Cl |
| 4.660 | H | H | H | 2 | $CH_3$ | H | $CH_3$ | H | $C=NOCH_3$ | H | Cl |
| 4.661 | H | H | H | 0 | $CH_3$ | H | $CH_3$ | H | $C=NOC_2H_5$ | H | Cl |
| 4.662 | H | H | H | 1 | $CH_3$ | H | $CH_3$ | H | $C=NOC_2H_5$ | H | Cl |
| 4.663 | H | H | H | 2 | $CH_3$ | H | $CH_3$ | H | $C=NOC_2H_5$ | H | Cl |
| 4.664 | H | H | H | 0 | $CH_3$ | H | $CH_3$ | H | C=NOiPr | H | Cl |
| 4.665 | H | H | H | 1 | $CH_3$ | H | $CH_3$ | H | C=NOiPr | H | Cl |
| 4.666 | H | H | H | 2 | $CH_3$ | H | $CH_3$ | H | C=NOiPr | H | Cl |
| 4.667 | H | H | H | 0 | $CH_3$ | H | $CH_3$ | H | $C=NOCH_2CH=CHCl$ | H | Cl |
| 4.668 | H | H | H | 1 | $CH_3$ | H | $CH_3$ | H | $C=NOCH_2CH=CHCl$ | H | Cl |
| 4.669 | H | H | H | 2 | $CH_3$ | H | $CH_3$ | H | $C=NOCH_2CH=CHCl$ | H | Cl |
| 4.670 | H | H | H | 0 | $CH_3$ | H | $CH_3$ | H | $C=NOCH_2C_6H_5$ | H | Cl |
| 4.671 | H | H | H | 1 | $CH_3$ | H | $CH_3$ | H | $C=NOCH_2C_6H_5$ | H | Cl |
| 4.672 | H | H | H | 2 | $CH_3$ | H | $CH_3$ | H | $C=NOCH_2C_6H_5$ | H | Cl |
| 4.673 | H | H | H | 0 | $CH_3$ | H | $CH_3$ | H | $C(CH_3)_2$ | H | Cl |
| 4.674 | H | H | H | 1 | $CH_3$ | H | $CH_3$ | H | $C(CH_3)_2$ | H | Cl |
| 4.675 | H | H | H | 2 | $CH_3$ | H | $CH_3$ | H | $C(CH_3)_2$ | H | Cl |
| 4.676 | H | H | H | 0 | $CH_3$ | H | $CH_3$ | H | 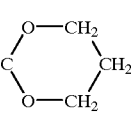 | H | Cl |
| 4.677 | H | H | H | 1 | $CH_3$ | H | $CH_3$ | H | 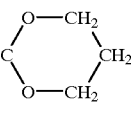 | H | Cl |
| 4.678 | H | H | H | 2 | $CH_3$ | H | $CH_3$ | H | 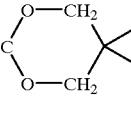 | H | Cl |
| 4.679 | H | H | H | 0 | $CH_3$ | H | $CH_3$ | H | 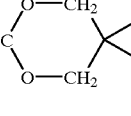 | H | Cl |
| 4.680 | H | H | H | 1 | $CH_3$ | H | $CH_3$ | H | 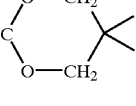 | H | Cl |
| 4.681 | H | H | H | 2 | $CH_3$ | H | $CH_3$ | H | | H | Cl |
| 4.682 | H | H | H | 0 | $CH_3$ | H | $CH_3$ | H | $C=N-CH_3$ | H | Cl |
| 4.683 | H | H | H | 1 | $CH_3$ | H | $CH_3$ | H | $C=N-CH_3$ | H | Cl |

TABLE 4-continued

Compounds of the formula

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.684 | H | H | H | 2 | CH$_3$ | H | CH$_3$ | H | C=N—CH$_3$ | H | Cl |
| 4.685 | H | H | H | 0 | CH$_3$ | H | CH$_3$ | H | C=NC$_2$H$_5$ | H | Cl |
| 4.686 | H | H | H | 1 | CH$_3$ | H | CH$_3$ | H | C=NC$_2$H$_5$ | H | Cl |
| 4.687 | H | H | H | 2 | CH$_3$ | H | CH$_3$ | H | C=NC$_2$H$_5$ | H | Cl |
| 4.688 | H | H | H | 0 | CH$_3$ | H | CH$_3$ | H | CH—NHCH$_3$ | H | Cl |
| 4.689 | H | H | H | 1 | CH$_3$ | H | CH$_3$ | H | CH—NHCH$_3$ | H | Cl |
| 4.690 | H | H | H | 2 | CH$_3$ | H | CH$_3$ | H | CH—NHCH$_3$ | H | Cl |
| 4.691 | H | H | H | 0 | CH$_3$ | H | CH$_3$ | H | CH—NHC$_2$H$_5$ | H | Cl |
| 4.692 | H | H | H | 1 | CH$_3$ | H | CH$_3$ | H | CH—NHC$_2$H$_5$ | H | Cl |
| 4.693 | H | H | H | 2 | CH$_3$ | H | CH$_3$ | H | CH—NHC$_2$H$_5$ | H | Cl |
| 4.694 | H | H | H | 0 | CH$_3$ | H | CH$_3$ | H | CH—N(CH$_3$)$_2$ | H | Cl |
| 4.695 | H | H | H | 1 | CH$_3$ | H | CH$_3$ | H | CH—N(CH$_3$)$_2$ | H | Cl |
| 4.696 | H | H | H | 2 | CH$_3$ | H | CH$_3$ | H | CH—N(CH$_3$)$_2$ | H | Cl |
| 4.697 | H | H | H | 0 | CH$_3$ | H | CH$_3$ | H | CH—NHOC$_2$H$_5$ | H | Cl |
| 4.698 | H | H | H | 1 | CH$_3$ | H | CH$_3$ | H | CH—NHOC$_2$H$_5$ | H | Cl |
| 4.699 | H | H | H | 2 | CH$_3$ | H | CH$_3$ | H | CH—NHOC$_2$H$_5$ | H | Cl |
| 4.700 | H | H | H | 0 | CH$_3$ | H | CH$_3$ | H | CH—N(CH$_3$)OC$_2$H$_5$ | H | Cl |
| 4.701 | H | H | H | 1 | CH$_3$ | H | CH$_3$ | H | CH—N(CH$_3$)OC$_2$H$_5$ | H | Cl |
| 4.702 | H | H | H | 2 | CH$_3$ | H | CH$_3$ | H | CH—N(CH$_3$)OC$_2$H$_5$ | H | Cl |
| 4.703 | H | H | H | 0 | CH$_3$ | H | CH$_3$ | H | C=N—NH$_2$ | H | Cl |
| 4.704 | H | H | H | 1 | CH$_3$ | H | CH$_3$ | H | C=N—NH$_2$ | H | Cl |
| 4.705 | H | H | H | 2 | CH$_3$ | H | CH$_3$ | H | C=N—NH$_2$ | H | Cl |
| 4.706 | H | H | H | 0 | CH$_3$ | H | CH$_3$ | H | C=N—N(CH$_3$)$_2$ | H | Cl |
| 4.707 | H | H | H | 1 | CH$_3$ | H | CH$_3$ | H | C=N—N(CH$_3$)$_2$ | H | Cl |
| 4.708 | H | H | H | 2 | CH$_3$ | H | CH$_3$ | H | C=N—N(CH$_3$)$_2$ | H | Cl |
| 4.709 | H | H | H | 0 | CH$_3$ | H | CH$_3$ | H | CH—N(CH$_3$)OCH$_2$C$_6$H$_5$ | H | Cl |
| 4.710 | H | H | H | 1 | CH$_3$ | H | CH$_3$ | H | CH—N(CH$_3$)OCH$_2$C$_6$H$_5$ | H | Cl |
| 4.711 | H | H | H | 2 | CH$_3$ | H | CH$_3$ | H | CH—N(CH$_3$)OCH$_2$C$_6$H$_5$ | H | Cl |
| 4.712 | H | H | H | 0 | CH$_3$ | H | CH$_3$ | H | C(CH$_3$)—OCH$_3$ | H | Cl |
| 4.713 | H | H | H | 1 | CH$_3$ | H | CH$_3$ | H | C(CH$_3$)—OCH$_3$ | H | Cl |
| 4.714 | H | H | H | 2 | CH$_3$ | H | CH$_3$ | H | C(CH$_3$)—OCH$_3$ | H | Cl |
| 4.715 | H | H | H | 0 | CH$_3$ | H | CH$_3$ | H | O | H | Cl |
| 4.716 | H | H | H | 2 | CH$_3$ | H | CH$_3$ | H | O | H | Cl |
| 4.717 | CH$_3$ | H | H | 0 | CH$_3$ | H | CH$_3$ | H | C=O | H | Cl |
| 4.718 | CH$_3$ | H | H | 1 | CH$_3$ | H | CH$_3$ | H | C=O | H | Cl |
| 4.719 | CH$_3$ | H | H | 2 | CH$_3$ | H | CH$_3$ | H | C=O | H | Cl |
| 4.720 | CH$_3$ | H | H | 0 | CH$_3$ | H | CH$_3$ | H | CHOCH$_3$ | H | Cl |
| 4.721 | CH$_3$ | H | H | 1 | CH$_3$ | H | CH$_3$ | H | CHOCH$_3$ | H | Cl |
| 4.722 | CH$_3$ | H | H | 2 | CH$_3$ | H | CH$_3$ | H | CHOCH$_3$ | H | Cl |
| 4.723 | CH$_3$ | H | H | 0 | CH$_3$ | H | CH$_3$ | H | CHOC$_2$H$_5$ | H | Cl |
| 4.724 | CH$_3$ | H | H | 1 | CH$_3$ | H | CH$_3$ | H | CHOC$_2$H$_5$ | H | Cl |
| 4.725 | CH$_3$ | H | H | 2 | CH$_3$ | H | CH$_3$ | H | CHOC$_2$H$_5$ | H | Cl |
| 4.726 | CH$_3$ | H | H | 0 | CH$_3$ | H | CH$_3$ | H | CHOiPr | H | Cl |
| 4.727 | CH$_3$ | H | H | 1 | CH$_3$ | H | CH$_3$ | H | CHOiPr | H | Cl |
| 4.728 | CH$_3$ | H | H | 2 | CH$_3$ | H | CH$_3$ | H | CHOiPr | H | Cl |
| 4.729 | CH$_3$ | H | H | 0 | CH$_3$ | H | CH$_3$ | H | C=NOCH$_3$ | H | Cl |
| 4.730 | CH$_3$ | H | H | 1 | CH$_3$ | H | CH$_3$ | H | C=NOCH$_3$ | H | Cl |
| 4.731 | CH$_3$ | H | H | 2 | CH$_3$ | H | CH$_3$ | H | C=NOCH$_3$ | H | Cl |
| 4.732 | CH$_3$ | H | H | 0 | CH$_3$ | H | CH$_3$ | H | C=NOC$_2$H$_5$ | H | Cl |
| 4.733 | CH$_3$ | H | H | 1 | CH$_3$ | H | CH$_3$ | H | C=NOC$_2$H$_5$ | H | Cl |
| 4.734 | CH$_3$ | H | H | 2 | CH$_3$ | H | CH$_3$ | H | C=NOC$_2$H$_5$ | H | Cl |
| 4.735 | CH$_3$ | H | H | 0 | CH$_3$ | H | CH$_3$ | H | C=NOiPr | H | Cl |
| 4.736 | CH$_3$ | H | H | 1 | CH$_3$ | H | CH$_3$ | H | C=NOiPr | H | Cl |
| 4.737 | CH$_3$ | H | H | 2 | CH$_3$ | H | CH$_3$ | H | C=NOiPr | H | Cl |
| 4.738 | CH$_3$ | H | H | 0 | CH$_3$ | H | CH$_3$ | H | C=NOCH$_2$CH=CHCl | H | Cl |
| 4.739 | CH$_3$ | H | H | 1 | CH$_3$ | H | CH$_3$ | H | C=NOCH$_2$CH=CHCl | H | Cl |
| 4.740 | CH$_3$ | H | H | 2 | CH$_3$ | H | CH$_3$ | H | C=NOCH$_2$CH=CHCl | H | Cl |
| 4.741 | CH$_3$ | H | H | 0 | CH$_3$ | H | CH$_3$ | H | C=NOCH$_2$C$_6$H$_5$ | H | Cl |
| 4.742 | CH$_3$ | H | H | 1 | CH$_3$ | H | CH$_3$ | H | C=NOCH$_2$C$_6$H$_5$ | H | Cl |
| 4.743 | CH$_3$ | H | H | 2 | CH$_3$ | H | CH$_3$ | H | C=NOCH$_2$C$_6$H$_5$ | H | Cl |
| 4.744 | CH$_3$ | H | H | 0 | CH$_3$ | H | CH$_3$ | H | C(CH$_3$)$_2$ | H | Cl |
| 4.745 | CH$_3$ | H | H | 1 | CH$_3$ | H | CH$_3$ | H | C(CH$_3$)$_2$ | H | Cl |
| 4.746 | CH$_3$ | H | H | 2 | CH$_3$ | H | CH$_3$ | H | C(CH$_3$)$_2$ | H | Cl |

TABLE 4-continued

Compounds of the formula

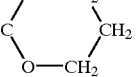

| No. | R17 | R18 | R19 | n | R12 | R13 | R21 | R22 | Y | L | M |
|---|---|---|---|---|---|---|---|---|---|---|---|
| 4.747 | CH3 | H | H | 0 | CH3 | H | CH3 | H | 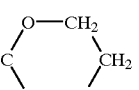 | H | Cl |
| 4.748 | CH3 | H | H | 1 | CH3 | H | CH3 | H | 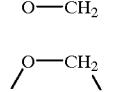 | H | Cl |
| 4.749 | CH3 | H | H | 2 | CH3 | H | CH3 | H | 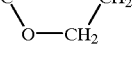 | H | Cl |
| 4.750 | CH3 | H | H | 0 | CH3 | H | CH3 | H | 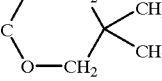 | H | Cl |
| 4.751 | CH3 | H | H | 1 | CH3 | H | CH3 | H | | H | Cl |
| 4.752 | CH3 | H | H | 2 | CH3 | H | CH3 | H | 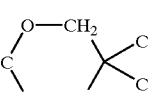 | H | Cl |
| 4.753 | CH3 | H | H | 0 | CH3 | H | CH3 | H | C=N—CH3 | H | Cl |
| 4.754 | CH3 | H | H | 1 | CH3 | H | CH3 | H | C=N—CH3 | H | Cl |
| 4.755 | CH3 | H | H | 2 | CH3 | H | CH3 | H | C=N—CH3 | H | Cl |
| 4.756 | CH3 | H | H | 0 | CH3 | H | CH3 | H | C=NC2H5 | H | Cl |
| 4.757 | CH3 | H | H | 1 | CH3 | H | CH3 | H | C=NC2H5 | H | Cl |
| 4.758 | CH3 | H | H | 2 | CH3 | H | CH3 | H | C=NC2H5 | H | Cl |
| 4.759 | CH3 | H | H | 0 | CH3 | H | CH3 | H | CH—NHCH3 | H | Cl |
| 4.760 | CH3 | H | H | 1 | CH3 | H | CH3 | H | CH—NHCH3 | H | Cl |
| 4.761 | CH3 | H | H | 2 | CH3 | H | CH3 | H | CH—NHCH3 | H | Cl |
| 4.762 | CH3 | H | H | 0 | CH3 | H | CH3 | H | CH—NHC2H5 | H | Cl |
| 4.763 | CH3 | H | H | 1 | CH3 | H | CH3 | H | CH—NHC2H5 | H | Cl |
| 4.764 | CH3 | H | H | 2 | CH3 | H | CH3 | H | CH—NHC2H5 | H | Cl |
| 4.765 | CH3 | H | H | 0 | CH3 | H | CH3 | H | CH—N(CH3)2 | H | Cl |
| 4.766 | CH3 | H | H | 1 | CH3 | H | CH3 | H | CH—N(CH3)2 | H | Cl |
| 4.767 | CH3 | H | H | 2 | CH3 | H | CH3 | H | CH—N(CH3)2 | H | Cl |
| 4.768 | CH3 | H | H | 0 | CH3 | H | CH3 | H | CH—NHOC2H5 | H | Cl |
| 4.769 | CH3 | H | H | 1 | CH3 | H | CH3 | H | CH—NHOC2H5 | H | Cl |
| 4.770 | CH3 | H | H | 2 | CH3 | H | CH3 | H | CH—NHOC2H5 | H | Cl |
| 4.771 | CH3 | H | H | 0 | CH3 | H | CH3 | H | CH—N(CH3)OC2H5 | H | Cl |
| 4.772 | CH3 | H | H | 1 | CH3 | H | CH3 | H | CH—N(CH3)OC2H5 | H | Cl |
| 4.773 | CH3 | H | H | 2 | CH3 | H | CH3 | H | CH—N(CH3)OC2H5 | H | Cl |
| 4.774 | CH3 | H | H | 0 | CH3 | H | CH3 | H | C=N—NH2 | H | Cl |
| 4.775 | CH3 | H | H | 1 | CH3 | H | CH3 | H | C=N—NH2 | H | Cl |
| 4.776 | CH3 | H | H | 2 | CH3 | H | CH3 | H | C=N—NH2 | H | Cl |
| 4.777 | CH3 | H | H | 0 | CH3 | H | CH3 | H | C=N—N(CH3)2 | H | Cl |
| 4.778 | CH3 | H | H | 1 | CH3 | H | CH3 | H | C=N—N(CH3)2 | H | Cl |
| 4.779 | CH3 | H | H | 2 | CH3 | H | CH3 | H | C=N—N(CH3)2 | H | Cl |
| 4.780 | CH3 | H | H | 0 | CH3 | H | CH3 | H | CH—N(CH3)OCH2C6H5 | H | Cl |

TABLE 4-continued

Compounds of the formula

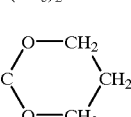

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.781 | $CH_3$ | H | H | 1 | $CH_3$ | H | $CH_3$ | H | $CH-N(CH_3)OCH_2C_6H_5$ | H | Cl |
| 4.782 | $CH_3$ | H | H | 2 | $CH_3$ | H | $CH_3$ | H | $CH-N(CH_3)OCH_2C_6H_5$ | H | Cl |
| 4.783 | $CH_3$ | H | H | 0 | $CH_3$ | H | $CH_3$ | H | $C(CH_3)-OCH_3$ | H | Cl |
| 4.784 | $CH_3$ | H | H | 1 | $CH_3$ | H | $CH_3$ | H | $C(CH_3)-OCH_3$ | H | Cl |
| 4.785 | $CH_3$ | H | H | 2 | $CH_3$ | H | $CH_3$ | H | $C(CH_3)-OCH_3$ | H | Cl |
| 4.786 | $CH_3$ | H | H | 0 | $CH_3$ | H | $CH_3$ | H | O | H | Cl |
| 4.787 | $CH_3$ | H | H | 2 | $CH_3$ | H | $CH_3$ | H | O | H | Cl |
| 4.788 | $CH_3$ | $CH_3$ | H | 0 | $CH_3$ | H | $CH_3$ | H | C=O | H | Cl |
| 4.789 | $CH_3$ | $CH_3$ | H | 1 | $CH_3$ | H | $CH_3$ | H | C=O | H | Cl |
| 4.790 | $CH_3$ | $CH_3$ | H | 2 | $CH_3$ | H | $CH_3$ | H | C=O | H | Cl |
| 4.791 | $CH_3$ | $CH_3$ | H | 0 | $CH_3$ | H | $CH_3$ | H | $CHOCH_3$ | H | Cl |
| 4.792 | $CH_3$ | $CH_3$ | H | 1 | $CH_3$ | H | $CH_3$ | H | $CHOCH_3$ | H | Cl |
| 4.793 | $CH_3$ | $CH_3$ | H | 2 | $CH_3$ | H | $CH_3$ | H | $CHOCH_3$ | H | Cl |
| 4.794 | $CH_3$ | $CH_3$ | H | 0 | $CH_3$ | H | $CH_3$ | H | $CHOC_2H_5$ | H | Cl |
| 4.795 | $CH_3$ | $CH_3$ | H | 1 | $CH_3$ | H | $CH_3$ | H | $CHOC_2H_5$ | H | Cl |
| 4.796 | $CH_3$ | $CH_3$ | H | 2 | $CH_3$ | H | $CH_3$ | H | $CHOC_2H_5$ | H | Cl |
| 4.797 | $CH_3$ | $CH_3$ | H | 0 | $CH_3$ | H | $CH_3$ | H | CHOiPr | H | Cl |
| 4.798 | $CH_3$ | $CH_3$ | H | 1 | $CH_3$ | H | $CH_3$ | H | CHOiPr | H | Cl |
| 4.799 | $CH_3$ | $CH_3$ | H | 2 | $CH_3$ | H | $CH_3$ | H | CHOiPr | H | Cl |
| 4.800 | $CH_3$ | $CH_3$ | H | 0 | $CH_3$ | H | $CH_3$ | H | $C=NOCH_3$ | H | Cl |
| 4.801 | $CH_3$ | $CH_3$ | H | 1 | $CH_3$ | H | $CH_3$ | H | $C=NOCH_3$ | H | Cl |
| 4.802 | $CH_3$ | $CH_3$ | H | 2 | $CH_3$ | H | $CH_3$ | H | $C=NOCH_3$ | H | Cl |
| 4.803 | $CH_3$ | $CH_3$ | H | 0 | $CH_3$ | H | $CH_3$ | H | $C=NOC_2H_5$ | H | Cl |
| 4.804 | $CH_3$ | $CH_3$ | H | 1 | $CH_3$ | H | $CH_3$ | H | $C=NOC_2H_5$ | H | Cl |
| 4.805 | $CH_3$ | $CH_3$ | H | 2 | $CH_3$ | H | $CH_3$ | H | $C=NOC_2H_5$ | H | Cl |
| 4.806 | $CH_3$ | $CH_3$ | H | 0 | $CH_3$ | H | $CH_3$ | H | C=NOiPr | H | Cl |
| 4.807 | $CH_3$ | $CH_3$ | H | 1 | $CH_3$ | H | $CH_3$ | H | C=NOiPr | H | Cl |
| 4.808 | $CH_3$ | $CH_3$ | H | 2 | $CH_3$ | H | $CH_3$ | H | C=NOiPr | H | Cl |
| 4.809 | $CH_3$ | $CH_3$ | H | 0 | $CH_3$ | H | $CH_3$ | H | $C=NOCH_2CH=CHCl$ | H | Cl |
| 4.810 | $CH_3$ | $CH_3$ | H | 1 | $CH_3$ | H | $CH_3$ | H | $C=NOCH_2CH=CHCl$ | H | Cl |
| 4.811 | $CH_3$ | $CH_3$ | H | 2 | $CH_3$ | H | $CH_3$ | H | $C=NOCH_2CH=CHCl$ | H | Cl |
| 4.812 | $CH_3$ | $CH_3$ | H | 0 | $CH_3$ | H | $CH_3$ | H | $C=NOCH_2C_6H_5$ | H | Cl |
| 4.813 | $CH_3$ | $CH_3$ | H | 1 | $CH_3$ | H | $CH_3$ | H | $C=NOCH_2C_6H_5$ | H | Cl |
| 4.814 | $CH_3$ | $CH_3$ | H | 2 | $CH_3$ | H | $CH_3$ | H | $C=NOCH_2C_6H_5$ | H | Cl |
| 4.815 | $CH_3$ | $CH_3$ | H | 0 | $CH_3$ | H | $CH_3$ | H | $C(CH_3)_2$ | H | Cl |
| 4.816 | $CH_3$ | $CH_3$ | H | 1 | $CH_3$ | H | $CH_3$ | H | $C(CH_3)_2$ | H | Cl |
| 4.817 | $CH_3$ | $CH_3$ | H | 2 | $CH_3$ | H | $CH_3$ | H | $C(CH_3)_2$ | H | Cl |
| 4.818 | $CH_3$ | $CH_3$ | H | 0 | $CH_3$ | H | $CH_3$ | H | 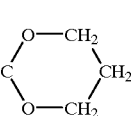 | H | Cl |
| 4.819 | $CH_3$ | $CH_3$ | H | 1 | $CH_3$ | H | $CH_3$ | H | 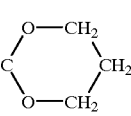 | H | Cl |
| 4.820 | $CH_3$ | $CH_3$ | H | 2 | $CH_3$ | H | $CH_3$ | H | 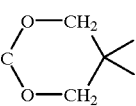 | H | Cl |
| 4.821 | $CH_3$ | $CH_3$ | H | 0 | $CH_3$ | H | $CH_3$ | H |  | H | Cl |

TABLE 4-continued

Compounds of the formula

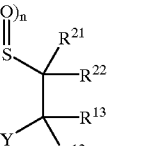

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.822 | $CH_3$ | $CH_3$ | H | 1 | $CH_3$ | H | $CH_3$ | H | 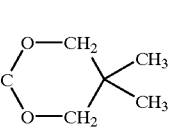 | H | Cl |
| 4.823 | $CH_3$ | $CH_3$ | H | 2 | $CH_3$ | H | $CH_3$ | H | (same dioxane group) | H | Cl |
| 4.824 | $CH_3$ | $CH_3$ | H | 0 | $CH_3$ | H | $CH_3$ | H | C=N—$CH_3$ | H | Cl |
| 4.825 | $CH_3$ | $CH_3$ | H | 1 | $CH_3$ | H | $CH_3$ | H | C=N—$CH_3$ | H | Cl |
| 4.826 | $CH_3$ | $CH_3$ | H | 2 | $CH_3$ | H | $CH_3$ | H | C=N—$CH_3$ | H | Cl |
| 4.827 | $CH_3$ | $CH_3$ | H | 0 | $CH_3$ | H | $CH_3$ | H | C=N$C_2H_5$ | H | Cl |
| 4.828 | $CH_3$ | $CH_3$ | H | 1 | $CH_3$ | H | $CH_3$ | H | C=N$C_2H_5$ | H | Cl |
| 4.829 | $CH_3$ | $CH_3$ | H | 2 | $CH_3$ | H | $CH_3$ | H | C=N$C_2H_5$ | H | Cl |
| 4.830 | $CH_3$ | $CH_3$ | H | 0 | $CH_3$ | H | $CH_3$ | H | CH—NH$CH_3$ | H | Cl |
| 4.831 | $CH_3$ | $CH_3$ | H | 1 | $CH_3$ | H | $CH_3$ | H | CH—NH$CH_3$ | H | Cl |
| 4.832 | $CH_3$ | $CH_3$ | H | 2 | $CH_3$ | H | $CH_3$ | H | CH—NH$CH_3$ | H | Cl |
| 4.833 | $CH_3$ | $CH_3$ | H | 0 | $CH_3$ | H | $CH_3$ | H | CH—NH$C_2H_5$ | H | Cl |
| 4.834 | $CH_3$ | $CH_3$ | H | 1 | $CH_3$ | H | $CH_3$ | H | CH—NH$C_2H_5$ | H | Cl |
| 4.835 | $CH_3$ | $CH_3$ | H | 2 | $CH_3$ | H | $CH_3$ | H | CH—NH$C_2H_5$ | H | Cl |
| 4.836 | $CH_3$ | $CH_3$ | H | 0 | $CH_3$ | H | $CH_3$ | H | CH—N$(CH_3)_2$ | H | Cl |
| 4.837 | $CH_3$ | $CH_3$ | H | 1 | $CH_3$ | H | $CH_3$ | H | CH—N$(CH_3)_2$ | H | Cl |
| 4.838 | $CH_3$ | $CH_3$ | H | 2 | $CH_3$ | H | $CH_3$ | H | CH—N$(CH_3)_2$ | H | Cl |
| 4.839 | $CH_3$ | $CH_3$ | H | 0 | $CH_3$ | H | $CH_3$ | H | CH—NHO$C_2H_5$ | H | Cl |
| 4.840 | $CH_3$ | $CH_3$ | H | 1 | $CH_3$ | H | $CH_3$ | H | CH—NHO$C_2H_5$ | H | Cl |
| 4.841 | $CH_3$ | $CH_3$ | H | 2 | $CH_3$ | H | $CH_3$ | H | CH—NHO$C_2H_5$ | H | Cl |
| 4.842 | $CH_3$ | $CH_3$ | H | 0 | $CH_3$ | H | $CH_3$ | H | CH—N$(CH_3)$O$C_2H_5$ | H | Cl |
| 4.843 | $CH_3$ | $CH_3$ | H | 1 | $CH_3$ | H | $CH_3$ | H | CH—N$(CH_3)$O$C_2H_5$ | H | Cl |
| 4.844 | $CH_3$ | $CH_3$ | H | 2 | $CH_3$ | H | $CH_3$ | H | CH—N$(CH_3)$O$C_2H_5$ | H | Cl |
| 4.845 | $CH_3$ | $CH_3$ | H | 0 | $CH_3$ | H | $CH_3$ | H | C=N—$NH_2$ | H | Cl |
| 4.846 | $CH_3$ | $CH_3$ | H | 1 | $CH_3$ | H | $CH_3$ | H | C=N—$NH_2$ | H | Cl |
| 4.847 | $CH_3$ | $CH_3$ | H | 2 | $CH_3$ | H | $CH_3$ | H | C=N—$NH_2$ | H | Cl |
| 4.848 | $CH_3$ | $CH_3$ | H | 0 | $CH_3$ | H | $CH_3$ | H | C=N—N$(CH_3)_2$ | H | Cl |
| 4.849 | $CH_3$ | $CH_3$ | H | 1 | $CH_3$ | H | $CH_3$ | H | C=N—N$(CH_3)_2$ | H | Cl |
| 4.850 | $CH_3$ | $CH_3$ | H | 2 | $CH_3$ | H | $CH_3$ | H | C=N—N$(CH_3)_2$ | H | Cl |
| 4.851 | $CH_3$ | $CH_3$ | H | 0 | $CH_3$ | H | $CH_3$ | H | CH—N$(CH_3)$OCH$_2C_6H_5$ | H | Cl |
| 4.852 | $CH_3$ | $CH_3$ | H | 1 | $CH_3$ | H | $CH_3$ | H | CH—N$(CH_3)$OCH$_2C_6H_5$ | H | Cl |
| 4.853 | $CH_3$ | $CH_3$ | H | 2 | $CH_3$ | H | $CH_3$ | H | CH—N$(CH_3)$OCH$_2C_6H_5$ | H | Cl |
| 4.854 | $CH_3$ | $CH_3$ | H | 0 | $CH_3$ | H | $CH_3$ | H | C$(CH_3)$—O$CH_3$ | H | Cl |
| 4.855 | $CH_3$ | $CH_3$ | H | 1 | $CH_3$ | H | $CH_3$ | H | C$(CH_3)$—O$CH_3$ | H | Cl |
| 4.856 | $CH_3$ | $CH_3$ | H | 2 | $CH_3$ | H | $CH_3$ | H | C$(CH_3)$—O$CH_3$ | H | Cl |
| 4.857 | $CH_3$ | $CH_3$ | H | 0 | $CH_3$ | H | $CH_3$ | H | O | H | Cl |
| 4.858 | $CH_3$ | $CH_3$ | H | 2 | $CH_3$ | H | $CH_3$ | H | O | H | Cl |
| 4.859 | H | H | H | 0 | $CH_3$ | H | H | H | C=O | H | $CH_3$ |
| 4.860 | H | H | H | 1 | $CH_3$ | H | H | H | C=O | H | $CH_3$ |
| 4.861 | H | H | H | 2 | $CH_3$ | H | H | H | C=O | H | $CH_3$ |
| 4.862 | H | H | H | 0 | $CH_3$ | H | H | H | CH—O$CH_3$ | H | $CH_3$ |
| 4.863 | H | H | H | 1 | $CH_3$ | H | H | H | CH—O$CH_3$ | H | $CH_3$ |
| 4.864 | H | H | H | 2 | $CH_3$ | H | H | H | CH—O$CH_3$ | H | $CH_3$ |
| 4.865 | H | H | H | 0 | $CH_3$ | H | H | H | CHO$C_2H_5$ | H | $CH_3$ |
| 4.866 | H | H | H | 1 | $CH_3$ | H | H | H | CHO$C_2H_5$ | H | $CH_3$ |
| 4.867 | H | H | H | 2 | $CH_3$ | H | H | H | CHO$C_2H_5$ | H | $CH_3$ |
| 4.868 | H | H | H | 0 | $CH_3$ | H | H | H | CHOiPr | H | $CH_3$ |
| 4.869 | H | H | H | 1 | $CH_3$ | H | H | H | CHOiPr | H | $CH_3$ |
| 4.870 | H | H | H | 2 | $CH_3$ | H | H | H | CHOiPr | H | $CH_3$ |
| 4.871 | H | H | H | 0 | $CH_3$ | H | H | H | C=NO$CH_3$ | H | $CH_3$ |
| 4.872 | H | H | H | 1 | $CH_3$ | H | H | H | C=NO$CH_3$ | H | $CH_3$ |
| 4.873 | H | H | H | 2 | $CH_3$ | H | H | H | C=NO$CH_3$ | H | $CH_3$ |
| 4.874 | H | H | H | 0 | $CH_3$ | H | H | H | C=NO$C_2H_5$ | H | $CH_3$ |
| 4.875 | H | H | H | 1 | $CH_3$ | H | H | H | C=NO$C_2H_5$ | H | $CH_3$ |

TABLE 4-continued

Compounds of the formula

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.876 | H | H | H | 2 | CH$_3$ | H | H | H | C=NOC$_2$H$_5$ | H | CH$_3$ |
| 4.877 | H | H | H | 0 | CH$_3$ | H | H | H | C=NOiPr | H | CH$_3$ |
| 4.878 | H | H | H | 1 | CH$_3$ | H | H | H | C=NOiPr | H | CH$_3$ |
| 4.879 | H | H | H | 2 | CH$_3$ | H | H | H | C=NOiPr | H | CH$_3$ |
| 4.880 | H | H | H | 0 | CH$_3$ | H | H | H | C=NOCH$_2$CH=CHCl | H | CH$_3$ |
| 4.881 | H | H | H | 1 | CH$_3$ | H | H | H | C=NOCH$_2$CH=CHCl | H | CH$_3$ |
| 4.882 | H | H | H | 2 | CH$_3$ | H | H | H | C=NOCH$_2$CH=CHCl | H | CH$_3$ |
| 4.883 | H | H | H | 0 | CH$_3$ | H | H | H | C=NOCH$_2$C$_6$H$_5$ | H | CH$_3$ |
| 4.884 | H | H | H | 1 | CH$_3$ | H | H | H | C=NOCH$_2$C$_6$H$_5$ | H | CH$_3$ |
| 4.885 | H | H | H | 2 | CH$_3$ | H | H | H | C=NOCH$_2$C$_6$H$_5$ | H | CH$_3$ |
| 4.886 | H | H | H | 0 | CH$_3$ | H | H | H | C(CH$_3$)$_2$ | H | CH$_3$ |
| 4.887 | H | H | H | 1 | CH$_3$ | H | H | H | C(CH$_3$)$_2$ | H | CH$_3$ |
| 4.888 | H | H | H | 2 | CH$_3$ | H | H | H | C(CH$_3$)$_2$ | H | CH$_3$ |
| 4.889 | H | H | H | 0 | CH$_3$ | H | H | H | 1,3-dioxane (unsubstituted) | H | CH$_3$ |
| 4.890 | H | H | H | 1 | CH$_3$ | H | H | H | 1,3-dioxane (unsubstituted) | H | CH$_3$ |
| 4.891 | H | H | H | 2 | CH$_3$ | H | H | H | 1,3-dioxane (unsubstituted) | H | CH$_3$ |
| 4.892 | H | H | H | 0 | CH$_3$ | H | H | H | 1,3-dioxane (gem-diCH$_3$) | H | CH$_3$ |
| 4.893 | H | H | H | 1 | CH$_3$ | H | H | H | 1,3-dioxane (gem-diCH$_3$) | H | CH$_3$ |
| 4.894 | H | H | H | 2 | CH$_3$ | H | H | H | 1,3-dioxane (gem-diCH$_3$) | H | CH$_3$ |
| 4.895 | H | H | H | 0 | CH$_3$ | H | H | H | C=N—CH$_3$ | H | CH$_3$ |
| 4.896 | H | H | H | 1 | CH$_3$ | H | H | H | C=N—CH$_3$ | H | CH$_3$ |
| 4.897 | H | H | H | 2 | CH$_3$ | H | H | H | C=N—CH$_3$ | H | CH$_3$ |
| 4.898 | H | H | H | 0 | CH$_3$ | H | H | H | C=NC$_2$H$_5$ | H | CH$_3$ |
| 4.899 | H | H | H | 1 | CH$_3$ | H | H | H | C=NC$_2$H$_5$ | H | CH$_3$ |
| 4.900 | H | H | H | 2 | CH$_3$ | H | H | H | C=NC$_2$H$_5$ | H | CH$_3$ |
| 4.901 | H | H | H | 0 | CH$_3$ | H | H | H | CH—NHCH$_3$ | H | CH$_3$ |
| 4.902 | H | H | H | 1 | CH$_3$ | H | H | H | CH—NHCH$_3$ | H | CH$_3$ |
| 4.903 | H | H | H | 2 | CH$_3$ | H | H | H | CH—NHCH$_3$ | H | CH$_3$ |
| 4.904 | H | H | H | 0 | CH$_3$ | H | H | H | CH—NHC$_2$H$_5$ | H | CH$_3$ |
| 4.905 | H | H | H | 1 | CH$_3$ | H | H | H | CH—NHC$_2$H$_5$ | H | CH$_3$ |
| 4.906 | H | H | H | 2 | CH$_3$ | H | H | H | CH—NHC$_2$H$_5$ | H | CH$_3$ |
| 4.907 | H | H | H | 0 | CH$_3$ | H | H | H | CH—N(CH$_3$)$_2$ | H | CH$_3$ |
| 4.908 | H | H | H | 1 | CH$_3$ | H | H | H | CH—N(CH$_3$)$_2$ | H | CH$_3$ |

TABLE 4-continued

Compounds of the formula

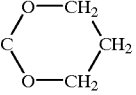

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.909 | H | H | H | 2 | $CH_3$ | H | H | H | CH—N($CH_3$)$_2$ | H | $CH_3$ |
| 4.910 | H | H | H | 0 | $CH_3$ | H | H | H | CH—NHO$C_2H_5$ | H | $CH_3$ |
| 4.911 | H | H | H | 1 | $CH_3$ | H | H | H | CH—NHO$C_2H_5$ | H | $CH_3$ |
| 4.912 | H | H | H | 2 | $CH_3$ | H | H | H | CH—NHO$C_2H_5$ | H | $CH_3$ |
| 4.913 | H | H | H | 0 | $CH_3$ | H | H | H | CH—N($CH_3$)O$C_2H_5$ | H | $CH_3$ |
| 4.914 | H | H | H | 1 | $CH_3$ | H | H | H | CH—N($CH_3$)O$C_2H_5$ | H | $CH_3$ |
| 4.915 | H | H | H | 2 | $CH_3$ | H | H | H | CH—N($CH_3$)O$C_2H_5$ | H | $CH_3$ |
| 4.916 | H | H | H | 0 | $CH_3$ | H | H | H | C=N—$NH_2$ | H | $CH_3$ |
| 4.917 | H | H | H | 1 | $CH_3$ | H | H | H | C=N—$NH_2$ | H | $CH_3$ |
| 4.918 | H | H | H | 2 | $CH_3$ | H | H | H | C=N—$NH_2$ | H | $CH_3$ |
| 4.919 | H | H | H | 0 | $CH_3$ | H | H | H | C=N—N($CH_3$)$_2$ | H | $CH_3$ |
| 4.920 | H | H | H | 1 | $CH_3$ | H | H | H | C=N—N($CH_3$)$_2$ | H | $CH_3$ |
| 4.921 | H | H | H | 2 | $CH_3$ | H | H | H | C=N—N($CH_3$)$_2$ | H | $CH_3$ |
| 4.922 | H | H | H | 0 | $CH_3$ | H | H | H | CH—N($CH_3$)OC$H_2C_6H_5$ | H | $CH_3$ |
| 4.923 | H | H | H | 1 | $CH_3$ | H | H | H | CH—N($CH_3$)OC$H_2C_6H_5$ | H | $CH_3$ |
| 4.924 | H | H | H | 2 | $CH_3$ | H | H | H | CH—N($CH_3$)OC$H_2C_6H_5$ | H | $CH_3$ |
| 4.925 | H | H | H | 0 | $CH_3$ | H | H | H | C($CH_3$)—O$CH_3$ | H | $CH_3$ |
| 4.926 | H | H | H | 1 | $CH_3$ | H | H | H | C($CH_3$)—O$CH_3$ | H | $CH_3$ |
| 4.927 | H | H | H | 2 | $CH_3$ | H | H | H | C($CH_3$)—O$CH_3$ | H | $CH_3$ |
| 4.928 | H | H | H | 0 | $CH_3$ | H | H | H | O | H | $CH_3$ |
| 4.929 | H | H | H | 2 | $CH_3$ | H | H | H | O | H | $CH_3$ |
| 4.930 | $CH_3$ | H | H | 0 | $CH_3$ | H | H | H | C=O | H | $CH_3$ |
| 4.931 | $CH_3$ | H | H | 1 | $CH_3$ | H | H | H | C=O | H | $CH_3$ |
| 4.932 | $CH_3$ | H | H | 2 | $CH_3$ | H | H | H | C=O | H | $CH_3$ |
| 4.933 | $CH_3$ | H | H | 0 | $CH_3$ | H | H | H | CHO$CH_3$ | H | $CH_3$ |
| 4.934 | $CH_3$ | H | H | 1 | $CH_3$ | H | H | H | CHO$CH_3$ | H | $CH_3$ |
| 4.935 | $CH_3$ | H | H | 2 | $CH_3$ | H | H | H | CHO$CH_3$ | H | $CH_3$ |
| 4.936 | $CH_3$ | H | H | 0 | $CH_3$ | H | H | H | CHO$C_2H_5$ | H | $CH_3$ |
| 4.937 | $CH_3$ | H | H | 1 | $CH_3$ | H | H | H | CHO$C_2H_5$ | H | $CH_3$ |
| 4.938 | $CH_3$ | H | H | 2 | $CH_3$ | H | H | H | CHO$C_2H_5$ | H | $CH_3$ |
| 4.939 | $CH_3$ | H | H | 0 | $CH_3$ | H | H | H | CHOiPr | H | $CH_3$ |
| 4.940 | $CH_3$ | H | H | 1 | $CH_3$ | H | H | H | CHOiPr | H | $CH_3$ |
| 4.941 | $CH_3$ | H | H | 2 | $CH_3$ | H | H | H | CHOiPr | H | $CH_3$ |
| 4.942 | $CH_3$ | H | H | 0 | $CH_3$ | H | H | H | C=NO$CH_3$ | H | $CH_3$ |
| 4.943 | $CH_3$ | H | H | 1 | $CH_3$ | H | H | H | C=NO$CH_3$ | H | $CH_3$ |
| 4.944 | $CH_3$ | H | H | 2 | $CH_3$ | H | H | H | C=NO$CH_3$ | H | $CH_3$ |
| 4.945 | $CH_3$ | H | H | 0 | $CH_3$ | H | H | H | C=NO$C_2H_5$ | H | $CH_3$ |
| 4.946 | $CH_3$ | H | H | 1 | $CH_3$ | H | H | H | C=NO$C_2H_5$ | H | $CH_3$ |
| 4.947 | $CH_3$ | H | H | 2 | $CH_3$ | H | H | H | C=NO$C_2H_5$ | H | $CH_3$ |
| 4.948 | $CH_3$ | H | H | 0 | $CH_3$ | H | H | H | C=NOiPr | H | $CH_3$ |
| 4.949 | $CH_3$ | H | H | 1 | $CH_3$ | H | H | H | C=NOiPr | H | $CH_3$ |
| 4.950 | $CH_3$ | H | H | 2 | $CH_3$ | H | H | H | C=NOiPr | H | $CH_3$ |
| 4.951 | $CH_3$ | H | H | 0 | $CH_3$ | H | H | H | C=NO$CH_2$CH=CHCl | H | $CH_3$ |
| 4.952 | $CH_3$ | H | H | 1 | $CH_3$ | H | H | H | C=NO$CH_2$CH=CHCl | H | $CH_3$ |
| 4.953 | $CH_3$ | H | H | 2 | $CH_3$ | H | H | H | C=NO$CH_2$CH=CHCl | H | $CH_3$ |
| 4.954 | $CH_3$ | H | H | 0 | $CH_3$ | H | H | H | C=NO$CH_2C_6H_5$ | H | $CH_3$ |
| 4.955 | $CH_3$ | H | H | 1 | $CH_3$ | H | H | H | C=NO$CH_2C_6H_5$ | H | $CH_3$ |
| 4.956 | $CH_3$ | H | H | 2 | $CH_3$ | H | H | H | C=NO$CH_2C_6H_5$ | H | $CH_3$ |
| 4.957 | $CH_3$ | H | H | 0 | $CH_3$ | H | H | H | C($CH_3$)$_2$ | H | $CH_3$ |
| 4.958 | $CH_3$ | H | H | 1 | $CH_3$ | H | H | H | C($CH_3$)$_2$ | H | $CH_3$ |
| 4.959 | $CH_3$ | H | H | 2 | $CH_3$ | H | H | H | C($CH_3$)$_2$ | H | $CH_3$ |
| 4.960 | $CH_3$ | $CH_3$ | H | 0 | $CH_3$ | H | H | H | 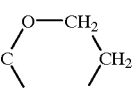 | H | $CH_3$ |
| 4.961 | $CH_3$ | $CH_3$ | H | 1 | $CH_3$ | H | H | H | 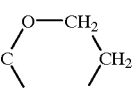 | H | $CH_3$ |

TABLE 4-continued

Compounds of the formula

[Structure: cyclohexanedione with OH and C=O groups connected via carbonyl to a benzene ring fused with a thiazine/dithiine ring bearing S(O)n, R21, R22, R13, R12, Y substituents; R17, R18, R19 on cyclohexanedione; L and M on benzene ring]

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.962 | CH₃ | CH₃ | H | 2 | CH₃ | H | H | H | O—CH₂—C—CH₂—O—CH₂ (1,3-dioxane) | H | CH₃ |
| 4.963 | CH₃ | CH₃ | H | 0 | CH₃ | H | H | H | O—CH₂—C(CH₃)₂—CH₂—O (dimethyl dioxane) | H | CH₃ |
| 4.964 | CH₃ | CH₃ | H | 1 | CH₃ | H | H | H | O—CH₂—C(CH₃)₂—CH₂—O | H | CH₃ |
| 4.965 | CH₃ | CH₃ | H | 2 | CH₃ | H | H | H | O—CH₂—C(CH₃)₂—CH₂—O | H | CH₃ |
| 4.966 | CH₃ | CH₃ | H | 0 | CH₃ | H | H | H | C=N—CH₃ | H | CH₃ |
| 4.967 | CH₃ | CH₃ | H | 1 | CH₃ | H | H | H | C=N—CH₃ | H | CH₃ |
| 4.968 | CH₃ | CH₃ | H | 2 | CH₃ | H | H | H | C=N—CH₃ | H | CH₃ |
| 4.969 | CH₃ | CH₃ | H | 0 | CH₃ | H | H | H | C=NC₂H₅ | H | CH₃ |
| 4.970 | CH₃ | H | H | 1 | CH₃ | H | H | H | C=NC₂H₅ | H | CH₃ |
| 4.971 | CH₃ | H | H | 2 | CH₃ | H | H | H | C=NC₂H₅ | H | CH₃ |
| 4.972 | CH₃ | H | H | 0 | CH₃ | H | H | H | CH—NHCH₃ | H | CH₃ |
| 4.973 | CH₃ | H | H | 1 | CH₃ | H | H | H | CH—NHCH₃ | H | CH₃ |
| 4.974 | CH₃ | H | H | 2 | CH₃ | H | H | H | CH—NHCH₃ | H | CH₃ |
| 4.975 | CH₃ | H | H | 0 | CH₃ | H | H | H | CH—NHC₂H₅ | H | CH₃ |
| 4.976 | CH₃ | H | H | 1 | CH₃ | H | H | H | CH—NHC₂H₅ | H | CH₃ |
| 4.977 | CH₃ | H | H | 2 | CH₃ | H | H | H | CH—NHC₂H₅ | H | CH₃ |
| 4.978 | CH₃ | H | H | 0 | CH₃ | H | H | H | CH—N(CH₃)₂ | H | CH₃ |
| 4.979 | CH₃ | H | H | 1 | CH₃ | H | H | H | CH—N(CH₃)₂ | H | CH₃ |
| 4.980 | CH₃ | H | H | 2 | CH₃ | H | H | H | CH—N(CH₃)₂ | H | CH₃ |
| 4.981 | CH₃ | H | H | 0 | CH₃ | H | H | H | CH—NHOC₂H₅ | H | CH₃ |
| 4.982 | CH₃ | H | H | 1 | CH₃ | H | H | H | CH—NHOC₂H₅ | H | CH₃ |
| 4.983 | CH₃ | H | H | 2 | CH₃ | H | H | H | CH—NHOC₂H₅ | H | CH₃ |
| 4.984 | CH₃ | H | H | 0 | CH₃ | H | H | H | CH—N(CH₃)OC₂H₅ | H | CH₃ |
| 4.985 | CH₃ | H | H | 1 | CH₃ | H | H | H | CH—N(CH₃)OC₂H₅ | H | CH₃ |
| 4.986 | CH₃ | H | H | 2 | CH₃ | H | H | H | CH—N(CH₃)OC₂H₅ | H | CH₃ |
| 4.987 | CH₃ | H | H | 0 | CH₃ | H | H | H | C=N—NH₂ | H | CH₃ |
| 4.988 | CH₃ | H | H | 1 | CH₃ | H | H | H | C=N—NH₂ | H | CH₃ |
| 4.989 | CH₃ | H | H | 2 | CH₃ | H | H | H | C=N—NH₂ | H | CH₃ |
| 4.990 | CH₃ | H | H | 0 | CH₃ | H | H | H | C=N—N(CH₃)₂ | H | CH₃ |
| 4.991 | CH₃ | H | H | 1 | CH₃ | H | H | H | C=N—N(CH₃)₂ | H | CH₃ |
| 4.992 | CH₃ | H | H | 2 | CH₃ | H | H | H | C=N—N(CH₃)₂ | H | CH₃ |
| 4.993 | CH₃ | H | H | 0 | CH₃ | H | H | H | CH—N(CH₃)OCH₂C₆H₅ | H | CH₃ |
| 4.994 | CH₃ | H | H | 1 | CH₃ | H | H | H | CH—N(CH₃)OCH₂C₆H₅ | H | CH₃ |
| 4.995 | CH₃ | H | H | 2 | CH₃ | H | H | H | CH—N(CH₃)OCH₂C₆H₅ | H | CH₃ |
| 4.996 | CH₃ | H | H | 0 | CH₃ | H | H | H | C(CH₃)—OCH₃ | H | CH₃ |
| 4.997 | CH₃ | H | H | 1 | CH₃ | H | H | H | C(CH₃)—OCH₃ | H | CH₃ |
| 4.998 | CH₃ | H | H | 2 | CH₃ | H | H | H | C(CH₃)—OCH₃ | H | CH₃ |
| 4.999 | CH₃ | H | H | 0 | CH₃ | H | H | H | O | H | CH₃ |
| 4.1000 | CH₃ | H | H | 2 | CH₃ | H | H | H | O | H | CH₃ |
| 4.1001 | CH₃ | CH₃ | H | 0 | CH₃ | H | H | H | C=O | H | CH₃ |
| 4.1002 | CH₃ | CH₃ | H | 1 | CH₃ | H | H | H | C=O | H | CH₃ |
| 4.1003 | CH₃ | CH₃ | H | 2 | CH₃ | H | H | H | C=O | H | CH₃ |
| 4.1004 | CH₃ | CH₃ | H | 0 | CH₃ | H | H | H | CHOCH₃ | H | CH₃ |
| 4.1005 | CH₃ | CH₃ | H | 1 | CH₃ | H | H | H | CHOCH₃ | H | CH₃ |

TABLE 4-continued

Compounds of the formula

[Structure: cyclohexanedione with OH, C=O substituents, connected via C(=O) to a benzene ring bearing M, L substituents, fused to a thiazine-type ring with S(=O)$_n$, R$^{21}$, R$^{22}$, R$^{13}$, R$^{12}$, Y; cyclohexanedione carries R$^{17}$, R$^{18}$, R$^{19}$]

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.1006 | CH$_3$ | CH$_3$ | H | 2 | CH$_3$ | H | H | H | CHOCH$_3$ | H | CH$_3$ |
| 4.1007 | CH$_3$ | CH$_3$ | H | 0 | CH$_3$ | H | H | H | CHOC$_2$H$_5$ | H | CH$_3$ |
| 4.1008 | CH$_3$ | CH$_3$ | H | 1 | CH$_3$ | H | H | H | CHOC$_2$H$_5$ | H | CH$_3$ |
| 4.1009 | CH$_3$ | CH$_3$ | H | 2 | CH$_3$ | H | H | H | CHOC$_2$H$_5$ | H | CH$_3$ |
| 4.1010 | CH$_3$ | CH$_3$ | H | 0 | CH$_3$ | H | H | H | CHOiPr | H | CH$_3$ |
| 4.1011 | CH$_3$ | CH$_3$ | H | 1 | CH$_3$ | H | H | H | CHOiPr | H | CH$_3$ |
| 4.1012 | CH$_3$ | CH$_3$ | H | 2 | CH$_3$ | H | H | H | CHOiPr | H | CH$_3$ |
| 4.1013 | CH$_3$ | CH$_3$ | H | 0 | CH$_3$ | H | H | H | C=NOCH$_3$ | H | CH$_3$ |
| 4.1014 | CH$_3$ | CH$_3$ | H | 1 | CH$_3$ | H | H | H | C=NOCH$_3$ | H | CH$_3$ |
| 4.1015 | CH$_3$ | CH$_3$ | H | 2 | CH$_3$ | H | H | H | C=NOCH$_3$ | H | CH$_3$ |
| 4.1016 | CH$_3$ | CH$_3$ | H | 0 | CH$_3$ | H | H | H | C=NOC$_2$H$_5$ | H | CH$_3$ |
| 4.1017 | CH$_3$ | CH$_3$ | H | 1 | CH$_3$ | H | H | H | C=NOC$_2$H$_5$ | H | CH$_3$ |
| 4.1018 | CH$_3$ | CH$_3$ | H | 2 | CH$_3$ | H | H | H | C=NOC$_2$H$_5$ | H | CH$_3$ |
| 4.1019 | CH$_3$ | CH$_3$ | H | 0 | CH$_3$ | H | H | H | C=NOiPr | H | CH$_3$ |
| 4.1020 | CH$_3$ | CH$_3$ | H | 1 | CH$_3$ | H | H | H | C=NOiPr | H | CH$_3$ |
| 4.1021 | CH$_3$ | CH$_3$ | H | 2 | CH$_3$ | H | H | H | C=NOiPr | H | CH$_3$ |
| 4.1022 | CH$_3$ | CH$_3$ | H | 0 | CH$_3$ | H | H | H | C=NOCH$_2$CH=CHCl | H | CH$_3$ |
| 4.1023 | CH$_3$ | CH$_3$ | H | 1 | CH$_3$ | H | H | H | C=NOCH$_2$CH=CHCl | H | CH$_3$ |
| 4.1024 | CH$_3$ | CH$_3$ | H | 2 | CH$_3$ | H | H | H | C=NOCH$_2$CH=CHCl | H | CH$_3$ |
| 4.1025 | CH$_3$ | CH$_3$ | H | 0 | CH$_3$ | H | H | H | C=NOCH$_2$C$_6$H$_5$ | H | CH$_3$ |
| 4.1026 | CH$_3$ | CH$_3$ | H | 1 | CH$_3$ | H | H | H | C=NOCH$_2$C$_6$H$_5$ | H | CH$_3$ |
| 4.1027 | CH$_3$ | CH$_3$ | H | 2 | CH$_3$ | H | H | H | C=NOCH$_2$C$_6$H$_5$ | H | CH$_3$ |
| 4.1028 | CH$_3$ | CH$_3$ | H | 0 | CH$_3$ | H | H | H | C(CH$_3$)$_2$ | H | CH$_3$ |
| 4.1029 | CH$_3$ | CH$_3$ | H | 1 | CH$_3$ | H | H | H | C(CH$_3$)$_2$ | H | CH$_3$ |
| 4.1030 | CH$_3$ | CH$_3$ | H | 2 | CH$_3$ | H | H | H | C(CH$_3$)$_2$ | H | CH$_3$ |
| 4.1031 | CH$_3$ | CH$_3$ | H | 0 | CH$_3$ | H | H | H | 1,3-dioxane-2-spiro (O—CH$_2$—CH$_2$—CH$_2$—O) | H | CH$_3$ |
| 4.1032 | CH$_3$ | CH$_3$ | H | 1 | CH$_3$ | H | H | H | 1,3-dioxane-2-spiro | H | CH$_3$ |
| 4.1033 | CH$_3$ | CH$_3$ | H | 2 | CH$_3$ | H | H | H | 1,3-dioxane-2-spiro | H | CH$_3$ |
| 4.1034 | CH$_3$ | CH$_3$ | H | 0 | CH$_3$ | H | H | H | 5,5-dimethyl-1,3-dioxane-2-spiro | H | CH$_3$ |
| 4.1035 | CH$_3$ | CH$_3$ | H | 1 | CH$_3$ | H | H | H | 5,5-dimethyl-1,3-dioxane-2-spiro | H | CH$_3$ |
| 4.1036 | CH$_3$ | CH$_3$ | H | 2 | CH$_3$ | H | H | H | 5,5-dimethyl-1,3-dioxane-2-spiro | H | CH$_3$ |
| 4.1037 | CH$_3$ | CH$_3$ | H | 0 | CH$_3$ | H | H | H | C=N—CH$_3$ | H | CH$_3$ |
| 4.1038 | CH$_3$ | CH$_3$ | H | 1 | CH$_3$ | H | H | H | C=N—CH$_3$ | H | CH$_3$ |

TABLE 4-continued

Compounds of the formula

[Structure: cyclohexenone with OH, connected via C=O to benzene ring with M substituent, fused to thiazine ring with S(O)n, R21, R22, R13, R12, Y; cyclohexenone has R17, R18, R19 substituents; benzene has L substituent]

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.1039 | CH$_3$ | CH$_3$ | H | 2 | CH$_3$ | H | H | H | C=N—CH$_3$ | H | CH$_3$ |
| 4.1040 | CH$_3$ | CH$_3$ | H | 0 | CH$_3$ | H | H | H | C=NC$_2$H$_5$ | H | CH$_3$ |
| 4.1041 | CH$_3$ | CH$_3$ | H | 1 | CH$_3$ | H | H | H | C=NC$_2$H$_5$ | H | CH$_3$ |
| 4.1042 | CH$_3$ | CH$_3$ | H | 2 | CH$_3$ | H | H | H | C=NC$_2$H$_5$ | H | CH$_3$ |
| 4.1043 | CH$_3$ | CH$_3$ | H | 0 | CH$_3$ | H | H | H | CH—NHCH$_3$ | H | CH$_3$ |
| 4.1044 | CH$_3$ | CH$_3$ | H | 1 | CH$_3$ | H | H | H | CH—NHCH$_3$ | H | CH$_3$ |
| 4.1045 | CH$_3$ | CH$_3$ | H | 2 | CH$_3$ | H | H | H | CH—NHCH$_3$ | H | CH$_3$ |
| 4.1046 | CH$_3$ | CH$_3$ | H | 0 | CH$_3$ | H | H | H | CH—NHC$_2$H$_5$ | H | CH$_3$ |
| 4.1047 | CH$_3$ | CH$_3$ | H | 1 | CH$_3$ | H | H | H | CH—NHC$_2$H$_5$ | H | CH$_3$ |
| 4.1048 | CH$_3$ | CH$_3$ | H | 2 | CH$_3$ | H | H | H | CH—NHC$_2$H$_5$ | H | CH$_3$ |
| 4.1049 | CH$_3$ | CH$_3$ | H | 0 | CH$_3$ | H | H | H | CH—N(CH$_3$)$_2$ | H | CH$_3$ |
| 4.1050 | CH$_3$ | CH$_3$ | H | 1 | CH$_3$ | H | H | H | CH—N(CH$_3$)$_2$ | H | CH$_3$ |
| 4.1051 | CH$_3$ | CH$_3$ | H | 2 | CH$_3$ | H | H | H | CH—N(CH$_3$)$_2$ | H | CH$_3$ |
| 4.1052 | CH$_3$ | CH$_3$ | H | 0 | CH$_3$ | H | H | H | CH—NHOC$_2$H$_5$ | H | CH$_3$ |
| 4.1053 | CH$_3$ | CH$_3$ | H | 1 | CH$_3$ | H | H | H | CH—NHOC$_2$H$_5$ | H | CH$_3$ |
| 4.1054 | CH$_3$ | CH$_3$ | H | 2 | CH$_3$ | H | H | H | CH—NHOC$_2$H$_5$ | H | CH$_3$ |
| 4.1055 | CH$_3$ | CH$_3$ | H | 0 | CH$_3$ | H | H | H | CH—N(CH$_3$)OC$_2$H$_5$ | H | CH$_3$ |
| 4.1056 | CH$_3$ | CH$_3$ | H | 1 | CH$_3$ | H | H | H | CH—N(CH$_3$)OC$_2$H$_5$ | H | CH$_3$ |
| 4.1057 | CH$_3$ | CH$_3$ | H | 2 | CH$_3$ | H | H | H | CH—N(CH$_3$)OC$_2$H$_5$ | H | CH$_3$ |
| 4.1058 | CH$_3$ | CH$_3$ | H | 0 | CH$_3$ | H | H | H | C=N—NH$_2$ | H | CH$_3$ |
| 4.1059 | CH$_3$ | CH$_3$ | H | 1 | CH$_3$ | H | H | H | C=N—NH$_2$ | H | CH$_3$ |
| 4.1060 | CH$_3$ | CH$_3$ | H | 2 | CH$_3$ | H | H | H | C=N—NH$_2$ | H | CH$_3$ |
| 4.1061 | CH$_3$ | CH$_3$ | H | 0 | CH$_3$ | H | H | H | C=N—N(CH$_3$)$_2$ | H | CH$_3$ |
| 4.1062 | CH$_3$ | CH$_3$ | H | 1 | CH$_3$ | H | H | H | C=N—N(CH$_3$)$_2$ | H | CH$_3$ |
| 4.1063 | CH$_3$ | CH$_3$ | H | 2 | CH$_3$ | H | H | H | C=N—N(CH$_3$)$_2$ | H | CH$_3$ |
| 4.1064 | CH$_3$ | CH$_3$ | H | 0 | CH$_3$ | H | H | H | CH—N(CH$_3$)OCH$_2$C$_6$H$_5$ | H | CH$_3$ |
| 4.1065 | CH$_3$ | CH$_3$ | H | 1 | CH$_3$ | H | H | H | CH—N(CH$_3$)OCH$_2$C$_6$H$_5$ | H | CH$_3$ |
| 4.1066 | CH$_3$ | CH$_3$ | H | 2 | CH$_3$ | H | H | H | CH—N(CH$_3$)OCH$_2$C$_6$H$_5$ | H | CH$_3$ |
| 4.1067 | CH$_3$ | CH$_3$ | H | 0 | CH$_3$ | H | H | H | C(CH$_3$)—OCH$_3$ | H | CH$_3$ |
| 4.1068 | CH$_3$ | CH$_3$ | H | 1 | CH$_3$ | H | H | H | C(CH$_3$)—OCH$_3$ | H | CH$_3$ |
| 4.1069 | CH$_3$ | CH$_3$ | H | 2 | CH$_3$ | H | H | H | C(CH$_3$)—OCH$_3$ | H | CH$_3$ |
| 4.1070 | CH$_3$ | CH$_3$ | H | 0 | CH$_3$ | H | H | H | O | H | CH$_3$ |
| 4.1071 | CH$_3$ | CH$_3$ | H | 2 | CH$_3$ | H | H | H | O | H | CH$_3$ |
| 4.1072 | H | H | H | 0 | CH$_3$ | CH$_3$ | H | H | C=O | H | Cl |
| 4.1073 | H | H | H | 1 | CH$_3$ | CH$_3$ | H | H | C=O | H | Cl |
| 4.1074 | H | H | H | 2 | CH$_3$ | CH$_3$ | H | H | C=O | H | Cl |
| 4.1075 | H | H | H | 0 | CH$_3$ | CH$_3$ | H | H | CHOCH$_3$ | H | Cl |
| 4.1076 | H | H | H | 1 | CH$_3$ | CH$_3$ | H | H | CHOCH$_3$ | H | Cl |
| 4.1077 | H | H | H | 2 | CH$_3$ | CH$_3$ | H | H | CHOCH$_3$ | H | Cl |
| 4.1078 | H | H | H | 0 | CH$_3$ | CH$_3$ | H | H | CHOC$_2$H$_5$ | H | Cl |
| 4.1079 | H | H | H | 1 | CH$_3$ | CH$_3$ | H | H | CHOC$_2$H$_5$ | H | Cl |
| 4.1080 | H | H | H | 2 | CH$_3$ | CH$_3$ | H | H | CHOC$_2$H$_5$ | H | Cl |
| 4.1081 | H | H | H | 0 | CH$_3$ | CH$_3$ | H | H | CHOiPr | H | Cl |
| 4.1082 | H | H | H | 1 | CH$_3$ | CH$_3$ | H | H | CHOiPr | H | Cl |
| 4.1083 | H | H | H | 2 | CH$_3$ | CH$_3$ | H | H | CHOiPr | H | Cl |
| 4.1084 | H | H | H | 0 | CH$_3$ | CH$_3$ | H | H | C=NOCH$_3$ | H | Cl |
| 4.1085 | H | H | H | 1 | CH$_3$ | CH$_3$ | H | H | C=NOCH$_3$ | H | Cl |
| 4.1086 | H | H | H | 2 | CH$_3$ | CH$_3$ | H | H | C=NOCH$_3$ | H | Cl |
| 4.1087 | H | H | H | 0 | CH$_3$ | CH$_3$ | H | H | C=NOC$_2$H$_5$ | H | Cl |
| 4.1088 | H | H | H | 1 | CH$_3$ | CH$_3$ | H | H | C=NOC$_2$H$_5$ | H | Cl |
| 4.1089 | H | H | H | 2 | CH$_3$ | CH$_3$ | H | H | C=NOC$_2$H$_5$ | H | Cl |
| 4.1090 | H | H | H | 0 | CH$_3$ | CH$_3$ | H | H | C=NOiPr | H | Cl |
| 4.1091 | H | H | H | 1 | CH$_3$ | CH$_3$ | H | H | C=NOiPr | H | Cl |
| 4.1092 | H | H | H | 2 | CH$_3$ | CH$_3$ | H | H | C=NOiPr | H | Cl |
| 4.1093 | H | H | H | 0 | CH$_3$ | CH$_3$ | H | H | C=NOCH$_2$CH=CHCl | H | Cl |
| 4.1094 | H | H | H | 1 | CH$_3$ | CH$_3$ | H | H | C=NOCH$_2$CH=CHCl | H | Cl |
| 4.1095 | H | H | H | 2 | CH$_3$ | CH$_3$ | H | H | C=NOCH$_2$CH=CHCl | H | Cl |
| 4.1096 | H | H | H | 0 | CH$_3$ | CH$_3$ | H | H | C=NOCH$_2$C$_6$H$_5$ | H | Cl |
| 4.1097 | H | H | H | 1 | CH$_3$ | CH$_3$ | H | H | C=NOCH$_2$C$_6$H$_5$ | H | Cl |
| 4.1098 | H | H | H | 2 | CH$_3$ | CH$_3$ | H | H | C=NOCH$_2$C$_6$H$_5$ | H | Cl |
| 4.1099 | H | H | H | 0 | CH$_3$ | CH$_3$ | H | H | C(CH$_3$)$_2$ | H | Cl |
| 4.1100 | H | H | H | 1 | CH$_3$ | CH$_3$ | H | H | C(CH$_3$)$_2$ | H | Cl |
| 4.1101 | H | H | H | 2 | CH$_3$ | CH$_3$ | H | H | C(CH$_3$)$_2$ | H | Cl |

TABLE 4-continued

Compounds of the formula

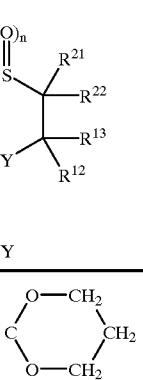

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.1102 | H | H | H | 0 | CH$_3$ | CH$_3$ | H | H | 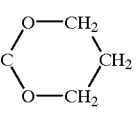 | H | Cl |
| 4.1103 | H | H | H | 1 | CH$_3$ | CH$_3$ | H | H | 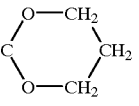 | H | Cl |
| 4.1104 | H | H | H | 2 | CH$_3$ | CH$_3$ | H | H | 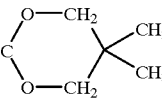 | H | Cl |
| 4.1105 | H | H | H | 0 | CH$_3$ | CH$_3$ | H | H | 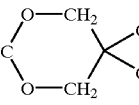 | H | Cl |
| 4.1106 | H | H | H | 1 | CH$_3$ | CH$_3$ | H | H | 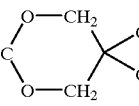 | H | Cl |
| 4.1107 | H | H | H | 2 | CH$_3$ | CH$_3$ | H | H |  | H | Cl |
| 4.1108 | H | H | H | 0 | CH$_3$ | CH$_3$ | H | H | C=N—CH$_3$ | H | Cl |
| 4.1109 | H | H | H | 1 | CH$_3$ | CH$_3$ | H | H | C=N—CH$_3$ | H | Cl |
| 4.1110 | H | H | H | 2 | CH$_3$ | CH$_3$ | H | H | C=N—CH$_3$ | H | Cl |
| 4.1111 | H | H | H | 0 | CH$_3$ | CH$_3$ | H | H | C=NC$_2$H$_5$ | H | Cl |
| 4.1112 | H | H | H | 1 | CH$_3$ | CH$_3$ | H | H | C=NC$_2$H$_5$ | H | Cl |
| 4.1113 | H | H | H | 2 | CH$_3$ | CH$_3$ | H | H | C=NC$_2$H$_5$ | H | Cl |
| 4.1114 | H | H | H | 0 | CH$_3$ | CH$_3$ | H | H | CH—NHCH$_3$ | H | Cl |
| 4.1115 | H | H | H | 1 | CH$_3$ | CH$_3$ | H | H | CH—NHCH$_3$ | H | Cl |
| 4.1116 | H | H | H | 2 | CH$_3$ | CH$_3$ | H | H | CH—NHCH$_3$ | H | Cl |
| 4.1117 | H | H | H | 0 | CH$_3$ | CH$_3$ | H | H | CH—NHC$_2$H$_5$ | H | Cl |
| 4.1118 | H | H | H | 1 | CH$_3$ | CH$_3$ | H | H | CH—NHC$_2$H$_5$ | H | Cl |
| 4.1119 | H | H | H | 2 | CH$_3$ | CH$_3$ | H | H | CH—NHC$_2$H$_5$ | H | Cl |
| 4.1120 | H | H | H | 0 | CH$_3$ | CH$_3$ | H | H | CH—N(CH$_3$)$_2$ | H | Cl |
| 4.1121 | H | H | H | 1 | CH$_3$ | CH$_3$ | H | H | CH—N(CH$_3$)$_2$ | H | Cl |
| 4.1122 | H | H | H | 2 | CH$_3$ | CH$_3$ | H | H | CH—N(CH$_3$)$_2$ | H | Cl |
| 4.1123 | H | H | H | 0 | CH$_3$ | CH$_3$ | H | H | CH—NHOC$_2$H$_5$ | H | Cl |
| 4.1124 | H | H | H | 1 | CH$_3$ | CH$_3$ | H | H | CH—NHOC$_2$H$_5$ | H | Cl |
| 4.1125 | H | H | H | 2 | CH$_3$ | CH$_3$ | H | H | CH—NHOC$_2$H$_5$ | H | Cl |
| 4.1126 | H | H | H | 0 | CH$_3$ | CH$_3$ | H | H | CH—N(CH$_3$)OC$_2$H$_5$ | H | Cl |
| 4.1127 | H | H | H | 1 | CH$_3$ | CH$_3$ | H | H | CH—N(CH$_3$)OC$_2$H$_5$ | H | Cl |
| 4.1128 | H | H | H | 2 | CH$_3$ | CH$_3$ | H | H | CH—N(CH$_3$)OC$_2$H$_5$ | H | Cl |
| 4.1129 | H | H | H | 0 | CH$_3$ | CH$_3$ | H | H | C=N—NH$_2$ | H | Cl |
| 4.1130 | H | H | H | 1 | CH$_3$ | CH$_3$ | H | H | C=N—NH$_2$ | H | Cl |
| 4.1131 | H | H | H | 2 | CH$_3$ | CH$_3$ | H | H | C=N—NH$_2$ | H | Cl |
| 4.1132 | H | H | H | 0 | CH$_3$ | CH$_3$ | H | H | C=N—N(CH$_3$)$_2$ | H | Cl |
| 4.1133 | H | H | H | 1 | CH$_3$ | CH$_3$ | H | H | C=N—N(CH$_3$)$_2$ | H | Cl |
| 4.1134 | H | H | H | 2 | CH$_3$ | CH$_3$ | H | H | C=N—N(CH$_3$)$_2$ | H | Cl |
| 4.1135 | H | H | H | 0 | CH$_3$ | CH$_3$ | H | H | CH—N(CH$_3$)OCH$_2$C$_6$H$_5$ | H | Cl |

TABLE 4-continued

Compounds of the formula

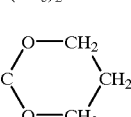

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.1136 | H | H | H | 1 | $CH_3$ | $CH_3$ | H | H | CH—N($CH_3$)$OCH_2C_6H_5$ | H | Cl |
| 4.1137 | H | H | H | 2 | $CH_3$ | $CH_3$ | H | H | CH—N($CH_3$)$OCH_2C_6H_5$ | H | Cl |
| 4.1138 | H | H | H | 0 | $CH_3$ | $CH_3$ | H | H | C($CH_3$)—$OCH_3$ | H | Cl |
| 4.1139 | H | H | H | 1 | $CH_3$ | $CH_3$ | H | H | C($CH_3$)—$OCH_3$ | H | Cl |
| 4.1140 | H | H | H | 2 | $CH_3$ | $CH_3$ | H | H | C($CH_3$)—$OCH_3$ | H | Cl |
| 4.1141 | H | H | H | 0 | $CH_3$ | $CH_3$ | H | H | O | H | Cl |
| 4.1142 | H | H | H | 2 | $CH_3$ | $CH_3$ | H | H | O | H | Cl |
| 4.1143 | $CH_3$ | H | H | 0 | $CH_3$ | $CH_3$ | H | H | C=O | H | Cl |
| 4.1144 | $CH_3$ | H | H | 1 | $CH_3$ | $CH_3$ | H | H | C=O | H | Cl |
| 4.1145 | $CH_3$ | H | H | 2 | $CH_3$ | $CH_3$ | H | H | C=O | H | Cl |
| 4.1146 | $CH_3$ | H | H | 0 | $CH_3$ | $CH_3$ | H | H | $CHOCH_3$ | H | Cl |
| 4.1147 | $CH_3$ | H | H | 1 | $CH_3$ | $CH_3$ | H | H | $CHOCH_3$ | H | Cl |
| 4.1148 | $CH_3$ | H | H | 2 | $CH_3$ | $CH_3$ | H | H | $CHOCH_3$ | H | Cl |
| 4.1149 | $CH_3$ | H | H | 0 | $CH_3$ | $CH_3$ | H | H | $CHOC_2H_5$ | H | Cl |
| 4.1150 | $CH_3$ | H | H | 1 | $CH_3$ | $CH_3$ | H | H | $CHOC_2H_5$ | H | Cl |
| 4.1151 | $CH_3$ | H | H | 2 | $CH_3$ | $CH_3$ | H | H | $CHOC_2H_5$ | H | Cl |
| 4.1152 | $CH_3$ | H | H | 0 | $CH_3$ | $CH_3$ | H | H | CHOiPr | H | Cl |
| 4.1153 | $CH_3$ | H | H | 1 | $CH_3$ | $CH_3$ | H | H | CHOiPr | H | Cl |
| 4.1154 | $CH_3$ | H | H | 2 | $CH_3$ | $CH_3$ | H | H | CHOiPr | H | Cl |
| 4.1155 | $CH_3$ | H | H | 0 | $CH_3$ | $CH_3$ | H | H | C=$NOCH_3$ | H | Cl |
| 4.1156 | $CH_3$ | H | H | 1 | $CH_3$ | $CH_3$ | H | H | C=$NOCH_3$ | H | Cl |
| 4.1157 | $CH_3$ | H | H | 2 | $CH_3$ | $CH_3$ | H | H | C=$NOCH_3$ | H | Cl |
| 4.1158 | $CH_3$ | H | H | 0 | $CH_3$ | $CH_3$ | H | H | C=$NOC_2H_5$ | H | Cl |
| 4.1159 | $CH_3$ | H | H | 1 | $CH_3$ | $CH_3$ | H | H | C=$NOC_2H_5$ | H | Cl |
| 4.1160 | $CH_3$ | H | H | 2 | $CH_3$ | $CH_3$ | H | H | C=$NOC_2H_5$ | H | Cl |
| 4.1161 | $CH_3$ | H | H | 0 | $CH_3$ | $CH_3$ | H | H | C=NOiPr | H | Cl |
| 4.1162 | $CH_3$ | H | H | 1 | $CH_3$ | $CH_3$ | H | H | C=NOiPr | H | Cl |
| 4.1163 | $CH_3$ | H | H | 2 | $CH_3$ | $CH_3$ | H | H | C=NOiPr | H | Cl |
| 4.1164 | $CH_3$ | H | H | 0 | $CH_3$ | $CH_3$ | H | H | C=$NOCH_2CH$=CHCl | H | Cl |
| 4.1165 | $CH_3$ | H | H | 1 | $CH_3$ | $CH_3$ | H | H | C=$NOCH_2CH$=CHCl | H | Cl |
| 4.1166 | $CH_3$ | H | H | 2 | $CH_3$ | $CH_3$ | H | H | C=$NOCH_2CH$=CHCl | H | Cl |
| 4.1167 | $CH_3$ | H | H | 0 | $CH_3$ | $CH_3$ | H | H | C=$NOCH_2C_6H_5$ | H | Cl |
| 4.1168 | $CH_3$ | H | H | 1 | $CH_3$ | $CH_3$ | H | H | C=$NOCH_2C_6H_5$ | H | Cl |
| 4.1169 | $CH_3$ | H | H | 2 | $CH_3$ | $CH_3$ | H | H | C=$NOCH_2C_6H_5$ | H | Cl |
| 4.1170 | $CH_3$ | H | H | 0 | $CH_3$ | $CH_3$ | H | H | C($CH_3$)$_2$ | H | Cl |
| 4.1171 | $CH_3$ | H | H | 1 | $CH_3$ | $CH_3$ | H | H | C($CH_3$)$_2$ | H | Cl |
| 4.1172 | $CH_3$ | H | H | 2 | $CH_3$ | $CH_3$ | H | H | C($CH_3$)$_2$ | H | Cl |
| 4.1173 | $CH_3$ | H | H | 0 | $CH_3$ | $CH_3$ | H | H | 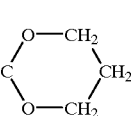 | H | Cl |
| 4.1174 | $CH_3$ | H | H | 1 | $CH_3$ | $CH_3$ | H | H | 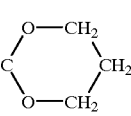 | H | Cl |
| 4.1175 | $CH_3$ | H | H | 2 | $CH_3$ | $CH_3$ | H | H | 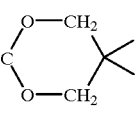 | H | Cl |
| 4.1176 | $CH_3$ | H | H | 0 | $CH_3$ | $CH_3$ | H | H |  | H | Cl |

TABLE 4-continued

Compounds of the formula

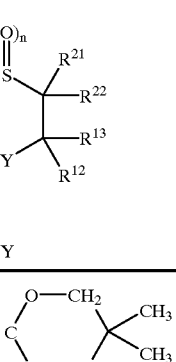

| No. | R$^{17}$ | R$^{18}$ | R$^{19}$ | n | R$^{12}$ | R$^{13}$ | R$^{21}$ | R$^{22}$ | Y | L | M |
|---|---|---|---|---|---|---|---|---|---|---|---|
| 4.1177 | CH$_3$ | H | H | 1 | CH$_3$ | CH$_3$ | H | H | (dioxane-CMe$_2$ group) | H | Cl |
| 4.1178 | CH$_3$ | H | H | 2 | CH$_3$ | CH$_3$ | H | H | (dioxane-CMe$_2$ group) | H | Cl |
| 4.1179 | CH$_3$ | H | H | 0 | CH$_3$ | CH$_3$ | H | H | C=N—CH$_3$ | H | Cl |
| 4.1180 | CH$_3$ | H | H | 1 | CH$_3$ | CH$_3$ | H | H | C=N—CH$_3$ | H | Cl |
| 4.1181 | CH$_3$ | H | H | 2 | CH$_3$ | CH$_3$ | H | H | C=N—CH$_3$ | H | Cl |
| 4.1182 | CH$_3$ | H | H | 0 | CH$_3$ | CH$_3$ | H | H | C=NC$_2$H$_5$ | H | Cl |
| 4.1183 | CH$_3$ | H | H | 1 | CH$_3$ | CH$_3$ | H | H | C=NC$_2$H$_5$ | H | Cl |
| 4.1184 | CH$_3$ | H | H | 2 | CH$_3$ | CH$_3$ | H | H | C=NC$_2$H$_5$ | H | Cl |
| 4.1185 | CH$_3$ | H | H | 0 | CH$_3$ | CH$_3$ | H | H | CH—NHCH$_3$ | H | Cl |
| 4.1186 | CH$_3$ | H | H | 1 | CH$_3$ | CH$_3$ | H | H | CH—NHCH$_3$ | H | Cl |
| 4.1187 | CH$_3$ | H | H | 2 | CH$_3$ | CH$_3$ | H | H | CH—NHCH$_3$ | H | Cl |
| 4.1188 | CH$_3$ | H | H | 0 | CH$_3$ | CH$_3$ | H | H | CH—NHC$_2$H$_5$ | H | Cl |
| 4.1189 | CH$_3$ | H | H | 1 | CH$_3$ | CH$_3$ | H | H | CH—NHC$_2$H$_5$ | H | Cl |
| 4.1190 | CH$_3$ | H | H | 2 | CH$_3$ | CH$_3$ | H | H | CH—NHC$_2$H$_5$ | H | Cl |
| 4.1191 | CH$_3$ | H | H | 0 | CH$_3$ | CH$_3$ | H | H | CH—N(CH$_3$)$_2$ | H | Cl |
| 4.1192 | CH$_3$ | H | H | 1 | CH$_3$ | CH$_3$ | H | H | CH—N(CH$_3$)$_2$ | H | Cl |
| 4.1193 | CH$_3$ | H | H | 2 | CH$_3$ | CH$_3$ | H | H | CH—N(CH$_3$)$_2$ | H | Cl |
| 4.1194 | CH$_3$ | H | H | 0 | CH$_3$ | CH$_3$ | H | H | CH—NHOC$_2$H$_5$ | H | Cl |
| 4.1195 | CH$_3$ | H | H | 1 | CH$_3$ | CH$_3$ | H | H | CH—NHOC$_2$H$_5$ | H | Cl |
| 4.1196 | CH$_3$ | H | H | 2 | CH$_3$ | CH$_3$ | H | H | CH—NHOC$_2$H$_5$ | H | Cl |
| 4.1197 | CH$_3$ | H | H | 0 | CH$_3$ | CH$_3$ | H | H | CH—N(CH$_3$)OC$_2$H$_5$ | H | Cl |
| 4.1198 | CH$_3$ | H | H | 1 | CH$_3$ | CH$_3$ | H | H | CH—N(CH$_3$)OC$_2$H$_5$ | H | Cl |
| 4.1199 | CH$_3$ | H | H | 2 | CH$_3$ | CH$_3$ | H | H | CH—N(CH$_3$)OC$_2$H$_5$ | H | Cl |
| 4.1200 | CH$_3$ | H | H | 0 | CH$_3$ | CH$_3$ | H | H | C=N—NH$_2$ | H | Cl |
| 4.1201 | CH$_3$ | H | H | 1 | CH$_3$ | CH$_3$ | H | H | C=N—NH$_2$ | H | Cl |
| 4.1202 | CH$_3$ | H | H | 2 | CH$_3$ | CH$_3$ | H | H | C=N—NH$_2$ | H | Cl |
| 4.1203 | CH$_3$ | H | H | 0 | CH$_3$ | CH$_3$ | H | H | C=N—N(CH$_3$)$_2$ | H | Cl |
| 4.1204 | CH$_3$ | H | H | 1 | CH$_3$ | CH$_3$ | H | H | C=N—N(CH$_3$)$_2$ | H | Cl |
| 4.1205 | CH$_3$ | H | H | 2 | CH$_3$ | CH$_3$ | H | H | C=N—N(CH$_3$)$_2$ | H | Cl |
| 4.1206 | CH$_3$ | H | H | 0 | CH$_3$ | CH$_3$ | H | H | CH—N(CH$_3$)OCH$_2$C$_6$H$_5$ | H | Cl |
| 4.1207 | CH$_3$ | H | H | 1 | CH$_3$ | CH$_3$ | H | H | CH—N(CH$_3$)OCH$_2$C$_6$H$_5$ | H | Cl |
| 4.1208 | CH$_3$ | H | H | 2 | CH$_3$ | CH$_3$ | H | H | CH—N(CH$_3$)OCH$_2$C$_6$H$_5$ | H | Cl |
| 4.1209 | CH$_3$ | H | H | 0 | CH$_3$ | CH$_3$ | H | H | C(CH$_3$)—OCH$_3$ | H | Cl |
| 4.1210 | CH$_3$ | H | H | 1 | CH$_3$ | CH$_3$ | H | H | C(CH$_3$)—OCH$_3$ | H | Cl |
| 4.1211 | CH$_3$ | H | H | 2 | CH$_3$ | CH$_3$ | H | H | C(CH$_3$)—OCH$_3$ | H | Cl |
| 4.1212 | CH$_3$ | H | H | 0 | CH$_3$ | CH$_3$ | H | H | O | H | Cl |
| 4.1213 | CH$_3$ | H | H | 2 | CH$_3$ | CH$_3$ | H | H | O | H | Cl |
| 4.1214 | CH$_3$ | CH$_3$ | H | 0 | CH$_3$ | CH$_3$ | H | H | C=O | H | Cl |
| 4.1215 | CH$_3$ | CH$_3$ | H | 1 | CH$_3$ | CH$_3$ | H | H | C=O | H | Cl |
| 4.1216 | CH$_3$ | CH$_3$ | H | 2 | CH$_3$ | CH$_3$ | H | H | C=O | H | Cl |
| 4.1217 | CH$_3$ | CH$_3$ | H | 0 | CH$_3$ | CH$_3$ | H | H | CHOCH$_3$ | H | Cl |
| 4.1218 | CH$_3$ | CH$_3$ | H | 1 | CH$_3$ | CH$_3$ | H | H | CHOCH$_3$ | H | Cl |
| 4.1219 | CH$_3$ | CH$_3$ | H | 2 | CH$_3$ | CH$_3$ | H | H | CHOCH$_3$ | H | Cl |
| 4.1220 | CH$_3$ | CH$_3$ | H | 0 | CH$_3$ | CH$_3$ | H | H | CHOC$_2$H$_5$ | H | Cl |
| 4.1221 | CH$_3$ | CH$_3$ | H | 1 | CH$_3$ | CH$_3$ | H | H | CHOC$_2$H$_5$ | H | Cl |
| 4.1222 | CH$_3$ | CH$_3$ | H | 2 | CH$_3$ | CH$_3$ | H | H | CHOC$_2$H$_5$ | H | Cl |
| 4.1223 | CH$_3$ | CH$_3$ | H | 0 | CH$_3$ | CH$_3$ | H | H | CHOiPr | H | Cl |
| 4.1224 | CH$_3$ | CH$_3$ | H | 1 | CH$_3$ | CH$_3$ | H | H | CHOiPr | H | Cl |
| 4.1225 | CH$_3$ | CH$_3$ | H | 2 | CH$_3$ | CH$_3$ | H | H | CHOiPr | H | Cl |
| 4.1226 | CH$_3$ | CH$_3$ | H | 0 | CH$_3$ | CH$_3$ | H | H | C=NOCH$_3$ | H | Cl |
| 4.1227 | CH$_3$ | CH$_3$ | H | 1 | CH$_3$ | CH$_3$ | H | H | C=NOCH$_3$ | H | Cl |
| 4.1228 | CH$_3$ | CH$_3$ | H | 2 | CH$_3$ | CH$_3$ | H | H | C=NOCH$_3$ | H | Cl |
| 4.1229 | CH$_3$ | CH$_3$ | H | 0 | CH$_3$ | CH$_3$ | H | H | C=NOC$_2$H$_5$ | H | Cl |
| 4.1230 | CH$_3$ | CH$_3$ | H | 1 | CH$_3$ | CH$_3$ | H | H | C=NOC$_2$H$_5$ | H | Cl |

TABLE 4-continued

Compounds of the formula

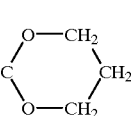

| No. | R17 | R18 | R19 | n | R12 | R13 | R21 | R22 | Y | L | M |
|---|---|---|---|---|---|---|---|---|---|---|---|
| 4.1231 | CH₃ | CH₃ | H | 2 | CH₃ | CH₃ | H | H | C=NOC₂H₅ | H | Cl |
| 4.1232 | CH₃ | CH₃ | H | 0 | CH₃ | CH₃ | H | H | C=NOiPr | H | Cl |
| 4.1233 | CH₃ | CH₃ | H | 1 | CH₃ | CH₃ | H | H | C=NOiPr | H | Cl |
| 4.1234 | CH₃ | CH₃ | H | 2 | CH₃ | CH₃ | H | H | C=NOiPr | H | Cl |
| 4.1235 | CH₃ | CH₃ | H | 0 | CH₃ | CH₃ | H | H | C=NOCH₂CH=CHCl | H | Cl |
| 4.1236 | CH₃ | CH₃ | H | 1 | CH₃ | CH₃ | H | H | C=NOCH₂CH=CHCl | H | Cl |
| 4.1237 | CH₃ | CH₃ | H | 2 | CH₃ | CH₃ | H | H | C=NOCH₂CH=CHCl | H | Cl |
| 4.1238 | CH₃ | CH₃ | H | 0 | CH₃ | CH₃ | H | H | C=NOCH₂C₆H₅ | H | Cl |
| 4.1239 | CH₃ | CH₃ | H | 1 | CH₃ | CH₃ | H | H | C=NOCH₂C₆H₅ | H | Cl |
| 4.1240 | CH₃ | CH₃ | H | 2 | CH₃ | CH₃ | H | H | C=NOCH₂C₆H₅ | H | Cl |
| 4.1241 | CH₃ | CH₃ | H | 0 | CH₃ | CH₃ | H | H | C(CH₃)₂ | H | Cl |
| 4.1242 | CH₃ | CH₃ | H | 1 | CH₃ | CH₃ | H | H | C(CH₃)₂ | H | Cl |
| 4.1243 | CH₃ | CH₃ | H | 2 | CH₃ | CH₃ | H | H | C(CH₃)₂ | H | Cl |
| 4.1244 | CH₃ | CH₃ | H | 0 | CH₃ | CH₃ | H | H | 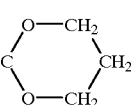 | H | ClCl |
| 4.1245 | CH₃ | CH₃ | H | 1 | CH₃ | CH₃ | H | H | 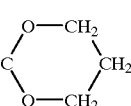 | H | Cl |
| 4.1246 | CH₃ | CH₃ | H | 2 | CH₃ | CH₃ | H | H | 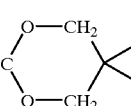 | H | Cl |
| 4.1247 | CH₃ | CH₃ | H | 0 | CH₃ | CH₃ | H | H | 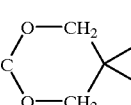 | H | Cl |
| 4.1248 | CH₃ | CH₃ | H | 1 | CH₃ | CH₃ | H | H | 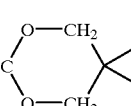 | H | Cl |
| 4.1249 | CH₃ | CH₃ | H | 2 | CH₃ | CH₃ | H | H |  | H | Cl |
| 4.1250 | CH₃ | CH₃ | H | 0 | CH₃ | CH₃ | H | H | C=N—CH₃ | H | Cl |
| 4.1251 | CH₃ | CH₃ | H | 1 | CH₃ | CH₃ | H | H | C=N—CH₃ | H | Cl |
| 4.1252 | CH₃ | CH₃ | H | 2 | CH₃ | CH₃ | H | H | C=N—CH₃ | H | Cl |
| 4.1253 | CH₃ | CH₃ | H | 0 | CH₃ | CH₃ | H | H | C=NC₂H₅ | H | Cl |
| 4.1254 | CH₃ | CH₃ | H | 1 | CH₃ | CH₃ | H | H | C=NC₂H₅ | H | Cl |
| 4.1255 | CH₃ | CH₃ | H | 2 | CH₃ | CH₃ | H | H | C=NC₂H₅ | H | Cl |
| 4.1256 | CH₃ | CH₃ | H | 0 | CH₃ | CH₃ | H | H | CH—NHCH₃ | H | Cl |
| 4.1257 | CH₃ | CH₃ | H | 1 | CH₃ | CH₃ | H | H | CH—NHCH₃ | H | Cl |
| 4.1258 | CH₃ | CH₃ | H | 2 | CH₃ | CH₃ | H | H | CH—NHCH₃ | H | Cl |
| 4.1259 | CH₃ | CH₃ | H | 0 | CH₃ | CH₃ | H | H | CH—NHC₂H₅ | H | Cl |
| 4.1260 | CH₃ | CH₃ | H | 1 | CH₃ | CH₃ | H | H | CH—NHC₂H₅ | H | Cl |
| 4.1261 | CH₃ | CH₃ | H | 2 | CH₃ | CH₃ | H | H | CH—NHC₂H₅ | H | Cl |
| 4.1262 | CH₃ | CH₃ | H | 0 | CH₃ | CH₃ | H | H | CH—N(CH₃)₂ | H | Cl |
| 4.1263 | CH₃ | CH₃ | H | 1 | CH₃ | CH₃ | H | H | CH—N(CH₃)₂ | H | Cl |

TABLE 4-continued

Compounds of the formula

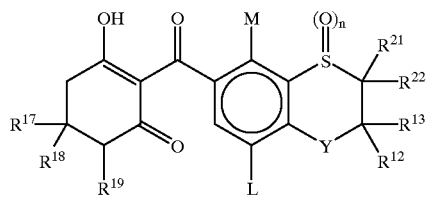

| No. | $R^{17}$ | $R^{18}$ | $R^{19}$ | n | $R^{12}$ | $R^{13}$ | $R^{21}$ | $R^{22}$ | Y | L | M |
|---|---|---|---|---|---|---|---|---|---|---|---|
| 4.1264 | $CH_3$ | $CH_3$ | H | 2 | $CH_3$ | $CH_3$ | H | H | CH—N(CH$_3$)$_2$ | H | Cl |
| 4.1265 | $CH_3$ | $CH_3$ | H | 0 | $CH_3$ | $CH_3$ | H | H | CH—NHOC$_2$H$_5$ | H | Cl |
| 4.1266 | $CH_3$ | $CH_3$ | H | 1 | $CH_3$ | $CH_3$ | H | H | CH—NHOC$_2$H$_5$ | H | Cl |
| 4.1267 | $CH_3$ | $CH_3$ | H | 2 | $CH_3$ | $CH_3$ | H | H | CH—NHOC$_2$H$_5$ | H | Cl |
| 4.1268 | $CH_3$ | $CH_3$ | H | 0 | $CH_3$ | $CH_3$ | H | H | CH—N(CH$_3$)OC$_2$H$_5$ | H | Cl |
| 4.1269 | $CH_3$ | $CH_3$ | H | 1 | $CH_3$ | $CH_3$ | H | H | CH—N(CH$_3$)OC$_2$H$_5$ | H | Cl |
| 4.1270 | $CH_3$ | $CH_3$ | H | 2 | $CH_3$ | $CH_3$ | H | H | CH—N(CH$_3$)OC$_2$H$_5$ | H | Cl |
| 4.1271 | $CH_3$ | $CH_3$ | H | 0 | $CH_3$ | $CH_3$ | H | H | C=N—NH$_2$ | H | Cl |
| 4.1272 | $CH_3$ | $CH_3$ | H | 1 | $CH_3$ | $CH_3$ | H | H | C=N—NH$_2$ | H | Cl |
| 4.1273 | $CH_3$ | $CH_3$ | H | 2 | $CH_3$ | $CH_3$ | H | H | C=N—NH$_2$ | H | Cl |
| 4.1274 | $CH_3$ | $CH_3$ | H | 0 | $CH_3$ | $CH_3$ | H | H | C=N—N(CH$_3$)$_2$ | H | Cl |
| 4.1275 | $CH_3$ | $CH_3$ | H | 1 | $CH_3$ | $CH_3$ | H | H | C=N—N(CH$_3$)$_2$ | H | Cl |
| 4.1276 | $CH_3$ | $CH_3$ | H | 2 | $CH_3$ | $CH_3$ | H | H | C=N—N(CH$_3$)$_2$ | H | Cl |
| 4.1277 | $CH_3$ | $CH_3$ | H | 0 | $CH_3$ | $CH_3$ | H | H | CH—N(CH$_3$)OCH$_2$C$_6$H$_5$ | H | Cl |
| 4.1278 | $CH_3$ | $CH_3$ | H | 1 | $CH_3$ | $CH_3$ | H | H | CH—N(CH$_3$)OCH$_2$C$_6$H$_5$ | H | Cl |
| 4.1279 | $CH_3$ | $CH_3$ | H | 2 | $CH_3$ | $CH_3$ | H | H | CH—N(CH$_3$)OCH$_2$C$_6$H$_5$ | H | Cl |
| 4.1280 | $CH_3$ | $CH_3$ | H | 0 | $CH_3$ | $CH_3$ | H | H | C(CH$_3$)—OCH$_3$ | H | Cl |
| 4.1281 | $CH_3$ | $CH_3$ | H | 1 | $CH_3$ | $CH_3$ | H | H | C(CH$_3$)—OCH$_3$ | H | Cl |
| 4.1282 | $CH_3$ | $CH_3$ | H | 2 | $CH_3$ | $CH_3$ | H | H | C(CH$_3$)—OCH$_3$ | H | Cl |
| 4.1283 | $CH_3$ | $CH_3$ | H | 0 | $CH_3$ | $CH_3$ | H | H | O | H | Cl |
| 4.1284 | $CH_3$ | $CH_3$ | H | 2 | $CH_3$ | $CH_3$ | H | H | O | H | Cl |

TABLE 5

Compounds of the formula

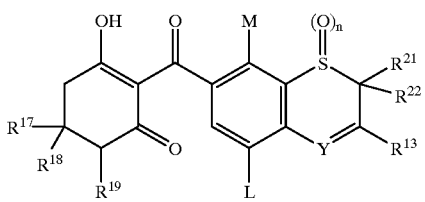

The radicals $R^{12}$ of X and R7 of Y form a bond

| No. | $R^{17}$ | $R^{18}$ | $R^{19}$ | n | $R^{21}$ | $R^{22}$ | $R^{13}$ | Y | L | M |
|---|---|---|---|---|---|---|---|---|---|---|
| 5.1 | H | H | H | 0 | H | H | H | COCH$_3$ | H | H |
| 5.2 | H | H | H | 2 | H | H | H | COCH$_3$ | H | H |
| 5.3 | H | H | H | 0 | H | H | H | COC$_2$H$_5$ | H | H |
| 5.4 | H | H | H | 2 | H | H | H | COC$_2$H$_5$ | H | H |
| 5.5 | H | H | H | 0 | H | H | H | COiPr | H | H |
| 5.6 | H | H | H | 2 | H | H | H | COiPr | H | H |
| 5.7 | $CH_3$ | H | H | 0 | H | H | H | COCH$_3$ | H | H |
| 5.8 | $CH_3$ | H | H | 2 | H | H | H | COCH$_3$ | H | H |
| 5.9 | $CH_3$ | H | H | 0 | H | H | H | COC$_2$H$_5$ | H | H |
| 5.10 | $CH_3$ | H | H | 2 | H | H | H | COC$_2$H$_5$ | H | H |
| 5.11 | $CH_3$ | H | H | 0 | H | H | H | COiPr | H | H |
| 5.12 | $CH_3$ | H | H | 2 | H | H | H | COiPr | H | H |
| 5.13 | $CH_3$ | $CH_3$ | H | 0 | H | H | H | COCH$_3$ | H | H |
| 5.14 | $CH_3$ | $CH_3$ | H | 2 | H | H | H | COCH$_3$ | H | H |
| 5.15 | $CH_3$ | $CH_3$ | H | 0 | H | H | H | COC$_2$H$_5$ | H | H |
| 5.16 | $CH_3$ | $CH_3$ | H | 2 | H | H | H | COC$_2$H$_5$ | H | H |
| 5.17 | $CH_3$ | $CH_3$ | H | 0 | H | H | H | COiPr | H | H |
| 5.18 | $CH_3$ | $CH_3$ | H | 2 | H | H | H | COiPr | H | H |
| 5.19 | H | H | H | 0 | H | H | H | COCH$_3$ | H | $CH_3$ |
| 5.20 | H | H | H | 2 | H | H | H | COCH$_3$ | H | $CH_3$ |
| 5.21 | H | H | H | 0 | H | H | H | COC$_2$H$_5$ | H | $CH_3$ |

TABLE 5-continued

Compounds of the formula

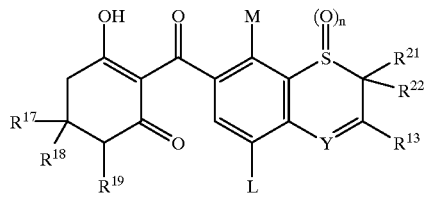

The radicals $R^{12}$ of X and R7 of Y form a bond

| No. | $R^{17}$ | $R^{18}$ | $R^{19}$ | n | $R^{21}$ | $R^{22}$ | $R^{13}$ | Y | L | M |
|---|---|---|---|---|---|---|---|---|---|---|
| 5.22 | H | H | H | 2 | H | H | H | $COC_2H_5$ | H | $CH_3$ |
| 5.23 | H | H | H | 0 | H | H | H | COiPr | H | $CH_3$ |
| 5.24 | H | H | H | 2 | H | H | H | COiPr | H | $CH_3$ |
| 5.25 | $CH_3$ | H | H | 0 | H | H | H | $COCH_3$ | H | $CH_3$ |
| 5.26 | $CH_3$ | H | H | 2 | H | H | H | $COCH_3$ | H | $CH_3$ |
| 5.27 | $CH_3$ | H | H | 0 | H | H | H | $COC_2H_5$ | H | $CH_3$ |
| 5.28 | $CH_3$ | H | H | 2 | H | H | H | $COC_2H_5$ | H | $CH_3$ |
| 5.29 | $CH_3$ | H | H | 0 | H | H | H | COiPr | H | $CH_3$ |
| 5.30 | $CH_3$ | H | H | 2 | H | H | H | COiPr | H | $CH_3$ |
| 5.31 | $CH_3$ | $CH_3$ | H | 0 | H | H | H | $COCH_3$ | H | $CH_3$ |
| 5.32 | $CH_3$ | $CH_3$ | H | 2 | H | H | H | $COCH_3$ | H | $CH_3$ |
| 5.33 | $CH_3$ | $CH_3$ | H | 0 | H | H | H | $COC_2H_5$ | H | $CH_3$ |
| 5.34 | $CH_3$ | $CH_3$ | H | 2 | H | H | H | $COC_2H_5$ | H | $CH_3$ |
| 5.35 | $CH_3$ | $CH_3$ | H | 0 | H | H | H | COiPr | H | $CH_3$ |
| 5.36 | $CH_3$ | $CH_3$ | H | 2 | H | H | H | COiPr | H | $CH_3$ |
| 5.37 | H | H | H | 0 | H | H | H | $COCH_3$ | H | Cl |
| 5.38 | H | H | H | 2 | H | H | H | $COCH_3$ | H | Cl |
| 5.39 | H | H | H | 0 | H | H | H | $COC_2H_5$ | H | Cl |
| 5.40 | H | H | H | 2 | H | H | H | $COC_2H_5$ | H | Cl |
| 5.41 | H | H | H | 0 | H | H | H | COiPr | H | Cl |
| 5.42 | H | H | H | 2 | H | H | H | COiPr | H | Cl |
| 5.43 | $CH_3$ | H | H | 0 | H | H | H | $COCH_3$ | H | Cl |
| 5.44 | $CH_3$ | H | H | 2 | H | H | H | $COCH_3$ | H | Cl |
| 5.45 | $CH_3$ | H | H | 0 | H | H | H | $COC_2H_5$ | H | Cl |
| 5.46 | $CH_3$ | H | H | 2 | H | H | H | $COC_2H_5$ | H | Cl |
| 5.47 | $CH_3$ | H | H | 0 | H | H | H | COiPr | H | Cl |
| 5.48 | $CH_3$ | H | H | 2 | H | H | H | COiPr | H | Cl |
| 5.49 | $CH_3$ | $CH_3$ | H | 0 | H | H | H | $COCH_3$ | H | Cl |
| 5.50 | $CH_3$ | $CH_3$ | H | 2 | H | H | H | $COCH_3$ | H | Cl |
| 5.51 | $CH_3$ | $CH_3$ | H | 0 | H | H | H | $COC_2H_5$ | H | Cl |
| 5.52 | $CH_3$ | $CH_3$ | H | 2 | H | H | H | $COC_2H_5$ | H | Cl |
| 5.53 | $CH_3$ | $CH_3$ | H | 0 | H | H | H | COiPr | H | Cl |
| 5.54 | $CH_3$ | $CH_3$ | H | 2 | H | H | H | COiPr | H | Cl |

TABLE 6

Compounds of the formula

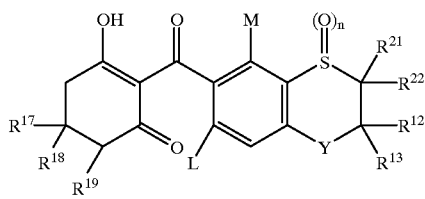

| No. | $R^{17}$ | $R^{18}$ | $R^{19}$ | n | $R^{21}$ | $R^{22}$ | $R^{12}$ | $R^{13}$ | Y | M | L |
|---|---|---|---|---|---|---|---|---|---|---|---|
| 6.1 | H | H | H | 0 | H | H | H | H | C=O | H | $CH_3$ |
| 6.2 | H | H | H | 1 | H | H | H | H | C=O | H | $CH_3$ |
| 6.3 | H | H | H | 2 | H | H | H | H | C=O | H | $CH_3$ |
| 6.4 | H | H | H | 0 | H | H | H | H | CH—$OCH_3$ | H | $CH_3$ |
| 6.5 | H | H | H | 1 | H | H | H | H | CH—$OCH_3$ | H | $CH_3$ |
| 6.6 | H | H | H | 2 | H | H | H | H | CH—$OCH_3$ | H | $CH_3$ |
| 6.7 | H | H | H | 0 | H | H | H | H | $CHOC_2H_5$ | H | $CH_3$ |
| 6.8 | H | H | H | 1 | H | H | H | H | $CHOC_2H_5$ | H | $CH_3$ |
| 6.9 | H | H | H | 2 | H | H | H | H | $CHOC_2H_5$ | H | $CH_3$ |
| 6.10 | H | H | H | 0 | H | H | H | H | CHOiPr | H | $CH_3$ |

TABLE 6-continued

Compounds of the formula

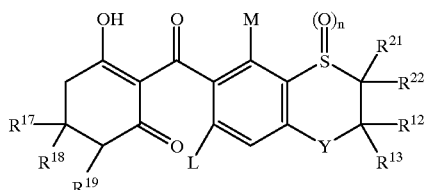

| No. | R¹⁷ | R¹⁸ | R¹⁹ | n | R²¹ | R²² | R¹² | R¹³ | Y | M | L |
|---|---|---|---|---|---|---|---|---|---|---|---|
| 6.11 | H | H | H | 1 | H | H | H | H | CHOiPr | H | CH₃ |
| 6.12 | H | H | H | 2 | H | H | H | H | CHOiPr | H | CH₃ |
| 6.13 | H | H | H | 0 | H | H | H | H | C=NOCH₃ | H | CH₃ |
| 6.14 | H | H | H | 1 | H | H | H | H | C=NOCH₃ | H | CH₃ |
| 6.15 | H | H | H | 2 | H | H | H | H | C=NOCH₃ | H | CH₃ |
| 6.16 | H | H | H | 0 | H | H | H | H | C=NOC₂H₅ | H | CH₃ |
| 6.17 | H | H | H | 1 | H | H | H | H | C=NOC₂H₅ | H | CH₃ |
| 6.18 | H | H | H | 2 | H | H | H | H | C=NOC₂H₅ | H | CH₃ |
| 6.19 | H | H | H | 0 | H | H | H | H | C=NOiPr | H | CH₃ |
| 6.20 | H | H | H | 1 | H | H | H | H | C=NOiPr | H | CH₃ |
| 6.21 | H | H | H | 2 | H | H | H | H | C=NOiPr | H | CH₃ |
| 6.22 | H | H | H | 0 | H | H | H | H | C=NOCH₂CH=CHCl | H | CH₃ |
| 6.23 | H | H | H | 1 | H | H | H | H | C=NOCH₂CH=CHCl | H | CH₃ |
| 6.24 | H | H | H | 2 | H | H | H | H | C=NOCH₂CH=CHCl | H | CH₃ |
| 6.25 | H | H | H | 0 | H | H | H | H | C=NOCH₂C₆H₅ | H | CH₃ |
| 6.26 | H | H | H | 1 | H | H | H | H | C=NOCH₂C₆H₅ | H | CH₃ |
| 6.27 | H | H | H | 2 | H | H | H | H | C=NOCH₂C₆H₅ | H | CH₃ |
| 6.28 | H | H | H | 0 | H | H | H | H | C(CH₃)₂ | H | CH₃ |
| 6.29 | H | H | H | 1 | H | H | H | H | C(CH₃)₂ | H | CH₃ |
| 6.30 | H | H | H | 2 | H | H | H | H | C(CH₃)₂ | H | CH₃ |
| 6.31 | H | H | H | 0 | H | H | H | H | (1,3-dioxane, O-CH₂-CH₂-CH₂-O) | H | CH₃ |
| 6.32 | H | H | H | 1 | H | H | H | H | (1,3-dioxane, O-CH₂-CH₂-CH₂-O) | H | CH₃ |
| 6.33 | H | H | H | 2 | H | H | H | H | (1,3-dioxane, O-CH₂-CH₂-CH₂-O) | H | CH₃ |
| 6.34 | H | H | H | 0 | H | H | H | H | (1,3-dioxane with C(CH₃)₂) | H | CH₃ |
| 6.35 | H | H | H | 1 | H | H | H | H | (1,3-dioxane with C(CH₃)₂) | H | CH₃ |
| 6.36 | H | H | H | 2 | H | H | H | H | (1,3-dioxane with C(CH₃)₂) | H | CH₃ |
| 6.37 | H | H | H | 0 | H | H | H | H | C=N—CH₃ | H | CH₃ |
| 6.38 | H | H | H | 1 | H | H | H | H | C=N—CH₃ | H | CH₃ |
| 6.39 | H | H | H | 2 | H | H | H | H | C=N—CH₃ | H | CH₃ |
| 6.40 | H | H | H | 0 | H | H | H | H | C=NC₂H₅ | H | CH₃ |
| 6.41 | H | H | H | 1 | H | H | H | H | C=NC₂H₅ | H | CH₃ |
| 6.42 | H | H | H | 2 | H | H | H | H | C=NC₂H₅ | H | CH₃ |
| 6.43 | H | H | H | 0 | H | H | H | H | CH—NHCH₃ | H | CH₃ |

TABLE 6-continued

Compounds of the formula

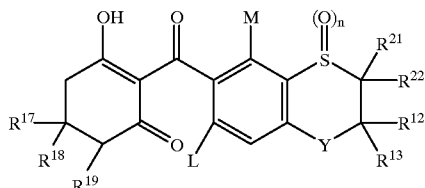

| No. | $R^{17}$ | $R^{18}$ | $R^{19}$ | n | $R^{21}$ | $R^{22}$ | $R^{12}$ | $R^{13}$ | Y | M | L |
|---|---|---|---|---|---|---|---|---|---|---|---|
| 6.44 | H | H | H | 1 | H | H | H | H | CH—NHCH$_3$ | H | CH$_3$ |
| 6.45 | H | H | H | 2 | H | H | H | H | CH—NHCH$_3$ | H | CH$_3$ |
| 6.46 | H | H | H | 0 | H | H | H | H | CH—NHC$_2$H$_5$ | H | CH$_3$ |
| 6.47 | H | H | H | 1 | H | H | H | H | CH—NHC$_2$H$_5$ | H | CH$_3$ |
| 6.48 | H | H | H | 2 | H | H | H | H | CH—NHC$_2$H$_5$ | H | CH$_3$ |
| 6.49 | H | H | H | 0 | H | H | H | H | CH—N(CH$_3$)$_2$ | H | CH$_3$ |
| 6.50 | H | H | H | 1 | H | H | H | H | CH—N(CH$_3$)$_2$ | H | CH$_3$ |
| 6.51 | H | H | H | 2 | H | H | H | H | CH—N(CH$_3$)$_2$ | H | CH$_3$ |
| 6.52 | H | H | H | 0 | H | H | H | H | CH—NHOC$_2$H$_5$ | H | CH$_3$ |
| 6.53 | H | H | H | 1 | H | H | H | H | CH—NHOC$_2$H$_5$ | H | CH$_3$ |
| 6.54 | H | H | H | 2 | H | H | H | H | CH—NHOC$_2$H$_5$ | H | CH$_3$ |
| 6.55 | H | H | H | 0 | H | H | H | H | CH—N(CH$_3$)OC$_2$H$_5$ | H | CH$_3$ |
| 6.56 | H | H | H | 1 | H | H | H | H | CH—N(CH$_3$)OC$_2$H$_5$ | H | CH$_3$ |
| 6.57 | H | H | H | 2 | H | H | H | H | CH—N(CH$_3$)OC$_2$H$_5$ | H | CH$_3$ |
| 6.58 | H | H | H | 0 | H | H | H | H | C=N—NH$_2$ | H | CH$_3$ |
| 6.59 | H | H | H | 1 | H | H | H | H | C=N—NH$_2$ | H | CH$_3$ |
| 6.60 | H | H | H | 2 | H | H | H | H | C=N—NH$_2$ | H | CH$_3$ |
| 6.61 | H | H | H | 0 | H | H | H | H | C=N—N(CH$_3$)$_2$ | H | CH$_3$ |
| 6.62 | H | H | H | 1 | H | H | H | H | C=N—N(CH$_3$)$_2$ | H | CH$_3$ |
| 6.63 | H | H | H | 2 | H | H | H | H | C=N—N(CH$_3$)$_2$ | H | CH$_3$ |
| 6.64 | H | H | H | 0 | H | H | H | H | CH—N(CH$_3$)OCH$_2$C$_6$H$_5$ | H | CH$_3$ |
| 6.65 | H | H | H | 1 | H | H | H | H | CH—N(CH$_3$)OCH$_2$C$_6$H$_5$ | H | CH$_3$ |
| 6.66 | H | H | H | 2 | H | H | H | H | CH—N(CH$_3$)OCH$_2$C$_6$H$_5$ | H | CH$_3$ |
| 6.67 | H | H | H | 0 | H | H | H | H | C(CH$_3$)—OCH$_3$ | H | CH$_3$ |
| 6.68 | H | H | H | 1 | H | H | H | H | C(CH$_3$)—OCH$_3$ | H | CH$_3$ |
| 6.69 | H | H | H | 2 | H | H | H | H | C(CH$_3$)—OCH$_3$ | H | CH$_3$ |
| 6.70 | H | H | H | 0 | H | H | H | H | O | H | CH$_3$ |
| 6.71 | H | H | H | 1 | H | H | H | H | O | H | CH$_3$ |
| 6.72 | H | H | H | 2 | H | H | H | H | O | H | CH$_3$ |
| 6.73 | CH$_3$ | H | H | 0 | H | H | H | H | C=O | H | CH$_3$ |
| 6.74 | CH$_3$ | H | H | 1 | H | H | H | H | C=O | H | CH$_3$ |
| 6.75 | CH$_3$ | H | H | 2 | H | H | H | H | C=O | H | CH$_3$ |
| 6.76 | CH$_3$ | H | H | 0 | H | H | H | H | CHOCH$_3$ | H | CH$_3$ |
| 6.77 | CH$_3$ | H | H | 1 | H | H | H | H | CHOCH$_3$ | H | CH$_3$ |
| 6.78 | CH$_3$ | H | H | 2 | H | H | H | H | CHOCH$_3$ | H | CH$_3$ |
| 6.79 | CH$_3$ | H | H | 0 | H | H | H | H | CHOC$_2$H$_5$ | H | CH$_3$ |
| 6.80 | CH$_3$ | H | H | 1 | H | H | H | H | CHOC$_2$H$_5$ | H | CH$_3$ |
| 6.81 | CH$_3$ | H | H | 2 | H | H | H | H | CHOC$_2$H$_5$ | H | CH$_3$ |
| 6.82 | CH$_3$ | H | H | 0 | H | H | H | H | CHOiPr | H | CH$_3$ |
| 6.83 | CH$_3$ | H | H | 1 | H | H | H | H | CHOiPr | H | CH$_3$ |
| 6.84 | CH$_3$ | H | H | 2 | H | H | H | H | CHOiPr | H | CH$_3$ |
| 6.85 | CH$_3$ | H | H | 0 | H | H | H | H | C=NOCH$_3$ | H | CH$_3$ |
| 6.86 | CH$_3$ | H | H | 1 | H | H | H | H | C=NOCH$_3$ | H | CH$_3$ |
| 6.87 | CH$_3$ | H | H | 2 | H | H | H | H | C=NOCH$_3$ | H | CH$_3$ |
| 6.88 | CH$_3$ | H | H | 0 | H | H | H | H | C=NOC$_2$H$_5$ | H | CH$_3$ |
| 6.89 | CH$_3$ | H | H | 1 | H | H | H | H | C=NOC$_2$H$_5$ | H | CH$_3$ |
| 6.90 | CH$_3$ | H | H | 2 | H | H | H | H | C=NOC$_2$H$_5$ | H | CH$_3$ |
| 6.91 | CH$_3$ | H | H | 0 | H | H | H | H | C=NOiPr | H | CH$_3$ |
| 6.92 | CH$_3$ | H | H | 1 | H | H | H | H | C=NOiPr | H | CH$_3$ |
| 6.93 | CH$_3$ | H | H | 2 | H | H | H | H | C=NOiPr | H | CH$_3$ |
| 6.94 | CH$_3$ | H | H | 0 | H | H | H | H | C=NOCH$_2$CH=CHCl | H | CH$_3$ |
| 6.95 | CH$_3$ | H | H | 1 | H | H | H | H | C=NOCH$_2$CH=CHCl | H | CH$_3$ |
| 6.96 | CH$_3$ | H | H | 2 | H | H | H | H | C=NOCH$_2$CH=CHCl | H | CH$_3$ |
| 6.97 | CH$_3$ | H | H | 0 | H | H | H | H | C=NOCH$_2$C$_6$H$_5$ | H | CH$_3$ |
| 6.98 | CH$_3$ | H | H | 1 | H | H | H | H | C=NOCH$_2$C$_6$H$_5$ | H | CH$_3$ |
| 6.99 | CH$_3$ | H | H | 2 | H | H | H | H | C=NOCH$_2$C$_6$H$_5$ | H | CH$_3$ |
| 6.100 | CH$_3$ | H | H | 0 | H | H | H | H | C(CH$_3$)$_2$ | H | CH$_3$ |
| 6.101 | CH$_3$ | H | H | 1 | H | H | H | H | C(CH$_3$)$_2$ | H | CH$_3$ |
| 6.102 | CH$_3$ | H | H | 2 | H | H | H | H | C(CH$_3$)$_2$ | H | CH$_3$ |

TABLE 6-continued

Compounds of the formula

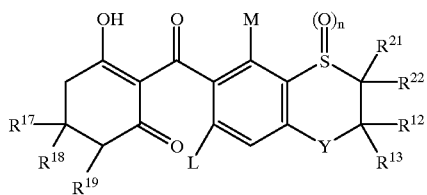

| No. | R17 | R18 | R19 | n | R21 | R22 | R12 | R13 | Y | M | L |
|---|---|---|---|---|---|---|---|---|---|---|---|
| 6.103 | CH3 | H | H | 0 | H | H | H | H | O—CH2 / C(O—CH2)(CH2) | H | CH3 |
| 6.104 | CH3 | H | H | 1 | H | H | H | H | O—CH2 / C(O—CH2)(CH2) | H | CH3 |
| 6.105 | CH3 | H | H | 2 | H | H | H | H | O—CH2 / C(O—CH2)(CH2) | H | CH3 |
| 6.106 | CH3 | H | H | 0 | H | H | H | H | O—CH2 / C(CH3)(CH3)(O—CH2) | H | CH3 |
| 6.107 | CH3 | H | H | 1 | H | H | H | H | O—CH2 / C(CH3)(CH3)(O—CH2) | H | CH3 |
| 6.108 | CH3 | H | H | 2 | H | H | H | H | O—CH2 / C(CH3)(CH3)(O—CH2) | H | CH3 |
| 6.109 | CH3 | H | H | 0 | H | H | H | H | C=N—CH3 | H | CH3 |
| 6.110 | CH3 | H | H | 1 | H | H | H | H | C=N—CH3 | H | CH3 |
| 6.111 | CH3 | H | H | 2 | H | H | H | H | C=N—CH3 | H | CH3 |
| 6.112 | CH3 | H | H | 0 | H | H | H | H | C=NC2H5 | H | CH3 |
| 6.113 | CH3 | H | H | 1 | H | H | H | H | C=NC2H5 | H | CH3 |
| 6.114 | CH3 | H | H | 2 | H | H | H | H | C=NC2H5 | H | CH3 |
| 6.115 | CH3 | H | H | 0 | H | H | H | H | CH—NHCH3 | H | CH3 |
| 6.116 | CH3 | H | H | 1 | H | H | H | H | CH—NHCH3 | H | CH3 |
| 6.117 | CH3 | H | H | 2 | H | H | H | H | CH—NHCH3 | H | CH3 |
| 6.118 | CH3 | H | H | 0 | H | H | H | H | CH—NHC2H5 | H | CH3 |
| 6.119 | CH3 | H | H | 1 | H | H | H | H | CH—NHC2H5 | H | CH3 |
| 6.120 | CH3 | H | H | 2 | H | H | H | H | CH—NHC2H5 | H | CH3 |
| 6.121 | CH3 | H | H | 0 | H | H | H | H | CH—N(CH3)2 | H | CH3 |
| 6.122 | CH3 | H | H | 1 | H | H | H | H | CH—N(CH3)2 | H | CH3 |
| 6.123 | CH3 | H | H | 2 | H | H | H | H | CH—N(CH3)2 | H | CH3 |
| 6.124 | CH3 | H | H | 0 | H | H | H | H | CH—NHOC2H5 | H | CH3 |
| 6.125 | CH3 | H | H | 1 | H | H | H | H | CH—NHOC2H5 | H | CH3 |
| 6.126 | CH3 | H | H | 2 | H | H | H | H | CH—NHOC2H5 | H | CH3 |
| 6.127 | CH3 | H | H | 0 | H | H | H | H | CH—N(CH3)OC2H5 | H | CH3 |
| 6.128 | CH3 | H | H | 1 | H | H | H | H | CH—N(CH3)OC2H5 | H | CH3 |
| 6.129 | CH3 | H | H | 2 | H | H | H | H | CH—N(CH3)OC2H5 | H | CH3 |
| 6.130 | CH3 | H | H | 0 | H | H | H | H | C=N—NH2 | H | CH3 |
| 6.131 | CH3 | H | H | 1 | H | H | H | H | C=N—NH2 | H | CH3 |
| 6.132 | CH3 | H | H | 2 | H | H | H | H | C=N—NH2 | H | CH3 |
| 6.133 | CH3 | H | H | 0 | H | H | H | H | C=N—N(CH3)2 | H | CH3 |
| 6.134 | CH3 | H | H | 1 | H | H | H | H | C=N—N(CH3)2 | H | CH3 |
| 6.135 | CH3 | H | H | 2 | H | H | H | H | C=N—N(CH3)2 | H | CH3 |
| 6.136 | CH3 | H | H | 0 | H | H | H | H | CH—N(CH3)OCH2C6H5 | H | CH3 |

TABLE 6-continued

Compounds of the formula

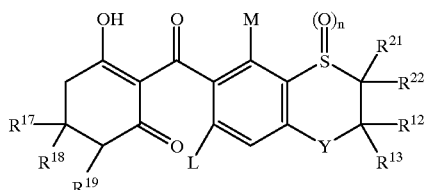

| No. | $R^{17}$ | $R^{18}$ | $R^{19}$ | n | $R^{21}$ | $R^{22}$ | $R^{12}$ | $R^{13}$ | Y | M | L |
|---|---|---|---|---|---|---|---|---|---|---|---|
| 6.137 | $CH_3$ | H | H | 1 | H | H | H | H | CH—N($CH_3$)O$CH_2C_6H_5$ | H | $CH_3$ |
| 6.138 | $CH_3$ | H | H | 2 | H | H | H | H | CH—N($CH_3$)O$CH_2C_6H_5$ | H | $CH_3$ |
| 6.139 | $CH_3$ | H | H | 0 | H | H | H | H | C($CH_3$)—O$CH_3$ | H | $CH_3$ |
| 6.140 | $CH_3$ | H | H | 1 | H | H | H | H | C($CH_3$)—O$CH_3$ | H | $CH_3$ |
| 6.141 | $CH_3$ | H | H | 2 | H | H | H | H | C($CH_3$)—O$CH_3$ | H | $CH_3$ |
| 6.142 | $CH_3$ | H | H | 0 | H | H | H | H | O | H | $CH_3$ |
| 6.143 | $CH_3$ | H | H | 1 | H | H | H | H | O | H | $CH_3$ |
| 6.144 | $CH_3$ | H | H | 2 | H | H | H | H | O | H | $CH_3$ |
| 6.145 | $CH_3$ | $CH_3$ | H | 0 | H | H | H | H | C=O | H | $CH_3$ |
| 6.146 | $CH_3$ | $CH_3$ | H | 1 | H | H | H | H | C=O | H | $CH_3$ |
| 6.147 | $CH_3$ | $CH_3$ | H | 2 | H | H | H | H | C=O | H | $CH_3$ |
| 6.148 | $CH_3$ | $CH_3$ | H | 0 | H | H | H | H | CHO$CH_3$ | H | $CH_3$ |
| 6.149 | $CH_3$ | $CH_3$ | H | 1 | H | H | H | H | CHO$CH_3$ | H | $CH_3$ |
| 6.150 | $CH_3$ | $CH_3$ | H | 2 | H | H | H | H | CHO$CH_3$ | H | $CH_3$ |
| 6.151 | $CH_3$ | $CH_3$ | H | 0 | H | H | H | H | CHO$C_2H_5$ | H | $CH_3$ |
| 6.152 | $CH_3$ | $CH_3$ | H | 1 | H | H | H | H | CHO$C_2H_5$ | H | $CH_3$ |
| 6.153 | $CH_3$ | $CH_3$ | H | 2 | H | H | H | H | CHO$C_2H_5$ | H | $CH_3$ |
| 6.154 | $CH_3$ | $CH_3$ | H | 0 | H | H | H | H | CHOiPr | H | $CH_3$ |
| 6.155 | $CH_3$ | $CH_3$ | H | 1 | H | H | H | H | CHOiPr | H | $CH_3$ |
| 6.156 | $CH_3$ | $CH_3$ | H | 2 | H | H | H | H | CHOiPr | H | $CH_3$ |
| 6.157 | $CH_3$ | $CH_3$ | H | 0 | H | H | H | H | C=NO$CH_3$ | H | $CH_3$ |
| 6.158 | $CH_3$ | $CH_3$ | H | 1 | H | H | H | H | C=NO$CH_3$ | H | $CH_3$ |
| 6.159 | $CH_3$ | $CH_3$ | H | 2 | H | H | H | H | C=NO$CH_3$ | H | $CH_3$ |
| 6.160 | $CH_3$ | $CH_3$ | H | 0 | H | H | H | H | C=NO$C_2H_5$ | H | $CH_3$ |
| 6.161 | $CH_3$ | $CH_3$ | H | 1 | H | H | H | H | C=NO$C_2H_5$ | H | $CH_3$ |
| 6.162 | $CH_3$ | $CH_3$ | H | 2 | H | H | H | H | C=NO$C_2H_5$ | H | $CH_3$ |
| 6.163 | $CH_3$ | $CH_3$ | H | 0 | H | H | H | H | C=NOiPr | H | $CH_3$ |
| 6.164 | $CH_3$ | $CH_3$ | H | 1 | H | H | H | H | C=NOiPr | H | $CH_3$ |
| 6.165 | $CH_3$ | $CH_3$ | H | 2 | H | H | H | H | C=NOiPr | H | $CH_3$ |
| 6.166 | $CH_3$ | $CH_3$ | H | 0 | H | H | H | H | C=NO$CH_2$CH=CHCl | H | $CH_3$ |
| 6.167 | $CH_3$ | $CH_3$ | H | 1 | H | H | H | H | C=NO$CH_2$CH=CHCl | H | $CH_3$ |
| 6.168 | $CH_3$ | $CH_3$ | H | 2 | H | H | H | H | C=NO$CH_2$CH=CHCl | H | $CH_3$ |
| 6.169 | $CH_3$ | $CH_3$ | H | 0 | H | H | H | H | C=NO$CH_2C_6H_5$ | H | $CH_3$ |
| 6.170 | $CH_3$ | $CH_3$ | H | 1 | H | H | H | H | C=NO$CH_2C_6H_5$ | H | $CH_3$ |
| 6.171 | $CH_3$ | $CH_3$ | H | 2 | H | H | H | H | C=NO$CH_2C_6H_5$ | H | $CH_3$ |
| 6.172 | $CH_3$ | $CH_3$ | H | 0 | H | H | H | H | C($CH_3$)$_2$ | H | $CH_3$ |
| 6.173 | $CH_3$ | $CH_3$ | H | 1 | H | H | H | H | C($CH_3$)$_2$ | H | $CH_3$ |
| 6.174 | $CH_3$ | $CH_3$ | H | 2 | H | H | H | H | C($CH_3$)$_2$ | H | $CH_3$ |
| 6.175 | $CH_3$ | $CH_3$ | H | 0 | H | H | H | H | ![dioxane ring] | H | $CH_3$ |
| 6.176 | $CH_3$ | $CH_3$ | H | 1 | H | H | H | H | ![dioxane ring] | H | $CH_3$ |
| 6.177 | $CH_3$ | $CH_3$ | H | 2 | H | H | H | H | ![dioxane ring] | H | $CH_3$ |
| 6.178 | $CH_3$ | $CH_3$ | H | 0 | H | H | H | H | ![dimethyl dioxane ring] | H | $CH_3$ |

TABLE 6-continued

Compounds of the formula

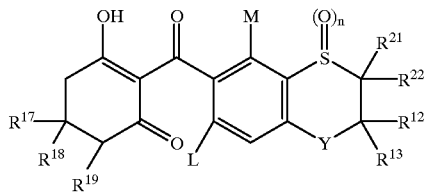

| No. | R17 | R18 | R19 | n | R21 | R22 | R12 | R13 | Y | M | L |
|---|---|---|---|---|---|---|---|---|---|---|---|
| 6.179 | CH₃ | CH₃ | H | 1 | H | H | H | H | O—CH₂<br>C(CH₃)(CH₃)<br>O—CH₂ | H | CH₃ |
| 6.180 | CH₃ | CH₃ | H | 2 | H | H | H | H | O—CH₂<br>C(CH₃)(CH₃)<br>O—CH₂ | H | CH₃ |
| 6.181 | CH₃ | CH₃ | H | 0 | H | H | H | H | C=N—CH₃ | H | CH₃ |
| 6.182 | CH₃ | CH₃ | H | 1 | H | H | H | H | C=N—CH₃ | H | CH₃ |
| 6.183 | CH₃ | CH₃ | H | 2 | H | H | H | H | C=N—CH₃ | H | CH₃ |
| 6.184 | CH₃ | CH₃ | H | 0 | H | H | H | H | C=NC₂H₅ | H | CH₃ |
| 6.185 | CH₃ | CH₃ | H | 1 | H | H | H | H | C=NC₂H₅ | H | CH₃ |
| 6.186 | CH₃ | CH₃ | H | 2 | H | H | H | H | C=NC₂H₅ | H | CH₃ |
| 6.187 | CH₃ | CH₃ | H | 0 | H | H | H | H | CH—NHCH₃ | H | CH₃ |
| 6.188 | CH₃ | CH₃ | H | 1 | H | H | H | H | CH—NHCH₃ | H | CH₃ |
| 6.189 | CH₃ | CH₃ | H | 2 | H | H | H | H | CH—NHCH₃ | H | CH₃ |
| 6.190 | CH₃ | CH₃ | H | 0 | H | H | H | H | CH—NHC₂H₅ | H | CH₃ |
| 6.191 | CH₃ | CH₃ | H | 1 | H | H | H | H | CH—NHC₂H₅ | H | CH₃ |
| 6.192 | CH₃ | CH₃ | H | 2 | H | H | H | H | CH—NHC₂H₅ | H | CH₃ |
| 6.193 | CH₃ | CH₃ | H | 0 | H | H | H | H | CH—N(CH₃)₂ | H | CH₃ |
| 6.194 | CH₃ | CH₃ | H | 1 | H | H | H | H | CH—N(CH₃)₂ | H | CH₃ |
| 6.195 | CH₃ | CH₃ | H | 2 | H | H | H | H | CH—N(CH₃)₂ | H | CH₃ |
| 6.196 | CH₃ | CH₃ | H | 0 | H | H | H | H | CH—NHOC₂H₅ | H | CH₃ |
| 6.197 | CH₃ | CH₃ | H | 1 | H | H | H | H | CH—NHOC₂H₅ | H | CH₃ |
| 6.198 | CH₃ | CH₃ | H | 2 | H | H | H | H | CH—NHOC₂H₅ | H | CH₃ |
| 6.199 | CH₃ | CH₃ | H | 0 | H | H | H | H | CH—N(CH₃)OC₂H₅ | H | CH₃ |
| 6.200 | CH₃ | CH₃ | H | 1 | H | H | H | H | CH—N(CH₃)OC₂H₅ | H | CH₃ |
| 6.201 | CH₃ | CH₃ | H | 2 | H | H | H | H | CH—N(CH₃)OC₂H₅ | H | CH₃ |
| 6.202 | CH₃ | CH₃ | H | 0 | H | H | H | H | C=N—NH₂ | H | CH₃ |
| 6.203 | CH₃ | CH₃ | H | 1 | H | H | H | H | C=N—NH₂ | H | CH₃ |
| 6.204 | CH₃ | CH₃ | H | 2 | H | H | H | H | C=N—NH₂ | H | CH₃ |
| 6.205 | CH₃ | CH₃ | H | 0 | H | H | H | H | C=N—N(CH₃)₂ | H | CH₃ |
| 6.206 | CH₃ | CH₃ | H | 1 | H | H | H | H | C=N—N(CH₃)₂ | H | CH₃ |
| 6.207 | CH₃ | CH₃ | H | 2 | H | H | H | H | C=N—N(CH₃)₂ | H | CH₃ |
| 6.208 | CH₃ | CH₃ | H | 0 | H | H | H | H | CH—N(CH₃)OCH₂C₆H₅ | H | CH₃ |
| 6.209 | CH₃ | CH₃ | H | 1 | H | H | H | H | CH—N(CH₃)OCH₂C₆H₅ | H | CH₃ |
| 6.210 | CH₃ | CH₃ | H | 2 | H | H | H | H | CH—N(CH₃)OCH₂C₆H₅ | H | CH₃ |
| 6.211 | CH₃ | CH₃ | H | 0 | H | H | H | H | C(CH₃)—OCH₃ | H | CH₃ |
| 6.212 | CH₃ | CH₃ | H | 1 | H | H | H | H | C(CH₃)—OCH₃ | H | CH₃ |
| 6.213 | CH₃ | CH₃ | H | 2 | H | H | H | H | C(CH₃)—OCh₃ | H | CH₃ |
| 6.214 | CH₃ | CH₃ | H | 0 | H | H | H | H | O | H | CH₃ |
| 6.215 | CH₃ | CH₃ | H | 1 | H | H | H | H | O | H | CH₃ |
| 6.216 | CH₃ | CH₃ | H | 2 | H | H | H | H | O | H | CH₃ |
| 6.217 | H | H | H | 0 | H | H | H | H | C=O | H | Cl |
| 6.218 | H | H | H | 1 | H | H | H | H | C=O | H | Cl |
| 6.219 | H | H | H | 2 | H | H | H | H | C=O | H | Cl |
| 6.220 | H | H | H | 0 | H | H | H | H | CHOCH₃ | H | Cl |
| 6.221 | H | H | H | 1 | H | H | H | H | CHOCH₃ | H | Cl |
| 6.222 | H | H | H | 2 | H | H | H | H | CHOCH₃ | H | Cl |
| 6.223 | H | H | H | 0 | H | H | H | H | CHOC₂H₅ | H | Cl |
| 6.224 | H | H | H | 1 | H | H | H | H | CHOC₂H₅ | H | Cl |
| 6.225 | H | H | H | 2 | H | H | H | H | CHOC₂H₅ | H | Cl |
| 6.226 | H | H | H | 0 | H | H | H | H | CHOiPr | H | Cl |
| 6.227 | H | H | H | 1 | H | H | H | H | CHOiPr | H | Cl |
| 6.228 | H | H | H | 2 | H | H | H | H | CHOiPr | H | Cl |
| 6.229 | H | H | H | 0 | H | H | H | H | C=NOCH₃ | H | Cl |
| 6.230 | H | H | H | 1 | H | H | H | H | C=NOCH₃ | H | Cl |
| 6.231 | H | H | H | 2 | H | H | H | H | C=NOCH₃ | H | Cl |
| 6.232 | H | H | H | 0 | H | H | H | H | C=NOC₂H₅ | H | Cl |

TABLE 6-continued

Compounds of the formula

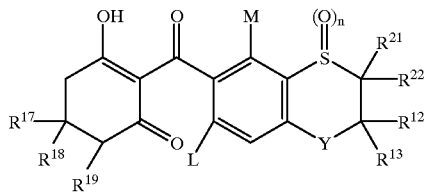

| No. | R¹⁷ | R¹⁸ | R¹⁹ | n | R²¹ | R²² | R¹² | R¹³ | Y | M | L |
|---|---|---|---|---|---|---|---|---|---|---|---|
| 6.233 | H | H | H | 1 | H | H | H | H | C=NOC$_2$H$_5$ | H | Cl |
| 6.234 | H | H | H | 2 | H | H | H | H | C=NOC$_2$H$_5$ | H | Cl |
| 6.235 | H | H | H | 0 | H | H | H | H | C=NOiPr | H | Cl |
| 6.236 | H | H | H | 1 | H | H | H | H | C=NOiPr | H | Cl |
| 6.237 | H | H | H | 2 | H | H | H | H | C=NOiPr | H | Cl |
| 6.238 | H | H | H | 0 | H | H | H | H | C=NOCH$_2$CH=CHCl | H | Cl |
| 6.239 | H | H | H | 1 | H | H | H | H | C=NOCH$_2$CH=CHCl | H | Cl |
| 6.240 | H | H | H | 2 | H | H | H | H | C=NOCH$_2$CH=CHCl | H | Cl |
| 6.241 | H | H | H | 0 | H | H | H | H | C=NOCH$_2$C$_6$H$_5$ | H | Cl |
| 6.242 | H | H | H | 1 | H | H | H | H | C=NOCH$_2$C$_6$H$_5$ | H | Cl |
| 6.243 | H | H | H | 2 | H | H | H | H | C=NOCH$_2$C$_6$H$_5$ | H | Cl |
| 6.244 | H | H | H | 0 | H | H | H | H | C(CH$_3$)$_2$ | H | Cl |
| 6.245 | H | H | H | 1 | H | H | H | H | C(CH$_3$)$_2$ | H | Cl |
| 6.246 | H | H | H | 2 | H | H | H | H | C(CH$_3$)$_2$ | H | Cl |
| 6.247 | H | H | H | 0 | H | H | H | H | ![dioxane ring](O-CH$_2$-CH$_2$-O-CH$_2$ cyclic) | H | Cl |
| 6.248 | H | H | H | 1 | H | H | H | H | (dioxane ring) | H | Cl |
| 6.249 | H | H | H | 2 | H | H | H | H | (dioxane ring) | H | Cl |
| 6.250 | H | H | H | 0 | H | H | H | H | (dioxane ring with C(CH$_3$)$_2$) | H | Cl |
| 6.251 | H | H | H | 1 | H | H | H | H | (dioxane ring with C(CH$_3$)$_2$) | H | Cl |
| 6.252 | H | H | H | 2 | H | H | H | H | (dioxane ring with C(CH$_3$)$_2$) | H | Cl |
| 6.253 | H | H | H | 0 | H | H | H | H | C=N—CH$_3$ | H | Cl |
| 6.254 | H | H | H | 1 | H | H | H | H | C=N—CH$_3$ | H | Cl |
| 6.255 | H | H | H | 2 | H | H | H | H | C=N—CH$_3$ | H | Cl |
| 6.256 | H | H | H | 0 | H | H | H | H | C=NC$_2$H$_5$ | H | Cl |
| 6.257 | H | H | H | 1 | H | H | H | H | C=NC$_2$H$_5$ | H | Cl |
| 6.258 | H | H | H | 2 | H | H | H | H | C=NC$_2$H$_5$ | H | Cl |
| 6.259 | H | H | H | 0 | H | H | H | H | CH—NHCH$_3$ | H | Cl |
| 6.260 | H | H | H | 1 | H | H | H | H | CH—NHCH$_3$ | H | Cl |
| 6.261 | H | H | H | 2 | H | H | H | H | CH—NHCH$_3$ | H | Cl |
| 6.262 | H | H | H | 0 | H | H | H | H | CH—NHC$_2$H$_5$ | H | Cl |
| 6.263 | H | H | H | 1 | H | H | H | H | CH—NHC$_2$H$_5$ | H | Cl |
| 6.264 | H | H | H | 2 | H | H | H | H | CH—NHC$_2$H$_5$ | H | Cl |
| 6.265 | H | H | H | 0 | H | H | H | H | CH—N(CH$_3$)$_2$ | H | Cl |

TABLE 6-continued

Compounds of the formula

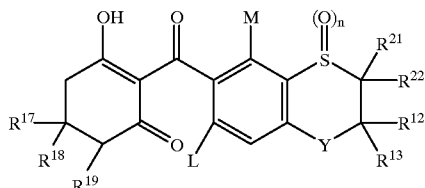

| No. | R$^{17}$ | R$^{18}$ | R$^{19}$ | n | R$^{21}$ | R$^{22}$ | R$^{12}$ | R$^{13}$ | Y | M | L |
|---|---|---|---|---|---|---|---|---|---|---|---|
| 6.266 | H | H | H | 1 | H | H | H | H | CH—N(CH$_3$)$_2$ | H | Cl |
| 6.267 | H | H | H | 2 | H | H | H | H | CH—N(CH$_3$)$_2$ | H | Cl |
| 6.268 | H | H | H | 0 | H | H | H | H | CH—NHOC$_2$H$_5$ | H | Cl |
| 6.269 | H | H | H | 1 | H | H | H | H | CH—NHOC$_2$H$_5$ | H | Cl |
| 6.270 | H | H | H | 2 | H | H | H | H | CH—NHOC$_2$H$_5$ | H | Cl |
| 6.271 | H | H | H | 0 | H | H | H | H | CH—N(CH$_3$)OC$_2$H$_5$ | H | Cl |
| 6.272 | H | H | H | 1 | H | H | H | H | CH—N(CH$_3$)OC$_2$H$_5$ | H | Cl |
| 6.273 | H | H | H | 2 | H | H | H | H | CH—N(CH$_3$)OC$_2$H$_5$ | H | Cl |
| 6.274 | H | H | H | 0 | H | H | H | H | C=N—NH$_2$ | H | Cl |
| 6.275 | H | H | H | 1 | H | H | H | H | C=N—NH$_2$ | H | Cl |
| 6.276 | H | H | H | 2 | H | H | H | H | C=N—NH$_2$ | H | Cl |
| 6.277 | H | H | H | 0 | H | H | H | H | C=N—N(CH$_3$)$_2$ | H | Cl |
| 6.278 | H | H | H | 1 | H | H | H | H | C=N—N(CH$_3$)$_2$ | H | Cl |
| 6.279 | H | H | H | 2 | H | H | H | H | C=N—N(CH$_3$)$_2$ | H | Cl |
| 6.280 | H | H | H | 0 | H | H | H | H | CH—N(CH$_3$)OCH$_2$C$_6$H$_5$ | H | Cl |
| 6.281 | H | H | H | 1 | H | H | H | H | CH—N(CH$_3$)OCH$_2$C$_6$H$_5$ | H | Cl |
| 6.282 | H | H | H | 2 | H | H | H | H | CH—N(CH$_3$)OCH$_2$C$_6$H$_5$ | H | Cl |
| 6.283 | H | H | H | 0 | H | H | H | H | C(CH$_3$)—OCH$_3$ | H | Cl |
| 6.284 | H | H | H | 1 | H | H | H | H | C(CH$_3$)—OCH$_3$ | H | Cl |
| 6.285 | H | H | H | 2 | H | H | H | H | C(CH$_3$)—OCH$_3$ | H | Cl |
| 6.286 | H | H | H | 0 | H | H | H | H | O | H | Cl |
| 6.287 | H | H | H | 1 | H | H | H | H | O | H | Cl |
| 6.288 | H | H | H | 2 | H | H | H | H | O | H | Cl |
| 6.289 | CH$_3$ | H | H | 0 | H | H | H | H | C=O | H | Cl |
| 6.290 | CH$_3$ | H | H | 1 | H | H | H | H | C=O | H | Cl |
| 6.291 | CH$_3$ | H | H | 2 | H | H | H | H | C=O | H | Cl |
| 6.292 | CH$_3$ | H | H | 0 | H | H | H | H | CHOCH$_3$ | H | Cl |
| 6.293 | CH$_3$ | H | H | 1 | H | H | H | H | CHOCH$_3$ | H | Cl |
| 6.294 | CH$_3$ | H | H | 2 | H | H | H | H | CHOCH$_3$ | H | Cl |
| 6.295 | CH$_3$ | H | H | 0 | H | H | H | H | CHOC$_2$H$_5$ | H | Cl |
| 6.296 | CH$_3$ | H | H | 1 | H | H | H | H | CHOC$_2$H$_5$ | H | Cl |
| 6.297 | CH$_3$ | H | H | 2 | H | H | H | H | CHOC$_2$H$_5$ | H | Cl |
| 6.298 | CH$_3$ | H | H | 0 | H | H | H | H | CHOiPr | H | Cl |
| 6.299 | CH$_3$ | H | H | 1 | H | H | H | H | CHOiPr | H | Cl |
| 6.300 | CH$_3$ | H | H | 2 | H | H | H | H | CHOiPr | H | Cl |
| 6.301 | CH$_3$ | H | H | 0 | H | H | H | H | C=NOCH$_3$ | H | Cl |
| 6.302 | CH$_3$ | H | H | 1 | H | H | H | H | C=NOCH$_3$ | H | Cl |
| 6.303 | CH$_3$ | H | H | 2 | H | H | H | H | C=NOCH$_3$ | H | Cl |
| 6.304 | CH$_3$ | H | H | 0 | H | H | H | H | C=NOC$_2$H$_5$ | H | Cl |
| 6.305 | CH$_3$ | H | H | 1 | H | H | H | H | C=NOC$_2$H$_5$ | H | Cl |
| 6.306 | CH$_3$ | H | H | 2 | H | H | H | H | C=NOC$_2$H$_5$ | H | Cl |
| 6.307 | CH$_3$ | H | H | 0 | H | H | H | H | C=NOiPr | H | Cl |
| 6.308 | CH$_3$ | H | H | 1 | H | H | H | H | C=NOiPr | H | Cl |
| 6.309 | CH$_3$ | H | H | 2 | H | H | H | H | C=NOiPr | H | Cl |
| 6.310 | CH$_3$ | H | H | 0 | H | H | H | H | C=NOCH$_2$CH=CHCl | H | Cl |
| 6.311 | CH$_3$ | H | H | 1 | H | H | H | H | C=NOCH$_2$CH=CHCl | H | Cl |
| 6.312 | CH$_3$ | H | H | 2 | H | H | H | H | C=NOCH$_2$CH=CHCl | H | Cl |
| 6.313 | CH$_3$ | H | H | 0 | H | H | H | H | C=NOCH$_2$C$_6$H$_5$ | H | Cl |
| 6.314 | CH$_3$ | H | H | 1 | H | H | H | H | C=NOCH$_2$C$_6$H$_5$ | H | Cl |
| 6.315 | CH$_3$ | H | H | 2 | H | H | H | H | C=NOCH$_2$C$_6$H$_5$ | H | Cl |
| 6.316 | CH$_3$ | H | H | 0 | H | H | H | H | C(CH$_3$)$_2$ | H | Cl |
| 6.317 | CH$_3$ | H | H | 1 | H | H | H | H | C(CH$_3$)$_2$ | H | Cl |
| 6.318 | CH$_3$ | H | H | 2 | H | H | H | H | C(CH$_3$)$_2$ | H | Cl |
| 6.319 | CH$_3$ | H | H | 0 | H | H | H | H | 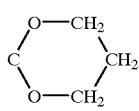 | H | Cl |

TABLE 6-continued

Compounds of the formula

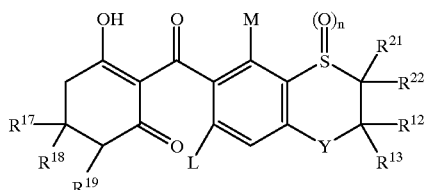

| No. | R¹⁷ | R¹⁸ | R¹⁹ | n | R²¹ | R²² | R¹² | R¹³ | Y | M | L |
|---|---|---|---|---|---|---|---|---|---|---|---|
| 6.320 | $CH_3$ | H | H | 1 | H | H | H | H | (dioxane-CH₂ ring) | H | Cl |
| 6.321 | $CH_3$ | H | H | 2 | H | H | H | H | (dioxane-CH₂ ring) | H | Cl |
| 6.322 | $CH_3$ | H | H | 0 | H | H | H | H | (dioxane-C(CH₃)₂ ring) | H | Cl |
| 6.323 | $CH_3$ | H | H | 1 | H | H | H | H | (dioxane-C(CH₃)₂ ring) | H | Cl |
| 6.324 | $CH_3$ | H | H | 2 | H | H | H | H | (dioxane-C(CH₃)₂ ring) | H | Cl |
| 6.325 | $CH_3$ | H | H | 0 | H | H | H | H | $C=N-CH_3$ | H | Cl |
| 6.326 | $CH_3$ | H | H | 1 | H | H | H | H | $C=N-CH_3$ | H | Cl |
| 6.327 | $CH_3$ | H | H | 2 | H | H | H | H | $C=N-CH_3$ | H | Cl |
| 6.328 | $CH_3$ | H | H | 0 | H | H | H | H | $C=NC_2H_5$ | H | Cl |
| 6.329 | $CH_3$ | H | H | 1 | H | H | H | H | $C=NC_2H_5$ | H | Cl |
| 6.330 | $CH_3$ | H | H | 2 | H | H | H | H | $C=NC_2H_5$ | H | Cl |
| 6.331 | $CH_3$ | H | H | 0 | H | H | H | H | $CH-NHCH_3$ | H | Cl |
| 6.332 | $CH_3$ | H | H | 1 | H | H | H | H | $CH-NHCH_3$ | H | Cl |
| 6.333 | $CH_3$ | H | H | 2 | H | H | H | H | $CH-NHCH_3$ | H | Cl |
| 6.334 | $CH_3$ | H | H | 0 | H | H | H | H | $CH-NHC_2H_5$ | H | Cl |
| 6.335 | $CH_3$ | H | H | 1 | H | H | H | H | $CH-NHC_2H_5$ | H | Cl |
| 6.336 | $CH_3$ | H | H | 2 | H | H | H | H | $CH-NHC_2H_5$ | H | Cl |
| 6.337 | $CH_3$ | H | H | 0 | H | H | H | H | $CH-N(CH_3)_2$ | H | Cl |
| 6.338 | $CH_3$ | H | H | 1 | H | H | H | H | $CH-N(CH_3)_2$ | H | Cl |
| 6.339 | $CH_3$ | H | H | 2 | H | H | H | H | $CH-N(CH_3)_2$ | H | Cl |
| 6.340 | $CH_3$ | H | H | 0 | H | H | H | H | $CH-NHOC_2H_5$ | H | Cl |
| 6.341 | $CH_3$ | H | H | 1 | H | H | H | H | $CH-NHOC_2H_5$ | H | Cl |
| 6.342 | $CH_3$ | H | H | 2 | H | H | H | H | $CH-NHOC_2H_5$ | H | Cl |
| 6.343 | $CH_3$ | H | H | 0 | H | H | H | H | $CH-N(CH_3)OC_2H_5$ | H | Cl |
| 6.344 | $CH_3$ | H | H | 1 | H | H | H | H | $CH-N(CH_3)OC_2H_5$ | H | Cl |
| 6.345 | $CH_3$ | H | H | 2 | H | H | H | H | $CH-N(CH_3)OC_2H_5$ | H | Cl |
| 6.346 | $CH_3$ | H | H | 0 | H | H | H | H | $C=N-NH_2$ | H | Cl |
| 6.347 | $CH_3$ | H | H | 1 | H | H | H | H | $C=N-NH_2$ | H | Cl |
| 6.348 | $CH_3$ | H | H | 2 | H | H | H | H | $C=N-NH_2$ | H | Cl |
| 6.349 | $CH_3$ | H | H | 0 | H | H | H | H | $C=N-N(CH_3)_2$ | H | Cl |
| 6.350 | $CH_3$ | H | H | 1 | H | H | H | H | $C=N-N(CH_3)_2$ | H | Cl |
| 6.351 | $CH_3$ | H | H | 2 | H | H | H | H | $C=N-N(CH_3)_2$ | H | Cl |
| 6.352 | $CH_3$ | H | H | 0 | H | H | H | H | $CH-N(CH_3)OCH_2C_6H_5$ | H | Cl |
| 6.353 | $CH_3$ | H | H | 1 | H | H | H | H | $CH-N(CH_3)OCH_2C_6H_5$ | H | Cl |
| 6.354 | $CH_3$ | H | H | 2 | H | H | H | H | $CH-N(CH_3)OCH_2C_6H_5$ | H | Cl |
| 6.355 | $CH_3$ | H | H | 0 | H | H | H | H | $C(CH_3)-OCH_3$ | H | Cl |
| 6.356 | $CH_3$ | H | H | 1 | H | H | H | H | $C(CH_3)-OCH_3$ | H | Cl |
| 6.357 | $CH_3$ | H | H | 2 | H | H | H | H | $C(CH_3)-OCH_3$ | H | Cl |
| 6.358 | $CH_3$ | H | H | 0 | H | H | H | H | O | H | Cl |

TABLE 6-continued

Compounds of the formula

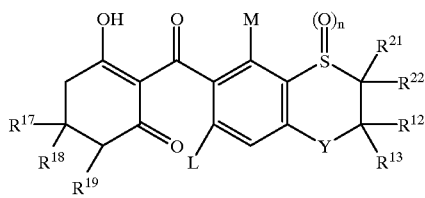

| No. | R17 | R18 | R19 | n | R21 | R22 | R12 | R13 | Y | M | L |
|---|---|---|---|---|---|---|---|---|---|---|---|
| 6.359 | CH3 | H | H | 1 | H | H | H | H | O | H | Cl |
| 6.360 | CH3 | H | H | 2 | H | H | H | H | O | H | Cl |
| 6.361 | CH3 | CH3 | H | 0 | H | H | H | H | C=O | H | Cl |
| 6.362 | CH3 | CH3 | H | 1 | H | H | H | H | C=O | H | Cl |
| 6.363 | CH3 | CH3 | H | 2 | H | H | H | H | C=O | H | Cl |
| 6.364 | CH3 | CH3 | H | 0 | H | H | H | H | CHOCH3 | H | Cl |
| 6.365 | CH3 | CH3 | H | 1 | H | H | H | H | CHOCH3 | H | Cl |
| 6.366 | CH3 | CH3 | H | 2 | H | H | H | H | CHOCH3 | H | Cl |
| 6.367 | CH3 | CH3 | H | 0 | H | H | H | H | CHOC2H5 | H | Cl |
| 6.368 | CH3 | CH3 | H | 1 | H | H | H | H | CHOC2H5 | H | Cl |
| 6.369 | CH3 | CH3 | H | 2 | H | H | H | H | CHOC2H5 | H | Cl |
| 6.370 | CH3 | CH3 | H | 0 | H | H | H | H | CHOiPr | H | Cl |
| 6.371 | CH3 | CH3 | H | 1 | H | H | H | H | CHOiPr | H | Cl |
| 6.372 | CH3 | CH3 | H | 2 | H | H | H | H | CHOiPr | H | Cl |
| 6.373 | CH3 | CH3 | H | 0 | H | H | H | H | C=NOCH3 | H | Cl |
| 6.374 | CH3 | CH3 | H | 1 | H | H | H | H | C=NOCH3 | H | Cl |
| 6.375 | CH3 | CH3 | H | 2 | H | H | H | H | C=NOCH3 | H | Cl |
| 6.376 | CH3 | CH3 | H | 0 | H | H | H | H | C=NOC2H5 | H | Cl |
| 6.377 | CH3 | CH3 | H | 1 | H | H | H | H | C=NOC2H5 | H | Cl |
| 6.378 | CH3 | CH3 | H | 2 | H | H | H | H | C=NOC2H5 | H | Cl |
| 6.379 | CH3 | CH3 | H | 0 | H | H | H | H | C=NOiPr | H | Cl |
| 6.380 | CH3 | CH3 | H | 1 | H | H | H | H | C=NOiPr | H | Cl |
| 6.381 | CH3 | CH3 | H | 2 | H | H | H | H | C=NOiPr | H | Cl |
| 6.382 | CH3 | CH3 | H | 0 | H | H | H | H | C=NOCH2CH=CHCl | H | Cl |
| 6.383 | CH3 | CH3 | H | 1 | H | H | H | H | C=NOCH2CH=CHCl | H | Cl |
| 6.384 | CH3 | CH3 | H | 2 | H | H | H | H | C=NOCH2CH=CHCl | H | Cl |
| 6.385 | CH3 | CH3 | H | 0 | H | H | H | H | C=NOCH2C6H5 | H | Cl |
| 6.386 | CH3 | CH3 | H | 1 | H | H | H | H | C=NOCH2C6H5 | H | Cl |
| 6.387 | CH3 | CH3 | H | 2 | H | H | H | H | C=NOCH2C6H5 | H | Cl |
| 6.388 | CH3 | CH3 | H | 0 | H | H | H | H | C(CH3)2 | H | Cl |
| 6.389 | CH3 | CH3 | H | 1 | H | H | H | H | C(CH3)2 | H | Cl |
| 6.390 | CH3 | CH3 | H | 2 | H | H | H | H | C(CH3)2 | H | Cl |
| 6.391 | CH3 | CH3 | H | 0 | H | H | H | H | (dioxane ring) | H | Cl |
| 6.392 | CH3 | CH3 | H | 1 | H | H | H | H | (dioxane ring) | H | Cl |
| 6.393 | CH3 | CH3 | H | 2 | H | H | H | H | (dioxane ring) | H | Cl |
| 6.394 | CH3 | CH3 | H | 0 | H | H | H | H | (dimethyl dioxane ring) | H | Cl |
| 6.395 | CH3 | CH3 | H | 1 | H | H | H | H | (dimethyl dioxane ring) | H | Cl |

TABLE 6-continued

Compounds of the formula

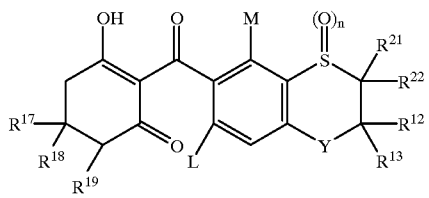

| No. | $R^{17}$ | $R^{18}$ | $R^{19}$ | n | $R^{21}$ | $R^{22}$ | $R^{12}$ | $R^{13}$ | Y | M | L |
|---|---|---|---|---|---|---|---|---|---|---|---|
| 6.396 | $CH_3$ | $CH_3$ | H | 2 | H | H | H | H | | H | Cl |
| 6.397 | $CH_3$ | $CH_3$ | H | 0 | H | H | H | H | C=N—$CH_3$ | H | Cl |
| 6.398 | $CH_3$ | $CH_3$ | H | 1 | H | H | H | H | C=N—$CH_3$ | H | Cl |
| 6.399 | $CH_3$ | $CH_3$ | H | 2 | H | H | H | H | C=N—$CH_3$ | H | Cl |
| 6.400 | $CH_3$ | $CH_3$ | H | 0 | H | H | H | H | C=N$C_2H_5$ | H | Cl |
| 6.401 | $CH_3$ | $CH_3$ | H | 1 | H | H | H | H | C=N$C_2H_5$ | H | Cl |
| 6.402 | $CH_3$ | $CH_3$ | H | 2 | H | H | H | H | C=N$C_2H_5$ | H | Cl |
| 6.403 | $CH_3$ | $CH_3$ | H | 0 | H | H | H | H | CH—NH$CH_3$ | H | Cl |
| 6.404 | $CH_3$ | $CH_3$ | H | 1 | H | H | H | H | CH—NH$CH_3$ | H | Cl |
| 6.405 | $CH_3$ | $CH_3$ | H | 2 | H | H | H | H | CH—NH$CH_3$ | H | Cl |
| 6.406 | $CH_3$ | $CH_3$ | H | 0 | H | H | H | H | CH—NH$C_2H_5$ | H | Cl |
| 6.407 | $CH_3$ | $CH_3$ | H | 1 | H | H | H | H | CH—NH$C_2H_5$ | H | Cl |
| 6.408 | $CH_3$ | $CH_3$ | H | 2 | H | H | H | H | CH—NH$C_2H_5$ | H | Cl |
| 6.409 | $CH_3$ | $CH_3$ | H | 0 | H | H | H | H | CH—N($CH_3$)$_2$ | H | Cl |
| 6.410 | $CH_3$ | $CH_3$ | H | 1 | H | H | H | H | CH—N(Cf3)2 | H | Cl |
| 6.411 | $CH_3$ | $CH_3$ | H | 2 | H | H | H | H | CH—N($CH_3$)$_2$ | H | Cl |
| 6.412 | $CH_3$ | $CH_3$ | H | 0 | H | H | H | H | CH—NHO$C_2H_5$ | H | Cl |
| 6.413 | $CH_3$ | $CH_3$ | H | 1 | H | H | H | H | CH—NHO$C_2H_5$ | H | Cl |
| 6.414 | $CH_3$ | $CH_3$ | H | 2 | H | H | H | H | CH—NHO$C_2H_5$ | H | Cl |
| 6.415 | $CH_3$ | $CH_3$ | H | 0 | H | H | H | H | CH—N($CH_3$)O$C_2H_5$ | H | Cl |
| 6.416 | $CH_3$ | $CH_3$ | H | 1 | H | H | H | H | CH—N($CH_3$)O$C_2H_5$ | H | Cl |
| 6.417 | $CH_3$ | $CH_3$ | H | 2 | H | H | H | H | CH—N($CH_3$)O$C_2H_5$ | H | Cl |
| 6.418 | $CH_3$ | $CH_3$ | H | 0 | H | H | H | H | C=N—$NH_2$ | H | Cl |
| 6.419 | $CH_3$ | $CH_3$ | H | 1 | H | H | H | H | C=N—$NH_2$ | H | Cl |
| 6.420 | $CH_3$ | $CH_3$ | H | 2 | H | H | H | H | C=N—$NH_2$ | H | Cl |
| 6.421 | $CH_3$ | $CH_3$ | H | 0 | H | H | H | H | C=N—N($CH_3$)$_2$ | H | Cl |
| 6.422 | $CH_3$ | $CH_3$ | H | 1 | H | H | H | H | C=N—N($CH_3$)$_2$ | H | Cl |
| 6.423 | $CH_3$ | $CH_3$ | H | 2 | H | H | H | H | C=N—N($CH_3$)$_2$ | H | Cl |
| 6.424 | $CH_3$ | $CH_3$ | H | 0 | H | H | H | H | CH—N($CH_3$)O$CH_2C_6H_5$ | H | Cl |
| 6.425 | $CH_3$ | $CH_3$ | H | 1 | H | H | H | H | CH—N($CH_3$)O$CH_2C_6H_5$ | H | Cl |
| 6.426 | $CH_3$ | $CH_3$ | H | 2 | H | H | H | H | CH—N($CH_3$)O$CH_2C_6H_5$ | H | Cl |
| 6.427 | $CH_3$ | $CH_3$ | H | 0 | H | H | H | H | C($CH_3$)—O$CH_3$ | H | Cl |
| 6.428 | $CH_3$ | $CH_3$ | H | 1 | H | H | H | H | C($CH_3$)—O$CH_3$ | H | Cl |
| 6.429 | $CH_3$ | $CH_3$ | H | 2 | H | H | H | H | C($CH_3$)—O$CH_3$ | H | Cl |
| 6.430 | $CH_3$ | $CH_3$ | H | 1 | H | H | H | H | O | H | Cl |
| 6.431 | $CH_3$ | $CH_3$ | H | 0 | H | H | H | H | O | H | Cl |
| 6.432 | $CH_3$ | $CH_3$ | H | 2 | H | H | H | H | O | H | Cl |

TABLE 7

Compounds of the formula

[Chemical structure with OH, M, (O)n, R17, R18, R19, L, Y, S, N substituents]

The radicals R⁷ and R²³ form a bond.

| No. | $R^{17}$ | $R^{18}$ | $R^{19}$ | n | Y | L | M |
|---|---|---|---|---|---|---|---|
| 7.1 | H | H | H | 2 | $COCH_3$ | H | H |
| 7.2 | H | H | H | 2 | $COC_2H_5$ | H | H |
| 7.3 | $CH_3$ | H | H | 2 | $COCH_3$ | H | H |
| 7.4 | $CH_3$ | H | H | 2 | $COC_2H_5$ | H | H |
| 7.5 | $CH_3$ | $CH_3$ | H | 2 | $COCH_3$ | H | H |
| 7.6 | $CH_3$ | $CH_3$ | H | 2 | $COC_2H_5$ | H | H |
| 7.7 | H | H | H | 2 | $COCH_3$ | H | $CH_3$ |
| 7.8 | H | H | H | 2 | $COC_2H_5$ | H | $CH_3$ |
| 7.9 | $CH_3$ | H | H | 2 | $COCH_3$ | H | $CH_3$ |
| 7.10 | $CH_3$ | H | H | 2 | $COC_2H_5$ | H | $CH_3$ |
| 7.11 | $CH_3$ | $CH_3$ | H | 2 | $COCH_3$ | H | $CH_3$ |
| 7.12 | $CH_3$ | $CH_3$ | H | 2 | $COC_2H_5$ | H | $CH_3$ |
| 7.13 | H | H | H | 2 | $COCH_3$ | H | Cl |
| 7.14 | H | H | H | 2 | $COC_2H_5$ | H | Cl |
| 7.15 | $CH_3$ | H | H | 2 | $COCH_3$ | H | Cl |
| 7.16 | $CH_3$ | H | H | 2 | $COC_2H_5$ | H | Cl |
| 7.17 | $CH_3$ | $CH_3$ | H | 2 | $COCH_3$ | H | Cl |
| 7.18 | $CH_3$ | $CH_3$ | H | 2 | $COC_2H_5$ | H | Cl |
| 7.19 | H | H | H | 2 | $COCH_3$ | H | $NO_2$ |
| 7.20 | H | H | H | 2 | $COC_2H_5$ | H | $NO_2$ |
| 7.21 | $CH_3$ | H | H | 2 | $COCH_3$ | H | $NO_2$ |
| 7.22 | $CH_3$ | H | H | 2 | $COC_2H_5$ | H | $NO_2$ |
| 7.23 | $CH_3$ | $CH_3$ | H | 2 | $COCH_3$ | H | $NO_2$ |
| 7.24 | $CH_3$ | $CH_3$ | H | 2 | $COC_2H_5$ | H | $NO_2$ |
| 7.25 | H | H | H | 2 | $COCH_3$ | H | $SO_2CH_3$ |
| 7.26 | H | H | H | 2 | $COC_2H_5$ | H | $SO_2CH_3$ |
| 7.27 | $CH_3$ | H | H | 2 | $COCH_3$ | H | $SO_2CH_3$ |
| 7.28 | $CH_3$ | H | H | 2 | $COC_2H_5$ | H | $SO_2CH_3$ |
| 7.29 | $CH_3$ | $CH_3$ | H | 2 | $COCH_3$ | H | $SO_2CH_3$ |
| 7.30 | $CH_3$ | $CH_3$ | H | 2 | $COC_2H_5$ | H | $SO_2CH_3$ |
| 7.31 | H | H | H | 2 | $COCH_3$ | $CH_3$ | $CH_3$ |
| 7.32 | H | H | H | 2 | $COC_2H_5$ | $CH_3$ | $CH_3$ |
| 7.33 | $CH_3$ | H | H | 2 | $COCH_3$ | $CH_3$ | $CH_3$ |
| 7.34 | $CH_3$ | H | H | 2 | $COC_2H_5$ | $CH_3$ | $CH_3$ |
| 7.35 | $CH_3$ | $CH_3$ | H | 2 | $COCH_3$ | $CH_3$ | $CH_3$ |
| 7.36 | $CH_3$ | $CH_3$ | H | 2 | $COC_2H_5$ | $CH_3$ | $CH_3$ |
| 7.37 | H | H | H | 2 | $COCH_3$ | Cl | Cl |
| 7.38 | H | H | H | 2 | $COC_2H_5$ | Cl | Cl |
| 7.39 | $CH_3$ | H | H | 2 | $COCH_3$ | Cl | Cl |
| 7.40 | $CH_3$ | H | H | 2 | $COC_2H_5$ | Cl | Cl |
| 7.41 | $CH_3$ | $CH_3$ | H | 2 | $COCH_3$ | Cl | Cl |
| 7.42 | $CH_3$ | $CH_3$ | H | 2 | $COC_2H_5$ | Cl | Cl |

TABLE 8

Compounds of the formula

[Chemical structure with OH, M, (O)n, R17, R18, R19, L, Y, S, N substituents]

| No. | $R^{17}$ | $R^{18}$ | $R^{19}$ | n | Y | M | L |
|---|---|---|---|---|---|---|---|
| 8.1 | H | H | H | 2 | $COCH_3$ | H | $CH_3$ |
| 8.2 | H | H | H | 2 | $COC_2H_5$ | H | $CH_3$ |
| 8.3 | $CH_3$ | H | H | 2 | $COCH_3$ | H | $CH_3$ |
| 8.4 | $CH_3$ | H | H | 2 | $COC_2H_5$ | H | $CH_3$ |
| 8.5 | $CH_3$ | $CH_3$ | H | 2 | $COCH_3$ | H | $CH_3$ |
| 8.6 | $CH_3$ | $CH_3$ | H | 2 | $COC_2H_5$ | H | $CH_3$ |
| 8.7 | H | H | H | 2 | $COCH_3$ | H | Cl |
| 8.8 | H | H | H | 2 | $COC_2H_5$ | H | Cl |
| 8.9 | $CH_3$ | H | H | 2 | $COCH_3$ | H | Cl |
| 8.10 | $CH_3$ | H | H | 2 | $COC_2H_5$ | H | Cl |
| 8.11 | $CH_3$ | $CH_3$ | H | 2 | $COCH_3$ | H | Cl |
| 8.12 | $CH_3$ | $CH_3$ | H | 2 | $COC_2H_5$ | H | Cl |
| 8.13 | H | H | H | 2 | $COCH_3$ | H | $NO_2$ |
| 8.14 | H | H | H | 2 | $COC_2H_5$ | H | $NO_2$ |
| 8.15 | $CH_3$ | H | H | 2 | $COCH_3$ | H | $NO_2$ |
| 8.16 | $CH_3$ | H | H | 2 | $COC_2H_5$ | H | $NO_2$ |
| 8.17 | $CH_3$ | $CH_3$ | H | 2 | $COCH_3$ | H | $NO_2$ |
| 8.18 | $CH_3$ | $CH_3$ | H | 2 | $COC_2H_5$ | H | $NO_2$ |
| 8.19 | H | H | H | 2 | $COCH_3$ | H | $SO_2CH_3$ |
| 8.20 | H | H | H | 2 | $COC_2H_5$ | H | $SO_2CH_3$ |
| 8.21 | $CH_3$ | H | H | 2 | $COCH_3$ | H | $SO_2CH_3$ |
| 8.22 | $CH_3$ | H | H | 2 | $COC_2H_5$ | H | $SO_2CH_3$ |
| 8.23 | $CH_3$ | $CH_3$ | H | 2 | $COCH_3$ | H | $SO_2CH_3$ |
| 8.24 | $CH_3$ | $CH_3$ | H | 2 | $COC_2H_5$ | H | $SO_2CH_3$ |
| 8.25 | H | H | H | 2 | $COCH_3$ | $CH_3$ | $CH_3$ |
| 8.26 | H | H | H | 2 | $COC_2H_5$ | $CH_3$ | $CH_3$ |
| 8.27 | $CH_3$ | H | H | 2 | $COCH_3$ | $CH_3$ | $CH_3$ |
| 8.28 | $CH_3$ | H | H | 2 | $COC_2H_5$ | $CH_3$ | $CH_3$ |
| 8.29 | $CH_3$ | $CH_3$ | H | 2 | $COCH_3$ | $CH_3$ | $CH_3$ |
| 8.30 | $CH_3$ | $CH_3$ | H | 2 | $COC_2H_5$ | $CH_3$ | $CH_3$ |
| 8.31 | H | H | H | 2 | $COCH_3$ | Cl | Cl |
| 8.32 | H | H | H | 2 | $COC_2H_5$ | Cl | Cl |
| 8.33 | $CH_3$ | H | H | 2 | $COCH_3$ | Cl | Cl |
| 8.34 | $CH_3$ | H | H | 2 | $COC_2H_5$ | Cl | Cl |
| 8.35 | $CH_3$ | $CH_3$ | H | 2 | $COCH_3$ | Cl | Cl |
| 8.36 | $CH_3$ | $CH_3$ | H | 2 | $COC_2H_5$ | Cl | Cl |

TABLE 9

Compounds of the formula

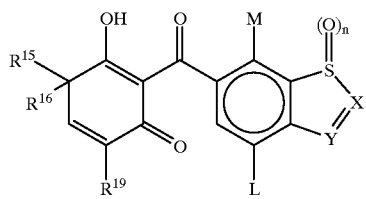

| No. | $R^{15}$ | $R^{16}$ | $R^{19}$ | n | X | Y | M | L |
|---|---|---|---|---|---|---|---|---|
| 9.1 | $CH_3$ | $CH_3$ | H | 2 | $CH_2$ | C=O | H | $CH_3$ |
| 9.2 | $CH_3$ | $CH_3$ | H | 0 | $(CH_2)_2$ | C=O | H | $CH_3$ |
| 9.3 | $CH_3$ | $CH_3$ | H | 2 | $(CH_2)_2$ | C=O | H | $CH_3$ |
| 9.4 | $CH_3$ | $CH_3$ | H | 2 | $CH_2$ | $CHOCH_3$ | H | $CH_3$ |
| 9.5 | $CH_3$ | $CH_3$ | H | 0 | $(CH_2)_2$ | $CHOCH_3$ | H | $CH_3$ |
| 9.6 | $CH_3$ | $CH_3$ | H | 2 | $(CH_2)_2$ | $CHOCH_3$ | H | $CH_3$ |
| 9.7 | $CH_3$ | $CH_3$ | H | 2 | $CH_2$ | $CHOC_2H_5$ | H | $CH_3$ |
| 9.8 | $CH_3$ | $CH_3$ | H | 0 | $(CH_2)_2$ | $CHOC_2H_5$ | H | $CH_3$ |
| 9.9 | $CH_3$ | $CH_3$ | H | 2 | $(CH_2)_2$ | $CHOC_2H_5$ | H | $CH_3$ |
| 9.10 | $CH_3$ | $CH_3$ | H | 2 | $CH_2$ | CHOiPr | H | $CH_3$ |
| 9.11 | $CH_3$ | $CH_3$ | H | 0 | $(CH_2)_2$ | CHOiPr | H | $CH_3$ |
| 9.12 | $CH_3$ | $CH_3$ | H | 2 | $(CH_2)_2$ | CHOiPr | H | $CH_3$ |
| 9.13 | $CH_3$ | $CH_3$ | H | 2 | $CH_2$ | $C=NOCH_3$ | H | $CH_3$ |
| 9.14 | $CH_3$ | $CH_3$ | H | 2 | $(CH_2)_2$ | $C=NOCH_3$ | H | $CH_3$ |
| 9.15 | $CH_3$ | $CH_3$ | H | 0 | $(CH_2)_2$ | $C=NOCH_3$ | H | $CH_3$ |
| 9.16 | $CH_3$ | $CH_3$ | H | 2 | $CH_2$ | $C=NOC_2H_5$ | H | $CH_3$ |
| 9.17 | $CH_3$ | $CH_3$ | H | 2 | $(CH_2)_2$ | $C=NOC_2H_5$ | H | $CH_3$ |
| 9.18 | $CH_3$ | $CH_3$ | H | 0 | $(CH_2)_2$ | $C=NOC_2H_5$ | H | $CH_3$ |
| 9.19 | $CH_3$ | $CH_3$ | H | 2 | $CH_2$ | C=NOiPr | H | $CH_3$ |
| 9.20 | $CH_3$ | $CH_3$ | H | 2 | $(CH_2)_2$ | C=NOiPr | H | $CH_3$ |
| 9.21 | $CH_3$ | $CH_3$ | H | 0 | $(CH_2)_2$ | C=NOiPr | H | $CH_3$ |
| 9.22 | $CH_3$ | $CH_3$ | H | 2 | $CH_2$ | $C=NOCH_2CH=CHCl$ | H | $CH_3$ |
| 9.23 | $CH_3$ | $CH_3$ | H | 2 | $(CH_2)_2$ | $C=NOCH_2CH=CHCl$ | H | $CH_3$ |
| 9.24 | $CH_3$ | $CH_3$ | H | 0 | $(CH_2)_2$ | $C=NOCH_2CH=CHCl$ | H | $CH_3$ |
| 9.25 | $CH_3$ | $CH_3$ | H | 2 | $CH_2$ | $C=NOCH_2C_6H_5$ | H | $CH_3$ |
| 9.26 | $CH_3$ | $CH_3$ | H | 2 | $(CH_2)_2$ | $C=NOCH_2C_6H_5$ | H | $CH_3$ |
| 9.27 | $CH_3$ | $CH_3$ | H | 0 | $(CH_2)_2$ | $C=NOCH_2C_6H_5$ | H | $CH_3$ |
| 9.28 | $CH_3$ | $CH_3$ | H | 2 | $CH_2$ | $C(CH_3)_2$ | H | $CH_3$ |
| 9.29 | $CH_3$ | $CH_3$ | H | 2 | $(CH_2)_2$ | $C(CH_3)_2$ | H | $CH_3$ |
| 9.30 | $CH_3$ | $CH_3$ | H | 0 | $(CH_2)_2$ | $C(CH_3)_2$ | H | $CH_3$ |
| 9.31 | $CH_3$ | $CH_3$ | H | 2 | $CH_2$ | ![dioxane] | H | $CH_3$ |
| 9.32 | $CH_3$ | $CH_3$ | H | 2 | $(CH_2)_2$ | ![dioxane] | H | $CH_3$ |
| 9.33 | $CH_3$ | $CH_3$ | H | 0 | $(CH_2)_2$ | ![dioxane] | H | $CH_3$ |
| 9.34 | $CH_3$ | $CH_3$ | H | 2 | $CH_2$ | ![dimethyldioxane] | H | $CH_3$ |
| 9.35 | $CH_3$ | $CH_3$ | H | 2 | $(CH_2)_2$ | ![dimethyldioxane] | H | $CH_3$ |

TABLE 9-continued

Compounds of the formula

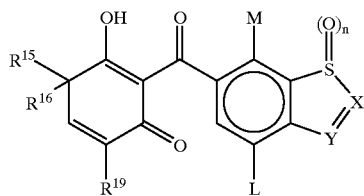

| No. | R15 | R16 | R19 | n | X | Y | M | L |
|---|---|---|---|---|---|---|---|---|
| 9.36 | CH3 | CH3 | H | 0 | (CH2)2 | (dioxane with C(CH3)2) | H | CH3 |
| 9.37 | CH3 | CH3 | H | 2 | CH2 | CH—NHCH3 | H | CH3 |
| 9.38 | CH3 | CH3 | H | 2 | (CH2)2 | CH—NHCH3 | H | CH3 |
| 9.39 | CH3 | CH3 | H | 0 | (CH2)2 | CH—NHCH3 | H | CH3 |
| 9.40 | CH3 | CH3 | H | 2 | CH2 | CH—NHC2H5 | H | CH3 |
| 9.41 | CH3 | CH3 | H | 2 | (CH2)2 | CH—NHC2H5 | H | CH3 |
| 9.42 | CH3 | CH3 | H | 0 | (CH2)2 | CH—NHC2H5 | H | CH3 |
| 9.43 | CH3 | CH3 | H | 2 | CH2 | CH—N(CH3)2 | H | CH3 |
| 9.44 | CH3 | CH3 | H | 2 | (CH2)2 | CH—N(CH3)2 | H | CH3 |
| 9.45 | CH3 | CH3 | H | 0 | (CH2)2 | CH—N(CH3)2 | H | CH3 |
| 9.46 | CH3 | CH3 | H | 2 | CH2 | CH—NHOC2H5 | H | CH3 |
| 9.47 | CH3 | CH3 | H | 2 | (CH2)2 | CH—NHOC2H5 | H | CH3 |
| 9.48 | CH3 | CH3 | H | 0 | (CH2)2 | CH—NHOC2H5 | H | CH3 |
| 9.49 | CH3 | CH3 | H | 2 | CH2 | CH—N(CH3)OC2H5 | H | CH3 |
| 9.50 | CH3 | CH3 | H | 2 | (CH2)2 | CH—N(CH3)OC2H5 | H | CH3 |
| 9.51 | CH3 | CH3 | H | 0 | (CH2)2 | CH—N(CH3)OC2H5 | H | CH3 |
| 9.52 | CH3 | CH3 | H | 2 | CH2 | C=N—NH2 | H | CH3 |
| 9.53 | CH3 | CH3 | H | 2 | (CH2)2 | C=N—NH2 | H | CH3 |
| 9.54 | CH3 | CH3 | H | 0 | (CH2)2 | C=N—NH2 | H | CH3 |
| 9.55 | CH3 | CH3 | H | 2 | CH2 | C=N—N(CH3)2 | H | CH3 |
| 9.56 | CH3 | CH3 | H | 2 | (CH2)2 | C=N—N(CH3)2 | H | CH3 |
| 9.57 | CH3 | CH3 | H | 0 | (CH2)2 | C=N—N(CH3)2 | H | CH3 |
| 9.58 | CH3 | CH3 | H | 2 | CH2 | CH—N(CH3)OCH2C6H5 | H | CH3 |
| 9.59 | CH3 | CH3 | H | 2 | (CH2)2 | CH—N(CH3)OCH2C6H5 | H | CH3 |
| 9.60 | CH3 | CH3 | H | 0 | (CH2)2 | CH—N(CH3)OCH2C6H5 | H | CH3 |
| 9.61 | CH3 | CH3 | H | 2 | CH2 | C(CH3)—OCH3 | H | CH3 |
| 9.62 | CH3 | CH3 | H | 2 | (CH2)2 | C(CH3)—OCH3 | H | CH3 |
| 9.63 | CH3 | CH3 | H | 0 | (CH2)2 | C(CH3)—OCH3 | H | CH3 |
| 9.64 | CH3 | CH3 | H | 2 | CH2 | O | H | CH3 |
| 9.65 | CH3 | CH3 | H | 2 | (CH2)2 | O | H | CH3 |
| 9.66 | CH3 | CH3 | H | 0 | (CH2)2 | O | H | CH3 |
| 9.67 | CH3 | CH3 | Br | 2 | CH2 | CHOCH3 | H | CH3 |
| 9.68 | CH3 | CH3 | Br | 2 | (CH2)2 | CHOCH3 | H | CH3 |
| 9.69 | CH3 | CH3 | Br | 0 | (CH2)2 | CHOCH3 | H | CH3 |
| 9.70 | CH3 | CH3 | Br | 2 | CH2 | CHOC2H5 | H | CH3 |
| 9.71 | CH3 | CH3 | Br | 2 | (CH2)2 | CHOC2H5 | H | CH3 |
| 9.72 | CH3 | CH3 | Br | 0 | (CH2)2 | CHOC2H5 | H | CH3 |
| 9.73 | CH3 | CH3 | Br | 2 | CH2 | CHOiPr | H | CH3 |
| 9.74 | CH3 | CH3 | Brr [sic] | 2 | (CH2)2 | CHOiPr | H | CH3 |
| 9.75 | CH3 | CH3 | Br | 0 | (CH2)2 | CHOiPr | H | CH3 |
| 9.76 | CH3 | CH3 | Cl | 2 | CH2 | CHOCH3 | H | CH3 |
| 9.77 | CH3 | CH3 | Cl | 2 | (CH2)2 | CHOCH3 | H | CH3 |
| 9.78 | CH3 | CH3 | Cl | 0 | (CH2)2 | CHOCH3 | H | CH3 |
| 9.79 | CH3 | CH3 | Cl | 2 | CH2 | CHOC2H5 | H | CH3 |
| 9.80 | CH3 | CH3 | Cl | 2 | (CH2)2 | CHOC2H5 | H | CH3 |
| 9.81 | CH3 | CH3 | Cl | 0 | (CH2)2 | CHOC2H5 | H | CH3 |
| 9.82 | CH3 | CH3 | Cl | 2 | CH2 | CHOiPr | H | CH3 |
| 9.83 | CH3 | CH3 | Cl | 2 | (CH2)2 | CHOiPr | H | CH3 |
| 9.84 | CH3 | CH3 | Cl | 0 | (CH2)2 | CHOiPr | H | CH3 |

TABLE 10

Compounds of the formula

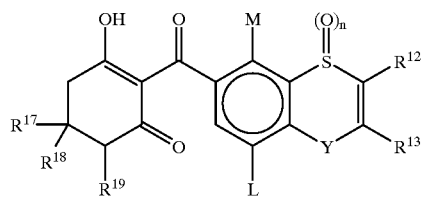

| No. | $R^{17}$ | $R^{18}$ | $R^{19}$ | n | $R^{12}$ | $R^{13}$ | Y | L | M |
|---|---|---|---|---|---|---|---|---|---|
| 10.1 | H | H | H | 0 | H | H | C=O | H | $CH_3$ |
| 10.2 | $CH_3$ | H | H | 0 | H | H | C=O | H | $CH_3$ |
| 10.3 | $CH_3$ | $CH_3$ | H | 0 | H | H | C=O | H | $CH_3$ |
| 10.4 | H | H | H | 2 | H | H | C=O | H | $CH_3$ |
| 10.5 | $CH_3$ | H | H | 2 | H | H | C=O | H | $CH_3$ |
| 10.6 | $CH_3$ | $CH_3$ | H | 2 | H | H | C=O | H | $CH_3$ |
| 10.7 | H | H | H | 0 | H | H | C=O | H | Cl |
| 10.8 | $CH_3$ | H | H | 0 | H | H | C=O | H | Cl |
| 10.9 | $CH_3$ | $CH_3$ | H | 0 | H | H | C=O | H | Cl |
| 10.10 | H | H | H | 2 | H | H | C=O | H | Cl |
| 10.11 | $CH_3$ | H | H | 2 | H | H | C=O | H | Cl |
| 10.12 | $CH_3$ | $CH_3$ | H | 2 | H | H | C=O | H | Cl |
| 10.13 | H | H | H | 0 | H | H | $CHOCH_3$ | H | $CH_3$ |
| 10.14 | $CH_3$ | H | H | 0 | H | H | $CHOCH_3$ | H | $CH_3$ |
| 10.15 | $CH_3$ | $CH_3$ | H | 0 | H | H | $CHOCH_3$ | H | $CH_3$ |
| 10.16 | H | H | H | 2 | H | H | $CHOCH_3$ | H | $CH_3$ |
| 10.17 | $CH_3$ | H | H | 2 | H | H | $CHOCH_3$ | H | $CH_3$ |
| 10.18 | $CH_3$ | $CH_3$ | H | 2 | H | H | $CHOCH_3$ | H | $CH_3$ |
| 10.19 | H | H | H | 0 | H | H | $CHOCH_3$ | H | Cl |
| 10.20 | $CH_3$ | H | H | 0 | H | H | $CHOCH_3$ | H | Cl |
| 10.21 | $CH_3$ | $CH_3$ | H | 0 | H | H | $CHOCH_3$ | H | Cl |
| 10.22 | H | H | H | 2 | H | H | $CHOCH_3$ | H | Cl |
| 10.23 | $CH_3$ | H | H | 2 | H | H | $CHOCH_3$ | H | Cl |
| 10.24 | $CH_3$ | $CH_3$ | H | 2 | H | H | $CHOCH_3$ | H | Cl |
| 10.25 | H | H | H | 0 | $CH_3$ | C=O | H | $CH_3$ | |
| 10.26 | $CH_3$ | H | H | 0 | $CH_3$ | C=O | H | $CH_3$ | |
| 10.27 | $CH_3$ | $CH_3$ | H | 0 | $CH_3$ | C=O | H | $CH_3$ | |
| 10.28 | H | H | H | 2 | $CH_3$ | C=O | H | $CH_3$ | |
| 10.29 | $CH_3$ | H | H | 2 | $CH_3$ | C=O | H | $CH_3$ | |
| 10.30 | $CH_3$ | $CH_3$ | H | 2 | $CH_3$ | C=O | H | $CH_3$ | |
| 10.31 | H | H | H | 0 | $CH_3$ | C=O | H | Cl | |
| 10.32 | $CH_3$ | H | H | 0 | $CH_3$ | C=O | H | Cl | |
| 10.33 | $CH_3$ | $CH_3$ | H | 0 | $CH_3$ | C=O | H | Cl | |
| 10.34 | H | H | H | 2 | $CH_3$ | C=O | H | Cl | |
| 10.35 | $CH_3$ | H | H | 2 | $CH_3$ | C=O | H | Cl | |
| 10.36 | $CH_3$ | $CH_3$ | H | 2 | $CH_3$ | C=O | H | Cl | |
| 10.37 | H | H | H | 0 | $CH_3$ | $CHOCH_3$ | H | $CH_3$ | |
| 10.38 | $CH_3$ | H | H | 0 | $CH_3$ | $CHOCH_3$ | H | $CH_3$ | |
| 10.39 | $CH_3$ | $CH_3$ | H | 0 | $CH_3$ | $CHOCH_3$ | H | $CH_3$ | |
| 10.40 | H | H | H | 2 | $CH_3$ | $CHOCH_3$ | H | $CH_3$ | |
| 10.41 | $CH_3$ | H | H | 2 | $CH_3$ | $CHOCH_3$ | H | $CH_3$ | |
| 10.42 | $CH_3$ | $CH_3$ | H | 2 | $CH_3$ | $CHOCH_3$ | H | $CH_3$ | |
| 10.43 | H | H | H | 0 | $CH_3$ | $CHOCH_3$ | H | Cl | |
| 10.44 | $CH_3$ | H | H | 0 | $CH_3$ | $CHOCH_3$ | H | Cl | |
| 10.45 | $CH_3$ | $CH_3$ | H | 0 | $CH_3$ | $CHOCH_3$ | H | Cl | |

TABLE 10-continued

Compounds of the formula

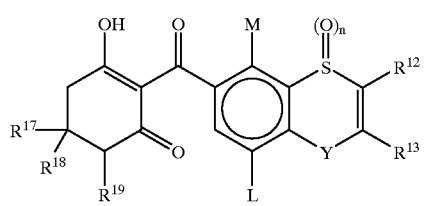

| No. | $R^{17}$ | $R^{18}$ | $R^{19}$ | n | $R^{12}$ | $R^{13}$ | Y | L | M |
|---|---|---|---|---|---|---|---|---|---|
| 10.46 | H | H | H | 2 | $CH_3$ | $CHOCH_3$ | H | Cl | |
| 10.47 | $CH_3$ | H | H | 2 | $CH_3$ | $CHOCH_3$ | H | Cl | |
| 10.48 | $CH_3$ | $CH_3$ | H | 2 | $CH_3$ | $CHOCH_3$ | H | Cl | |
| 10.49 | H | H | H | 0 | H | $C_6H_5$ | C=O | H | $CH_3$ |
| 10.50 | $CH_3$ | H | H | 0 | H | $C_6H_5$ | C=O | H | $CH_3$ |
| 10.51 | $CH_3$ | $CH_3$ | H | 0 | H | $C_6H_5$ | C=O | H | $CH_3$ |
| 10.52 | H | H | H | 2 | H | $C_6H_5$ | C=O | H | $CH_3$ |
| 10.53 | $CH_3$ | H | H | 2 | H | $C_6H_5$ | C=O | H | $CH_3$ |
| 10.54 | $CH_3$ | $CH_3$ | H | 2 | H | $C_6H_5$ | C=O | H | $CH_3$ |
| 10.55 | H | H | H | 0 | H | $C_6H_5$ | C=O | H | Cl |
| 10.56 | $CH_3$ | H | H | 0 | H | $C_6H_5$ | C=O | H | Cl |
| 10.57 | $CH_3$ | $CH_3$ | H | 0 | H | $C_6H_5$ | C=O | H | Cl |
| 10.58 | H | H | H | 2 | H | $C_6H_5$ | C=O | H | Cl |
| 10.59 | $CH_3$ | H | H | 2 | H | $C_6H_5$ | C=O | H | Cl |
| 10.60 | $CH_3$ | $CH_3$ | H | 2 | H | $C_6H_5$ | C=O | H | Cl |
| 10.61 | H | H | H | 0 | H | $C_6H_5$ | $CHOCH_3$ | H | $CH_3$ |
| 10.62 | $CH_3$ | H | H | 0 | H | $C_6H_5$ | $CHOCH_3$ | H | $CH_3$ |
| 10.63 | $CH_3$ | $CH_3$ | H | 0 | H | $C_6H_5$ | $CHOCH_3$ | H | $CH_3$ |
| 10.64 | H | H | H | 2 | H | $C_6H_5$ | $CHOCH_3$ | H | $CH_3$ |
| 10.65 | $CH_3$ | H | H | 2 | H | $C_6H_5$ | $CHOCH_3$ | H | $CH_3$ |
| 10.66 | $CH_3$ | $CH_3$ | H | 2 | H | $C_6H_5$ | $CHOCH_3$ | H | $CH_3$ |
| 10.67 | H | H | H | 0 | H | $C_6H_5$ | $CHOCH_3$ | H | Cl |
| 10.68 | $CH_3$ | H | H | 0 | H | $C_6H_5$ | $CHOCH_3$ | H | Cl |
| 10.69 | $CH_3$ | $CH_3$ | H | 0 | H | $C_6H_5$ | $CHOCH_3$ | H | Cl |
| 10.70 | H | H | H | 2 | H | $C_6H_5$ | $CHOCH_3$ | H | Cl |
| 10.71 | $CH_3$ | H | H | 2 | H | $C_6H_5$ | $CHOCH_3$ | H | Cl |
| 10.72 | $CH_3$ | $CH_3$ | H | 2 | H | $C_6H_5$ | $CHOCH_3$ | H | Cl |
| 10.73 | H | H | H | 0 | H | H | $CH_2$ | H | $CH_3$ |
| 10.74 | $CH_3$ | H | H | 0 | H | H | $CH_2$ | H | $CH_3$ |
| 10.75 | $CH_3$ | $CH_3$ | H | 0 | H | H | $CH_2$ | H | $CH_3$ |
| 10.76 | H | H | H | 2 | H | H | $CH_2$ | H | $CH_3$ |
| 10.77 | $CH_3$ | H | H | 2 | H | H | $CH_2$ | H | $CH_3$ |
| 10.78 | $CH_3$ | $CH_3$ | H | 2 | H | H | $CH_2$ | H | $CH_3$ |
| 10.79 | H | H | H | 0 | H | H | $CH_2$ | H | Cl |
| 10.80 | $CH_3$ | H | H | 0 | H | H | $CH_2$ | H | Cl |
| 10.81 | $CH_3$ | $CH_3$ | H | 0 | H | H | $CH_2$ | H | Cl |
| 10.82 | H | H | H | 2 | H | H | $CH_2$ | H | Cl |
| 10.83 | $CH_3$ | H | H | 2 | H | H | $CH_2$ | H | Cl |
| 10.84 | $CH_3$ | $CH_3$ | H | 2 | H | H | $CH_2$ | H | Cl |

TABLE 11

Compounds of the formula

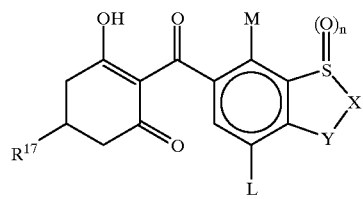

| No. | R$^{17}$ | n | X | Y | L | M |
|---|---|---|---|---|---|---|
| 11.1 | 2-Ethylthiopropyl | 2 | CH$_2$ | C=O | H | CH$_3$ |
| 11.2 | 2-Ethylthiopropyl | 0 | (CH$_2$)$_2$ | C=O | H | CH$_3$ |
| 11.3 | 2-Ethylthiopropyl | 2 | (CH$_2$)$_2$ | C=O | H | CH$_3$ |
| 11.4 | 2-Ethylthiopropyl | 2 | CH$_2$ | CHOCH$_3$ | H | CH$_3$ |
| 11.5 | 2-Ethylthiopropyl | 0 | (CH$_2$)$_2$ | CHOCH$_3$ | H | CH$_3$ |
| 11.6 | 2-Ethylthiopropyl | 2 | (CH$_2$)$_2$ | CHOCH$_3$ | H | CH$_3$ |
| 11.7 | 2-Ethylthiopropyl | 2 | CH$_2$ | CHOC$_2$H$_5$ | H | CH$_3$ |
| 11.8 | 2-Ethylthiopropyl | 0 | (CH$_2$)$_2$ | CHOC$_2$H$_5$ | H | CH$_3$ |
| 11.9 | 2-Ethylthiopropyl | 2 | (CH$_2$)$_2$ | CHOC$_2$H$_5$ | H | CH$_3$ |
| 11.10 | 2-Ethylthiopropyl | 2 | CH$_2$ | CHOiPr | H | CH$_3$ |
| 11.11 | 2-Ethylthiopropyl | 0 | (CH$_2$)$_2$ | CHOiPr | H | CH$_3$ |
| 11.12 | 2-Ethylthiopropyl | 2 | (CH$_2$)$_2$ | CHOiPr | H | CH$_3$ |
| 11.13 | 2-Ethylthiopropyl | 2 | CH$_2$ | C=NOCH$_3$ | H | CH$_3$ |
| 11.14 | 2-Ethylthiopropyl | 2 | (CH$_2$)$_2$ | C=NOCH$_3$ | H | CH$_3$ |
| 11.15 | 2-Ethylthiopropyl | 0 | (CH$_2$)$_2$ | C=NOCH$_3$ | H | CH$_3$ |
| 11.16 | 2-Ethylthiopropyl | 2 | CH$_2$ | C=NOC$_2$H$_5$ | H | CH$_3$ |
| 11.17 | 2-Ethylthiopropyl | 2 | (CH$_2$)$_2$ | C=NOC$_2$H$_5$ | H | CH$_3$ |
| 11.18 | 2-Ethylthiopropyl | 0 | (CH$_2$)$_2$ | C=NOC$_2$H$_5$ | H | CH$_3$ |
| 11.19 | 2-Ethylthiopropyl | 2 | CH$_2$ | C=NOiPr | H | CH$_3$ |
| 11.20 | 2-Ethylthiopropyl | 2 | (CH$_2$)$_2$ | C=NOiPr | H | CH$_3$ |
| 11.21 | 2-Ethylthiopropyl | 0 | (CH$_2$)$_2$ | C=NOiPr | H | CH$_3$ |
| 11.22 | 2-Ethylthiopropyl | 2 | CH$_2$ | C=NOCH$_2$CH=CHCl | H | CH$_3$ |
| 11.23 | 2-Ethylthiopropyl | 2 | (CH$_2$)$_2$ | C=NOCH$_2$CH=CHCl | H | CH$_3$ |
| 11.24 | 2-Ethylthiopropyl | 0 | (CH$_2$)$_2$ | C=NOCH$_2$CH=CHCl | H | CH$_3$ |
| 11.25 | 2-Ethylthiopropyl | 2 | CH$_2$ | C=NOCH$_2$C$_6$H$_5$ | H | CH$_3$ |
| 11.26 | 2-Ethylthiopropyl | 2 | (CH$_2$)$_2$ | C=NOCH$_2$C$_6$H$_5$ | H | CH$_3$ |
| 11.27 | 2-Ethylthiopropyl | 0 | (CH$_2$)$_2$ | C=NOCH$_2$C$_6$H$_5$ | H | CH$_3$ |
| 11.28 | 2-Ethylthiopropyl | 2 | CH$_2$ | C(CH$_3$)$_2$ | H | CH$_3$ |
| 11.29 | 2-Ethylthiopropyl | 2 | (CH$_2$)$_2$ | C(CH$_3$)$_2$ | H | CH$_3$ |
| 11.30 | 2-Ethylthiopropyl | 0 | (CH$_2$)$_2$ | C(CH$_3$)$_2$ | H | CH$_3$ |
| 11.31 | 2-Ethylthiopropyl | 2 | CH$_2$ | CH—NHCH$_3$ | H | CH$_3$ |
| 11.32 | 2-Ethylthiopropyl | 2 | (CH$_2$)$_2$ | CH—NHCH$_3$ | H | CH$_3$ |
| 11.33 | 2-Ethylthiopropyl | 0 | (CH$_2$)$_2$ | CH—NHCH$_3$ | H | CH$_3$ |
| 11.34 | 2-Ethylthiopropyl | 2 | CH$_2$ | CH—NHC$_2$H$_5$ | H | CH$_3$ |
| 11.35 | 2-Ethylthiopropyl | 2 | (CH$_2$)$_2$ | CH—NHC$_2$H$_5$ | H | CH$_3$ |
| 11.36 | 2-Ethylthiopropyl | 0 | (CH$_2$)$_2$ | CH—NHC$_2$H$_5$ | H | CH$_3$ |
| 11.37 | 2-Ethylthiopropyl | 2 | CH$_2$ | CH—N(CH$_3$)$_2$ | H | CH$_3$ |
| 11.38 | 2-Ethylthiopropyl | 2 | (CH$_2$)$_2$ | CH—N(CH$_3$)$_2$ | H | CH$_3$ |
| 11.39 | 2-Ethylthiopropyl | 0 | (CH$_2$)$_2$ | CH—N(CH$_3$)$_2$ | H | CH$_3$ |
| 11.40 | 2-Ethylthiopropyl | 2 | CH$_2$ | CH—NHOC$_2$H$_5$ | H | CH$_3$ |
| 11.41 | 2-Ethylthiopropyl | 2 | (CH$_2$)$_2$ | CH—NHOC$_2$H$_5$ | H | CH$_3$ |
| 11.42 | 2-Ethylthiopropyl | 0 | (CH$_2$)$_2$ | CH—NHOC$_2$H$_5$ | H | CH$_3$ |
| 11.43 | 2-Ethylthiopropyl | 2 | CH$_2$ | CH—N(CH$_3$)OC$_2$H$_5$ | H | CH$_3$ |
| 11.44 | 2-Ethylthiopropyl | 2 | (CH$_2$)$_2$ | CH—N(CH$_3$)OC$_2$H$_5$ | H | CH$_3$ |
| 11.45 | 2-Ethylthiopropyl | 0 | (CH$_2$)$_2$ | CH—N(CH$_3$)OC$_2$H$_5$ | H | CH$_3$ |
| 11.46 | 2-Ethylthiopropyl | 2 | CH$_2$ | C=N—NH$_2$ | H | CH$_3$ |
| 11.47 | 2-Ethylthiopropyl | 2 | (CH$_2$)$_2$ | C=N—NH$_2$ | H | CH$_3$ |
| 11.48 | 2-Ethylthiopropyl | 0 | (CH$_2$)$_2$ | C=N—NH$_2$ | H | CH$_3$ |
| 11.49 | 2-Ethylthiopropyl | 2 | CH$_2$ | C=N—N(CH$_3$)$_2$ | H | CH$_3$ |
| 11.50 | 2-Ethylthiopropyl | 2 | (CH$_2$)$_2$ | C=N—N(CH$_3$)$_2$ | H | CH$_3$ |
| 11.51 | 2-Ethylthiopropyl | 0 | (CH$_2$)$_2$ | C=N—N(CH$_3$)$_2$ | H | CH$_3$ |
| 11.52 | 2-Ethylthiopropyl | 2 | CH$_2$ | CH—N(CH$_3$)OCH$_2$C$_6$H$_5$ | H | CH$_3$ |
| 11.53 | 2-Ethylthiopropyl | 2 | (CH$_2$)$_2$ | CH—N(CH$_3$)OCH$_2$C$_6$H$_5$ | H | CH$_3$ |
| 11.54 | 2-Ethylthiopropyl | 0 | (CH$_2$)$_2$ | CH—N(CH$_3$)OCH$_2$C$_6$H$_5$ | H | CH$_3$ |
| 11.55 | 2-Ethylthiopropyl | 2 | CH$_2$ | C(CH$_3$)—OCH$_3$ | H | CH$_3$ |
| 11.56 | 2-Ethylthiopropyl | 2 | (CH$_2$)$_2$ | C(CH$_3$)—OCH$_3$ | H | CH$_3$ |
| 11.57 | 2-Ethylthiopropyl | 0 | (CH$_2$)$_2$ | C(CH$_3$)—OCH$_3$ | H | CH$_3$ |
| 11.58 | 2-Ethylthiopropyl | 2 | CH$_2$ | O | H | CH$_3$ |
| 11.59 | 2-Ethylthiopropyl | 0 | (CH$_2$)$_2$ | O | H | CH$_3$ |
| 11.60 | 2-Ethylthiopropyl | 2 | (CH$_2$)$_2$ | O | H | CH$_3$ |
| 11.61 | Tetrahydropyran-3-yl | 2 | CH$_2$ | C=O | H | CH$_3$ |
| 11.62 | Tetrahydropyran-3-yl | 0 | (CH$_2$)$_2$ | C=O | H | CH$_3$ |
| 11.63 | Tetrahydropyran-3-yl | 2 | (CH$_2$)$_2$ | C=O | H | CH$_3$ |
| 11.64 | Tetrahydropyran-3-yl | 2 | CH$_2$ | CHOCH$_3$ | H | CH$_3$ |

TABLE 11-continued

Compounds of the formula

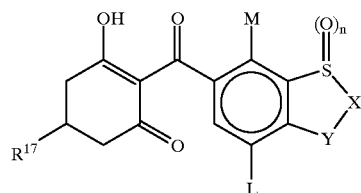

| No. | R$^{17}$ | n | X | Y | L | M |
|---|---|---|---|---|---|---|
| 11.65 | Tetrahydropyran-3-yl | 0 | (CH$_2$)$_2$ | CHOCH$_3$ | H | CH$_3$ |
| 11.66 | Tetrahydropyran-3-yl | 2 | (CH$_2$)$_2$ | CHOCH$_3$ | H | CH$_3$ |
| 11.67 | Tetrahydropyran-3-yl | 2 | CH$_2$ | CHOC$_2$H$_5$ | H | CH$_3$ |
| 11.68 | Tetrahydropyran-3-yl | 0 | (CH$_2$)$_2$ | CHOC$_2$H$_5$ | H | CH$_3$ |
| 11.69 | Tetrahydropyran-3-yl | 2 | (CH$_2$)$_2$ | CHOC$_2$H$_5$ | H | CH$_3$ |
| 11.70 | Tetrahydropyran-3-yl | 2 | CH$_2$ | CHOiPr | H | CH$_3$ |
| 11.71 | Tetrahydropyran-3-yl | 0 | (CH$_2$)$_2$ | CHOiPr | H | CH$_3$ |
| 11.72 | Tetrahydropyran-3-yl | 2 | (CH$_2$)$_2$ | CHOiPr | H | CH$_3$ |
| 11.73 | Tetrahydropyran-3-yl | 2 | CH$_2$ | C=NOCH$_3$ | H | CH$_3$ |
| 11.74 | Tetrahydropyran-3-yl | 2 | (CH$_2$)$_2$ | C=NOCH$_3$ | H | CH$_3$ |
| 11.75 | Tetrahydropyran-3-yl | 0 | (CH$_2$)$_2$ | C=NOCH$_3$ | H | CH$_3$ |
| 11.76 | Tetrahydropyran-3-yl | 2 | CH$_2$ | C=NOC$_2$H$_5$ | H | CH$_3$ |
| 11.77 | Tetrahydropyran-3-yl | 2 | (CH$_2$)$_2$ | C=NOC$_2$H$_5$ | H | CH$_3$ |
| 11.78 | Tetrahydropyran-3-yl | 0 | (CH$_2$)$_2$ | C=NOC$_2$H$_5$ | H | CH$_3$ |
| 11.79 | Tetrahydropyran-3-yl | 2 | CH$_2$ | C=NOiPr | H | CH$_3$ |
| 11.80 | Tetrahydropyran-3-yl | 2 | (CH$_2$)$_2$ | C=NOiPr | H | CH$_3$ |
| 11.81 | Tetrahydropyran-3-yl | 0 | (CH$_2$)$_2$ | C=NOiPr | H | CH$_3$ |
| 11.82 | Tetrahydropyran-4-yl | 2 | CH$_2$ | C=O | H | CH$_3$ |
| 11.83 | Tetrahydropyran-4-yl | 0 | (CH$_2$)$_2$ | C=O | H | CH$_3$ |
| 11.84 | Tetrahydropyran-4-yl | 2 | (CH$_2$)$_2$ | C=O | H | CH$_3$ |
| 11.85 | Tetrahydropyran-4-yl | 2 | CH$_2$ | CHOCH$_3$ | H | CH$_3$ |
| 11.86 | Tetrahydropyran-4-yl | 0 | (CH$_2$)$_2$ | CHOCH$_3$ | H | CH$_3$ |
| 11.87 | Tetrahydropyran-4-yl | 2 | (CH$_2$)$_2$ | CHOCH$_3$ | H | CH$_3$ |
| 11.88 | Tetrahydropyran-4-yl | 2 | CH$_2$ | CHOC$_2$H$_5$ | H | CH$_3$ |
| 11.89 | Tetrahydropyran-4-yl | 0 | (CH$_2$)$_2$ | CHOC$_2$H$_5$ | H | CH$_3$ |
| 11.90 | Tetrahydropyran-4-yl | 2 | (CH$_2$)$_2$ | CHOC$_2$H$_5$ | H | CH$_3$ |
| 11.91 | Tetrahydropyran-4-yl | 2 | CH$_2$ | CHOiPr | H | CH$_3$ |
| 11.92 | Tetrahydropyran-4-yl | 0 | (CH$_2$)$_2$ | CHOiPr | H | CH$_3$ |
| 11.93 | Tetrahydropyran-4-yl | 2 | (CH$_2$)$_2$ | CHOiPr | H | CH$_3$ |
| 11.94 | Tetrahydropyran-4-yl | 2 | CH$_2$ | C=NOCH$_3$ | H | CH$_3$ |
| 11.95 | Tetrahydropyran-4-yl | 2 | (CH$_2$)$_2$ | C=NOCH$_3$ | H | CH$_3$ |
| 11.96 | Tetrahydropyran-4-yl | 0 | (CH$_2$)$_2$ | C=NOCH$_3$ | H | CH$_3$ |
| 11.97 | Tetrahydropyran-4-yl | 2 | CH$_2$ | C=NOC$_2$H$_5$ | H | CH$_3$ |
| 11.98 | Tetrahydropyran-4-yl | 2 | (CH$_2$)$_2$ | C=NOC$_2$H$_5$ | H | CH$_3$ |
| 11.99 | Tetrahydropyran-4-yl | 0 | (CH$_2$)$_2$ | C=NOC$_2$H$_5$ | H | CH$_3$ |
| 11.100 | Tetrahydropyran-4-yl | 2 | CH$_2$ | C=NOiPr | H | CH$_3$ |
| 11.101 | Tetrahydropyran-4-yl | 2 | (CH$_2$)$_2$ | C=NOiPr | H | CH$_3$ |
| 11.102 | Tetrahydropyran-4-yl | 0 | (CH$_2$)$_2$ | C=NOiPr | H | CH$_3$ |
| 11.103 | Tetrahydrothiopyran-3-yl | 2 | CH$_2$ | C=O | H | CH$_3$ |
| 11.104 | Tetrahydrothiopyran-3-yl | 0 | (CH$_2$)$_2$ | C=O | H | CH$_3$ |
| 11.105 | Tetrahydrothiopyran-3-yl | 2 | (CH$_2$)$_2$ | C=O | H | CH$_3$ |
| 11.106 | Tetrahydrothiopyran-3-yl | 2 | CH$_2$ | CHOCH$_3$ | H | CH$_3$ |
| 11.107 | Tetrahydrothiopyran-3-yl | 0 | (CH$_2$)$_2$ | CHOCH$_3$ | H | CH$_3$ |
| 11.108 | Tetrahydrothiopyran-3-yl | 2 | (CH$_2$)$_2$ | CHOCH$_3$ | H | CH$_3$ |
| 11.109 | Tetrahydrothiopyran-3-yl | 2 | CH$_2$ | CHOC$_2$H$_5$ | H | CH$_3$ |
| 11.110 | Tetrahydrothiopyran-3-yl | 0 | (CH$_2$)$_2$ | CHOC$_2$H$_5$ | H | CH$_3$ |
| 11.111 | Tetrahydrothiopyran-3-yl | 2 | (CH$_2$)$_2$ | CHOC$_2$H$_5$ | H | CH$_3$ |
| 11.112 | Tetrahydrothiopyran-3-yl | 2 | CH$_2$ | CHOiPr | H | CH$_3$ |
| 11.113 | Tetrahydrothiopyran-3-yl | 0 | (CH$_2$)$_2$ | CHOiPr | H | CH$_3$ |
| 11.114 | Tetrahydrothiopyran-3-yl | 2 | (CH$_2$)$_2$ | CHOiPr | H | CH$_3$ |
| 11.115 | Tetrahydrothiopyran-3-yl | 2 | CH$_2$ | C=NOCH$_3$ | H | CH$_3$ |
| 11.116 | Tetrahydrothiopyran-3-yl | 2 | (CH$_2$)$_2$ | C=NOCH$_3$ | H | CH$_3$ |
| 11.117 | Tetrahydrothiopyran-3-yl | 0 | (CH$_2$)$_2$ | C=NOCH$_3$ | H | CH$_3$ |
| 11.118 | Tetrahydrothiopyran-3-yl | 2 | CH$_2$ | C=NOC$_2$H$_5$ | H | CH$_3$ |
| 11.119 | Tetrahydrothiopyran-3-yl | 2 | (CH$_2$)$_2$ | C=NOC$_2$H$_5$ | H | CH$_3$ |
| 11.120 | Tetrahydrothiopyran-3-yl | 0 | (CH$_2$)$_2$ | C=NOC$_2$H$_5$ | H | CH$_3$ |
| 11.121 | Tetrahydrothiopyran-3-yl | 2 | CH$_2$ | C=NOiPr | H | CH$_3$ |
| 11.122 | Tetrahydrothiopyran-3-yl | 2 | (CH$_2$)$_2$ | C=NOiPr | H | CH$_3$ |
| 11.123 | Tetrahydrothiopyran-3-yl | 0 | (CH$_2$)$_2$ | C=NOiPr | H | CH$_3$ |
| 11.124 | 1-Methylthiocyclopropyl | 2 | CH$_2$ | C=O | H | CH$_3$ |
| 11.125 | 1-Methylthiocyclopropyl | 0 | (CH$_2$)$_2$ | C=O | H | CH$_3$ |
| 11.126 | 1-Methylthiocyclopropyl | 2 | (CH$_2$)$_2$ | C=O | H | CH$_3$ |
| 11.127 | 1-Methylthiocyclopropyl | 2 | CH$_2$ | CHOCH$_3$ | H | CH$_3$ |
| 11.128 | 1-Methylthiocyclopropyl | 0 | (CH$_2$)$_2$ | CHOCH$_3$ | H | CH$_3$ |

TABLE 11-continued

Compounds of the formula

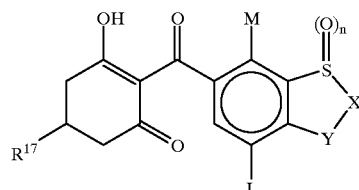

| No. | R[17] | n | X | Y | L | M |
|---|---|---|---|---|---|---|
| 11.129 | 1-Methylthiocyclopropyl | 2 | (CH$_2$)$_2$ | CHOCH$_3$ | H | CH$_3$ |
| 11.130 | 1-Methylthiocyclopropyl | 2 | CH$_2$ | CHOC$_2$H$_5$ | H | CH$_3$ |
| 11.131 | 1-Methylthiocyclopropyl | 2 | (CH$_2$)$_2$ | CHOC$_2$H$_5$ | H | CH$_3$ |
| 11.132 | 1-Methylthiocyclopropyl | 0 | (CH$_2$)$_2$ | CHOC$_2$H$_5$ | H | CH$_3$ |
| 11.133 | 1-Methylthiocyclopropyl | 2 | CH$_2$ | CHOiPr | H | CH$_3$ |
| 11.134 | 1-Methylthiocyclopropyl | 0 | (CH$_2$)$_2$ | CHOiPr | H | CH$_3$ |
| 11.135 | 1-Methylthiocyclopropyl | 2 | (CH$_2$)$_2$ | CHOiPr | H | CH$_3$ |
| 11.136 | 1-Methylthiocyclopropyl | 2 | CH$_2$ | C=NOCH$_3$ | H | CH$_3$ |
| 11.137 | 1-Methylthiocyclopropyl | 2 | (CH$_2$)$_2$ | C=NOCH$_3$ | H | CH$_3$ |
| 11.138 | 1-Methylthiocyclopropyl | 0 | (CH$_2$)$_2$ | C=NOCH$_3$ | H | CH$_3$ |
| 11.139 | 1-Methylthiocyclopropyl | 2 | CH$_2$ | C=NOC$_2$H$_5$ | H | CH$_3$ |
| 11.140 | 1-Methylthiocyclopropyl | 2 | (CH$_2$)$_2$ | C=NOC$_2$H$_5$ | H | CH$_3$ |
| 11.141 | 1-Methylthiocyclopropyl | 0 | (CH$_2$)$_2$ | C=NOC$_2$H$_5$ | H | CH$_3$ |
| 11.142 | 1-Methylthiocyclopropyl | 2 | CH$_2$ | C=NOiPr | H | CH$_3$ |
| 11.143 | 1-Methylthiocyclopropyl | 2 | (CH$_2$)$_2$ | C=NOiPr | H | CH$_3$ |
| 11.144 | 1-Methylthiocyclopropyl | 0 | (CH$_2$)$_2$ | C=NOiPr | H | CH$_3$ |
| 11.145 | (Dimethoxy)methyl | 2 | CH$_2$ | C=O | H | CH$_3$ |
| 11.146 | (Dimethoxy)methyl | 0 | (CH$_2$)$_2$ | C=O | H | CH$_3$ |
| 11.147 | (Dimethoxy)methyl | 2 | (CH$_2$)$_2$ | C=O | H | CH$_3$ |
| 11.148 | (Dimethoxy)methyl | 2 | CH$_2$ | CHOCH$_3$ | H | CH$_3$ |
| 11.149 | (Dimethoxy)methyl | 0 | (CH$_2$)$_2$ | CHOCH$_3$ | H | CH$_3$ |
| 11.150 | (Dimethoxy)methyl | 2 | (CH$_2$)$_2$ | CHOCH$_3$ | H | CH$_3$ |
| 11.151 | (Dimethoxy)methyl | 2 | CH$_2$ | CHOC$_2$H$_5$ | H | CH$_3$ |
| 11.152 | (Dimethoxy)methyl | 0 | (CH$_2$)$_2$ | CHOC$_2$H$_5$ | H | CH$_3$ |
| 11.153 | (Dimethoxy)methyl | 2 | (CH$_2$)$_2$ | CHOC$_2$H$_5$ | H | CH$_3$ |
| 11.154 | (Dimethoxy)methyl | 2 | CH$_2$ | CHOiPr | H | CH$_3$ |
| 11.155 | (Dimethoxy)methyl | 0 | (CH$_2$)$_2$ | CHOiPr | H | CH$_3$ |
| 11.156 | (Dimethoxy)methyl | 2 | (CH$_2$)$_2$ | CHOiPr | H | CH$_3$ |
| 11.157 | (Dimethoxy)methyl | 2 | CH$_2$ | C=NOCH$_3$ | H | CH$_3$ |
| 11.158 | (Dimethoxy)methyl | 2 | (CH$_2$)$_2$ | C=NOCH$_3$ | H | CH$_3$ |
| 11.159 | (Dimethoxy)methyl | 0 | (CH$_2$)$_2$ | C=NOCH$_3$ | H | CH$_3$ |
| 11.160 | (Dimethoxy)methyl | 2 | CH$_2$ | C=NOC$_2$H$_5$ | H | CH$_3$ |
| 11.161 | (Dimethoxy)methyl | 2 | (CH$_2$)$_2$ | C=NOC$_2$H$_5$ | H | CH$_3$ |
| 11.162 | (Dimethoxy)methyl | 0 | (CH$_2$)$_2$ | C=NOC$_2$H$_5$ | H | CH$_3$ |
| 11.163 | (Dimethoxy)methyl | 2 | CH$_2$ | C=NOiPr | H | CH$_3$ |
| 11.164 | (Dimethoxy)methyl | 2 | (CH$_2$)$_2$ | C=NOiPr | H | CH$_3$ |
| 11.165 | (Dimethoxy)methyl | 0 | (CH$_2$)$_2$ | C=NOiPr | H | CH$_3$ |

PREPARATION EXAMPLES

A) Preparation of the Starting Materials and Intermediates 1. 3-Thio-2-methylbenzoic Acid 100 g (0.66 mol) of 3-amino-2-methylbenzoic acid are initially introduced together with 270 g of ice and 127 ml of concentrated hydrochloric acid. 45.7 g (0.66 mol) of sodium nitrite in 270 ml of water are then added dropwise at 0–10° C.

In a second vessel, 84.2 g (0.79 mol) of sodium carbonate and 106 g (0.66 mol) of potassium methylxanthate are dissolved in 450 ml of water and heated to 60–70° C. The diazonium solution is cautiously added dropwise. The mixture is subsequently stirred for 1 hour. 106 g (2.65 mol) of sodium hydroxide in 270 ml of water are then added, the mixture is stirred for a further 2 hours, the solution is rendered acidic using hydrochloric acid and the resulting precipitate is filtered off with suction. The solid is washed with water and dried.

Yield: 110 g (100% of theory) of 3-thio-2-methylbenzoic acid; melting point 155° C. $^1$H-NMR (d$^6$-DMSO): δ [ppm]= 13.0 (1H, bs), 7.7 (2H, m), 7.3 (1H, tr), 2.4 (3H, s).

2. Methyl 3-thio-2-methylbenzoate [sic]

110 g (0.66 mol) of 3-thio-2-methylbenzoic acid are dissolved in 1.6 l of methanol which contains 5% sulfuric acid and the mixture is refluxed for 5 hours. The alcohol is then distilled off, the residue is taken up in ethyl acetate, and the organic phase is washed with water and with sodium carbonate, dried using sodium sulfate and concentrated.

Yield: 104 g (87% of theory) of methyl 3-thio-2-methylbenzoate; $^1$H-NMR (CDCl$_3$):δ [ppm]=7.6 (1H, d), 7.4 (1H, d), 7.1 (1H, d), 3.9 (3H, s), 3.4 (1H, s), 2.5 (3H, s).

3. Methyl 3-thio(2'-propionic acid)-2-methylbenzoate

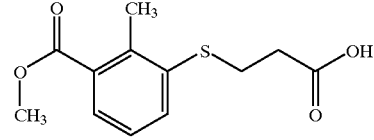

70 g (0.38 mol) of methyl 3-thio-2-methylbenzoate are dissolved in 400 ml of water and refluxed for 7 hours with 30.8 g (0.77 mol) of sodium hydroxide solution and 58.8 g (0.45 mol) of bromopropionic acid. After cooling, the aqueous phase is washed with methyl tert-butyl ether. The aqueous phase is then acidified with 2 N hydrochloric acid, the resulting precipitate is filtered off with suction and washed with water, and the product is dried.

Yield: 75.5 g (78% of theory) of methyl 3-thiopropionic acid-2-methylbenzoate; $^1$H-NMR (CDCl$_3$): δ [ppm]=7.66 (1H, d), 7.51 (1H, d), 7.20 (1H, tr), 3.96 (3H, s), 3.18 (2H, tr), 2.70 (2H, tr), 2.63 (3H, s).

4. Methyl 8-methylthiochroman-4-one-7-carboxylate

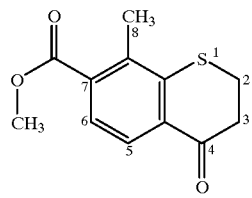

4 g (15.8 mmol) of methyl 3-thiopropionic acid-2-methylbenzoate are stirred at 70° C. for 15 minutes in 40 g of polyphosphoric acid. The reaction solution is then added to ice-water and the resulting precipitate is filtered off with suction. The product is washed with water and dried in a drying cabinet. As a by-product of the cyclization, methyl 8-methylthiochromen-4-one-carboxylate can be formed, which can be separated off by chromatography.

Yield: 3.1 g (83% of theory) of methyl 8-methylthiochroman-4-one-7-carboxylate; $^1$H-NMR (CDCl$_3$): δ [ppm]=8.00 (1H, d), 7.30 (1H, d), 3.94 (3H, s), 3.15 (2H, m), 2.98 (2H, m), 2.50 (3H, s);

Secondary component: methyl 8-methylthiochromen-4-one-carboxylate: $^1$H-NMR (CDCl$_3$): δ [ppm]=8.4 (1H, d), 7.9 (1H, d), 7.8 (1H, d), 7.0 (1H, d), 4.0 (3H, s), 2.7 (3H, s).

5. 8-Methylthiochroman-4-one-7-carboxylic acid 41.1 g (0.17 mol) of methyl 8-methylthiochroman-4-one-7-carboxylate are hydrolyzed under reflux with 10.3 g (0.26 mol) of NaOH in a mixture of 400 ml of water and methanol. The methanol is then distilled off and the residue is diluted with water and acidifed with 2N hydrochloric acid. The useful product precipitates out and is filtered off with suction, washed with water and dried.

Yield: 34.4 g (89% of theory) of 8-methylthiochroman-4-one-7-carboxylic acid; melting point: 243–246° C.

6. 8-Methyl-1,1-dioxothiochroman-4-one-7-carboxylic acid

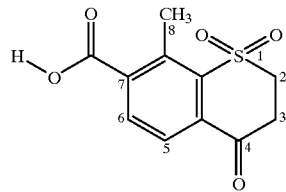

20 g (0.09 mol) of 8-methylthiochroman-4-one-7-carboxylic acid are dissolved in 100 ml of acetic acid. A spatula tipful of sodium tungstate is added. 24.9 g (0.22 mol) of 30% strength hydrogen peroxide solution are then added dropwise at 50° C. The mixture is subsequently stirred at about 20° C. for 1 hour. The reaction solution is then added to water, a precipitate being formed which is filtered off with suction. After washing the product with water, it is dried.

Yield: 18.4 g (80% of theory) of 8-methyl-1,1-dioxothiochroman-4-one-7-carboxylic acid; melting point: 224–225° C.

7. Methyl 4-hydroxy-8-methylthiochroman-7-carboxylate

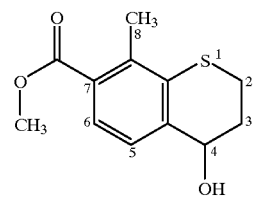

30 g (0.127 mol) of methyl 8-methylthiochroman-4-one-7-carboxylate are dissolved in a mixture of 120 ml of methylene chloride and 60 ml of methanol and cooled to 0–5° C. 2.4 g (0.064 mol) of sodium borohydride are then added in portions. The mixture is subsequently stirred at this temperature for 1 hour, and 200 ml of 2N hydrochloric acid are added to the reaction solution. Two phases are formed. The organic phase is separated off and dried, and the solvent is removed by distillation. The crude product is directly reacted further without further purification.

Yield: 27.6 g (91% of theory) of methyl 4-hydroxy-8-methylthiochroman-7-carboxylate.

8. Methyl 4-ethoxy-8-methylthiochroman-7-carboxylate 13.8 g (0.058 mol) of methyl 4-hydroxy-8-methylthiochroman-7-carboxylate are heated at boiling point for 4 hours in 60 ml of ethanol with addition of 1 g of sulfuric acid. The solvent is then distilled off and the residue is taken up with water. The aqueous phase is extracted with ethyl acetate. The organic phase is washed with sodium hydrogen carbonate solution, dried and concentrated. The product is purified by chromatography.

Yield: 10.1 g (60% of theory) of methyl 4-ethoxy-8-methylthiochroman-7-carboxylate; $^1$H-NMR (CDCl$_3$): δ [ppm]=7.44 (1H, d), 7.13 (1H, d), 4.40 (1H, m), 3.90 (3H, s), 3.60 (2H, m), 3.38 (1 H, dtr), 2.90 (1H, m), 2.50 (3H, g), 2.40 (1H, m), 1.98 (1H, m), 1.10 (3H, tr).

The reaction to give methyl 4-methoxy-8-methylthiochroman-4-one-7-carboxylate and methyl 4-isopropoxy-8-methylthiochroman-4-one-7-carboxylate is carried out analogously to the above procedure, in the case of methyl 4-methoxy-8-methylthiochroman-4-one-7-carboxylate ethanol being replaced by methanol and in the case of methyl 4-isopropoxy-8-methylthiochroman-4-one-7-carboxylate ethanol being replaced by isopropanol.

9. 4-Ethoxy-8-methylthiochroman-7-carboxylic acid 2.1 g of sodium hydroxide solution are dissolved in 20 ml of water. Methyl 4-ethoxy-8-methylthiochroman-4-one-7-carboxylate dissolved in 20 ml of methanol is added dropwise at about 20° C. The mixture is refluxed for 2 hours. The solvent is then distilled off and the residue is added to 2N hydrochloric acid. The aqueous phase is extracted with methylene chloride and the organic phase is dried and concentrated.

Yield: 9.3 g (100% of theory) of 4-ethoxy-8-methylthiochroman-7-carboxylic acid; melting point: 89–98° C.

Hydrolysis of the corresponding esters to 4-ethoxy-8-methylthiochroman-7-carboxylic acid and 4-isopropoxy-8-methylthiochroman-7-carboxylic acid proceeds in a similar manner. The same applies to the hydrolysis of the corresponding benzo[b]thiophene derivatives shown below.

10. 8-Methyl-4-ethoxy-1,1-dioxothiochroman-7-carboxylic acid 8.4 g (0.033 mol) of 4-ethoxy-8-methylthiochroman-7-carboxylic acid are initially introduced in 60 ml of acetic acid. A spatula tipful of sodium tungstate is added. 7.9 g (0.07 mol) is of 30% strength hydrogen peroxide solution are slowly added dropwise at 50° C. and the reaction mixture is subsequently stirred for 2 hours. It is then poured into water and the aqueous phase is extracted with ethyl acetate. The organic phase is washed with bisulfite solution, then dried and concentrated.

Yield: 9.5 g (100% of theory) of 8-methyl-4-ethoxy-1,1-dioxothiochroman-7-carboxylic acid; melting point: 150° C.

11. 8-Methylthiochroman-4-one-7-carboxylic acid O-ethyl oxime

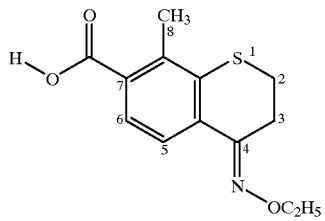

0.88 g (9 mmol) of ethylhydroxylamine is initially introduced in 20 ml of methanol. 0.62 g (4.5 mmol) of potassium carbonate is then added, followed by 2.0 g (9 mmol) of 8-methylthiochroman-4-one-7-carboxylic acid. The reaction is stirred at about 20° C. for 10 days. It is worked up by addition of water and 2N hydrochloric acid, and the resulting precipitate is filtered of f with suction and dried.

Yield: 2.2 g (92% of theory) of 8-methylthiochroman-4-one-7-carboxylic acid O-ethyl oxime; melting point: 166° C.

12. 8-Methyl-1,1-dioxothiochroman-4-one-7-carboxylic acid O-ethyl oxime 3.0 g (0.011 mol) of 8-methylthiochroman-4-one-7-carboxylic acid O-ethyl oxime are initially introduced into 30 ml of acetic acid together with a spatula tipful of sodium tungstate. 2.8 g (0.024 mol) of 30% strength hydrogen peroxide solution are added dropwise at 50° C. After stirring for 1 hour, the reaction mixture is poured into ice-water and the resulting precipitate is filtered off with suction. The product is washed with water and dried.

Yield: 2.5 g (74% of theory) of 8-methyl-1,1-dioxothiochroman-4-one-7-carboxylic acid O-ethyl oxime; melting point 198° C.

13. 8-Methyl-1-oxothiochroman-4-one-7-carboxylic Acid 7.0 g (31.5 mmol) of 8-methylthiochroman-4-one-7-carboxylic acid are initially introduced into 70 ml of acetic acid together with a spatula tipful of sodium tungstate. 3.6 g (31.5 mmol) of 30% strength hydrogen peroxide solution are added dropwise at 50° C. and the reaction solution is subsequently stirred for 3 hours. It is then stirred into water and the product is extracted with ethyl acetate. The organic phase is dried and the solvent is removed. The product is purified by chromatography.

Yield: 5.4 g (72% of theory) of 8-methyl-1-oxothiochroman-4-one-7-carboxylic acid; $^1$H-NMR (d$^6$-DMSO): δ [ppm]=8.0 (2H, m), 3.5 (3H, m), 2.8 (1H, m), 2.7 (3H, s).

14. Methyl 3-carboxymethylthio-2-methylbenzoate

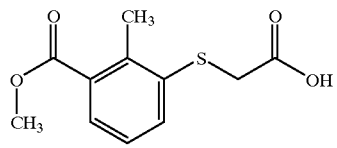

12.4 g (0.068 mmol) of methyl 3-mercapto-2-methylbenzoate in 80 ml of dimethylformamide are added dropwise to 1.6 g (0.068 mol) of sodium hydride in 40 ml of dimethylformamide and the mixture is stirred at about 20° C. for 60 min. 8 g (0.068 mol) of chloroacetic acid are then added and the mixture is stirred at about 20° C. for 4 hours.

The reaction mixture is worked up by stirring it into ice-water containing hydrochloric acid.

The resulting precipitate is filtered off with suction, washed with water and dried.

Yield: 14.6 g (89% of theory) of methyl 3-carboxymethylthio-2-methylbenzoate; $^1$H-NMR (d$^6$-DMSO): δ [ppm]=7.55 (1H, d), 7.45 (1H, d), 7.21 (1H, tr), 3.82 (2H, s), 2.50 (3H, s).

15. Methyl 7-methylbenzo[b]thiophene-3[2H]-one-6-carboxylate

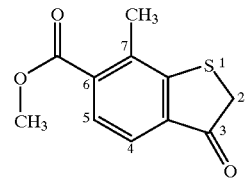

14.3 g (0.06 mmol) of 3-carboxymethylthio-2-methylbenzoic acid are dissolved in 300 ml of methylene chloride and 13.1 g (0.11 mmol) of thionyl chloride are added dropwise. The mixture is refluxed for 1 hour and the solvent and excess thionyl chloride are then distilled off. The residue is taken up in 100 ml of methylene chloride and treated with 31.8 g (0.24 mmol) of aluminum trichloride. The reaction is stirred at about 20° C. for 1 hour. The mixture is then added to ice-water and the organic phase is separated off. After washing and drying the organic phase, the solvent is removed. The product is reacted further without purification.

Yield: 12.9 g (97% of theory) of methyl 7-methylbenzo[b]thiophene-3[2H]-one-6-carboxylate; $^1$H-NMR (CDCl$_3$): δ [ppm]=7.65 (2H, m), 3.93 (3H, s), 3.88 (2H, s), 2.50 (3H, s).

16. Methyl 7-methyl-3-hydroxybenzo[b]thiophene-[2H]-6-carboxylate

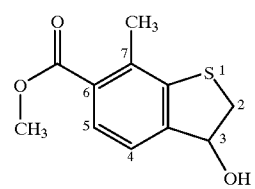

12.8 g (0.058 mol) of methyl 7-methylbenzo[b]thiophene-3[2H]-one-6-carboxylate are dissolved in 120 ml of methylene chloride and 60 ml of methanol and cooled to 0° C. 1.1 g (0.029 mol) of sodium borohydride is added in portions and the mixture is stirred for 3 hours. The reaction is terminated by adding water. The phases are separated and the aqueous phase is extracted with methylene chloride. The combined organic phases are dried and the solvent is distilled off. The crude product is reacted further.

Yield: 13.2 g (100% of theory) of methyl 7-methyl-3-hydroxybenzo[b]-thiophene-[2H]-6-carboxylate; $^1$H-NMR (CDCl$_3$): δ [ppm]=7.6 (2H, m), 5.3 (1H, m), 3.9 (3H, s), 3.7 (1H, m), 3.3 (1H, m), 2.4 (3H, s).

17. Methyl 7-methyl-3-methoxybenzo[b]thiophene-[2H]-6-carboxylate 2.4 g (0.059 mol) of NaH is dissolved in 50 ml of dimethylformamide. 13.2 g of methyl 7-methyl-3- hydroxybenzo[b]thiophene-[2H]-6-carboxylate dissolved in 50 ml are added dropwise and the mixture is subsequently stirred at about 20° C. for 2 hours. 8.4 g (0.059 mol) of iodomethane are then added and the mixture is stirred for a further 2 hours. The reaction solution is added to ice-water and extracted with ethyl acetate. The organic phase is dried and subsequently concentrated, and the product is purified by chromatography.

Yield: 3.5 g (25% of theory) of methyl 7-methyl-3-methoxybenzo[b]thiophene-[2H]-6-carboxylate; $^1$H-NMR (CDCl$_3$): δ [ppm]=7.60 (1H, d), 7.20 (1H, d), 5.04 (1H, m), 3.90 (3H, s),3.56 (1H, m), 3.40 (3H, s), 3.38 (1H, m), 2.50 (3H, s).

Similarly to the hydrolysis of the thiochromanone esters described above, the corresponding benzothiophene acids are also obtained.

The compounds shown in the following tables are obtained in a similar manner:

TABLE 12

Intermediates

| No. | T | n | X | Y | L | M | Physical data |
|---|---|---|---|---|---|---|---|
| 12.1 | HO | 0 | (CH$_2$)$_2$ | C=O | H | H | m.p. [° C.]: 226–231 |
| 12.2 | HO | 2 | (CH$_2$)$_2$ | C=O | H | H | m.p. [° C.]: 217–220 |
| 12.3 | HO | 0 | (CH$_2$)$_2$ | C=O | H | CH$_3$ | m.p. [° C.]: 243–246 |
| 12.4 | HO | 2 | (CH$_2$)$_2$ | C=O | H | CH$_3$ | m.p. [° C.]: 224–225 |
| 12.5 | HO | 0 | (CH$_2$)$_2$ | CHOCH$_3$ | H | CH$_3$ | m.p. [° C.]: 117–118 |
| 12.6 | HO | 2 | (CH$_2$)$_2$ | CHOCH$_3$ | H | CH$_3$ | m.p. [° C.]: 167–172 |
| 12.7 | HO | 0 | (CH$_2$)$_2$ | CHOC$_2$H$_5$ | H | CH$_3$ | m.p. [° C.]: 89–98 |
| 12.8 | HO | 2 | (CH$_2$)$_2$ | CHOC$_2$H$_5$ | H | CH$_3$ | m.p. [° C.]: 150 |
| 12.9 | HO | 0 | (CH$_2$)$_2$ | CHOiPropyl | H | CH$_3$ | m.p. [° C.]: 138 |
| 12.10 | HO | 2 | (CH$_2$)$_2$ | CHOiPropyl | H | CH$_3$ | m.p. [° C.]: 142 |
| 12.11 | HO | 0 | (CH$_2$)$_2$ | C=NOC$_2$H$_5$ | H | CH$_3$ | m.p. [° C.]: 166 |
| 12.12 | HO | 2 | (CH$_2$)$_2$ | C=NOC$_2$H$_5$ | H | CH$_3$ | m.p. [° C.]: 198 |
| 12.13 | HO | 0 | (CH$_2$)$_2$ | C=NOCH$_2$CH=CHCl | H | CH$_3$ | m.p. [° C.]: 163 |
| 12.14 | HO | 2 | (CH$_2$)$_2$ | C=NOCH$_2$CH=CHCl | H | CH$_3$ | m.p. [° C.]: 174 |
| 12.15 | HO | 0 | (CH$_2$)$_2$ | C=NOCH$_2$C$_6$H$_5$ | H | CH$_3$ | m.p. [° C.]: 178 |
| 12.16 | HO | 2 | (CH$_2$)$_2$ | C=NO-tButyl | H | CH$_3$ | m.p. [° C.]: 217 |
| 12.17 | H$_3$CO | 0 | (CH$_2$)$_2$ | C(CH$_3$)$_2$ | H | CH$_3$ | m.p. [° C.]: 63–65 |
| 12.18 | HO | 2 | (CH$_2$)$_2$ | CHOCH$_3$ | H | Cl | m.p. [° C.]: 137–139 |
| 12.19 | HO | 2 | (CH$_2$)$_2$ | C=NOC$_2$H$_5$ | H | Cl | m.p. [° C.]: 205 |
| 12.20 | HO | 0 | (CH$_2$) | CHOCH$_3$ | H | CH$_3$ | $^1$H-NMR, 300 MHz (d$^6$-DMSO): δ [ppm] = 13.0 (1H, s), 7.55 (1H, d), 7.25 (1H, d), 5.10 (1H, s), 3.62 (1H, m), 3.42 (1H, m), 3.41 (3H, s), 2.42 (3H, s) |
| 12.21 | HO | 2 | (CH$_2$) | CHOCH$_3$ | H | CH$_3$ | $^1$H-NMR, 300 MHz (d$^6$-DMSO): δ [ppm] = 13.5 (1H, bs), 8.10 (1H, d), 7.60 (1H, d), 5.18 (1H, m), 4.07 (1H, m), 3.75 (1H, m), 3.40 (3H, s), 2.70 (3H, s) |
| 12.22 | HO | 2 | (CH$_2$)$_2$ | C=O | H | Cl | $^1$H-NMR, 300 MHz (d$^6$-DMSO): δ [ppm] = 14.2 (1H, bs), 8.10 (1H, d), 7.98 (1H, d), 4.13 (2H, m), 3.30 (2H, m) |
| 12.23 | HO | 0 | (CH$_2$)$_2$ | C=O | H | Cl | $^1$H-NMR, 300 MHz (d$^6$-DMSO): δ [ppm] = 13.9 (1H, bs), 8.10 (1H, d), 7.52 (1H, d), 3.41 (2H, m), 2.90 (2H, m) |
| 12.24 | H$_3$CO | 0 | (CH$_2$)$_2$ | CHOCH$_3$ | H | CH$_3$ | $^1$H-NMR, 400 MHz (CDCl$_3$): δ [ppm] = 7.46, 7.13, 4.28, 3.87, 3.38, 3.30, 2.90, 2.48, 2.39, 1.91 |
| 12.25 | H$_3$CO | 0 | (CH$_2$)$_2$ | CHOC$_2$H$_5$ | H | CH$_3$ | m.p. [° C.]: 94–98 |
| 12.26 | H$_3$CO | 0 | (CH$_2$)$_2$ | CHOiPropyl | H | CH$_3$ | $^1$H-NMR, 250 MHz (CDCl$_3$): δ [ppm] = 7.47, 7.17, 4.48, 3.88, 3.79, 3.29, 2.90, 2.48, 2.29, 1.97, 1.21 |
| 12.27 | HO | 1 | (CH$_2$)$_2$ | C=O | H | CH$_3$ | m.p. [° C.]: 98 (decomp.) |
| 12.28 | H$_3$CO | 0 | CH=CH | C=O | H | CH$_3$ | m.p. [° C.]: 128–130 |

TABLE 12-continued

Intermediates

| No. | T | n | X | Y | L | M | Physical data |
|---|---|---|---|---|---|---|---|
| 12.29 | HO | 0 | CH=CH | C=O | H | $CH_3$ | $^1$H-NMR, 250 MHz ($d^6$-DMSO): δ [ppm] = 13.52, 8.48, 8.30, 7.87, 7.03, 2.66 |
| 12.30 | HO | 0 | $(CH_2)_2$ | C=NO-tButyl | H | $CH_3$ | m.p. [° C.]: 217 |
| 12.31 | HO | 2 | $(CH_2)_2$ | C=NOC$_2$H$_5$ | H | Cl | m.p. [° C.]: 205 |
| 12.32 | HO | 0 | $(CH_2)_2$ | C(CH$_3$)$_2$ | H | $CH_3$ | m.p. [° C.]: 212 |
| 12.33 | HO | 0 | $(CH_2)_2$ | $CH_2$ | H | $CH_3$ | m.p. [° C.]: 155 |
| 12.34 | HO | 0 | $(CH_2)_2$ | CH(C$_6$H$_5$) | H | $CH_3$ | m.p. [° C.]: 175 |
| 12.35 | HO | 2 | $(CH_2)_2$ | $CH_2$ | H | $CH_3$ | m.p. [° C.]: 204 |
| 12.36 | $H_3$CO | 0 | $(CH_2)_2$ | CH(C$_6$H$_5$) | H | $CH_3$ | m.p. [° C.]: 103 |
| 12.37 | HO | 2 | $(CH_2)_2$ | CH(C$_6$H$_5$) | H | $CH_3$ | m.p. [° C.]: 145 |
| 12.38 | HO | 0 | $(CH_2)_2$ | CHSC$_6$H$_5$ | H | $CH_3$ | m.p. [° C.]: 77 |
| 12.39 | HO | 2 | $(CH_2)_2$ | CHSO2C$_6$H$_5$ | H | $CH_3$ | m.p. [° C.]: 239 |
| 12.40 | HO | 0 | $(CH_2)_2$ | C=O | Cl | Cl | $^1$H-NMR, 250 MHz (CDCl$_3$): δ [ppm] = 7.69, 3.31, 3.01 |
| 12.41 | HO | 2 | $(CH_2)_2$ | C=O | Cl | Cl | $^1$H-NMR, 250 MHz ($d^6$-DMSO): δ [ppm]= 8.04, 4.16, 3.31 |
| 12.42 | $H_3$CO | 0 | $(CH_2)_2$ | CHOH | Cl | Cl | $^1$H-NMR, 250 MHz (CDCl$_3$): δ [ppm] = 7.50, 5.20, 4.92, 3.36, 2.89, 2.53, 1.85 |
| 12.43 | HO | 2 | $(CH_2)_2$ | CHOI | Cl | Cl | $^1$H-NMR, 250 MHz ($d^6$-DMSO): δ [ppm] = 8.03, 6.96, 5.08, 3.87, 3.62, 2.54, 2.37 |
| 12.44 | HO | 0 | $(CH_2)_2$ | CHOH | H | $CH_3$ | m.p. [° C.]: 209 |

TABLE 12a

Intermediates

| No. | T | n | $R^{12}$ | $R^{13}$ | $R^{21}$ | $R^{22}$ | Y | L | M | Physical data |
|---|---|---|---|---|---|---|---|---|---|---|
| 12.45 | $H_3$CO | 0 | $CH_3$ | $CH_3$ | H | H | C=O | H | $CH_3$ | $^1$H-NMR, 270 MHz (CDCl$_3$): δ [ppm] = 8.02, 7.50, 3.92, 3.09, 2.50, 1.33 |
| 12.46 | $H_3$CO | 0 | H | $CH_3$ | H | H | C=O | H | $CH_3$ | m.p. [° C.]: 79 |
| 12.47 | $H_3$CO | 0 | $CH_3$ | $CH_3$ | H | H | CHOCH$_3$ | H | $CH_3$ | $^1$H-NMR, 270 MHz (CDCl$_3$): δ [ppm] = 7.44, 7.02, 3.89, 3.59, 3.33, 3.28, 2.50, 2.48, 1.21, 0.88 |
| 12.48 | $H_3$CO | 0 | H | H | $CH_3$ | H | C=O | H | $CH_3$ | m.p. [° C.]: 83 |
| 12.49 | $H_3$CO | 0 | H | H | $CH_3$ | H | CHOCH$_3$ | H | $CH_3$ | $^1$H-NMR, 270 MHz (CDCl$_3$): δ [ppm] = 7.46, 7.11, 4.31, 3.89, 3.65, 3.37, 2.48, 2.44, 1.64, 1.44 |
| 12.50 | HO | 0 | H | $CH_3$ | H | H | CHOCH$_3$ | H | $CH_3$ | m.p. [° C.]: 124 |
| 12.51 | HO | 0 | $CH_3$ | $CH_3$ | H | H | CHOCH$_3$ | H | $CH_3$ | m.p. [° C.]: 168 |
| 12.52 | HO | 0 | H | H | $CH_3$ | H | CHOCH$_3$ | H | $CH_3$ | m.p. [° C.]: 145 |
| 12.53 | HO | 2 | H | $CH_3$ | H | H | CHOCH$_3$ (trans) | H | $CH_3$ | m.p. [° C.]: 184 |
| 12.54 | HO | 2 | $CH_3$ | $CH_3$ | H | H | CHOCH$_3$ | H | $CH_3$ | m.p. [° C.]: 161 |
| 12.55 | HO | 2 | H | H | $CH_3$ | H | CHOCH$_3$ | H | $CH_3$ | m.p. [° C.]: 182 |

Preparation of the Final Products
1. 2-(8-Methyl-1,1-dioxothiochroman-4-one-7-carbonyl)-1,3-cyclohexanedione

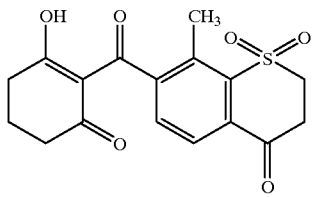

a) 17.4 g (0.0685 mol) of 8-methyl-1,1-dioxothiochroman-4-one-7-carboxylic acid are dissolved in 170 ml of toluene and treated with one drop of dimethylformamide, and 8.96 g (0.0753 mol) of thionyl chloride are added. After refluxing for 4 hours, the reaction mixture is concentrated. The reaction product is directly reacted further.

Yield: 18.6 g (99% of theory) of 8-methyl-1,1-dioxothiochroman-4-one-7-carbonyl chloride;

b) 0.62 g (5.5 mmol) of cyclohexane-1,3-dione is initially introduced into 10 ml of acetonitrile together with 0.56 g (5.5 mol) of triethylamine. 1.5 (5.5 mmol) of 8-methyl-1,1-dioxothiochroman-4-one-7-carbonyl chloride dissolved in 20 ml of acetonitrile are then added dropwise.

The mixture is subsequently stirred at about 20° C. for one hour. 0.31 g (3.7 mmol) of acetone cyanohydrin and 2.8 g (22.5 mmol) of triethylamine are then added and the mixture is stirred for 1 hour. For working-up, the reaction solution is stirred into 2N hydrochloric acid and the aqueous phase is extracted with ethyl acetate. The organic phase is then extracted with $Na_2CO_3$ solution and the alkaline aqueous phase is rendered acidic with cooling. The resulting precipitate is filtered off with suction, washed with water and dried.

Yield: 1.0 g (52% of theory) of 2-(8-methyl-1,1-dioxothiochroman-4-one-7-carbonyl)-1,3-cyclohexanedione melting point: 173–178° C.

2. 2-(8-Methyl-1,1-dioxothiochroman-4-one-7-carbonyl O-ethyl oxime)cyclohexane-1,3-dione

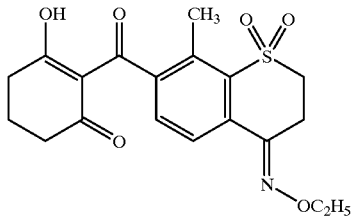

1.0 g (3.4 mmol) of 8-methyl-1,1-dioxochroman-4-one-7-carboxylic acid O-ethyl oxime is initially introduced into 10 ml of acetonitrile together with 0.39 g (3.5 mmol) of cyclohexane-1,3-dione, 0.75 g (3.6 mmol) of dicyclocarbodiimide (DCC) is added and the mixture is stirred for 2 hours. 0.1 ml of acetone cyanohydrin and 0.51 g (5.1 mmol) of triethylamine are then added and the reaction mixture is stirred for a further 2 hours. It is then stirred into sodium carbonate solution and extracted with ethyl acetate, and the organic phase is discarded. The aqueous phase is rendered acidic using hydrochloric acid and extracted again with ethyl acetate, the organic phase is dried and the solvent is distilled off. The product is purified by chromatography.

Yield: 600 mg (45% of theory) of 2-(8-methyl-1,1-dioxothiochroman-4-one-7-carbonyl O-ethyl oxime) cylohexane-1,3-dione; melting point: 143° C.

3. 2-(8-Methyl-4-ethoxy-1,1-dioxothiochroman-7-carbonyl)cyclohexane-1,3-dione

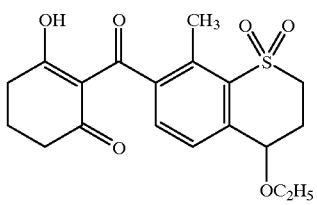

a) 8.8 g (0.031 mmol) of 8-methyl-4-ethoxy-1,1-dioxothiochroman-7-carboxylic acid are dissolved in 50 ml of toluene, the solution is treated with 2 drops of dimethylformamide and 4.4 g (0.04 mmol) of thionyl chloride are added. After refluxing for 4 hours, the reaction mixture is concentrated. The acid chloride is directly employed further.

b) 0.56 g of cyclohexane-1,3-dione is initially introduced into 10 ml of methylene chloride together with 0.47 g (6 mmol) of pyridine. 1.5 g (5 mmol) of the acid chloride from 3a) in 20 ml of methylene chloride are then added dropwise and the mixture is stirred for one hour. The reaction solution is added to water and rendered acidic with hydrochloric acid. The aqueous phase is extracted with ethyl acetate, the organic phase is dried and the solvent is removed.

Yield: 1.88 g (99% of theory) of O-acylated product.

c) 1.3 g (3.4 mmol) of the product from 3b are dissolved in 20 ml of acetonitrile. The reaction mixture is then treated with 0.19 g (2.3 mmol) of acetone cyanohydrin and 1.7 g (17.2 mmol) of triethylamine and stirred for 2 hours. It is then added to 2N hydrochloric acid and extracted with ethyl acetate. The organic phase is then washed with sodium carbonate solution and discarded. Finally, the alkaline aqueous phase is rendered acidic using hydrochloric acid. The resulting precipitate is filtered off with suction and dried.

Yield: 0.6 g (46% of theory) of 2-(8-methyl-4-ethoxy-1,1-dioxothiochroman-7-carbonyl)cyclohexane-1,3-dione; $^1$H-NMR ($CDCl_3$): δ ppm]=17.5 (1H, s), 7.30 (1H, d), 7.18 (1H, d), 4.47 (1H, m), 3.95–3.83 (1H, m), 3.70–3.50 (2H, m), 3.28 (1H, m), 2.81 (2H, tr), 2.71–2.50 (2H, m), 2.64 (3H,s), 2.43 (2H, tr), 2.05 (2H, m), 1.24 (3H, tr).

The compounds shown in the following tables are obtained in a similar manner:

TABLE 13

Compounds of the formula

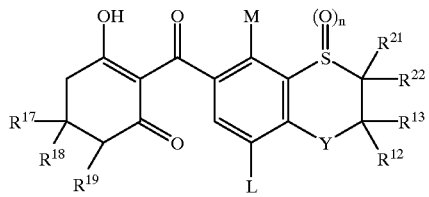

| No. | $R^{17}$ | $R^{18}$ | $R^{19}$ | n | $R^{12}$ | $R^{13}$ | $R^{21}$ | $R^{22}$ | Y | L | M | Physical data |
|---|---|---|---|---|---|---|---|---|---|---|---|---|
| 13.1 | CH₃ | CH₃ | H | 2 | H | H | H | H | C=O | H | H | m.p. [° C.]: 110 |
| 13.2 | CH₃ | H | H | 2 | H | H | H | H | C=O | H | CH₃ | m.p. [° C.]: 84–86 |
| 13.3 | H | H | H | 2 | H | H | H | H | C=O | H | CH₃ | m.p. [° C.]: 173–178 |
| 13.4 | CH₃ | CH₃ | H | 2 | H | H | H | H | C=O | H | CH₃ | m.p. [° C.]: 84–85 |
| 13.5 | H | H | H | 0 | H | H | H | H | C=O | H | CH₃ | m.p. [° C.]: 148–150 |
| 13.6 | CH₃ | H | H | 0 | H | H | H | H | C=O | H | CH₃ | m.p. [° C.]: 128–130 |
| 13.7 | CH₃ | CH₃ | H | 0 | H | H | H | H | C=O | H | CH₃ | NMR (CDCl₃), 300 MHz: δ [ppm] = 17.5 (1H, s), 8.06 (1H, d), 6.89 (1H, d), 3.25 (2H, m), 2.97 (2H, m), 2.68 (2H, s), 2.31 (2H, s), 2.19 (3H, s), 1.12 (6H, s) |
| 13.8 | H | H | H | 2 | H | H | H | H | C=O | H | H | m.p. [° C.]: 159–162 |
| 13.9 | CH₃ | H | H | 2 | H | H | H | H | C=O | H | H | m.p. [° C.]: 161–163 |
| 13.10 | CH₃ | CH₃ | H | 2 | H | H | H | H | CHOCH₃ | H | CH₃ | NMR (CDCl₃), 300 MHz: δ [ppm] = 17.5 (1H, s), 7.30 (1H, d), 7.19 (1H, d), 4.36 (1H, m), 3.41 (3H, s), 3.28 (1H, m), 2.70–2.59 (4H, m), 2.61 (3H, s), 2.30 (2H, m), 1.14 (6H, s) |
| 13.11 | H | H | H | 2 | H | H | H | H | CHOCH₃ | H | CH₃ | m.p. [° C.]: 80–84 |
| 13.12 | CH₃ | H | H | 2 | H | H | H | H | CHOCH₃ | H | CH₃ | m.p. [° C.]: 73 |
| 13.13 | H | H | H | 2 | H | H | H | H | CHOC₂H₅ | H | CH₃ | NMR (CDCl₃), 300 MHz: δ [ppm] = 17.5 (1H, s), 7.30 (1H, d), 7.18 (1H, d), 4.47 (1H, m), 3.95–3.83 (1H, m), 3.70–3.50 (2H, m), 3.28 (1H, m), 2.81 (2H, tr), 2.71–2.50 (2H, m), 2.64 (3H, s), 2.43 (2H, tr), 2.05 (2H, m), 1.24 (3H, tr) |
| 13.14 | CH₃ | H | H | 2 | H | H | H | H | CHOC₂H₅ | H | CH₃ | m.p. [° C.]: 68–72 |
| 13.15 | CH₃ | CH₃ | H | 2 | H | H | H | H | CHOC₂H₅ | H | CH₃ | NMR (CDCl₃), 300 MHz: δ [ppm] = 17.5 (1H, s), 7.31 (1H, d), 7.18 (1H, d), 4.47 (1H, m), 3.96–3.82 (1H, m), 3.69–3.50 (2H, m), 3.28 (1H, m), 2.81 (2H, tr), 2.72–2.49 (2H, m), 2.68 (2H, s), 2.60 (3H, s), 2.31 (2H, s), 1.24 (3H, tr), 1.11 (6H, s) |
| 13.16 | CH₃ | CH₃ | H | 2 | H | H | H | H | CHOiPropyl | H | CH₃ | m.p. [° C.]: 80–83 |
| 13.17 | H | H | H | 2 | H | H | H | H | CHOiPropyl | H | CH₃ | m.p. [° C.]: 144–146 |
| 13.18 | CH₃ | H | H | 2 | H | H | H | H | CHOiPropyl | H | CH₃ | m.p. [° C.]: 85 |
| 13.19 | H | H | H | 1 | H | H | H | H | C=O | H | CH₃ | NMR (CDCl₃), 300 MHz: δ [ppm] = 17.25 (1H, s), 8.14 (1H, d), 7.33 (1H, d), 3.90–3.57 (1H, m), 3.39–3.26 (1H, m), 2.99–2.79 (3H, m), 3.63 (3H, m), 2.44 (2H, tr), 2.13–2.03 (2H, m) |
| 13.20 | CH₃ | H | H | 1 | H | H | H | H | C=O | H | CH₃ | NMR (CDCl₃), 300 MHz: δ [ppm] = 17.25 (1H, s), 8.14 (1H, d), 7.33 (1H, d), 3.87 (1H, m), 3.69–3.58 (1H, m), 3.28 (1H, m), 2.96–2.79 (2H, m), 2.62 (3H, s), 2.57–2.44 (2H, m), 2.40–2.13 (2H, m), 1.15 (3H, d) |
| 13.21 | CH₃ | CH₃ | H | 1 | H | H | H | H | C=O | H | CH₃ | NMR (CDCl₃), 300 MHz: δ [ppm] = 17.30 (1H, m), 8.13 (1H, d), 7.34 (1H, d), 3.82 (1H, m), 3.64 (1H, m), 3.40–3.25 (1H, m), 2.91 (1H, m), 2.70 (2H, s), 2.64 (3H, s), 2.31 (2H, s), 1.15 (6H, s) |
| 13.22 | H | H | H | 2 | H | H | H | H | C=NOC₂H₅ | H | CH₃ | m.p. [° C.]: 143 |
| 13.23 | CH₃ | H | H | 2 | H | H | H | H | C=NOC₂H₅ | H | CH₃ | m.p. [° C.]: 62 |
| 13.24 | CH₃ | CH₃ | H | 2 | H | H | H | H | C=NOC₂H₅ | H | CH₃ | m.p. [° C.]: 75 |
| 13.25 | H | H | H | 2 | H | H | H | H | C=NOCH₂CH=CHCl | H | CH₃ | m.p. [° C.]: 75 |
| 13.26 | H | H | H | 2 | H | H | H | H | C=NOCH₂C₆H₅ | H | CH₃ | m.p. [° C.]: 192 |
| 13.27 | CH₃ | H | H | 2 | H | H | H | H | C=NOCH₂C₆H₅ | H | CH₃ | m.p. [° C.]: 143 |
| 13.28 | CH₃ | CH₃ | H | 2 | H | H | H | H | C=NOCH₂C₆H₅ | H | CH₃ | m.p. [° C.]: 126 |
| 13.29 | H | H | H | 2 | H | H | H | H | C=NO-tButyl | H | CH₃ | m.p. [° C.]: 98 |

TABLE 13-continued

Compounds of the formula

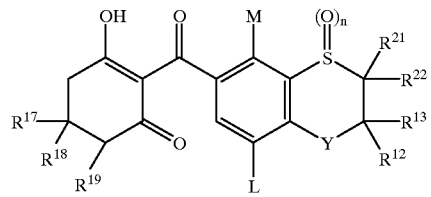

| No. | R17 | R18 | R19 | n | R12 | R13 | R21 | R22 | Y | L | M | Physical data |
|---|---|---|---|---|---|---|---|---|---|---|---|---|
| 13.30 | CH₃ | CH₃ | H | 2 | H | H | H | H | C=NO-tButyl | H | CH₃ | m.p. [° C.]: 91 |
| 13.31 | H | H | H | 2 | H | H | H | H | C=O | H | Cl | NMR (d⁶-DMSO), 300 MHz: δ [ppm] = 8.05 (1H, d), 7.69 (1H, d), 4.18 (2H, m), 3.31 (2H, m), 2.62 (4H, m), 1.96 (2H, m) |
| 13.32 | CH₃ | H | H | 2 | H | H | H | H | C=O | H | Cl | m.p. [° C.]: 66 |
| 13.33 | CH₃ | CH₃ | H | 2 | H | H | H | H | C=O | H | Cl | m.p. [° C.]: 104 |
| 13.34 | H | H | H | 2 | H | H | H | H | CHOCH₃ | H | Cl | m.p. [° C.]: 97 |
| 13.35 | CH₃ | H | H | 2 | H | H | H | H | CHOCH₃ | H | Cl | m.p. [° C.]: 86 |
| 13.36 | CH₃ | CH₃ | H | 2 | H | H | H | H | CHOCH₃ | H | Cl | m.p. [° C.]: 92 |
| 13.37 | H | H | H | 2 | H | H | H | H | C(CH₃)₂ | H | CH₃ | m.p. [° C.]: 165 |
| 13.38 | CH₃ | H | H | 2 | H | H | H | H | C(CH₃)₂ | H | CH₃ | m.p. [° C.]: 92 |
| 13.39 | CH₃ | CH₃ | H | 2 | H | H | H | H | C(CH₃)₂ | H | CH₃ | m.p. [° C.]: 107 |
| 13.40 | H | H | H | 2 | H | H | H | H | C=NOC₂H₅ | H | CH₃ | ¹H-NMR (CDCl₃), 250 MHz: δ [ppm] = 16.8, 8.20, 7.32, 4.33, 3.37, 2.82, 2.45, 2.08, 1.35 |
| 13.41 | H | H | H | 2 | H | H | H | H | CH₂ | H | CH₃ | m.p. [° C.]: 199 |
| 13.42 | H | H | H | 2 | H | CH₃ | H | H | CHOCH₃ (trans) | H | CH₃ | m.p. [° C.]: 95 (decomp.) |
| 13.43 | CH₃ | H | H | 2 | H | CH₃ | H | H | CHOCH₃ (trans) | H | CH₃ | m.p. [° C.]: 79–82 |
| 13.44 | CH₃ | CH₃ | H | 2 | H | CH₃ | H | H | CHOCH₃ (trans) | H | CH₃ | m.p. [° C.]: 136–137 |
| 13.45 | H | H | H | 2 | CH₃ | CH₃ | H | H | CHOCH₃ | H | CH₃ | m.p. [° C.]: 118 |
| 13.46 | CH₃ | H | H | 2 | CH₃ | CH₃ | H | H | CHOCH₃ | H | CH₃ | m.p. [° C.]: 110 |
| 13.47 | CH₃ | CH₃ | H | 2 | CH₃ | CH₃ | H | H | CHOCH₃ | H | CH₃ | m.p. [° C.]: 95 (decomp.) |
| 13.48 | H | H | H | 0 | H | H | H | H | CH(C₆H₅) | H | CH₃ | m.p. [° C.]: 81 |
| 13.49 | H | H | H | 2 | H | H | CH₃ | H | CHOCH₃ | H | CH₃ | m.p. [° C.]: 100 |
| 13.50 | CH₃ | H | H | 2 | H | H | CH₃ | H | CHOCH₃ | H | CH₃ | m.p. [° C.]: 86 |
| 13.51 | CH₃ | CH₃ | H | 2 | H | H | CH₃ | H | CHOCH₃ | H | CH₃ | m.p. [° C.]: 149 |
| 13.52 | H | H | H | 2 | H | H | H | H | CH(C₆H₅) | H | CH₃ | m.p. [° C.]: 124 |
| 13.53 | CH₃ | CH₃ | H | 2 | H | H | H | H | CH(C₆H₅) | H | CH₃ | m.p. [° C.]: 115 |
| 13.54 | H | H | H | 2 | H | H | H | H | CHNHOC₂H₅ | H | CH₃ | m.p. [° C.]: 98 |
| 13.55 | H | H | H | 2 | H | CH₃ | H | H | CHOCH₃ (cis) | H | CH₃ | m.p. [° C.]: 108 |
| 13.56 | CH₃ | CH₃ | H | 2 | H | H | H | H | CHSO₂C₆H₅ | H | CH₃ | m.p. [° C.]: 140 |
| 13.57 | H | H | H | 2 | H | H | H | H | CHSO₂C₆H₅ | H | CH₃ | m.p. [° C.]: 125 |
| 13.58 | CH₃ | CH₃ | H | 2 | H | H | H | H | CHOH | Cl | Cl | m.p. [° C.]: 88 |
| 13.59 | H | H | H | 2 | H | H | H | H | C(CH₃)₂ | Cl | Cl | m.p. [° C.]: 200 (decomp.) |

TABLE 14

Compounds of the formula

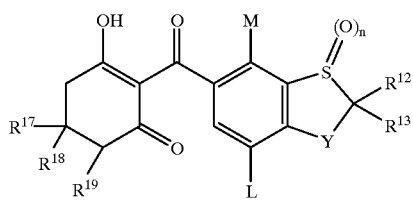

| No. | R17 | R18 | R19 | n | R12 | R13 | Y | L | M | Physical data m.p. [° C.] |
|---|---|---|---|---|---|---|---|---|---|---|
| 14.001 | H | H | H | 2 | H | H | CHOCH₃ | H | CH₃ | 70 |

TABLE 15

Compounds of the formula

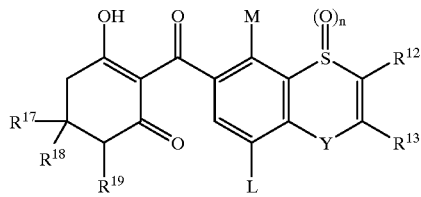

| No. | $R^{17}$ | $R^{18}$ | $R^{19}$ | n | $R^{12}$ | $R^{13}$ | Y | L | M | Physical data m.p. [° C.] |
|---|---|---|---|---|---|---|---|---|---|---|
| 15.1 | H | H | H | 0 | H | H | C=O | H | $CH_3$ | 184 |
| 15.2 | $CH_3$ | H | H | 0 | H | H | C=O | H | $CH_3$ | 178–180 |
| 15.3 | $CH_3$ | $CH_3$ | H | 0 | H | H | C=O | H | $CH_3$ | 198 |

TABLE 16

Compounds of the formula

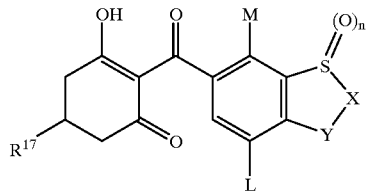

| No. | $R^3$ | n | X | Y | L | M | Physical data m.p. [° C.] |
|---|---|---|---|---|---|---|---|
| 16.1 | 1-Methylthiocyclopropyl | 0 | $(CH_2)_2$ | C=O | H | $CH_3$ | 151–153 |
| 16.2 | 1-Methylthiocyclopropyl | 2 | $(CH_2)_2$ | C=O | H | $CH_3$ | 133–135 |

The compounds I and their agriculturally utilizable salts are suitable as herbicides, both in the form of isomer mixtures and in pure isomer form. The isomer-containing herbicidal compositions provide highly effective control of plant growth on uncultivated areas, in particular at high application rates. They act against broad-leaved weeds and grass weeds in crops such as wheat, rice, maize, soybeans and cotton without significantly harming the crop plants. This effect occurs especially at low application rates.

In consideration of the versatility of the application methods, the compounds I or compositions containing them can additionally be employed in a further number of crop plants for the elimination of undesired plants. Suitable crops, for example, are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa, Phaseolus lunatus, Phaseolus vulgaris, Picea abies, Pinus spec., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays.

Moreover, the compounds I can also be used in crops which are tolerant to the action of herbicides as a result of breeding, including genetic engineering methods.

The compounds I and the herbicidal compositions containing them can be applied by spraying, atomizing, dusting, scattering or watering, for example in the form of directly sprayable aqueous solutions, powders, suspensions, even high-percentage aqueous, oily or other suspensions, or dispersions, emulsions, oil dispersions, pastes, dusting compositions, scattering compositions or granules. The application forms depend on the intended uses; in each case they should if possible ensure the finest dispersion of the active compounds according to the invention.

Suitable inert additives are mineral oil fractions of medium to high boiling point, such as kerosene or diesel oil, further coal tar oils and oils of vegetable or animal origin, aliphatic, cyclic and aromatic hydrocarbons, e.g. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, dispersions, pastes, wettable powders or water-dispersible granules by addition of water. To prepare emulsions, pastes or oil dispersions, the substrates can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Suitable surface-active substances (adjuvants) are the alkali metal, alkaline earth metal or ammonium salts of aromatic sulfonic acids, e.g. lignosulfonic, phenolsulfonic, naphthalenesulfonic and dibutylnaphthalenesulfonic acid, and also of fatty acids, alkyl and alkylarylsulfonates, alkyl, lauryl ether and fatty alcohol sulfates, as well as salts of sulfated hexa-, hepta- and octadecanols, and also of fatty alcohol glycol ether, condensation products of sulfonated naphthalene and its derivatives with formaldehyde, condensation products of naphthalene or of the naphthalenesulfonic acids with phenol and formaldehyde, polyoxyethylene octylphenol ethers, ethoxylated isooctyl-, octyl- or nonylphenol, alkylphenyl or tributylphenyl polyglycol ethers, alkyl-aryl polyether alcohols, isotridecyl alcohol, fatty alcohol-ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, e.g. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as grain flour, tree bark, wood and nutshell meal, cellulose powder or other solid carriers.

The concentrations of the active compounds I in the ready-to-use preparations can be varied within wide ranges. The formulations in general contain from 0.001 to 98% by weight, preferably from 0.01 to 95% by weight, of at least one active compound. The active compounds are employed here in a purity of from 90 to 100%, preferably 95 to 100% (according to NMR spectrum).

The compounds I according to the invention can be formulated, for example, as follows I. 20 parts by weight of the compound No. 13.1 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium dodecylbenzenesulfonate and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 13.3 are dissolved in a mixture which consists of 40 parts by weight of cyclohexanone, 30 parts by weight of isobutanol, 20 parts by weight of the addition product of 40 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 13.8 are dissolved in a mixture which consists of 25 parts by weight of cyclohexanone, 65 parts by weight of a mineral oil fraction of boiling point from 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 13.9 are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is contained obtained which contains 0.1% by weight of the active compound.

V. 3 parts by weight of the active compound No. 13.5 are mixed with 97 parts by weight of finely divided kaolin. In this manner, a dusting composition is obtained which contains 3% by weight of the active compound.

VI. 20 parts by weight of the active compound No. 13.15 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

VII. 1 part by weight of the active compound No. 13.16 is dissolved in a mixture which consists of 70 parts by weight of cyclohexanone, 20 parts by weight of ethoxylated isooctylphenol and 10 parts by weight of ethoxylated castor oil. A stable emulsion concentrate is obtained.

VIII. 1 part by weight of the active compound No. 13.17 is dissolved in a mixture which consists of 80 parts by weight of cyclohexanone and 20 parts by weight of Wettol® EM 31 (=nonionic emulsifier based on ethoxylated castor oil). A stable emulsion concentrate is obtained.

The application of the active compounds I or of the herbicidal compositions can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

Depending on the aim of control, time of year, target plants and stage of growth, the application rates of active compound are from 0.001 to 3.0, preferably from 0.01 to 1.0, kg/ha of active substance (a.s.).

To widen the spectrum of action and to achieve synergistic effects, the benzoyl derivatives I can be mixed and applied together with numerous representatives of other herbicidal or growth-regulating active compound groups. For example, suitable mixture components are 1,2,4- thiadiazoles, 1,3,4-thiadiazoles, amides, aminophosphoric acid and its derivatives, aminotriazoles, anilides, aryloxy-/heteroaryloxyalkanoic acids and their derivatives, benzoic acid and its derivatives, benzothiadiazinones, 2-(heteroaryl/aroyl)-1,3-cyclohexadiones, heteroaryl aryl ketones, benzylisoxazolidinones, meta-CF$_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic acid esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, tirazolecarboxamides and uracils.

Additionally, it may be useful to apply the compounds I on their own or in combination with other herbicides additionally mixed with further crop protection agents, for example with agents for controlling pests or phytopathogenic fungi or bacteria. Further of interest is the miscibility with mineral salt solutions, which are employed for the elimination of nutritional and trace element deficiencies. Nonphytotoxic oils and oil concentrates can also be added.

Use Examples

It was possible to show the herbicidal action of the benzoyl derivatives of the formula I by greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered to promote germination and growth and then covered with transparent plastic hoods until the plants had taken root. This covering causes uniform germination of the test plants if this has not been adversely affected by the active compounds.

For the purposes of post-emergence application, the test plants, depending on growth form, were first raised to a height growth of from 3 to 15 cm and only then treated with the active compounds suspended or emulsified in water. For this purpose, the test plants were either sown directly and grown in the same containers or they were first raised separately as seedlings and transplanted into the test containers a few days before treatment.

The application rate for post-emergence treatment was from 0.5 to 0.25 kg/ha of a.s.

The plants were kept species-specifically at from 10–25° C. or 20–35° C. The test period extended over 2 to 4 weeks. During this time, the plants were tended and their reaction to the individual treatments was assessed.

Assessment was carried out on a scale of from 0 to 100. 100 here means no emergence of the plants or complete destruction of at least the above-ground parts and 0 means no damage or normal course of growth.

The plants used in the greenhouse tests were made up of the following species:

| Botanical Name | English Name |
|---|---|
| Chenopodium album (CHEAL) | lambs-quarters (goosefoot) |
| Ipomoea subspecies (IPOSS) | morning glory |
| Sinapis alba (SINAL) | white mustard |
| Solanum nigrum (SOLNI) | black nightshade |
| Triticum aestivum (TRZAS) | summer wheat |
| Zea mays (ZEAMX) | Indian corn |

TABLE 17

Herbicidal activity in the case of post-emergence application in the greenhouse

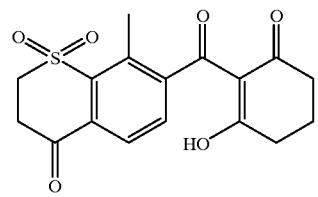

| | Ex. No. 13.3 | |
|---|---|---|
| | Application rate (kg/ha of a.s.) | |
| | 0.5 | 0.25 |
| Test plants | Damage in % | |
| TRZAS | 0 | 0 |
| CHEAL | 95 | 95 |
| SINAL | 95 | 95 |
| SOLNI | 100 | 95 |

TABLE 18

Herbicidal activity in the case of post-emergence application in the greenhouse

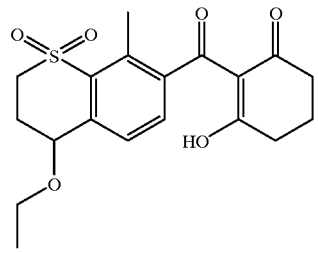

| | Ex. No. 13.13 | |
|---|---|---|
| | Application rate (kg/ha of a.s.) | |
| | 0.5 | 0.25 |
| Test plants | Damage in % | |
| ZEAMX | 10 | 0 |
| CHEAL | 95 | 95 |
| IPOSS | 100 | 100 |
| SOLNI | 100 | 100 |

We claim:
1. A benzoyl compound of the formula I

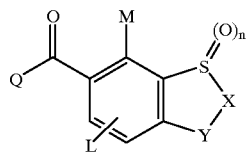

where the substituents have the following meanings:
L and M are hydrogen, $C_1$–$C_6$-alkyl, $C_2$–$C_6$-alkenyl, $C_2$–$C_6$-alkynyl, $C_1$–$C_4$-alkoxy, where these groups may carry one to five halogen atoms or $C_1$–$C_4$-alkoxy; halogen, cyano, nitro, a group —$(A)_m$—$S(O)_n R^1$ or a group —$(A)_m$—CO—$R^2$;
Y is $CR^{10}R^{11}$;
X is —$CR^{12}R^{13}$—$CR^{21}R^{22}$— or —$CR^{12}$=$CR^{13}$—;
the bond between X and Y can be saturated or unsaturated;
A is O or $NR^{14}$;
m is zero or one;
n is zero, one or two;
$R^1$ is $C_1$–$C_4$-alkyl, $C_1$–$C_4$-haloalkyl or $NR^{14}$;
$R^2$ is $C_1$–$C_4$-alkyl, $C_1$–$C_4$-haloalkyl, $C_1$–$C_4$-alkoxy or $NR^{14}$;
$R^{10}$, $R^{11}$ independently of one another are hydrogen, $C_1$–$C_6$-alkyl; unsubstituted or substituted phenyl, wherein the substituents are selected from the group consisting of one to three halogens, $C_1$–$C_4$-alkyl, $C_1$–$C_4$-alkoxy, $C_1$–$C_4$-haloalkoxy and nitro; $R^{10}$ and $R^{12}$ or $R^{10}$ and $R^{21}$ can form a bond;
$R^{12}$ and $R^{13}$ independently of one another are hydrogen, $C_1$–$C_6$-alkyl, $C_1$–$C_6$-haloalkyl, $C_1$–$C_6$-alkoxy, $C_1$–$C_6$-haloalkoxy; unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
$R^{14}$ is $C_1$–$C_4$-alkyl;
$R^{21}$ is hydrogen, $C_1$–$C_6$-alkyl, $C_1$–$C_6$-haloalkyl, $C_1$–$C_6$-alkoxy, $C_1$–$C_6$-haloalkoxy; unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
$R^{22}$ is hydrogen, $C_1$–$C_6$-alkyl, $C_1$–$C_6$-haloalkyl, $C_1$–$C_6$-alkoxy, $C_1$–$C_6$-haloalkoxy; unsubstituted or substituted phenyl, wherein the substituents are selected from the group consisting of $C_1$–$C_4$-alkyl, $C_1$–$C_4$-alkoxy, $C_1$–$C_4$-haloalkoxy, $C_1$–$C_4$-haloalkyl, halogen, cyano and nitro;
Q is a cyclohexane-1,3-dione ring, which is linked in the 2-position, of the formula II

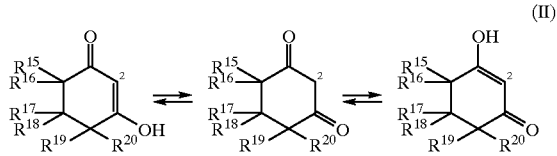

where
$R^{15}$, $R^{16}$, $R^{18}$ and $R^{20}$ are hydrogen or $C_1$–$C_4$-alkyl, $R^{19}$ is hydrogen, $C_1$–$C_4$-alkyl or a group —$COOR^{14}$,
$R^{17}$ is hydrogen, $C_1$–$C_4$-alkyl, $C_3$–$C_4$-cycloalkyl, where these groups may carry one to three of the following substituents: halogen, $C_1$–$C_4$-alkylthio or $C_1$–$C_4$-alkoxy, or
$R^{17}$ is tetrahydropyran-3-yl, tetrahydropyran-4-yl or tetrahydrothiopyran-3-yl, or
$R^{17}$ and $R^{20}$ together form a bond or a three to six-membered carbocyclic ring,
or an agriculturally utilizable salt thereof.

2. A benzoyl compound of the formula Ia

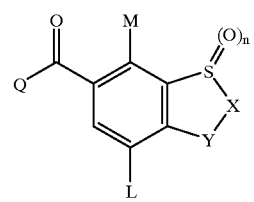

where
L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano,
M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano, and
Q, X, n and Y have the meanings given in claim 1.

3. A benzoyl compound of the formula Ib

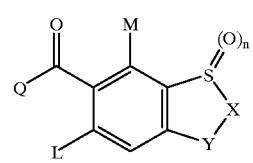

where
L is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano,
M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, and
Q, X, n and Y have the meanings given in claim 1.

4. The benzoyl compound of the formula I as defined in claim 1 where the radicals L and M are hydrogen, methyl, methoxy, chlorine, cyano, nitro or trifluoromethyl.

5. A benzoyl compound of the formula Ic

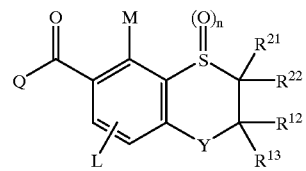

where
L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, and Q, n, Y and $R^{22}$, $R^{21}$, $R^{12}$ and $R^{13}$ have the meanings given in claim 1.

6. A benzoyl compound of the formula Ie

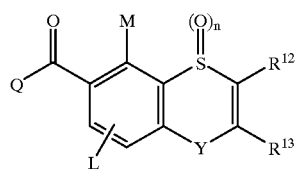

Ie where

L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, M is hydrogen, $C_1$–C–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, halogen, nitro or cyano, and Q, n, Y and $R^{12}$ and $R^{13}$ have the meanings given in claim 1.

7. A herbicidal composition comprising at least one benzoyl compound of the formula I as defined in claim 1 and customary inert additives.

8. A method of controlling undesirable vegetation, which comprises allowing a herbicidally active amount of a benzoyl compound of the formula I as defined in claim 1 to act on the plants or their environment.

9. A process for preparing a compound of the formula I as defined in claim 1, which comprises acylating a 1,3-cyclohexanedione of the formula II

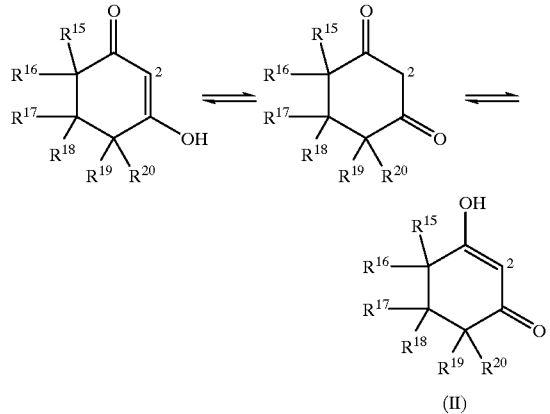

(II)

with an acid chloride of the formula IIIa or an acid IIIb,

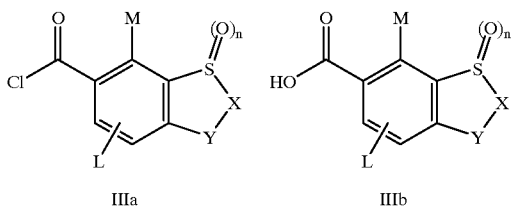

IIIa                IIIb and rearranging the acylation product in the presence of a catalyst to give the compound I.

10. A benzoyl compound of the formula IIIc

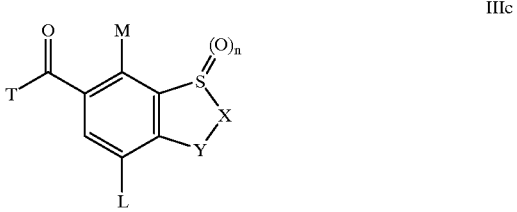

IIIc where T, L, M, X, n and Y have the following meanings:
T is chlorine, OH or $C_1$–$C_4$-alkoxy;
L is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-halothioalkyl, $C_1$–$C_4$-alkylsulfonyl, halogen, nitro or cyano;
M is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-halothioalkyl, $C_1$–$C_4$-alkylsulfonyl, halogen, nitro or cyano;
X is —$CR^{12}R^{13}$—$CR^{21}R^{22}$— or —$CR^{12}$=$CR^{13}$—;
Y is $CR^{10}R^{11}$;
n is zero, one or two.

11. A benzoyl compound of the formula IIId

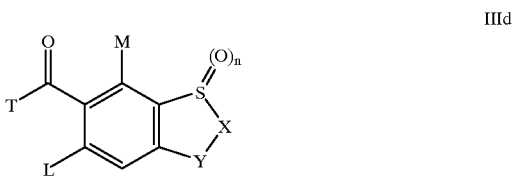

IIId where T, L, M, X, n and Y have the following meanings:
T is chlorine, OH or $C_1$–$C_4$-alkoxy;
L is $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-halothioalkyl, $C_1$–$C_4$-alkylsulfonyl, halogen or cyano;
M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-halothioalkyl, $C_1$–$C_4$-alkylsulfonyl, halogen, nitro or cyano;
X is —$CR^{12}R^{13}$—$CR^{21}R^{22}$— or —$CR^{12}$=$CR^{13}$—;
Y is $CR^{10}R^{11}$;
n is zero, one or two.

* * * * *

UNITED STATES PATENT AND TRADEMARK OFFICE
CERTIFICATE OF CORRECTION

PATENT NO.: 6,054,414

DATED: April 25, 2000

INVENTOR(S): OTTEN et al.

It is certified that error appears in the above-identified patent and that said Letters Patent is hereby corrected as shown below:

Col. 211, claim 6, line 25, "$C_1$-C-$C_6$-alkyl" should be --$C_1$-$C_6$-alkyl--.

Signed and Sealed this

Third Day of April, 2001

Attest:

NICHOLAS P. GODICI

*Attesting Officer*     *Acting Director of the United States Patent and Trademark Office*